(12) United States Patent
Sakamoto et al.

(10) Patent No.: US 11,787,877 B2
(45) Date of Patent: Oct. 17, 2023

(54) ANTIBODY WITH NON-NATURAL AMINO ACID INTRODUCED THEREIN

(71) Applicants: RIKEN, Wako (JP); KYOWA KIRIN CO., LTD., Tokyo (JP)

(72) Inventors: Kensaku Sakamoto, Saitama (JP); Kazumasa Ohtake, Saitama (JP); Yoshimi Yamaguchi, Saitama (JP); Shigeyuki Yokoyama, Saitama (JP); Tatsuo Yanagisawa, Saitama (JP); Akiko Matsumoto, Saitama (JP); Akifumi Kato, Tokyo (JP); Yasuhisa Shiraishi, Tokyo (JP); Kaname Kimura, Tokyo (JP); Masakazu Homma, Tokyo (JP)

(73) Assignees: RIKEN, Saitama (JP); KYOWA KIRIN CO., LTD., Tokyo (JP)

( * ) Notice: Subject to any disclaimer, the term of this patent is extended or adjusted under 35 U.S.C. 154(b) by 353 days.

(21) Appl. No.: 17/131,135

(22) Filed: Dec. 22, 2020

(65) Prior Publication Data
US 2021/0107997 A1   Apr. 15, 2021

Related U.S. Application Data

(62) Division of application No. 15/753,724, filed as application No. PCT/JP2016/074056 on Aug. 18, 2016, now Pat. No. 10,906,990.

(30) Foreign Application Priority Data

Aug. 19, 2015 (JP) ................. 2015-162160

(51) Int. Cl.
| | |
|---|---|
| C07K 16/46 | (2006.01) |
| C07K 16/28 | (2006.01) |
| C07K 16/32 | (2006.01) |
| A61K 39/395 | (2006.01) |
| C07K 16/00 | (2006.01) |
| C07K 16/24 | (2006.01) |
| A61K 47/68 | (2017.01) |
| C07K 16/22 | (2006.01) |
| A61K 47/60 | (2017.01) |

(52) U.S. Cl.
CPC .......... *C07K 16/467* (2013.01); *A61K 39/395* (2013.01); *A61K 47/60* (2017.08); *A61K 47/6803* (2017.08); *A61K 47/6849* (2017.08); *A61K 47/6855* (2017.08); *A61K 47/6875* (2017.08); *A61K 47/6889* (2017.08); *C07K 16/00* (2013.01); *C07K 16/22* (2013.01); *C07K 16/241* (2013.01); *C07K 16/28* (2013.01); *C07K 16/2863* (2013.01); *C07K 16/2887* (2013.01); *C07K 16/32* (2013.01); *C07K 16/46* (2013.01); *C07K 2317/14* (2013.01); *C07K 2317/20* (2013.01); *C07K 2317/21* (2013.01); *C07K 2317/24* (2013.01); *C07K 2317/33* (2013.01); *C07K 2317/52* (2013.01); *C07K 2317/522* (2013.01); *C07K 2317/55* (2013.01); *C07K 2317/71* (2013.01); *C07K 2317/72* (2013.01); *C07K 2317/732* (2013.01); *C07K 2317/734* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,219,996 A | 6/1993 | Bodmer et al. | |
| 10,906,990 B2 * | 2/2021 | Sakamoto ............ | A61K 39/395 |
| 2010/0267087 A1 | 10/2010 | Yokoyama et al. | |
| 2010/0304431 A1 | 12/2010 | Yokoyama et al. | |
| 2012/0009621 A1 | 1/2012 | Yamasaki et al. | |
| 2014/0127209 A1 | 5/2014 | Grabstein et al. | |
| 2015/0017187 A1 | 1/2015 | Thanos | |
| 2015/0259721 A1 | 9/2015 | Grabstein | |
| 2018/0154017 A1 | 6/2018 | Gomez De La Cuesta | |

FOREIGN PATENT DOCUMENTS

| | | |
|---|---|---|
| JP | 2007-037445 A | 2/2007 |
| JP | 2013-545438 A | 12/2013 |
| WO | 2006/034488 A2 | 3/2006 |
| WO | 2009/038195 A1 | 3/2009 |
| WO | 2011/118739 A1 | 9/2011 |

(Continued)

OTHER PUBLICATIONS

Atsushi Yamaguchi et al., "Incorporation of a Doubly Functionalized Synthetic Amino Acid into Proteins for Creating Chemical and Light-Induced Conjugates", Bioconjugate Chem., 2016, vol. 27, No. 1, pp. 198-206 (XP055549606).

Kline, et al., "Methods to Make Homogenous Antibody Drug Conjugates" Pharmaceutical Research, Published Dec. 16, 2014; vol. 32, No. 11, pp. 3480-3493.

Asher Mullard, "Maturing antibody-drug conjugate pipeline hits 30," Nature Reviews Drug Discovery, May 2013, pp. 329-332 (5 pages), vol. 12.

Tatsuo Yanagisawa et al., "Multistep Engineering of Pyrrolysyl-tRNA Synthetase to Genetically Encode N$^\varepsilon$-(o-Azidobenzyloxycarbonyl) lysine for Site-Specific Protein Modification," Chemistry & Biology, Nov. 24, 2008, pp. 1187-1197, vol. 15.

(Continued)

*Primary Examiner* — Phuong Huynh
(74) *Attorney, Agent, or Firm* — Sughrue Mion, PLLC

(57) ABSTRACT

The present invention relates to a monoclonal antibody or antibody fragment thereof as a human IgG antibody including at least one lysine derivative in a constant region of the human IgG antibody; a modified antibody or antibody fragment thereof, wherein the lysine derivative is modified; a nucleic acid including a nucleotide sequence encoding the antibody or antibody fragment thereof; a vector including the nucleic acid; a transformed cell obtained by introducing the vector into a host cell; a method for producing the antibody or antibody fragment thereof; and a composition containing the antibody or antibody fragment thereof.

14 Claims, 2 Drawing Sheets
Specification includes a Sequence Listing.

(56) References Cited

FOREIGN PATENT DOCUMENTS

| WO | 2013/068874 A1 | 5/2013 |
| WO | 2013/171485 A1 | 11/2013 |
| WO | 2014/004639 A1 | 1/2014 |
| WO | 2014/044872 A1 | 3/2014 |
| WO | 2014/124258 A2 | 8/2014 |

OTHER PUBLICATIONS

Communication dated Feb. 14, 2019, issued by the European Patent Office in corresponding European Application No. 16837145.8.

Communication dated Apr. 15, 2020, issued by European Patent Office in counterpart application No. 16837145.8.

Siler Panowski et al., "Site-Specific antibody drug conjugates for cancer therapy," mAbs, Jan./Feb. 2014, pp. 34-45, vol. 6, Issue 1.

Chan Hyuk Kim et al., "Synthesis of Bispecific Antibodies with Genetically Encoded Unnatural Amino Acids," J. Am. Chem. Soc., Jun. 20, 2012, pp. 9918-9921 (10 pages), vol. 134, No. 24.

Han Xiao et al., "Genetic Incorporation of Multiple Unnatural Amino Acids into Proteins in Mammalian Cells", Angew. Chem. Int. Ed., 2013, vol. 52, No. 52, pp. 14080-14083 (XP055122417).

Feng, et al., "Conjugates of Small Molecule Drugs with Antibodies and Other Proteins" Biomedicines, published Jan. 24, 2014, vol. 2, No. 1, pp. 1-13.

Jun Y. Axup et al., "Synthesis of site-specific antibody-drug conjugates using unnatural amino acids," PNAS, Oct. 2, 2012, pp. 16101-16106, vol. 109, No. 40.

Ivana Nikic et al., "Minimal Tags for Rapid-Dual-Color Live-Cell Labeling and Super-Resolution Microscopy," Angew. Chem. Int. Ed., 2014, pp. 2245-2249, vol. 53.

Tatsuo Yanagisawa et al., "Wide-range protein photo-crosslinking achieved by a genetically encoded Nε-(benzyloxycarbonyl)lysine derivative with a diazirinyl moiety", Mol. BioSyst., 2012, vol. 8, No. 4, pp. 1131-1135 (XP055549614).

Mueller, et al., "Determination of the Number of ε-Amino Groups Available for Conjugation of Effector Molecules to Monoclonal Antibodies" Hybridoma, 1988, vol. 7, No. 5 pp. 453-456.

International Search Report of PCT/JP2016/074056 dated Nov. 15, 2016.

Colman et al., Research in Immunology (145(1):33-36 (Year :1994).

Lederman et al., Molecular Immunology 28:1171-1181 (Year: 1991).

Stancovski et al., PNAS, 88: 8691-8695 (Year: 1991).

Golay et al., Archives of Biochemistry and Biophysics 526: 146-153 (Year: 2012).

Jubala et al., Vet Pathol 42: 468-476 (Year: 2005).

Yu et al. (Investigative Opthalmology & Visual Science 49 (2): 522-527 (Year: 2008).

Erik S. Zimmerman et al., "Production of Site-Specific Antibody-Drug Conjugates Using Optimized Non-Natural Amino Acids in a Cell-Free Expression System," Bioconjugate Chemistry, 2014, pp. 351-361, vol. 25.

* cited by examiner

SEQUENCE LISTING

```
<160> NUMBER OF SEQ ID NOS: 107

<210> SEQ ID NO 1
<211> LENGTH: 72
<212> TYPE: DNA
<213> ORGANISM: Methanosarcina mazeii

<400> SEQUENCE: 1
ggaaacctga tcatgtagat cgaatggact ctaaatccgt tcagccgggt tagattcccg      60
gggtttccgc ca                                                         72

<210> SEQ ID NO 2
<211> LENGTH: 214
<212> TYPE: PRT
<213> ORGANISM: Artificial Sequence
<220> FEATURE:
<223> OTHER INFORMATION: Synthetic amino acid sequence of light chain of
      Trastuzumab-Fab

<400> SEQUENCE: 2

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 3
<211> LENGTH: 232
<212> TYPE: PRT
<213> ORGANISM: Artificial Sequence
<220> FEATURE:
<223> OTHER INFORMATION: Synthetic amino acid sequence of heavy chain of
      Trastuzumab-Fab

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His His His His His His
225                 230

<210> SEQ ID NO 4
<211> LENGTH: 70
<212> TYPE: DNA
<213> ORGANISM: Artificial Sequence
<220> FEATURE:
<223> OTHER INFORMATION: Synthetic nucleotide sequence of Tac promoter
      and Shine-Dalgarno sequence

<400> SEQUENCE: 4
tgacaattaa tcatcggctc gtataatgtg tggaattgtg agcggataac aatttcacac    60
aggagatatc                                                          70

<210> SEQ ID NO 5
<211> LENGTH: 66
<212> TYPE: DNA
<213> ORGANISM: Artificial Sequence
<220> FEATURE:
<223> OTHER INFORMATION: Synthetic nucleotide sequence of PelB signal
      sequence
```

```
<400> SEQUENCE: 5
atgaaatacc tgctgccgac cgctgctgct ggtctgctgc tcctcgctgc ccagccggcg   60
atggcc                                                              66

<210> SEQ ID NO 6
<211> LENGTH: 727
<212> TYPE: DNA
<213> ORGANISM: Artificial Sequence
<220> FEATURE:
<223> OTHER INFORMATION: Synthetic nucleotide sequence of light chain of
      Trastuzumab-Fab

<400> SEQUENCE: 6
catatgaaat acctgctgcc gaccgctgct gctggtctgc tgctcctcgc tgcccagccg   60
gcgatggccg atattcaaat gacccagtcc ccgtcctccc tgtctgcctc cgttggtgat  120
cgtgttacga ttacctgccg cgcctctcaa gatgtcaaca ccgcagtggc ttggtatcag  180
caaaaaccgg gcaaagcgcc gaaactgctg atttattcag cctcgtttct gtactccggt  240
gttccgtcac gtttcagcgg ctctcgcagt ggtaccgatt taccctgac gatcagctct   300 ctgcagccgg aagacttcgc aacgtattac tgccagcaac attacaccac gccgccgacc  360
tttggccagg gtacgaaagt ggaaattaaa cgtacggttg cggccccgtc tgtctttatc  420
ttcccgccga gcgatgaaca gctgaaatcg ggcaccgcga gcgtggtttg tctgctgaac  480
aatttctatc cgcgcgaagc aaaagtccag tggaaagtgg acaacgctct gcagtccggt  540
aattcacaag aatcggtcac cgaacaagat agcaaagact ctacgtacag tctgagttcc  600
accctgacgc tgagcaaagc ggattatgaa aaacacaaag tttacgcctg cgaagttacg  660
catcagggtc tgtccagccc ggtgacgaaa tcttttaatc gtggtgaatg ttgagtcgcg  720
caagctt                                                            727

<210> SEQ ID NO 7
<211> LENGTH: 774
<212> TYPE: DNA
<213> ORGANISM: Artificial Sequence
<220> FEATURE:
<223> OTHER INFORMATION: Synthetic nucleotide sequence of heavy chain of
      Trastuzumab-Fab

<400> SEQUENCE: 7
catatgaaat acctgctgcc gaccgctgct gctggtctgc tgctcctcgc tgcccagccg   60
gcgatggccg aagtgcaact ggtggaaagt ggtggtggtc tggttcaacc gggtggctcc  120
ctgcgtctgt cctgtgctgc gtcgggtttt aacatcaaag ataccatat tcattgggtc   180 cgtcaggcac cgggcaaagg tctggaatgg gtggctcgca tctacccgac caacggctat  240
acgcgttacg cggattccgt gaaaggtcgc tttaccattt ccgcggacac ctcaaaaaac  300
acggcctatc tgcagatgaa cagcctgcgt gcagaagaca cggctgttta ttactgcagt  360
cgctggggcg gtgatggctt ttatgccatg gactactggg gccaaggtac cctggtcacc  420
gtgagctctg ctagcaccaa aggtccgagc gtgttccgc tggctccgag ttccaaatcg   480
accagcggcg gtacggcagc actgggttgt ctggttaaag attattttcc ggaaccggtt  540
accgtctctt ggaacagtgg cgcgctgacc tctggtgtgc atacgttccc ggccgttctg  600
cagtcatcgg gcctgtatag cctgagctct gtggttaccg ttccgagttc ctcactgggt  660
acccaaacgt acatctgcaa cgtcaatcac aaaccgagca atacgaaagt ggacaaaaaa  720
gttgaaccga atcctgcga taaaacccat catcaccatc atcattgagt cgac          774
```

<210> SEQ ID NO 8
<211> LENGTH: 454
<212> TYPE: PRT
<213> ORGANISM: Artificial Sequence
<220> FEATURE:
<223> OTHER INFORMATION: Synthetic amino acid sequence of Pyl aminoacyl-
      tRNA synthetase variant(Y306A/Y384F)

<400> SEQUENCE: 8

```
Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Lys His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Ala Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
```

His Leu Gly Ile Asp Phe Lys Ile Val Gly Asp Ser Cys Met Val Phe
370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
            405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Gly Ser Tyr Tyr Asn
            435                 440                 445

Gly Ile Ser Thr Asn Leu
        450

<210> SEQ ID NO 9
<211> LENGTH: 348
<212> TYPE: DNA
<213> ORGANISM: Artificial Sequence
<220> FEATURE:
<223> OTHER INFORMATION: Synthetic nucleotide sequence of K126
      amber_C_kappa of Trastuzumab-Fab

<400> SEQUENCE: 9
cgtacggttg cggccccgtc tgtctttatc ttcccgccga gcgatgaaca gctgtagtcg      60
ggcaccgcga gcgtggtttg tctgctgaac aatttctatc cgcgcgaagc aaaagtccag     120
tggaaagtgg acaacgctct gcagtccggt aattcacaag aatcggtcac cgaacaagat     180
agcaaagact ctacgtacag tctgagttcc accctgacgc tgagcaaagc ggattatgaa     240
aaacacaaag tttacgcctg cgaagttacg catcagggtc tgtccagccc ggtgacgaaa     300 tctttaatc gtggtgaatg ttgagtcgcg caagcttctc gagaattc                    348

<210> SEQ ID NO 10
<211> LENGTH: 348
<212> TYPE: DNA
<213> ORGANISM: Artificial Sequence
<220> FEATURE:
<223> OTHER INFORMATION: Synthetic nucleotide sequence of K145
      amber_C_kappa of Trastuzumab-Fab

<400> SEQUENCE: 10
cgtacggttg cggccccgtc tgtctttatc ttcccgccga gcgatgaaca gctgaaatcg      60
ggcaccgcga gcgtggtttg tctgctgaac aatttctatc cgcgcgaagc ataggtccag     120
tggaaagtgg acaacgctct gcagtccggt aattcacaag aatcggtcac cgaacaagat     180
agcaaagact ctacgtacag tctgagttcc accctgacgc tgagcaaagc ggattatgaa     240
aaacacaaag tttacgcctg cgaagttacg catcagggtc tgtccagccc ggtgacgaaa     300 tctttaatc gtggtgaatg ttgagtcgcg caagcttctc gagaattc                    348

<210> SEQ ID NO 11
<211> LENGTH: 348
<212> TYPE: DNA
<213> ORGANISM: Artificial Sequence
<220> FEATURE:
<223> OTHER INFORMATION: Synthetic nucleotide sequence of K149
      amber_C_kappa of Trastuzumab-Fab

<400> SEQUENCE: 11
cgtacggttg cggccccgtc tgtctttatc ttcccgccga gcgatgaaca gctgaaatcg      60

```
ggcaccgcga gcgtggtttg tctgctgaac aatttctatc cgcgcgaagc aaaagtccag      120
tggtaggtgg acaacgctct gcagtccggt aattcacaag aatcggtcac cgaacaagat      180
agcaaagact ctacgtacag tctgagttcc accctgacgc tgagcaaagc ggattatgaa      240
aaacacaaag tttacgcctg cgaagttacg catcagggtc tgtccagccc ggtgacgaaa      300
tcttttaatc gtggtgaatg ttgagtcgcg caagcttctc gagaattc                   348
```

<210> SEQ ID NO 12
<211> LENGTH: 348
<212> TYPE: DNA
<213> ORGANISM: Artificial Sequence
<220> FEATURE:
<223> OTHER INFORMATION: Synthetic nucleotide sequence of K169
       amber_C_kappa of Trastuzumab-Fab

<400> SEQUENCE: 12

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag     120
tggaaagtgg acaacgctct gcagtccggt aattcacaag aatcggtcac cgaacaagat     180
agctaggact ctacgtacag tctgagttcc accctgacgc tgagcaaagc ggattatgaa     240
aaacacaaag tttacgcctg cgaagttacg catcagggtc tgtccagccc ggtgacgaaa     300
tcttttaatc gtggtgaatg ttgagtcgcg caagcttctc gagaattc                   348
```

<210> SEQ ID NO 13
<211> LENGTH: 348
<212> TYPE: DNA
<213> ORGANISM: Artificial Sequence
<220> FEATURE:
<223> OTHER INFORMATION: Synthetic nucleotide sequence of K183
       amber_C_kappa of Trastuzumab-Fab

<400> SEQUENCE: 13

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag     120
tggaaagtgg acaacgctct gcagtccggt aattcacaag aatcggtcac cgaacaagat     180
agcaaagact ctacgtacag tctgagttcc accctgacgc tgagctaggc ggattatgaa     240
aaacacaaag tttacgcctg cgaagttacg catcagggtc tgtccagccc ggtgacgaaa     300
tcttttaatc gtggtgaatg ttgagtcgcg caagcttctc gagaattc                   348
```

<210> SEQ ID NO 14
<211> LENGTH: 348
<212> TYPE: DNA
<213> ORGANISM: Artificial Sequence
<220> FEATURE:
<223> OTHER INFORMATION: Synthetic nucleotide sequence of K188
       amber_C_kappa of Trastuzumab-Fab

<400> SEQUENCE: 14

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag     120
tggaaagtgg acaacgctct gcagtccggt aattcacaag aatcggtcac cgaacaagat     180
agcaaagact ctacgtacag tctgagttcc accctgacgc tgagcaaagc ggattatgaa     240
tagcacaaag tttacgcctg cgaagttacg catcagggtc tgtccagccc ggtgacgaaa     300
tcttttaatc gtggtgaatg ttgagtcgcg caagcttctc gagaattc                   348
```

<210> SEQ ID NO 15
<211> LENGTH: 348
<212> TYPE: DNA
<213> ORGANISM: Artificial Sequence
<220> FEATURE:
<223> OTHER INFORMATION: Synthetic nucleotide sequence of K190
      amber_C_kappa of Trastuzumab-Fab

<400> SEQUENCE: 15

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag     120
tggaaagtgg acaacgctct gcagtccggt aattcacaag aatcggtcac cgaacaagat     180
agcaaagact ctacgtacag tctgagttcc accctgacgc tgagcaaagc ggattatgaa     240
aaacactagg tttacgcctg cgaagttacg catcagggtc tgtccagccc ggtgacgaaa     300
tcttttaatc gtggtgaatg ttgagtcgcg caagcttctc gagaattc                  348
```

<210> SEQ ID NO 16
<211> LENGTH: 348
<212> TYPE: DNA
<213> ORGANISM: Artificial Sequence
<220> FEATURE:
<223> OTHER INFORMATION: Synthetic nucleotide sequence of K207
      amber_C_kappa of Trastuzumab-Fab

<400> SEQUENCE: 16

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag     120
tggaaagtgg acaacgctct gcagtccggt aattcacaag aatcggtcac cgaacaagat     180
agcaaagact ctacgtacag tctgagttcc accctgacgc tgagcaaagc ggattatgaa     240
aaacacaaag tttacgcctg cgaagttacg catcagggtc tgtccagccc ggtgacgtag     300
tcttttaatc gtggtgaatg ttgagtcgcg caagcttctc gagaattc                  348
```

<210> SEQ ID NO 17
<211> LENGTH: 345
<212> TYPE: DNA
<213> ORGANISM: Artificial Sequence
<220> FEATURE:
<223> OTHER INFORMATION: Synthetic nucleotide sequence of K121 amber_CH
      of Trastuzumab-Fab

<400> SEQUENCE: 17

```
gctagcacct agggtccgag cgtgttcccg ctggctccga gttccaaatc gaccagcggc      60
ggtacggcag cactgggttg tctggttaaa gattattttc cggaaccggt taccgtctct     120
tggaacagtg cgcgctgac ctctggtgtg catacgttcc cggccgttct gcagtcatcg      180
ggcctgtata gcctgagctc tgtggttacc gttccgagtt cctcactggg tacccaaacg     240
tacatctgca acgtcaatca caaaccgagc aatacgaaag tggacaaaaa agttgaaccg     300
aaatcctgcg ataaaaccca tcatcaccat catcattgag tcgac                     345
```

<210> SEQ ID NO 18
<211> LENGTH: 345
<212> TYPE: DNA
<213> ORGANISM: Artificial Sequence
<220> FEATURE:
<223> OTHER INFORMATION: Synthetic nucleotide sequence of K133 amber_CH
      of Trastuzumab-Fab

<400> SEQUENCE: 18

```
gctagcacca aaggtccgag cgtgttcccg ctggctccga gttcctagtc gaccagcggc    60
ggtacggcag cactgggttg tctggttaaa gattattttc cggaaccggt taccgtctct   120
tggaacagtg gcgcgctgac ctctggtgtg catacgttcc cggccgttct gcagtcatcg   180
ggcctgtata gcctgagctc tgtggttacc gttccgagtt cctcactggg tacccaaacg   240
tacatctgca acgtcaatca caaaccgagc aatacgaaag tggacaaaaa agttgaaccg   300
aaatcctgcg ataaaaccca tcatcaccat catcattgag tcgac                   345
```

<210> SEQ ID NO 19
<211> LENGTH: 345
<212> TYPE: DNA
<213> ORGANISM: Artificial Sequence
<220> FEATURE:
<223> OTHER INFORMATION: Synthetic nucleotide sequence of K147 amber_CH
      of Trastuzumab-Fab

<400> SEQUENCE: 19

```
gctagcacca aaggtccgag cgtgttcccg ctggctccga gttccaaatc gaccagcggc    60
ggtacggcag cactgggttg tctggtttag gattattttc cggaaccggt taccgtctct   120
tggaacagtg gcgcgctgac ctctggtgtg catacgttcc cggccgttct gcagtcatcg   180
ggcctgtata gcctgagctc tgtggttacc gttccgagtt cctcactggg tacccaaacg   240
tacatctgca acgtcaatca caaaccgagc aatacgaaag tggacaaaaa agttgaaccg   300
aaatcctgcg ataaaaccca tcatcaccat catcattgag tcgac                   345
```

<210> SEQ ID NO 20
<211> LENGTH: 345
<212> TYPE: DNA
<213> ORGANISM: Artificial Sequence
<220> FEATURE:
<223> OTHER INFORMATION: Synthetic nucleotide sequence of K205 amber_CH
      of Trastuzumab-Fab

<400> SEQUENCE: 20

```
gctagcacca aaggtccgag cgtgttcccg ctggctccga gttccaaatc gaccagcggc    60
ggtacggcag cactgggttg tctggttaaa gattattttc cggaaccggt taccgtctct   120
tggaacagtg gcgcgctgac ctctggtgtg catacgttcc cggccgttct gcagtcatcg   180
ggcctgtata gcctgagctc tgtggttacc gttccgagtt cctcactggg tacccaaacg   240
tacatctgca acgtcaatca ctagccgagc aatacgaaag tggacaaaaa agttgaaccg   300
aaatcctgcg ataaaaccca tcatcaccat catcattgag tcgac                   345
```

<210> SEQ ID NO 21
<211> LENGTH: 345
<212> TYPE: DNA
<213> ORGANISM: Artificial Sequence
<220> FEATURE:
<223> OTHER INFORMATION: Synthetic nucleotide sequence of K210 amber_CH
      of Trastuzumab-Fab

<400> SEQUENCE: 21

```
gctagcacca aaggtccgag cgtgttcccg ctggctccga gttccaaatc gaccagcggc    60
ggtacggcag cactgggttg tctggttaaa gattattttc cggaaccggt taccgtctct   120
tggaacagtg gcgcgctgac ctctggtgtg catacgttcc cggccgttct gcagtcatcg   180
ggcctgtata gcctgagctc tgtggttacc gttccgagtt cctcactggg tacccaaacg   240
tacatctgca acgtcaatca caaaccgagc aatacgtagg tggacaaaaa agttgaaccg   300
```
aaatcctgcg ataaaaccca tcatcaccat catcattgag tcgac          345

<210> SEQ ID NO 22
<211> LENGTH: 345
<212> TYPE: DNA
<213> ORGANISM: Artificial Sequence
<220> FEATURE:
<223> OTHER INFORMATION: Synthetic nucleotide sequence of K213 amber_CH
      of Trastuzumab-Fab

<400> SEQUENCE: 22
gctagcacca aggtccgag cgtgttcccg ctggctccga gttccaaatc gaccagcggc    60
ggtacggcag cactgggttg tctggttaaa gattattttc cggaaccggt taccgtctct   120
tggaacagtg gcgcgctgac ctctggtgtg catacgttcc cggccgttct gcagtcatcg   180
ggcctgtata gcctgagctc tgtggttacc gttccgagtt cctcactggg tacccaaacg   240
tacatctgca acgtcaatca caaaccgagc aatacgaaag tggactagaa agttgaaccg   300
aaatcctgcg ataaaaccca tcatcaccat catcattgag tcgac                   345

<210> SEQ ID NO 23
<211> LENGTH: 345
<212> TYPE: DNA
<213> ORGANISM: Artificial Sequence
<220> FEATURE:
<223> OTHER INFORMATION: Synthetic nucleotide sequence of K214 amber_CH
      of Trastuzumab-Fab

<400> SEQUENCE: 23
gctagcacca aggtccgag cgtgttcccg ctggctccga gttccaaatc gaccagcggc    60
ggtacggcag cactgggttg tctggttaaa gattattttc cggaaccggt taccgtctct   120
tggaacagtg gcgcgctgac ctctggtgtg catacgttcc cggccgttct gcagtcatcg   180
ggcctgtata gcctgagctc tgtggttacc gttccgagtt cctcactggg tacccaaacg   240
tacatctgca acgtcaatca caaaccgagc aatacgaaag tggacaaata ggttgaaccg   300
aaatcctgcg ataaaaccca tcatcaccat catcattgag tcgac                   345

<210> SEQ ID NO 24
<211> LENGTH: 774
<212> TYPE: DNA
<213> ORGANISM: Artificial Sequence
<220> FEATURE:
<223> OTHER INFORMATION: Synthetic nucleotide sequence of A118
      amber_heavy chain of Trastuzumab-Fab

<400> SEQUENCE: 24
catatgaaat acctgctgcc gaccgctgct gctggtctgc tgctcctcgc tgcccagccg    60
gcgatggccg aagtgcaact ggtggaaagt ggtggtggtc tggttcaacc gggtggctcc   120
ctgcgtctgt cctgtgctgc gtcgggtttt aacatcaaag ataccttatat tcattgggtc   180 cgtcaggcac cgggcaaagg tctggaatgg gtggctcgca tctacccgac caacggctat   240
acgcgttacg cggattccgt gaaaggtcgc tttaccattt ccgcggacac ctcaaaaaac   300
acggcctatc tgcagatgaa cagcctgcgt gcagaagaca cggctgttta ttactgcagt   360
cgctggggcg gtgatggctt ttatgccatg gactactggg gccaaggtac cctggtcacc   420
gtgagctctt agtcgaccaa aggtccgagc gtgttcccgc tggctccgag ttccaaatcg   480
accagcggcg gtacggcagc actggttgt ctggttaaag attattttcc ggaaccggtt   540
accgtctctt ggaacagtgg gcgcgctgacc tctggtgtgc atacgttccc ggccgttctg   600

```
cagtcatcgg gcctgtatag cctgagctct gtggttaccg ttccgagttc ctcactgggt    660
acccaaacgt acatctgcaa cgtcaatcac aaaccgagca atacgaaagt ggacaaaaaa    720
gttgaaccga atcctgcga taaaacccat catcaccatc atcattgagt cgac           774
```

<210> SEQ ID NO 25
<211> LENGTH: 774
<212> TYPE: DNA
<213> ORGANISM: Artificial Sequence
<220> FEATURE:
<223> OTHER INFORMATION: Synthetic nucleotide sequence of S119
      amber_heavy chain of Trastuzumab-Fab

<400> SEQUENCE: 25

```
catatgaaat acctgctgcc gaccgctgct gctggtctgc tgctcctcgc tgcccagccg    60
gcgatggccg aagtgcaact ggtggaaagt ggtggtggtc tggttcaacc gggtggctcc    120
ctgcgtctgt cctgtgctgc gtcgggtttt aacatcaaag ataccctatat tcattgggtc    180 cgtcaggcac cgggcaaagg tctggaatgg gtggctcgca tctacccgac caacggctat    240
acgcgttacg cggattccgt gaaaggtcgc tttaccattt ccgcggacac ctcaaaaaac    300
acggcctatc tgcagatgaa cagcctgcgt gcagaagaca cggctgttta ttactgcagt    360
cgctggggcg gtgatggctt ttatgccatg gactactggg gccaaggtac cctggtcacc    420
gtgagctctg catagaccaa aggtccgagc gtgttcccgc tggctccgag ttccaaatcg    480
accagcggcg gtacggcagc actgggttgt ctggttaaag attatttttc ggaaccggtt    540
accgtctctt ggaacagtgg cgcgctgacc tctggtgtgc atacgttccc ggccgttctg    600
cagtcatcgg gcctgtatag cctgagctct gtggttaccg ttccgagttc ctcactgggt    660
acccaaacgt acatctgcaa cgtcaatcac aaaccgagca atacgaaagt ggacaaaaaa    720
gttgaaccga atcctgcga taaaacccat catcaccatc atcattgagt cgac           774
```

<210> SEQ ID NO 26
<211> LENGTH: 345
<212> TYPE: DNA
<213> ORGANISM: Artificial Sequence
<220> FEATURE:
<223> OTHER INFORMATION: Synthetic nucleotide sequence of A162 amber_CH
      of Trastuzumab-Fab

<400> SEQUENCE: 26

```
gctagcacca aaggtccgag cgtgttcccg ctggctccga gttccaaatc gaccagcggc    60
ggtacggcag cactgggttg tctggttaaa gattatttttc cggaaccggt taccgtctct    120
tggaacagtg gctagctgac ctctggtgtg catacgttcc cggccgttct gcagtcatcg    180
ggcctgtata gcctgagctc tgtggttacc gttccgagtt cctcactggg tacccaaacg    240
tacatctgca acgtcaatca aaaccgagc aatacgaaag tggacaaaaa agttgaaccg    300
aaatcctgcg ataaaaccca tcatcaccat catcattgag tcgac                    345
```

<210> SEQ ID NO 27
<211> LENGTH: 345
<212> TYPE: DNA
<213> ORGANISM: Artificial Sequence
<220> FEATURE:
<223> OTHER INFORMATION: Synthetic nucleotide sequence of S176 amber_CH
      of Trastuzumab-Fab

<400> SEQUENCE: 27

```
gctagcacca aaggtccgag cgtgttcccg ctggctccga gttccaaatc gaccagcggc    60
```

```
ggtacggcag cactgggttg tctggttaaa gattattttc cggaaccggt taccgtctct    120
tggaacagtg gcgcgctgac ctctggtgtg catacgttcc cggccgttct gcagtagtcg    180
ggcctgtata gcctgagctc tgtggttacc gttccgagtt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345

<210> SEQ ID NO 28
<211> LENGTH: 337
<212> TYPE: DNA
<213> ORGANISM: Artificial Sequence
<220> FEATURE:
<223> OTHER INFORMATION: Synthetic nucleotide sequence of P119
      amber_C_kappa of Trastuzumab-Fab

<400> SEQUENCE: 28
cgtacggttg cggccccgtc tgtctttatc ttctagccga gcgatgaaca gctgaaatcg    60
ggcaccgcga gcgtggtttg tctgctgaac aatttctatc cgcgcgaagc aaaagtccag    120
tggaaagtgg acaacgctct gcagtccggt aattcacaag aatcggtcac cgaacaagat    180
agcaaagact ctacgtacag tctgagttcc accctgacgc tgagcaaagc ggattatgaa    240
aaacacaaag tttacgcctg cgaagttacg catcagggtc tgtccagccc ggtgacgaaa    300
tcttttaatc gtggtgaatg ttgagtcgcg caagctt                             337

<210> SEQ ID NO 29
<211> LENGTH: 337
<212> TYPE: DNA
<213> ORGANISM: Artificial Sequence
<220> FEATURE:
<223> OTHER INFORMATION: Synthetic nucleotide sequence of N138
      amber_C_kappa of Trastuzumab-Fab

<400> SEQUENCE: 29
cgtacggttg cggccccgtc tgtctttatc ttcccgccga gcgatgaaca gctgaaatcg    60
ggcaccgcga gcgtggtttg tctgctgaac tagttctatc cgcgcgaagc aaaagtccag    120
tggaaagtgg acaacgctct gcagtccggt aattcacaag aatcggtcac cgaacaagat    180
agcaaagact ctacgtacag tctgagttcc accctgacgc tgagcaaagc ggattatgaa    240
aaacacaaag tttacgcctg cgaagttacg catcagggtc tgtccagccc ggtgacgaaa    300
tcttttaatc gtggtgaatg ttgagtcgcg caagctt                             337

<210> SEQ ID NO 30
<211> LENGTH: 337
<212> TYPE: DNA
<213> ORGANISM: Artificial Sequence
<220> FEATURE:
<223> OTHER INFORMATION: Synthetic nucleotide sequence of P141
      amber_C_kappa of Trastuzumab-Fab

<400> SEQUENCE: 30
cgtacggttg cggccccgtc tgtctttatc ttcccgccga gcgatgaaca gctgaaatcg    60
ggcaccgcga gcgtggtttg tctgctgaac aatttctatt agcgcgaagc aaaagtccag    120
tggaaagtgg acaacgctct gcagtccggt aattcacaag aatcggtcac cgaacaagat    180
agcaaagact ctacgtacag tctgagttcc accctgacgc tgagcaaagc ggattatgaa    240
aaacacaaag tttacgcctg cgaagttacg catcagggtc tgtccagccc ggtgacgaaa    300
tcttttaatc gtggtgaatg ttgagtcgcg caagctt                             337
```

<210> SEQ ID NO 31
<211> LENGTH: 337
<212> TYPE: DNA
<213> ORGANISM: Artificial Sequence
<220> FEATURE:
<223> OTHER INFORMATION: Synthetic nucleotide sequence of Q147
      amber_C_kappa of Trastuzumab-Fab

<400> SEQUENCE: 31

| | | | | | | |
|---|---|---|---|---|---|---|
| cgtacggttg | cggccccgtc | tgtctttatc | ttcccgccga | gcgatgaaca | gctgaaatcg | 60 |
| ggcaccgcga | gcgtggtttg | tctgctgaac | aatttctatc | cgcgcgaagc | aaaagtctag | 120 |
| tggaaagtgg | acaacgctct | gcagtccggt | aattcacaag | aatcggtcac | cgaacaagat | 180 |
| agcaaagact | ctacgtacag | tctgagttcc | accctgacgc | tgagcaaagc | ggattatgaa | 240 |
| aaacacaaag | tttacgcctg | cgaagttacg | catcagggtc | tgtccagccc | ggtgacgaaa | 300 |
| tcttttaatc | gtggtgaatg | ttgagtcgcg | caagctt | | | 337 |

<210> SEQ ID NO 32
<211> LENGTH: 337
<212> TYPE: DNA
<213> ORGANISM: Artificial Sequence
<220> FEATURE:
<223> OTHER INFORMATION: Synthetic nucleotide sequence of Q155
      amber_C_kappa of Trastuzumab-Fab

<400> SEQUENCE: 32

| | | | | | | |
|---|---|---|---|---|---|---|
| cgtacggttg | cggccccgtc | tgtctttatc | ttcccgccga | gcgatgaaca | gctgaaatcg | 60 |
| ggcaccgcga | gcgtggtttg | tctgctgaac | aatttctatc | cgcgcgaagc | aaaagtccag | 120 |
| tggaaagtgg | acaacgctct | gtagtccggt | aattcacaag | aatcggtcac | cgaacaagat | 180 |
| agcaaagact | ctacgtacag | tctgagttcc | accctgacgc | tgagcaaagc | ggattatgaa | 240 |
| aaacacaaag | tttacgcctg | cgaagttacg | catcagggtc | tgtccagccc | ggtgacgaaa | 300 |
| tcttttaatc | gtggtgaatg | ttgagtcgcg | caagctt | | | 337 |

<210> SEQ ID NO 33
<211> LENGTH: 337
<212> TYPE: DNA
<213> ORGANISM: Artificial Sequence
<220> FEATURE:
<223> OTHER INFORMATION: Synthetic nucleotide sequence of N158
      amber_C_kappa of Trastuzumab-Fab

<400> SEQUENCE: 33

| | | | | | | |
|---|---|---|---|---|---|---|
| cgtacggttg | cggccccgtc | tgtctttatc | ttcccgccga | gcgatgaaca | gctgaaatcg | 60 |
| ggcaccgcga | gcgtggtttg | tctgctgaac | aatttctatc | cgcgcgaagc | aaaagtccag | 120 |
| tggaaagtgg | acaacgctct | gcagtccggt | tagtcacaag | aatcggtcac | cgaacaagat | 180 |
| agcaaagact | ctacgtacag | tctgagttcc | accctgacgc | tgagcaaagc | ggattatgaa | 240 |
| aaacacaaag | tttacgcctg | cgaagttacg | catcagggtc | tgtccagccc | ggtgacgaaa | 300 |
| tcttttaatc | gtggtgaatg | ttgagtcgcg | caagctt | | | 337 |

<210> SEQ ID NO 34
<211> LENGTH: 337
<212> TYPE: DNA
<213> ORGANISM: Artificial Sequence
<220> FEATURE:
<223> OTHER INFORMATION: Synthetic nucleotide sequence of E161
      amber_C_kappa of Trastuzumab-Fab

<400> SEQUENCE: 34

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag     120
tggaaagtgg acaacgctct gcagtccggt aattcacaat agtcggtcac cgaacaagat     180
agcaaagact ctacgtacag tctgagttcc accctgacgc tgagcaaagc ggattatgaa     240
aaacacaaag tttacgcctg cgaagttacg catcagggtc tgtccagccc ggtgacgaaa     300
tcttttaatc gtggtgaatg ttgagtcgcg caagctt                              337
```

<210> SEQ ID NO 35
<211> LENGTH: 337
<212> TYPE: DNA
<213> ORGANISM: Artificial Sequence
<220> FEATURE:
<223> OTHER INFORMATION: Synthetic nucleotide sequence of D167
    amber_C_kappa of Trastuzumab-Fab

<400> SEQUENCE: 35

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag     120
tggaaagtgg acaacgctct gcagtccggt aattcacaag aatcggtcac cgaacaatag     180
agcaaagact ctacgtacag tctgagttcc accctgacgc tgagcaaagc ggattatgaa     240
aaacacaaag tttacgcctg cgaagttacg catcagggtc tgtccagccc ggtgacgaaa     300
tcttttaatc gtggtgaatg ttgagtcgcg caagctt                              337
```

<210> SEQ ID NO 36
<211> LENGTH: 337
<212> TYPE: DNA
<213> ORGANISM: Artificial Sequence
<220> FEATURE:
<223> OTHER INFORMATION: Synthetic nucleotide sequence of T180
    amber_C_kappa of Trastuzumab-Fab

<400> SEQUENCE: 36

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag     120
tggaaagtgg acaacgctct gcagtccggt aattcacaag aatcggtcac cgaacaagat     180
agcaaagact ctacgtacag tctgagttcc accctgtagc tgagcaaagc ggattatgaa     240
aaacacaaag tttacgcctg cgaagttacg catcagggtc tgtccagccc ggtgacgaaa     300
tcttttaatc gtggtgaatg ttgagtcgcg caagctt                              337
```

<210> SEQ ID NO 37
<211> LENGTH: 337
<212> TYPE: DNA
<213> ORGANISM: Artificial Sequence
<220> FEATURE:
<223> OTHER INFORMATION: Synthetic nucleotide sequence of V191
    amber_C_kappa of Trastuzumab-Fab

<400> SEQUENCE: 37

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag     120
tggaaagtgg acaacgctct gcagtccggt aattcacaag aatcggtcac cgaacaagat     180
agcaaagact ctacgtacag tctgagttcc accctgacgc tgagcaaagc ggattatgaa     240
```

```
aaacacaaat agtacgcctg cgaagttacg catcagggtc tgtccagccc ggtgacgaaa    300
tcttttaatc gtggtgaatg ttgagtcgcg caagctt                            337
```

<210> SEQ ID NO 38
<211> LENGTH: 337
<212> TYPE: DNA
<213> ORGANISM: Artificial Sequence
<220> FEATURE:
<223> OTHER INFORMATION: Synthetic nucleotide sequence of E195
      amber_C_kappa of Trastuzumab-Fab

<400> SEQUENCE: 38

```
cgtacggttg cggccccgtc tgtctttatc ttcccgccga gcgatgaaca gctgaaatcg    60
ggcaccgcga gcgtggtttg tctgctgaac aatttctatc cgcgcgaagc aaaagtccag    120
tggaaagtgg acaacgctct gcagtccggt aattcacaag aatcggtcac cgaacaagat    180
agcaaagact ctacgtacag tctgagttcc accctgacgc tgagcaaagc ggattatgaa    240
aaacacaaag tttacgcctg ctaggttacg catcagggtc tgtccagccc ggtgacgaaa    300
tcttttaatc gtggtgaatg ttgagtcgcg caagctt                            337
```

<210> SEQ ID NO 39
<211> LENGTH: 337
<212> TYPE: DNA
<213> ORGANISM: Artificial Sequence
<220> FEATURE:
<223> OTHER INFORMATION: Synthetic nucleotide sequence of T197
      amber_C_kappa of Trastuzumab-Fab

<400> SEQUENCE: 39

```
cgtacggttg cggccccgtc tgtctttatc ttcccgccga gcgatgaaca gctgaaatcg    60
ggcaccgcga gcgtggtttg tctgctgaac aatttctatc cgcgcgaagc aaaagtccag    120
tggaaagtgg acaacgctct gcagtccggt aattcacaag aatcggtcac cgaacaagat    180
agcaaagact ctacgtacag tctgagttcc accctgacgc tgagcaaagc ggattatgaa    240
aaacacaaag tttacgcctg cgaagtttag catcagggtc tgtccagccc ggtgacgaaa    300
tcttttaatc gtggtgaatg ttgagtcgcg caagctt                            337
```

<210> SEQ ID NO 40
<211> LENGTH: 337
<212> TYPE: DNA
<213> ORGANISM: Artificial Sequence
<220> FEATURE:
<223> OTHER INFORMATION: Synthetic nucleotide sequence of N210
      amber_C_kappa of Trastuzumab-Fab

<400> SEQUENCE: 40

```
cgtacggttg cggccccgtc tgtctttatc ttcccgccga gcgatgaaca gctgaaatcg    60
ggcaccgcga gcgtggtttg tctgctgaac aatttctatc cgcgcgaagc aaaagtccag    120
tggaaagtgg acaacgctct gcagtccggt aattcacaag aatcggtcac cgaacaagat    180
agcaaagact ctacgtacag tctgagttcc accctgacgc tgagcaaagc ggattatgaa    240
aaacacaaag tttacgcctg cgaagttacg catcagggtc tgtccagccc ggtgacgaaa    300 tcttttagc gtggtgaatg ttgagtcgcg caagctt                             337
```

<210> SEQ ID NO 41
<211> LENGTH: 337
<212> TYPE: DNA
<213> ORGANISM: Artificial Sequence
<220> FEATURE:

```
<223> OTHER INFORMATION: Synthetic nucleotide sequence of R211
      amber_C_kappa of Trastuzumab-Fab

<400> SEQUENCE: 41
cgtacggttg cggccccgtc tgtctttatc ttcccgccga gcgatgaaca gctgaaatcg    60
ggcaccgcga gcgtggtttg tctgctgaac aatttctatc cgcgcgaagc aaaagtccag   120
tggaaagtgg acaacgctct gcagtccggt aattcacaag aatcggtcac cgaacaagat   180
agcaaagact ctacgtacag tctgagttcc accctgacgc tgagcaaagc ggattatgaa   240
aaacacaaag tttacgcctg cgaagttacg catcagggtc tgtccagccc ggtgacgaaa   300
tcttttaatt agggtgaatg ttgagtcgcg caagctt                            337

<210> SEQ ID NO 42
<211> LENGTH: 348
<212> TYPE: DNA
<213> ORGANISM: Artificial Sequence
<220> FEATURE:
<223> OTHER INFORMATION: Synthetic nucleotide sequence of V110
      amber_C_kappa of Trastuzumab-Fab

<400> SEQUENCE: 42
cgtacgtagg cggccccgtc tgtctttatc ttcccgccga gcgatgaaca gctgaaatcg    60
ggcaccgcga gcgtggtttg tctgctgaac aatttctatc cgcgcgaagc aaaagtccag   120
tggaaagtgg acaacgctct gcagtccggt aattcacaag aatcggtcac cgaacaagat   180
agcaaagact ctacgtacag tctgagttcc accctgacgc tgagcaaagc ggattatgaa   240
aaacacaaag tttacgcctg cgaagttacg catcagggtc tgtccagccc ggtgacgaaa   300
tcttttaatc gtggtgaatg ttgagtcgcg caagcttctc gagaattc                348

<210> SEQ ID NO 43
<211> LENGTH: 348
<212> TYPE: DNA
<213> ORGANISM: Artificial Sequence
<220> FEATURE:
<223> OTHER INFORMATION: Synthetic nucleotide sequence of A112 amber
      C_kappa of Trastuzumab-Fab

<400> SEQUENCE: 43
cgtacggttg cgtagccgtc tgtctttatc ttcccgccga gcgatgaaca gctgaaatcg    60
ggcaccgcga gcgtggtttg tctgctgaac aatttctatc cgcgcgaagc aaaagtccag   120
tggaaagtgg acaacgctct gcagtccggt aattcacaag aatcggtcac cgaacaagat   180
agcaaagact ctacgtacag tctgagttcc accctgacgc tgagcaaagc ggattatgaa   240
aaacacaaag tttacgcctg cgaagttacg catcagggtc tgtccagccc ggtgacgaaa   300
tcttttaatc gtggtgaatg ttgagtcgcg caagcttctc gagaattc                348

<210> SEQ ID NO 44
<211> LENGTH: 348
<212> TYPE: DNA
<213> ORGANISM: Artificial Sequence
<220> FEATURE:
<223> OTHER INFORMATION: Synthetic nucleotide sequence of A153
      amber_C_kappa of Trastuzumab-Fab

<400> SEQUENCE: 44
cgtacggttg cggccccgtc tgtctttatc ttcccgccga gcgatgaaca gctgaaatcg    60
ggcaccgcga gcgtggtttg tctgctgaac aatttctatc cgcgcgaagc aaaagtccag   120
tggaaagtgg acaactagct gcagtccggt aattcacaag aatcggtcac cgaacaagat   180
```

```
agcaaagact ctacgtacag tctgagttcc accctgacgc tgagcaaagc ggattatgaa      240
aaacacaaag tttacgcctg cgaagttacg catcagggtc tgtccagccc ggtgacgaaa      300
tcttttaatc gtggtgaatg ttgagtcgcg caagcttctc gagaattc                   348
```

```
<210> SEQ ID NO 45
<211> LENGTH: 348
<212> TYPE: DNA
<213> ORGANISM: Artificial Sequence
<220> FEATURE:
<223> OTHER INFORMATION: Synthetic nucleotide sequence of L154
      amber_C_kappa of Trastuzumab-Fab

<400> SEQUENCE: 45
```

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag      120
tggaaagtgg acaacgctta gcagtccggt aattcacaag aatcggtcac cgaacaagat      180
agcaaagact ctacgtacag tctgagttcc accctgacgc tgagcaaagc ggattatgaa      240
aaacacaaag tttacgcctg cgaagttacg catcagggtc tgtccagccc ggtgacgaaa      300
tcttttaatc gtggtgaatg ttgagtcgcg caagcttctc gagaattc                   348
```

```
<210> SEQ ID NO 46
<211> LENGTH: 348
<212> TYPE: DNA
<213> ORGANISM: Artificial Sequence
<220> FEATURE:
<223> OTHER INFORMATION: Synthetic nucleotide sequence of A184
      amber_C_kappa of Trastuzumab-Fab

<400> SEQUENCE: 46
```

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag      120
tggaaagtgg acaacgctct gcagtccggt aattcacaag aatcggtcac cgaacaagat      180
agcaaagact ctacgtacag tctgagttcc accctgacgc tgagcaaata ggattatgaa      240
aaacacaaag tttacgcctg cgaagttacg catcagggtc tgtccagccc ggtgacgaaa      300
tcttttaatc gtggtgaatg ttgagtcgcg caagcttctc gagaattc                   348
```

```
<210> SEQ ID NO 47
<211> LENGTH: 348
<212> TYPE: DNA
<213> ORGANISM: Artificial Sequence
<220> FEATURE:
<223> OTHER INFORMATION: Synthetic nucleotide sequence of V205
      amber_C_kappa of Trastuzumab-Fab

<400> SEQUENCE: 47
```

```
cgtacggttg cggccccgtc tgtctttatc ttcccgccga gcgatgaaca gctgaaatcg      60
ggcaccgcga gcgtggtttg tctgctgaac aatttctatc cgcgcgaagc aaaagtccag      120
tggaaagtgg acaacgctct gcagtccggt aattcacaag aatcggtcac cgaacaagat      180
agcaaagact ctacgtacag tctgagttcc accctgacgc tgagcaaagc ggattatgaa      240
aaacacaaag tttacgcctg cgaagttacg catcagggtc tgtccagccc gtagacgaaa      300
tcttttaatc gtggtgaatg ttgagtcgcg caagcttctc gagaattc                   348
```

```
<210> SEQ ID NO 48
<211> LENGTH: 345
```

```
<212> TYPE: DNA
<213> ORGANISM: Artificial Sequence
<220> FEATURE:
<223> OTHER INFORMATION: Synthetic nucleotide sequence of T120 amber_CH
      of Trastuzumab-Fab

<400> SEQUENCE: 48
gctagctaga aaggtccgag cgtgttcccg ctggctccga gttccaaatc gaccagcggc      60
ggtacggcag cactgggttg tctggttaaa gattattttc cggaaccggt taccgtctct     120
tggaacagtg gcgcgctgac ctctggtgtg catacgttcc cggccgttct gcagtcatcg     180
ggcctgtata gcctgagctc tgtggttacc gttccgagtt cctcactggg tacccaaacg     240
tacatctgca acgtcaatca caaaccgagc aatacgaaag tggacaaaaa agttgaaccg     300
aaatcctgcg ataaaaccca tcatcaccat catcattgag tcgac                     345

<210> SEQ ID NO 49
<211> LENGTH: 345
<212> TYPE: DNA
<213> ORGANISM: Artificial Sequence
<220> FEATURE:
<223> OTHER INFORMATION: Synthetic nucleotide sequence of P127 amber_CH
      of Trastuzumab-Fab

<400> SEQUENCE: 49
gctagcacca aaggtccgag cgtgttctag ctggctccga gttccaaatc gaccagcggc      60
ggtacggcag cactgggttg tctggttaaa gattattttc cggaaccggt taccgtctct     120
tggaacagtg gcgcgctgac ctctggtgtg catacgttcc cggccgttct gcagtcatcg     180
ggcctgtata gcctgagctc tgtggttacc gttccgagtt cctcactggg tacccaaacg     240
tacatctgca acgtcaatca caaaccgagc aatacgaaag tggacaaaaa agttgaaccg     300
aaatcctgcg ataaaaccca tcatcaccat catcattgag tcgac                     345

<210> SEQ ID NO 50
<211> LENGTH: 345
<212> TYPE: DNA
<213> ORGANISM: Artificial Sequence
<220> FEATURE:
<223> OTHER INFORMATION: Synthetic nucleotide sequence of S131 amber_CH
      of Trastuzumab-Fab

<400> SEQUENCE: 50
gctagcacca aaggtccgag cgtgttcccg ctggctccgt agtccaaatc gaccagcggc      60
ggtacggcag cactgggttg tctggttaaa gattattttc cggaaccggt taccgtctct     120
tggaacagtg gcgcgctgac ctctggtgtg catacgttcc cggccgttct gcagtcatcg     180
ggcctgtata gcctgagctc tgtggttacc gttccgagtt cctcactggg tacccaaacg     240
tacatctgca acgtcaatca caaaccgagc aatacgaaag tggacaaaaa agttgaaccg     300
aaatcctgcg ataaaaccca tcatcaccat catcattgag tcgac                     345

<210> SEQ ID NO 51
<211> LENGTH: 345
<212> TYPE: DNA
<213> ORGANISM: Artificial Sequence
<220> FEATURE:
<223> OTHER INFORMATION: Synthetic nucleotide sequence of T135 amber_CH
      of Trastuzumab-Fab

<400> SEQUENCE: 51
gctagcacca aaggtccgag cgtgttcccg ctggctccga gttccaaatc gtagagcggc      60
```

```
ggtacggcag cactgggttg tctggttaaa gattattttc cggaaccggt taccgtctct    120
tggaacagtg gcgcgctgac ctctggtgtg catacgttcc cggccgttct gcagtcatcg    180
ggcctgtata gcctgagctc tgtggttacc gttccgagtt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345
```

<210> SEQ ID NO 52
<211> LENGTH: 345
<212> TYPE: DNA
<213> ORGANISM: Artificial Sequence
<220> FEATURE:
<223> OTHER INFORMATION: Synthetic nucleotide sequence of D148 amber_CH
      of Trastuzumab-Fab

<400> SEQUENCE: 52

```
gctagcacca aggtccgag cgtgttcccg ctggctccga gttccaaatc gaccagcggc     60
ggtacggcag cactgggttg tctggttaaa tagtattttc cggaaccggt taccgtctct    120
tggaacagtg gcgcgctgac ctctggtgtg catacgttcc cggccgttct gcagtcatcg    180
ggcctgtata gcctgagctc tgtggttacc gttccgagtt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345
```

<210> SEQ ID NO 53
<211> LENGTH: 345
<212> TYPE: DNA
<213> ORGANISM: Artificial Sequence
<220> FEATURE:
<223> OTHER INFORMATION: Synthetic nucleotide sequence of E152 amber_CH
      of Trastuzumab-Fab

<400> SEQUENCE: 53

```
gctagcacca aggtccgag cgtgttcccg ctggctccga gttccaaatc gaccagcggc     60
ggtacggcag cactgggttg tctggttaaa gattattttc cgtagccggt taccgtctct    120
tggaacagtg gcgcgctgac ctctggtgtg catacgttcc cggccgttct gcagtcatcg    180
ggcctgtata gcctgagctc tgtggttacc gttccgagtt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345
```

<210> SEQ ID NO 54
<211> LENGTH: 345
<212> TYPE: DNA
<213> ORGANISM: Artificial Sequence
<220> FEATURE:
<223> OTHER INFORMATION: Synthetic nucleotide sequence of N159 amber_CH
      of Trastuzumab-Fab

<400> SEQUENCE: 54

```
gctagcacca aggtccgag cgtgttcccg ctggctccga gttccaaatc gaccagcggc     60
ggtacggcag cactgggttg tctggttaaa gattattttc cggaaccggt taccgtctct    120
tggtagagtg gcgcgctgac ctctggtgtg catacgttcc cggccgttct gcagtcatcg    180
ggcctgtata gcctgagctc tgtggttacc gttccgagtt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345
```

<210> SEQ ID NO 55
<211> LENGTH: 345
<212> TYPE: DNA
<213> ORGANISM: Artificial Sequence
<220> FEATURE:
<223> OTHER INFORMATION: Synthetic nucleotide sequence of T169 amber_CH of Trastuzumab-Fab

<400> SEQUENCE: 55

```
gctagcacca aaggtccgag cgtgttcccg ctggctccga gttccaaatc gaccagcggc     60
ggtacggcag cactgggttg tctggttaaa gattattttc cggaaccggt taccgtctct    120
tggaacagtg gcgcgctgac ctctggtgtg cattagttcc cggccgttct gcagtcatcg    180
ggcctgtata gcctgagctc tgtggttacc gttccgagtt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345
```

<210> SEQ ID NO 56
<211> LENGTH: 345
<212> TYPE: DNA
<213> ORGANISM: Artificial Sequence
<220> FEATURE:
<223> OTHER INFORMATION: Synthetic nucleotide sequence of V173 amber_CH of Trastuzumab-Fab

<400> SEQUENCE: 56

```
gctagcacca aaggtccgag cgtgttcccg ctggctccga gttccaaatc gaccagcggc     60
ggtacggcag cactgggttg tctggttaaa gattattttc cggaaccggt taccgtctct    120
tggaacagtg gcgcgctgac ctctggtgtg catacgttcc cggcctagct gcagtcatcg    180
ggcctgtata gcctgagctc tgtggttacc gttccgagtt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345
```

<210> SEQ ID NO 57
<211> LENGTH: 345
<212> TYPE: DNA
<213> ORGANISM: Artificial Sequence
<220> FEATURE:
<223> OTHER INFORMATION: Synthetic nucleotide sequence of S177 amber_CH of Trastuzumab-Fab

<400> SEQUENCE: 57

```
gctagcacca aaggtccgag cgtgttcccg ctggctccga gttccaaatc gaccagcggc     60
ggtacggcag cactgggttg tctggttaaa gattattttc cggaaccggt taccgtctct    120
tggaacagtg gcgcgctgac ctctggtgtg catacgttcc cggccgttct gcagtcatag    180
ggcctgtata gcctgagctc tgtggttacc gttccgagtt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345
```

<210> SEQ ID NO 58
<211> LENGTH: 345
<212> TYPE: DNA
<213> ORGANISM: Artificial Sequence
<220> FEATURE:
<223> OTHER INFORMATION: Synthetic nucleotide sequence of Y180 amber_CH of Trastuzumab-Fab

<400> SEQUENCE: 58

```
gctagcacca aaggtccgag cgtgttcccg ctggctccga gttccaaatc gaccagcggc      60
ggtacggcag cactgggttg tctggttaaa gattattttc cggaaccggt taccgtctct    120
tggaacagtg gcgcgctgac ctctggtgtg catacgttcc cggccgttct gcagtcatcg    180
ggcctgtaga gcctgagctc tgtggttacc gttccgagtt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345
```

<210> SEQ ID NO 59
<211> LENGTH: 345
<212> TYPE: DNA
<213> ORGANISM: Artificial Sequence
<220> FEATURE:
<223> OTHER INFORMATION: Synthetic nucleotide sequence of S190 amber_CH
      of Trastuzumab-Fab

<400> SEQUENCE: 59

```
gctagcacca aaggtccgag cgtgttcccg ctggctccga gttccaaatc gaccagcggc      60
ggtacggcag cactgggttg tctggttaaa gattattttc cggaaccggt taccgtctct    120
tggaacagtg gcgcgctgac ctctggtgtg catacgttcc cggccgttct gcagtcatcg    180
ggcctgtata gcctgagctc tgtggttacc gttccgtagt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345
```

<210> SEQ ID NO 60
<211> LENGTH: 345
<212> TYPE: DNA
<213> ORGANISM: Artificial Sequence
<220> FEATURE:
<223> OTHER INFORMATION: Synthetic nucleotide sequence of I199 amber_CH
      of Trastuzumab-Fab

<400> SEQUENCE: 60

```
gctagcacca aaggtccgag cgtgttcccg ctggctccga gttccaaatc gaccagcggc      60
ggtacggcag cactgggttg tctggttaaa gattattttc cggaaccggt taccgtctct    120
tggaacagtg gcgcgctgac ctctggtgtg catacgttcc cggccgttct gcagtcatcg    180
ggcctgtata gcctgagctc tgtggttacc gttccgagtt cctcactggg tacccaaacg    240
tactagtgca acgtcaatca caaaccgagc aatacgaaag tggacaaaaa agttgaaccg    300
aaatcctgcg ataaaaccca tcatcaccat catcattgag tcgac                    345
```

<210> SEQ ID NO 61
<211> LENGTH: 345
<212> TYPE: DNA
<213> ORGANISM: Artificial Sequence
<220> FEATURE:
<223> OTHER INFORMATION: Synthetic nucleotide sequence of A129 amber_CH
      of Trastuzumab-Fab

<400> SEQUENCE: 61

```
gctagcacca aaggtccgag cgtgttcccg ctgtagccga gttccaaatc gaccagcggc      60
ggtacggcag cactgggttg tctggttaaa gattattttc cggaaccggt taccgtctct    120
tggaacagtg gcgcgctgac ctctggtgtg catacgttcc cggccgttct gcagtcatcg    180
ggcctgtata gcctgagctc tgtggttacc gttccgagtt cctcactggg tacccaaacg    240
tacatctgca acgtcaatca caaaccgagc aatacgaaag tggacaaaaa agttgaaccg    300
```
aaatcctgcg ataaaaccca tcatcaccat catcattgag tcgac 345

<210> SEQ ID NO 62
<211> LENGTH: 345
<212> TYPE: DNA
<213> ORGANISM: Artificial Sequence
<220> FEATURE:
<223> OTHER INFORMATION: Synthetic nucleotide sequence of L174 amber_CH
    of Trastuzumab-Fab

<400> SEQUENCE: 62
gctagcacca aggtccgag cgtgttcccg ctggctccga gttccaaatc gaccagcggc    60
ggtacggcag cactgggttg tctggttaaa gattattttc cggaaccggt taccgtctct   120
tggaacagtg gcgcgctgac ctctggtgtg catacgttcc cggccgttta gcagtcatcg   180
ggcctgtata gcctgagctc tgtggttacc gttccgagtt cctcactggg tacccaaacg   240
tacatctgca acgtcaatca caaaccgagc aatacgaaag tggacaaaaa agttgaaccg   300
aaatcctgcg ataaaaccca tcatcaccat catcattgag tcgac                   345

<210> SEQ ID NO 63
<211> LENGTH: 214
<212> TYPE: PRT
<213> ORGANISM: Artificial Sequence
<220> FEATURE:
<223> OTHER INFORMATION: Synthetic amino acid sequence of light chain of
    Cixutumumab-Fab

<400> SEQUENCE: 63

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Ile Leu Val Ile Tyr
        35                  40                  45

Gly Glu Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Ala Glu Cys Ser
    210

<210> SEQ ID NO 64
<211> LENGTH: 242
<212> TYPE: PRT
<213> ORGANISM: Artificial Sequence
<220> FEATURE:
<223> OTHER INFORMATION: Synthetic amino acid sequence of heavy chain of Cixutumumab-Fab

<400> SEQUENCE: 64

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His His His His
225                 230                 235                 240

His His
```

<210> SEQ ID NO 65
<211> LENGTH: 727
<212> TYPE: DNA
<213> ORGANISM: Artificial Sequence
<220> FEATURE:
<223> OTHER INFORMATION: Synthetic nucleotide sequence of light chain of Cixutumumab-Fab

<400> SEQUENCE: 65

```
catatgaaat acctgctgcc gaccgctgct gctggtctgc tgctcctcgc tgcccagccg      60
gcgatggcca gtagtgaact gacccaagat ccggccgtct ccgttgctct gggtcaaacc     120
gtccgcatta cctgccaagg cgattccctg cgtagctatt acgcaacgtg gtatcagcaa     180
aaaccgggtc aggctccgat tctggtcatc tacggtgaaa acaaacgtcc gtccggcatt     240
ccggatcgct tctcaggtag ctctagtggc aataccgcga gcctgacgat caccggtgcg     300
```

| | |
|---|---:|
| caagccgaag atgaagccga ctattactgc aaatctcgtg acggtagtgg ccagcatctg | 360 |
| gtttttggcg gtggcacgaa actgaccgtc ctgggtcaac cgaaagcagc accgtctgtg | 420 |
| accctgttcc cgccgtcctc agaagaactg caggcaaaca agctacgct ggtttgtctg | 480 |
| attagcgatt tttatccggg tgcagtgacc gttgcgtgga agcagactc gagcccggtc | 540 |
| aaagccggcg tggaaaccac gaccccgtcg aaacagagca caataaata tgcagcttct | 600 |
| agttacctgt cgctgacccc ggaacaatgg aaaagccacc gctcctactc atgtcaagtc | 660 |
| acgcacgaag gtagcacggt ggaaaaaacg gtggccccgg cggaatgttc ataggtcgcg | 720 |
| caagctt | 727 |

<210> SEQ ID NO 66
<211> LENGTH: 804
<212> TYPE: DNA
<213> ORGANISM: Artificial Sequence
<220> FEATURE:
<223> OTHER INFORMATION: Synthetic nucleotide sequence of heavy chain of Cixutumumab-Fab

<400> SEQUENCE: 66

| | |
|---|---:|
| catatgaaat acctgctgcc gaccgctgct gctggtctgc tgctcctcgc tgcccagccg | 60 |
| gcgatggccg aagtccaact ggtccaatct ggcgcggaag tcaaaaaacc gggttcgtca | 120 |
| gtgaaagtct cctgtaaagc gtcggtggc acgttcagct cttacgcaat tagctgggtg | 180 |
| cgtcaggctc cgggtcaagg tctggaatgg atgggcggta ttatcccgat ttttggcacc | 240 |
| gcgaactacg cccagaaatt ccaaggtcgt gtgaccatca cggcggataa atccacctca | 300 |
| acggcctata tggaactgag ttccctgcgc tctgaagaca ccgcggttta ttactgcgca | 360 |
| cgtgctccgc tgcgcttct ggaatggagt acgcaggatc attactacta ctactacatg | 420 |
| gacgtttggg gcaaaggtac cacggtcacc gtgtcatcgg cgtccacgaa aggtccgtca | 480 |
| gtcttcccgc tggcaccgag ctctaaatcc accagcggcg gtacggcagc actgggttgc | 540 |
| ctggttaaag attattttcc ggaaccggtt accgtctctt ggaacagtgg cgcactgacc | 600 |
| tcgggtgtgc atacgttccc ggctgttctg cagagttccg gcctgtactc actgtcatcg | 660 |
| gtggttaccg tcccgagctc tagtctgggt acccaaacgt atatctgtaa cgtgaatcac | 720 |
| aaaccgagca ataccaaagt ggataaaaaa gttgaaccga atcttgcga taaaacccat | 780 |
| caccatcatc atcattgagt cgac | 804 |

<210> SEQ ID NO 67
<211> LENGTH: 738
<212> TYPE: DNA
<213> ORGANISM: Artificial Sequence
<220> FEATURE:
<223> OTHER INFORMATION: Synthetic nucleotide sequence of K110 amber_lambda light chain of Cixutumumab-Fab

<400> SEQUENCE: 67

| | |
|---|---:|
| catatgaaat acctgctgcc gaccgctgct gctggtctgc tgctcctcgc tgcccagccg | 60 |
| gcgatggcca gtagtgaact gacccaagat ccggctgtgt ctgttgctct gggccaaacc | 120 |
| gtccgtatta cctgccaagg cgattctctg cgtagctatt acgcaacgtg gtatcagcaa | 180 |
| aaaccgggtc aggctccgat tctggtcatc tacggtgaaa acaaacgtcc gtccggcatt | 240 |
| ccggatcgct ctctcaggta gctcagtggc aataccgcga gcctgacgat caccggtgcg | 300 |
| caagccgaag atgaagccga ctattactgc aaatctcgtg acggtagtgg ccagcatctg | 360 |
| gtttttggcg gtggcacgaa actgaccgtc ctgggtcaac cgtaggcagc accgtctgtg | 420 |

```
accctgttcc cgccgtcctc agaagaactg caggcaaaca aagctacgct ggtttgtctg    480
attagcgatt tttatccggg tgcagtgacc gttgcgtgga aagcagactc gagcccggtc    540
aaagccggcg tggaaaccac gaccccgtcg aaacagagca acaataaata tgcagcttct    600
agttacctgt cgctgacccc ggaacaatgg aaaagccacc gctcctactc atgtcaagtt    660
acgcacgaag gctctacggt ggaaaaaacg gtggctccga cggaatgctc ctgagtcgcg    720
caagcttctc gagaattc                                                   738
```

<210> SEQ ID NO 68
<211> LENGTH: 738
<212> TYPE: DNA
<213> ORGANISM: Artificial Sequence
<220> FEATURE:
<223> OTHER INFORMATION: Synthetic nucleotide sequence of K129
      amber_lambda light chain of Cixutumumab-Fab

<400> SEQUENCE: 68

```
catatgaaat acctgctgcc gaccgctgct gctggtctgc tgctcctcgc tgcccagccg     60
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360
gtttttggcg gtggcacgaa actgaccgtc ctgggtcaac cgaaagcagc accgtctgtg    420
accctgttcc cgccgtcctc agaagaactg caggcaaaac aggctacgct ggtttgtctg    480
attagcgatt tttatccggg tgcagtgacc gttgcgtgga aagcagactc gagcccggtc    540
aaagccggcg tggaaaccac gaccccgtcg aaacagagca acaataaata tgcagcttct    600
agttacctgt cgctgacccc ggaacaatgg aaaagccacc gctcctactc atgtcaagtt    660
acgcacgaag gctctacggt ggaaaaaacg gtggctccga cggaatgctc ctgagtcgcg    720
caagcttctc gagaattc                                                   738
```

<210> SEQ ID NO 69
<211> LENGTH: 738
<212> TYPE: DNA
<213> ORGANISM: Artificial Sequence
<220> FEATURE:
<223> OTHER INFORMATION: Synthetic nucleotide sequence of K149
      amber_lambda light chain of Cixutumumab-Fab

<400> SEQUENCE: 69

```
catatgaaat acctgctgcc gaccgctgct gctggtctgc tgctcctcgc tgcccagccg     60
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360
gtttttggcg gtggcacgaa actgaccgtc ctgggtcaac cgaaagcagc accgtctgtg    420
accctgttcc cgccgtcctc agaagaactg caggcaaaca aagctacgct ggtttgtctg    480
attagcgatt tttatccggg tgcagtgacc gttgcgtggt aggcagactc gagcccggtc    540
```

| | |
|---|---|
| aaagccggcg tggaaaccac gaccccgtcg aaacagagca acaataaata tgcagcttct | 600 |
| agttacctgt cgctgacccc ggaacaatgg aaaagccacc gctcctactc atgtcaagtt | 660 |
| acgcacgaag gctctacggt ggaaaaaacg gtggctccga cggaatgctc ctgagtcgcg | 720 |
| caagcttctc gagaattc | 738 |

<210> SEQ ID NO 70
<211> LENGTH: 738
<212> TYPE: DNA
<213> ORGANISM: Artificial Sequence
<220> FEATURE:
<223> OTHER INFORMATION: Synthetic nucleotide sequence of K156
      amber_lambda light chain of Cixutumumab-Fab

<400> SEQUENCE: 70

| | |
|---|---|
| catatgaaat acctgctgcc gaccgctgct gctggtctgc tgctcctcgc tgcccagccg | 60 |
| gcgatggcca gtagtgaact gacccaagat ccggctgtgt ctgttgctct gggccaaacc | 120 |
| gtccgtatta cctgccaagg cgattctctg cgtagctatt acgcaacgtg gtatcagcaa | 180 |
| aaaccgggtc aggctccgat tctggtcatc tacggtgaaa acaaacgtcc gtccggcatt | 240 |
| ccggatcgct tctcaggtag ctctagtggc aataccgcga gcctgacgat caccggtgcg | 300 |
| caagccgaag atgaagccga ctattactgc aaatctcgtg acggtagtgg ccagcatctg | 360 |
| gttttggcg gtggcacgaa actgaccgtc ctgggtcaac gaaagcagc accgtctgtg | 420 |
| accctgttcc cgccgtcctc agaagaactg caggcaaaca agctacgct ggtttgtctg | 480 |
| attagcgatt tttatccggg tgcagtgacc gttgcgtgga agcagactc gagcccggtc | 540 |
| taggccggcg tggaaaccac gaccccgtcg aaacagagca acaataaata tgcagcttct | 600 |
| agttacctgt cgctgacccc ggaacaatgg aaaagccacc gctcctactc atgtcaagtt | 660 |
| acgcacgaag gctctacggt ggaaaaaacg gtggctccga cggaatgctc ctgagtcgcg | 720 |
| caagcttctc gagaattc | 738 |

<210> SEQ ID NO 71
<211> LENGTH: 738
<212> TYPE: DNA
<213> ORGANISM: Artificial Sequence
<220> FEATURE:
<223> OTHER INFORMATION: Synthetic nucleotide sequence of K166
      amber_lambda light chain of Cixutumumab-Fab

<400> SEQUENCE: 71

| | |
|---|---|
| catatgaaat acctgctgcc gaccgctgct gctggtctgc tgctcctcgc tgcccagccg | 60 |
| gcgatggcca gtagtgaact gacccaagat ccggctgtgt ctgttgctct gggccaaacc | 120 |
| gtccgtatta cctgccaagg cgattctctg cgtagctatt acgcaacgtg gtatcagcaa | 180 |
| aaaccgggtc aggctccgat tctggtcatc tacggtgaaa acaaacgtcc gtccggcatt | 240 |
| ccggatcgct tctcaggtag ctctagtggc aataccgcga gcctgacgat caccggtgcg | 300 |
| caagccgaag atgaagccga ctattactgc aaatctcgtg acggtagtgg ccagcatctg | 360 |
| gttttggcg gtggcacgaa actgaccgtc ctgggtcaac gaaagcagc accgtctgtg | 420 |
| accctgttcc cgccgtcctc agaagaactg caggcaaaca agctacgct ggtttgtctg | 480 |
| attagcgatt tttatccggg tgcagtgacc gttgcgtgga agcagactc gagcccggtc | 540 |
| aaagccggcg tggaaaccac gaccccgtcg tagcagagca acaataaata tgcagcttct | 600 |
| agttacctgt cgctgacccc ggaacaatgg aaaagccacc gctcctactc atgtcaagtt | 660 |
| acgcacgaag gctctacggt ggaaaaaacg gtggctccga cggaatgctc ctgagtcgcg | 720 |

```
caagcttctc gagaattc                                               738

<210> SEQ ID NO 72
<211> LENGTH: 738
<212> TYPE: DNA
<213> ORGANISM: Artificial Sequence
<220> FEATURE:
<223> OTHER INFORMATION: Synthetic nucleotide sequence of K172
      amber_lambda light chain of Cixutumumab-Fab

<400> SEQUENCE: 72
catatgaaat acctgctgcc gaccgctgct gctggtctgc tgctcctcgc tgcccagccg    60
gcgatggcca gtagtgaact gacccaagat ccggctgtgt ctgttgctct gggccaaacc   120
gtccgtatta cctgccaagg cgattctctg cgtagctatt acgcaacgtg gtatcagcaa   180
aaaccgggtc aggctccgat tctggtcatc tacggtgaaa acaaacgtcc gtccggcatt   240
ccggatcgct tctcaggtag ctctagtggc aataccgcga gcctgacgat caccggtgcg   300
caagccgaag atgaagccga ctattactgc aaatctcgtg acggtagtgg ccagcatctg   360 gttttttggcg gtggcacgaa actgaccgtc ctgggtcaac gaaagcagc accgtctgtg   420 accctgttcc cgccgtcctc agaagaactg caggcaaaca agctacgct ggtttgtctg   480 attagcgatt tttatccggg tgcagtgacc gttgcgtgga agcagactc gagcccggtc   540 aaagccggcg tggaaaccac gaccccgtcg aaacagagca caattagta tgcagcttct   600 agttacctgt cgctgacccc ggaacaatgg aaaagccacc gctcctactc atgtcaagtt   660
acgcacgaag gctctacggt ggaaaaaacg gtggctccga cggaatgctc ctgagtcgcg   720
caagcttctc gagaattc                                               738

<210> SEQ ID NO 73
<211> LENGTH: 738
<212> TYPE: DNA
<213> ORGANISM: Artificial Sequence
<220> FEATURE:
<223> OTHER INFORMATION: Synthetic nucleotide sequence of K187
      amber_lambda light chain of Cixutumumab-Fab

<400> SEQUENCE: 73
catatgaaat acctgctgcc gaccgctgct gctggtctgc tgctcctcgc tgcccagccg    60
gcgatggcca gtagtgaact gacccaagat ccggctgtgt ctgttgctct gggccaaacc   120
gtccgtatta cctgccaagg cgattctctg cgtagctatt acgcaacgtg gtatcagcaa   180
aaaccgggtc aggctccgat tctggtcatc tacggtgaaa acaaacgtcc gtccggcatt   240
ccggatcgct tctcaggtag ctctagtggc aataccgcga gcctgacgat caccggtgcg   300
caagccgaag atgaagccga ctattactgc aaatctcgtg acggtagtgg ccagcatctg   360 gttttttggcg gtggcacgaa actgaccgtc ctgggtcaac gaaagcagc accgtctgtg   420 accctgttcc cgccgtcctc agaagaactg caggcaaaca agctacgct ggtttgtctg   480 attagcgatt tttatccggg tgcagtgacc gttgcgtgga agcagactc gagcccggtc   540 aaagccggcg tggaaaccac gaccccgtcg aaacagagca acaataaata tgcagcttct   600
agttacctgt cgctgacccc ggaacaatgg tagagccacc gctcctactc atgtcaagtt   660
acgcacgaag gctctacggt ggaaaaaacg gtggctccga cggaatgctc ctgagtcgcg   720
caagcttctc gagaattc                                               738

<210> SEQ ID NO 74
```

<211> LENGTH: 738
<212> TYPE: DNA
<213> ORGANISM: Artificial Sequence
<220> FEATURE:
<223> OTHER INFORMATION: Synthetic nucleotide sequence of K207
      amber_lambda light chain of Cixutumumab-Fab

<400> SEQUENCE: 74

| | | | | | |
|---|---|---|---|---|---|
| catatgaaat | acctgctgcc | gaccgctgct | gctggtctgc | tgctcctcgc | tgcccagccg | 60 |
| gcgatggcca | gtagtgaact | gacccaagat | ccggctgtgt | ctgttgctct | gggccaaacc | 120 |
| gtccgtatta | cctgccaagg | cgattctctg | cgtagctatt | acgaacgtg | gtatcagcaa | 180 |
| aaaccgggtc | aggctccgat | tctggtcatc | tacggtgaaa | acaaacgtcc | gtccggcatt | 240 |
| ccggatcgct | ctcaggtag | ctctagtggc | aataccgcga | gcctgacgat | caccggtgcg | 300 |
| caagccgaag | atgaagccga | ctattactgc | aaatctcgtg | acggtagtgg | ccagcatctg | 360 |
| gtttttggcg | gtggcacgaa | actgaccgtc | ctgggtcaac | gaaagcagc | accgtctgtg | 420 |
| accctgttcc | cgccgtcctc | agaagaactg | caggcaaaca | aagctacgct | ggtttgtctg | 480 |
| attagcgatt | tttatccggg | tgcagtgacc | gttgcgtgga | agcagactc | gagcccggtc | 540 |
| aaagccggcg | tggaaaccac | gacccgtcg | aaacagagca | caataaata | tgcagcttct | 600 |
| agttacctgt | cgctgacccc | ggaacaatgg | aaaagccacc | gctcctactc | atgtcaagtt | 660 |
| acgcacgaag | gctctacggt | ggaatagacg | gtggctccga | cggaatgctc | ctgagtcgcg | 720 |
| caagcttctc | gagaattc | | | | | 738 |

<210> SEQ ID NO 75
<211> LENGTH: 738
<212> TYPE: DNA
<213> ORGANISM: Artificial Sequence
<220> FEATURE:
<223> OTHER INFORMATION: Synthetic nucleotide sequence of P119
      amber_lambda light chain of Cixutumumab-Fab

<400> SEQUENCE: 75

| | | | | | |
|---|---|---|---|---|---|
| catatgaaat | acctgctgcc | gaccgctgct | gctggtctgc | tgctcctcgc | tgcccagccg | 60 |
| gcgatggcca | gtagtgaact | gacccaagat | ccggctgtgt | ctgttgctct | gggccaaacc | 120 |
| gtccgtatta | cctgccaagg | cgattctctg | cgtagctatt | acgaacgtg | gtatcagcaa | 180 |
| aaaccgggtc | aggctccgat | tctggtcatc | tacggtgaaa | acaaacgtcc | gtccggcatt | 240 |
| ccggatcgct | ctcaggtag | ctctagtggc | aataccgcga | gcctgacgat | caccggtgcg | 300 |
| caagccgaag | atgaagccga | ctattactgc | aaatctcgtg | acggtagtgg | ccagcatctg | 360 |
| gtttttggcg | gtggcacgaa | actgaccgtc | ctgggtcaac | gaaagcagc | accgtctgtg | 420 |
| accctgttct | agccgtcctc | agaagaactg | caggcaaaca | aagctacgct | ggtttgtctg | 480 |
| attagcgatt | tttatccggg | tgcagtgacc | gttgcgtgga | agcagactc | gagcccggtc | 540 |
| aaagccggcg | tggaaaccac | gacccgtcg | aaacagagca | caataaata | tgcagcttct | 600 |
| agttacctgt | cgctgacccc | ggaacaatgg | aaaagccacc | gctcctactc | atgtcaagtt | 660 |
| acgcacgaag | gctctacggt | ggaaaaaacg | gtggctccga | cggaatgctc | ctgagtcgcg | 720 |
| caagcttctc | gagaattc | | | | | 738 |

<210> SEQ ID NO 76
<211> LENGTH: 738
<212> TYPE: DNA
<213> ORGANISM: Artificial Sequence
<220> FEATURE:
<223> OTHER INFORMATION: Synthetic nucleotide sequence of L125 amber_lambda light chain of Cixutumumab-Fab

<400> SEQUENCE: 76

| catatgaaat acctgctgcc gaccgctgct gctggtctgc tgctcctcgc tgcccagccg | 60 |
| gcgatggcca gtagtgaact gacccaagat ccggctgtgt ctgttgctct gggccaaacc | 120 |
| gtccgtatta cctgccaagg cgattctctg cgtagctatt acgcaacgtg gtatcagcaa | 180 |
| aaaccgggtc aggctccgat tctggtcatc tacggtgaaa acaaacgtcc gtccggcatt | 240 |
| ccggatcgct tctcaggtag ctctagtggc aataccgcga gcctgacgat caccggtgcg | 300 |
| caagccgaag atgaagccga ctattactgc aaatctcgtg acggtagtgg ccagcatctg | 360 |
| gtttttggcg gtggcacgaa actgaccgtc ctgggtcaac cgaaagcagc accgtctgtg | 420 |
| accctgttcc cgccgtcctc agaagaatag caggcaaaca agctacgct ggtttgtctg | 480 |
| attagcgatt tttatccggg tgcagtgacc gttgcgtgga agcagactc gagcccggtc | 540 |
| aaagccggcg tggaaaccac gaccccgtcg aaacagagca acaataaata tgcagcttct | 600 |
| agttacctgt cgctgacccc ggaacaatgg aaaagccacc gctcctactc atgtcaagtt | 660 |
| acgcacgaag gctctacggt ggaaaaaacg gtggctccga cggaatgctc ctgagtcgcg | 720 |
| caagcttctc gagaattc | 738 |

<210> SEQ ID NO 77
<211> LENGTH: 738
<212> TYPE: DNA
<213> ORGANISM: Artificial Sequence
<220> FEATURE:
<223> OTHER INFORMATION: Synthetic nucleotide sequence of S137 amber_lambda light chain of Cixutumumab-Fab

<400> SEQUENCE: 77

| catatgaaat acctgctgcc gaccgctgct gctggtctgc tgctcctcgc tgcccagccg | 60 |
| gcgatggcca gtagtgaact gacccaagat ccggctgtgt ctgttgctct gggccaaacc | 120 |
| gtccgtatta cctgccaagg cgattctctg cgtagctatt acgcaacgtg gtatcagcaa | 180 |
| aaaccgggtc aggctccgat tctggtcatc tacggtgaaa acaaacgtcc gtccggcatt | 240 |
| ccggatcgct tctcaggtag ctctagtggc aataccgcga gcctgacgat caccggtgcg | 300 |
| caagccgaag atgaagccga ctattactgc aaatctcgtg acggtagtgg ccagcatctg | 360 |
| gtttttggcg gtggcacgaa actgaccgtc ctgggtcaac cgaaagcagc accgtctgtg | 420 |
| accctgttcc cgccgtcctc agaagaactg caggcaaaca agctacgct ggtttgtctg | 480 |
| atttaggatt tttatccggg tgcagtgacc gttgcgtgga agcagactc gagcccggtc | 540 |
| aaagccggcg tggaaaccac gaccccgtcg aaacagagca acaataaata tgcagcttct | 600 |
| agttacctgt cgctgacccc ggaacaatgg aaaagccacc gctcctactc atgtcaagtt | 660 |
| acgcacgaag gctctacggt ggaaaaaacg gtggctccga cggaatgctc ctgagtcgcg | 720 |
| caagcttctc gagaattc | 738 |

<210> SEQ ID NO 78
<211> LENGTH: 738
<212> TYPE: DNA
<213> ORGANISM: Artificial Sequence
<220> FEATURE:
<223> OTHER INFORMATION: Synthetic nucleotide sequence of E160 amber_lambda light chain of Cixutumumab-Fab

<400> SEQUENCE: 78

| catatgaaat acctgctgcc gaccgctgct gctggtctgc tgctcctcgc tgcccagccg | 60 |

```
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360
gtttttggcg gtggcacgaa actgaccgtc ctgggtcaac cgaaagcagc accgtctgtg    420
accctgttcc cgccgtcctc agaagaactg caggcaaaca agctacgct ggtttgtctg    480 attagcgatt tttatccggg tgcagtgacc gttgcgtgga agcagactc gagcccggtc    540 aaagccggcg tgtagaccac gaccccgtcg aaacagagca acaataaata tgcagcttct    600
agttacctgt cgctgacccc ggaacaatgg aaaagccacc gctcctactc atgtcaagtt    660
acgcacgaag gctctacggt ggaaaaaacg gtggctccga cggaatgctc ctgagtcgcg    720
caagcttctc gagaattc                                                  738
```

<210> SEQ ID NO 79
<211> LENGTH: 738
<212> TYPE: DNA
<213> ORGANISM: Artificial Sequence
<220> FEATURE:
<223> OTHER INFORMATION: Synthetic nucleotide sequence of T161
      amber_lambda light chain of Cixutumumab-Fab

<400> SEQUENCE: 79

```
catatgaaat acctgctgcc gaccgctgct gctggtctgc tgctcctcgc tgcccagccg     60
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360
gtttttggcg gtggcacgaa actgaccgtc ctgggtcaac cgaaagcagc accgtctgtg    420
accctgttcc cgccgtcctc agaagaactg caggcaaaca agctacgct ggtttgtctg    480 attagcgatt tttatccggg tgcagtgacc gttgcgtgga agcagactc gagcccggtc    540 aaagccggcg tggaatagac gaccccgtcg aaacagagca acaataaata tgcagcttct    600
agttacctgt cgctgacccc ggaacaatgg aaaagccacc gctcctactc atgtcaagtt    660
acgcacgaag gctctacggt ggaaaaaacg gtggctccga cggaatgctc ctgagtcgcg    720
caagcttctc gagaattc                                                  738
```

<210> SEQ ID NO 80
<211> LENGTH: 738
<212> TYPE: DNA
<213> ORGANISM: Artificial Sequence
<220> FEATURE:
<223> OTHER INFORMATION: Synthetic nucleotide sequence of S165
      amber_lambda light chain of Cixutumumab-Fab

<400> SEQUENCE: 80

```
catatgaaat acctgctgcc gaccgctgct gctggtctgc tgctcctcgc tgcccagccg     60
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
```

```
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360
gtttttggcg gtggcacgaa actgaccgtc ctgggtcaac cgaaagcagc accgtctgtg    420
accctgttcc cgccgtcctc agaagaactg caggcaaaca agctacgct ggtttgtctg     480 attagcgatt tttatccggg tgcagtgacc gttgcgtgga agcagactc gagcccggtc     540 aaagccggcg tggaaaccac gaccccgtag aaacagagca acaataaata tgcagcttct    600
agttacctgt cgctgacccc ggaacaatgg aaaagccacc gctcctactc atgtcaagtt    660
acgcacgaag gctctacggt ggaaaaaacg gtggctccga cggaatgctc ctgagtcgcg    720
caagcttctc gagaattc                                                  738

<210> SEQ ID NO 81
<211> LENGTH: 738
<212> TYPE: DNA
<213> ORGANISM: Artificial Sequence
<220> FEATURE:
<223> OTHER INFORMATION: Synthetic nucleotide sequence of Y173
      amber_lambda light chain of Cixutumumab-Fab

<400> SEQUENCE: 81
catatgaaat acctgctgcc gaccgctgct gctggtctgc tgctcctcgc tgcccagccg     60
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360
gtttttggcg gtggcacgaa actgaccgtc ctgggtcaac cgaaagcagc accgtctgtg    420
accctgttcc cgccgtcctc agaagaactg caggcaaaca agctacgct ggtttgtctg     480 attagcgatt tttatccggg tgcagtgacc gttgcgtgga agcagactc gagcccggtc     540 aaagccggcg tggaaaccac gaccccgtcg aaacagagca acaataaata ggcagcttct    600
agttacctgt cgctgacccc ggaacaatgg aaaagccacc gctcctactc atgtcaagtt    660
acgcacgaag gctctacggt ggaaaaaacg gtggctccga cggaatgctc ctgagtcgcg    720
caagcttctc gagaattc                                                  738

<210> SEQ ID NO 82
<211> LENGTH: 738
<212> TYPE: DNA
<213> ORGANISM: Artificial Sequence
<220> FEATURE:
<223> OTHER INFORMATION: Synthetic nucleotide sequence of S180
      amber_lambda light chain of Cixutumumab-Fab

<400> SEQUENCE: 82
catatgaaat acctgctgcc gaccgctgct gctggtctgc tgctcctcgc tgcccagccg     60
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360
```

```
gtttttggcg gtggcacgaa actgaccgtc ctgggtcaac cgaaagcagc accgtctgtg    420
accctgttcc cgccgtcctc agaagaactg caggcaaaca aagctacgct ggtttgtctg    480
attagcgatt tttatccggg tgcagtgacc gttgcgtgga agcagactc gagcccggtc     540 aaagccggcg tggaaaccac gaccccgtcg aaacagagca caataaata tgcagcttct    600 agttacctgt agctgacccc ggaacaatgg aaaagccacc gctcctactc atgtcaagtt    660
acgcacgaag gctctacggt ggaaaaaacg gtggctccga cggaatgctc ctgagtcgcg    720
caagcttctc gagaattc                                                   738
```

```
<210> SEQ ID NO 83
<211> LENGTH: 738
<212> TYPE: DNA
<213> ORGANISM: Artificial Sequence
<220> FEATURE:
<223> OTHER INFORMATION: Synthetic nucleotide sequence of H189
      amber_lambda light chain of Cixutumumab-Fab

<400> SEQUENCE: 83
catatgaaat acctgctgcc gaccgctgct gctggtctgc tgctcctcgc tgcccagccg    60
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360
gtttttggcg gtggcacgaa actgaccgtc ctgggtcaac cgaaagcagc accgtctgtg    420
accctgttcc cgccgtcctc agaagaactg caggcaaaca aagctacgct ggtttgtctg    480
attagcgatt tttatccggg tgcagtgacc gttgcgtgga agcagactc gagcccggtc     540 aaagccggcg tggaaaccac gaccccgtcg aaacagagca caataaata tgcagcttct    600 agttacctgt cgctgacccc ggaacaatgg aaaagctagc gctcctactc atgtcaagtt    660
acgcacgaag gctctacggt ggaaaaaacg gtggctccga cggaatgctc ctgagtcgcg    720
caagcttctc gagaattc                                                   738
```

```
<210> SEQ ID NO 84
<211> LENGTH: 738
<212> TYPE: DNA
<213> ORGANISM: Artificial Sequence
<220> FEATURE:
<223> OTHER INFORMATION: Synthetic nucleotide sequence of S191
      amber_lambda light chain of Cixutumumab-Fab

<400> SEQUENCE: 84
catatgaaat acctgctgcc gaccgctgct gctggtctgc tgctcctcgc tgcccagccg    60
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360
gtttttggcg gtggcacgaa actgaccgtc ctgggtcaac cgaaagcagc accgtctgtg    420
accctgttcc cgccgtcctc agaagaactg caggcaaaca aagctacgct ggtttgtctg    480
```

| | |
|---|---|
| attagcgatt tttatccggg tgcagtgacc gttgcgtgga aagcagactc gagcccggtc | 540 |
| aaagccggcg tggaaaccac gaccccgtcg aaacagagca acaataaata tgcagcttct | 600 |
| agttacctgt cgctgacccc ggaacaatgg aaaagccacc gctagtactc atgtcaagtt | 660 |
| acgcacgaag gctctacggt ggaaaaaacg gtggctccga cggaatgctc ctgagtcgcg | 720 |
| caagcttctc gagaattc | 738 |

<210> SEQ ID NO 85
<211> LENGTH: 738
<212> TYPE: DNA
<213> ORGANISM: Artificial Sequence
<220> FEATURE:
<223> OTHER INFORMATION: Synthetic nucleotide sequence of Q195
    amber_lambda light chain of Cixutumumab-Fab

<400> SEQUENCE: 85

| | |
|---|---|
| catatgaaat acctgctgcc gaccgctgct gctggtctgc tgctcctcgc tgcccagccg | 60 |
| gcgatggcca gtagtgaact gacccaagat ccggctgtgt ctgttgctct gggccaaacc | 120 |
| gtccgtatta cctgccaagg cgattctctg cgtagctatt acgaacgtg gtatcagcaa | 180 |
| aaaccgggtc aggctccgat tctggtcatc tacggtgaaa acaaacgtcc gtccggcatt | 240 |
| ccggatcgct tctcaggtag ctctagtggc aataccgcga gcctgacgat caccggtgcg | 300 |
| caagccgaag atgaagccga ctattactgc aaatctcgtg acggtagtgg ccagcatctg | 360 |
| gtttttggcg gtggcacgaa actgaccgtc ctgggtcaac gaaagcagc accgtctgtg | 420 |
| accctgttcc cgccgtcctc agaagaactg caggcaaaca agctacgct ggtttgtctg | 480 |
| attagcgatt tttatccggg tgcagtgacc gttgcgtgga agcagactc gagcccggtc | 540 |
| aaagccggcg tggaaaccac gaccccgtcg aaacagagca caataaata tgcagcttct | 600 |
| agttacctgt cgctgacccc ggaacaatgg aaaagccacc gctcctactc atgttaggtt | 660 |
| acgcacgaag gctctacggt ggaaaaaacg gtggctccga cggaatgctc ctgagtcgcg | 720 |
| caagcttctc gagaattc | 738 |

<210> SEQ ID NO 86
<211> LENGTH: 738
<212> TYPE: DNA
<213> ORGANISM: Artificial Sequence
<220> FEATURE:
<223> OTHER INFORMATION: Synthetic nucleotide sequence of T197
    amber_lambda light chain of Cixutumumab-Fab

<400> SEQUENCE: 86

| | |
|---|---|
| catatgaaat acctgctgcc gaccgctgct gctggtctgc tgctcctcgc tgcccagccg | 60 |
| gcgatggcca gtagtgaact gacccaagat ccggctgtgt ctgttgctct gggccaaacc | 120 |
| gtccgtatta cctgccaagg cgattctctg cgtagctatt acgaacgtg gtatcagcaa | 180 |
| aaaccgggtc aggctccgat tctggtcatc tacggtgaaa acaaacgtcc gtccggcatt | 240 |
| ccggatcgct tctcaggtag ctctagtggc aataccgcga gcctgacgat caccggtgcg | 300 |
| caagccgaag atgaagccga ctattactgc aaatctcgtg acggtagtgg ccagcatctg | 360 |
| gtttttggcg gtggcacgaa actgaccgtc ctgggtcaac gaaagcagc accgtctgtg | 420 |
| accctgttcc cgccgtcctc agaagaactg caggcaaaca agctacgct ggtttgtctg | 480 |
| attagcgatt tttatccggg tgcagtgacc gttgcgtgga agcagactc gagcccggtc | 540 |
| aaagccggcg tggaaaccac gaccccgtcg aaacagagca caataaata tgcagcttct | 600 |
| agttacctgt cgctgacccc ggaacaatgg aaaagccacc gctcctactc atgtcaagtt | 660 |

```
tagcacgaag gctctacggt ggaaaaaacg gtggctccga cggaatgctc ctgagtcgcg    720
caagcttctc gagaattc                                                  738

<210> SEQ ID NO 87
<211> LENGTH: 738
<212> TYPE: DNA
<213> ORGANISM: Artificial Sequence
<220> FEATURE:
<223> OTHER INFORMATION: Synthetic nucleotide sequence of V205
      amber_lambda light chain of Cixutumumab-Fab

<400> SEQUENCE: 87
catatgaaat acctgctgcc gaccgctgct gctggtctgc tgctcctcgc tgcccagccg     60
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360 gttttttggcg gtggcacgaa actgaccgtc ctgggtcaac cgaaagcagc accgtctgtg    420
accctgttcc cgccgtcctc agaagaactg caggcaaaca agctacgct ggtttgtctg    480 attagcgatt tttatccggg tgcagtgacc gttgcgtgga agcagactc gagcccggtc    540 aaagccggcg tggaaaccac gaccccgtcg aaacagagca acaataaata tgcagcttct    600
agttacctgt cgctgacccc ggaacaatgg aaaagccacc gctcctactc atgtcaagtt    660
acgcacgaag gctctacgta ggaaaaaacg gtggctccga cggaatgctc ctgagtcgcg    720
caagcttctc gagaattc                                                  738

<210> SEQ ID NO 88
<211> LENGTH: 738
<212> TYPE: DNA
<213> ORGANISM: Artificial Sequence
<220> FEATURE:
<223> OTHER INFORMATION: Synthetic nucleotide sequence of A210
      amber_lambda light chain of Cixutumumab-Fab

<400> SEQUENCE: 88
catatgaaat acctgctgcc gaccgctgct gctggtctgc tgctcctcgc tgcccagccg     60
gcgatggcca gtagtgaact gacccaagat ccggctgtgt ctgttgctct gggccaaacc    120
gtccgtatta cctgccaagg cgattctctg cgtagctatt acgcaacgtg gtatcagcaa    180
aaaccgggtc aggctccgat tctggtcatc tacggtgaaa acaaacgtcc gtccggcatt    240
ccggatcgct tctcaggtag ctctagtggc aataccgcga gcctgacgat caccggtgcg    300
caagccgaag atgaagccga ctattactgc aaatctcgtg acggtagtgg ccagcatctg    360 gttttttggcg gtggcacgaa actgaccgtc ctgggtcaac cgaaagcagc accgtctgtg    420
accctgttcc cgccgtcctc agaagaactg caggcaaaca agctacgct ggtttgtctg    480 attagcgatt tttatccggg tgcagtgacc gttgcgtgga agcagactc gagcccggtc    540 aaagccggcg tggaaaccac gaccccgtcg aaacagagca acaataaata tgcagcttct    600
agttacctgt cgctgacccc ggaacaatgg aaaagccacc gctcctactc atgtcaagtt    660
acgcacgaag gctctacggt ggaaaaaacg gtgtagccga cggaatgctc ctgagtcgcg    720
caagcttctc gagaattc                                                  738
```

<210> SEQ ID NO 89
<211> LENGTH: 738
<212> TYPE: DNA
<213> ORGANISM: Artificial Sequence
<220> FEATURE:
<223> OTHER INFORMATION: Synthetic nucleotide sequence of S215
      amber_lambda light chain of Cixutumumab-Fab

<400> SEQUENCE: 89

| | | | | | |
|---|---|---|---|---|---|
| catatgaaat | acctgctgcc | gaccgctgct | gctggtctgc | tgctcctcgc | tgcccagccg | 60 |
| gcgatggcca | gtagtgaact | gacccaagat | ccggctgtgt | ctgttgctct | gggccaaacc | 120 |
| gtccgtatta | cctgccaagg | cgattctctg | cgtagctatt | acgcaacgtg | gtatcagcaa | 180 |
| aaaccgggtc | aggctccgat | tctggtcatc | tacggtgaaa | acaaacgtcc | gtccggcatt | 240 |
| ccggatcgct | ctcaggtag | ctctagtggc | aataccgcga | gcctgacgat | caccggtgcg | 300 |
| caagccgaag | atgaagccga | ctattactgc | aaatctcgtg | acggtagtgg | ccagcatctg | 360 |
| gttttggcg | gtggcacgaa | actgaccgtc | ctgggtcaac | cgaaagcagc | accgtctgtg | 420 |
| accctgttcc | cgccgtcctc | agaagaactg | caggcaaaca | agctacgct | ggtttgtctg | 480 |
| attagcgatt | tttatccggg | tgcagtgacc | gttgcgtgga | agcagactc | gagcccggtc | 540 |
| aaagccggcg | tggaaaccac | gaccccgtcg | aaacagagca | acaataaata | tgcagcttct | 600 |
| agttacctgt | cgctgacccc | ggaacaatgg | aaaagccacc | gctcctactc | atgtcaagtt | 660 |
| acgcacgaag | gctctacggt | ggaaaaaacg | gtggctccga | cggaatgcta | gtgagtcgcg | 720 |
| caagcttctc | gagaattc | | | | | 738 |

<210> SEQ ID NO 90
<211> LENGTH: 738
<212> TYPE: DNA
<213> ORGANISM: Artificial Sequence
<220> FEATURE:
<223> OTHER INFORMATION: Synthetic nucleotide sequence of A127
      amber_lambda light chain of Cixutumumab-Fab

<400> SEQUENCE: 90

| | | | | | |
|---|---|---|---|---|---|
| catatgaaat | acctgctgcc | gaccgctgct | gctggtctgc | tgctcctcgc | tgcccagccg | 60 |
| gcgatggcca | gtagtgaact | gacccaagat | ccggctgtgt | ctgttgctct | gggccaaacc | 120 |
| gtccgtatta | cctgccaagg | cgattctctg | cgtagctatt | acgcaacgtg | gtatcagcaa | 180 |
| aaaccgggtc | aggctccgat | tctggtcatc | tacggtgaaa | acaaacgtcc | gtccggcatt | 240 |
| ccggatcgct | ctcaggtag | ctctagtggc | aataccgcga | gcctgacgat | caccggtgcg | 300 |
| caagccgaag | atgaagccga | ctattactgc | aaatctcgtg | acggtagtgg | ccagcatctg | 360 |
| gttttggcg | gtggcacgaa | actgaccgtc | ctgggtcaac | cgaaagcagc | accgtctgtg | 420 |
| accctgttcc | cgccgtcctc | agaagaactg | cagtagaaca | agctacgct | ggtttgtctg | 480 |
| attagcgatt | tttatccggg | tgcagtgacc | gttgcgtgga | agcagactc | gagcccggtc | 540 |
| aaagccggcg | tggaaaccac | gaccccgtcg | aaacagagca | acaataaata | tgcagcttct | 600 |
| agttacctgt | cgctgacccc | ggaacaatgg | aaaagccacc | gctcctactc | atgtcaagtt | 660 |
| acgcacgaag | gctctacggt | ggaaaaaacg | gtggctccga | cggaatgctc | ctgagtcgcg | 720 |
| caagcttctc | gagaattc | | | | | 738 |

<210> SEQ ID NO 91
<211> LENGTH: 738
<212> TYPE: DNA
<213> ORGANISM: Artificial Sequence
<220> FEATURE:
<223> OTHER INFORMATION: Synthetic nucleotide sequence of A143
      amber_lambda light chain of Cixutumumab-Fab

<400> SEQUENCE: 91

| | | | | | |
|---|---|---|---|---|---|
| catatgaaat | acctgctgcc | gaccgctgct | gctggtctgc | tgctcctcgc | tgcccagccg | 60 |
| gcgatggcca | gtagtgaact | gacccaagat | ccggctgtgt | ctgttgctct | gggccaaacc | 120 |
| gtccgtatta | cctgccaagg | cgattctctg | cgtagctatt | acgcaacgtg | gtatcagcaa | 180 |
| aaaccgggtc | aggctccgat | tctggtcatc | tacggtgaaa | acaaacgtcc | gtccggcatt | 240 |
| ccggatcgct | tctcaggtag | ctctagtggc | aataccgcga | gcctgacgat | caccggtgcg | 300 |
| caagccgaag | atgaagccga | ctattactgc | aaatctcgtg | acggtagtgg | ccagcatctg | 360 |
| gtttttggcg | gtggcacgaa | actgaccgtc | ctgggtcaac | cgaaagcagc | accgtctgtg | 420 |
| accctgttcc | cgccgtcctc | agaagaactg | caggcaaaca | agctacgct | ggtttgtctg | 480 |
| attagcgatt | tttatccggg | ttaggtgacc | gttgcgtgga | agcagactc | gagcccggtc | 540 |
| aaagccggcg | tggaaaccac | gaccccgtcg | aaacagagca | caataaata | tgcagcttct | 600 |
| agttacctgt | cgctgacccc | ggaacaatgg | aaaagccacc | gctcctactc | atgtcaagtt | 660 |
| acgcacgaag | gctctacggt | ggaaaaaacg | gtggctccga | cggaatgctc | ctgagtcgcg | 720 |
| caagcttctc | gagaattc | | | | | 738 |

<210> SEQ ID NO 92
<211> LENGTH: 738
<212> TYPE: DNA
<213> ORGANISM: Artificial Sequence
<220> FEATURE:
<223> OTHER INFORMATION: Synthetic nucleotide sequence of A147
      amber_lambda light chain of Cixutumumab-Fab

<400> SEQUENCE: 92

| | | | | | |
|---|---|---|---|---|---|
| catatgaaat | acctgctgcc | gaccgctgct | gctggtctgc | tgctcctcgc | tgcccagccg | 60 |
| gcgatggcca | gtagtgaact | gacccaagat | ccggctgtgt | ctgttgctct | gggccaaacc | 120 |
| gtccgtatta | cctgccaagg | cgattctctg | cgtagctatt | acgcaacgtg | gtatcagcaa | 180 |
| aaaccgggtc | aggctccgat | tctggtcatc | tacggtgaaa | acaaacgtcc | gtccggcatt | 240 |
| ccggatcgct | tctcaggtag | ctctagtggc | aataccgcga | gcctgacgat | caccggtgcg | 300 |
| caagccgaag | atgaagccga | ctattactgc | aaatctcgtg | acggtagtgg | ccagcatctg | 360 |
| gtttttggcg | gtggcacgaa | actgaccgtc | ctgggtcaac | cgaaagcagc | accgtctgtg | 420 |
| accctgttcc | cgccgtcctc | agaagaactg | caggcaaaca | agctacgct | ggtttgtctg | 480 |
| attagcgatt | tttatccggg | tgcagtgacc | gtttagtgga | agcagactc | gagcccggtc | 540 |
| aaagccggcg | tggaaaccac | gaccccgtcg | aaacagagca | caataaata | tgcagcttct | 600 |
| agttacctgt | cgctgacccc | ggaacaatgg | aaaagccacc | gctcctactc | atgtcaagtt | 660 |
| acgcacgaag | gctctacggt | ggaaaaaacg | gtggctccga | cggaatgctc | ctgagtcgcg | 720 |
| caagcttctc | gagaattc | | | | | 738 |

<210> SEQ ID NO 93
<211> LENGTH: 738
<212> TYPE: DNA
<213> ORGANISM: Artificial Sequence
<220> FEATURE:
<223> OTHER INFORMATION: Synthetic nucleotide sequence of A157
      amber_lambda light chain of Cixutumumab-Fab

<400> SEQUENCE: 93

```
catatgaaat acctgctgcc gaccgctgct gctggtctgc tgctcctcgc tgcccagccg    60
gcgatggcca gtagtgaact gacccaagat ccggctgtgt ctgttgctct gggccaaacc   120
gtccgtatta cctgccaagg cgattctctg cgtagctatt acgcaacgtg gtatcagcaa   180
aaaccgggtc aggctccgat tctggtcatc tacggtgaaa acaaacgtcc gtccggcatt   240
ccggatcgct ctctcaggtag ctctagtggc aataccgcga gcctgacgat caccggtgcg   300
caagccgaag atgaagccga ctattactgc aaatctcgtg acggtagtgg ccagcatctg   360 gttttggcg gtggcacgaa actgaccgtc ctgggtcaac cgaaagcagc accgtctgtg   420
accctgttcc cgccgtcctc agaagaactg caggcaaaca agctacgct ggtttgtctg   480 attagcgatt tttatccggg tgcagtgacc gttgcgtgga agcagactc gagcccggtc   540 aaatagggcg tggaaaccac gaccccgtcg aaacagagca caataaata tgcagcttct   600 agttacctgt cgctgacccc ggaacaatgg aaaagccacc gctcctactc atgtcaagtt   660
acgcacgaag gctctacggt ggaaaaaacg gtggctccga cggaatgctc ctgagtcgcg   720
caagcttctc gagaattc                                                  738

<210> SEQ ID NO 94
<211> LENGTH: 405
<212> TYPE: DNA
<213> ORGANISM: Artificial Sequence
<220> FEATURE:
<223> OTHER INFORMATION: Synthetic nucleotide sequence of VL of
      Farletuzumab-Fab

<400> SEQUENCE: 94
catatgaaat acctgctgcc gaccgctgct gctggtctgc tgctcctcgc tgcccagccg    60
gcgatggccg atattcaatt aactcagtcc cctagctcgc tgagcgcgtc ggttggtgac   120
cgcgtgacta ttacgtgttc agtgagcagc agcatctcca gtaacaacct gcactggtat   180
cagcaaaagc cgggtaaagc gccgaagcca tggatttacg gaacctcgaa cttagcctca   240
ggagtaccct ctcgcttctc gggcagcggc tcgggcacag actataccct tactatctcg   300
tccctgcaac cggaagacat tgccacgtat tattgccaac agtggagctc atatccgtac   360
atgtacacct tcggtcaggg gacaaaggtg gagatcaaac gtacg                    405

<210> SEQ ID NO 95
<211> LENGTH: 432
<212> TYPE: DNA
<213> ORGANISM: Artificial Sequence
<220> FEATURE:
<223> OTHER INFORMATION: Synthetic nucleotide sequence of VH of
      Farletuzumab-Fab

<400> SEQUENCE: 95
catatgaaat acctgctgcc gaccgctgct gctggtctgc tgctcctcgc tgcccagccg    60
gcgatggccg aggtgcaatt ggttgaatct ggtggtggcg tagtgcaacc aggccgcagc   120
ctgcgcttaa gttgttcagc aagcggcttt actttcagtg ggtatggttt atcttgggtg   180
cgccaggccc ctggcaaagg cctggagtgg gtgcgatga tttcaagtgg cggatcatac   240
acctactatg cggatagcgt gaaggggcgt tttgcgatta gccgtgataa cgccaaaaat   300
acattattcc tgcagatgga cagcctgcgc ccggaagaca ctggcgtgta cttctgtgca   360
cgtcatggtg atgatccagc ctggttcgca tattggggac aggggacccc tgtgaccgtg   420
agctcggcta gc                                                        432
```

<210> SEQ ID NO 96
<211> LENGTH: 396
<212> TYPE: DNA
<213> ORGANISM: Artificial Sequence
<220> FEATURE:
<223> OTHER INFORMATION: Synthetic nucleotide sequence of VL of
      Adalimumab-Fab

<400> SEQUENCE: 96

| catatgaaat acctgctgcc gaccgctgct gctggtctgc tgctcctcgc tgcccagccg | 60  |
| gcgatggccg atattgttct gacccagagc ccgagcagct taagcgcaag cctgggtgat | 120 |
| accatcacca ttacctgcca tgccagccag aacatcaacg tgtggctgag ctggtatcag | 180 |
| cagaaaccgg gcaacatccc gaaactgctg atctacaagg ccagcaatct gcacaccggt | 240 |
| gtgccgagtc gcttcagcgg tagcggtagc ggtaccggtt ttaccctgac cattagcagc | 300 |
| ctgcagccgg aagatatcgc cacctactat tgccagcagg gtcagagcta ccgctgacc | 360 |
| tttggcggtg gcaccaaact ggaaattaaa cgtacg | 396 |

<210> SEQ ID NO 97
<211> LENGTH: 429
<212> TYPE: DNA
<213> ORGANISM: Artificial Sequence
<220> FEATURE:
<223> OTHER INFORMATION: Synthetic nucleotide sequence of VH of
      Adalimumab-Fab

<400> SEQUENCE: 97

| catatgaaat acctgctgcc gaccgctgct gctggtctgc tgctcctcgc tgcccagccg | 60  |
| gcgatggccg aagtgaaact gcaggagagc ggtggtggtc tggttcagcc gggtggtagc | 120 |
| ctgaaactga gctgcgccac cagcggcttt accttcagcg actactacat gtattgggtg | 180 |
| cgccagaccc cggaaaaacg cctggagtgg gtggcatata tcagcaatgg tggcggcagc | 240 |
| acctattatc cggacaccgt gaaaggccgc tttaccatca gcgcgacaa cgccaaaaac | 300 |
| accctgtacc tgcagatgag ccgcctgaaa agcgaagaca ccgccatgta ctattgcgcc | 360 |
| cgccatggcg gctattatgc catggattac tggggtcagg gcaccaccgt gaccgtgagc | 420 |
| agcgctagc | 429 |

<210> SEQ ID NO 98
<211> LENGTH: 393
<212> TYPE: DNA
<213> ORGANISM: Artificial Sequence
<220> FEATURE:
<223> OTHER INFORMATION: Synthetic nucleotide sequence of VL of
      Rituximab-Fab

<400> SEQUENCE: 98

| catatgaaat acctgctgcc gaccgctgct gctggtctgc tgctcctcgc tgcccagccg | 60  |
| gcgatggccc aaattgttct ctcccagtct ccagcaatcc tgtctgcatc tccaggggag | 120 |
| aaggtcacaa tgacttgcag ggccagctca agtgtaagtt acatccactg gttccagcag | 180 |
| aagccaggat cctcccccaa acctggatt tatgccacat ccaacctggc ttctggagtc | 240 |
| cctgttcgct tcagtggcag tgggtctggg acttcttact ctctcaccat cagcagagtg | 300 |
| gaggctgaag atgctgccac ttattactgc cagcagtgga ctagtaaccc acccacgttc | 360 |
| ggaggggga ccaagctgga atcaaacgt acg | 393 |

<210> SEQ ID NO 99

<211> LENGTH: 438
<212> TYPE: DNA
<213> ORGANISM: Artificial Sequence
<220> FEATURE:
<223> OTHER INFORMATION: Synthetic nucleotide sequence of VH of
      Rituximab-Fab

<400> SEQUENCE: 99

| catatgaaat acctgctgcc gaccgctgct gctggtctgc tgctcctcgc tgcccagccg | 60 |
| gcgatggccc aggtacaact gcagcagcct ggggctgagc tggtgaagcc tggggcctca | 120 |
| gtgaagatgt cctgcaaggc ttctggctac acatttacca gttacaatat gcactgggta | 180 |
| aaacagacac tggtcgggg cctggaatgg attggagcta tttatcccgg aaatggtgat | 240 |
| acttcctaca atcagaagtt caaaggcaag gccacattga ctgcagacaa atcctccagc | 300 |
| acagcctaca tgcagctcag cagcctgaca tctgaggact ctgcggtcta ttactgtgca | 360 |
| agatcgactt actacggcgg tgactggtac ttcaatgtct ggggcgcagg gaccacggtc | 420 |
| accgtctctg cagctagc | 438 |

<210> SEQ ID NO 100
<211> LENGTH: 396
<212> TYPE: DNA
<213> ORGANISM: Artificial Sequence
<220> FEATURE:
<223> OTHER INFORMATION: Synthetic nucleotide sequence of VL of
      Bevacizumab-Fab

<400> SEQUENCE: 100

| catatgaaat acctgctgcc gaccgctgct gctggtctgc tgctcctcgc tgcccagccg | 60 |
| gcgatggccg atattcagat gacccagagc ccgagcagcc tgagcgcaag cgttggtgat | 120 |
| cgcgttacca ttacctgcag cgccagccag gatattagca actatctgaa ctggtatcag | 180 |
| cagaaaccgg gcaaagcccc gaaggtgctg atctatttca ccagcagcct gcatagcggt | 240 |
| gtgccgagcc gtttcagcgg tagcggtagc ggcaccgatt ttaccctgac cattagcagc | 300 |
| ctgcagccgg aagactttgc cacctactat tgccagcagt acagcaccgt tccgtggacc | 360 |
| tttggccagg gcaccaaagt ggaaattaaa cgtacg | 396 |

<210> SEQ ID NO 101
<211> LENGTH: 444
<212> TYPE: DNA
<213> ORGANISM: Artificial Sequence
<220> FEATURE:
<223> OTHER INFORMATION: Synthetic nucleotide sequence of VH of
      Bevacizumab-Fab

<400> SEQUENCE: 101

| catatgaaat acctgctgcc gaccgctgct gctggtctgc tgctcctcgc tgcccagccg | 60 |
| gcgatggccg aagtgcagct ggtggaaagc ggtggtggtc tggttcagcc gggtggtagt | 120 |
| ctgcgtctga gctgcgcagc cagcggctat accttcacca actatggcat gaattgggtg | 180 |
| cgtcaggccc cgggtaaagg tctggaatgg gtgggctgga tcaataccta taccggcgaa | 240 |
| ccgacctatg ccgccgattt taaacgcgc ttcaccttca gcctggatac cagcaaaagc | 300 |
| accgcctacc tgcagatgaa tagcctgcgc gccgaagaca ccgccgtgta ctactgcgca | 360 |
| aaatacccgc actactacgg tagcagccat ggtacttcg atgtgtgggg ccagggtacc | 420 |
| ctggtgaccg ttagcagcgc tagc | 444 |

<210> SEQ ID NO 102

```
<211> LENGTH: 345
<212> TYPE: DNA
<213> ORGANISM: Artificial Sequence
<220> FEATURE:
<223> OTHER INFORMATION: Synthetic nucleotide sequence of heavy chain of
      antibody No.2 or No.5

<400> SEQUENCE: 102
gctagcacca aaggtccgag cgtgttcccg ctggctccgt agtccaaatc gaccagcggc      60
ggtacggcag cactgggttg tctggttaaa gattattttc cggaaccggt taccgtctct    120
tggaacagtg gcgcgctgac ctctggtgtg catacgttcc cggccgttct gcagtcatag    180
ggcctgtata gcctgagctc tgtggttacc gttccgagtt cctcactggg tacccaaacg    240
tacatctgca acgtcaatca caaaccgagc aatacgaaag tggacaaaaa agttgaaccg    300
aaatcctgcg ataaaaccca tcatcaccat catcattgag tcgac                    345

<210> SEQ ID NO 103
<211> LENGTH: 346
<212> TYPE: DNA
<213> ORGANISM: Artificial Sequence
<220> FEATURE:
<223> OTHER INFORMATION: Synthetic nucleotide sequence of heavy chain of
      antibody No.3 or No.6

<400> SEQUENCE: 103
tgctagcacc aaaggtccga gcgtgttccc gctggctccg tagtccaaat cgaccagcgg     60
cggtacggca gcactgggtt gtctggttaa agattatttt ccggaaccgg ttaccgtctc    120
ttggaacagt ggcgcgctga cctctggtgt gcatacgttc ccggccgttc tgcagtcata    180
gggcctgtat agcctgagct ctgtggttac cgttccgagt tcctcactgg gtacccaaac    240
gtactagtgc aacgtcaatc acaaaccgag caatacgaaa gtggacaaaa aagttgaacc    300
gaaatcctgc gataaaaccc atcatcacca tcatcattga gtcgac                   346

<210> SEQ ID NO 104
<211> LENGTH: 711
<212> TYPE: DNA
<213> ORGANISM: Artificial Sequence
<220> FEATURE:
<223> OTHER INFORMATION: Synthetic nucleotide sequence of light chain of
      Trastuzuzumab

<400> SEQUENCE: 104
atggagacag acacactcct gctatgggta ctgctgctct gggttccagg ttccactggt     60
gacgatattc aaatgaccca gtccccgtcc tccctgtctg cctccgttgg tgatcgtgtt    120
acgattacct gccgcgcctc tcaagatgtc aacaccgcag tggcttggta tcagcaaaaa    180
ccgggcaaag cgccgaaact gctgatttat tcagcctcgt ttctgtactc cggtgttccg    240
tcacgtttca gcggctctcg cagtggtacc gattttaccc tgacgatcag ctctctgcag    300
ccggaagact tcgcaacgta ttactgccag caacattaca ccacgccgcc gacctttggc    360
cagggtacga agtggaaat taaacgtacg gttgcggccc cgtctgtctt tatcttcccg    420
ccgagcgatg aacagctgaa atcgggcacc gcgagcgtgg tttgtctgct gaacaatttc    480
tatccgcgcg aagcaaaagt ccagtggaaa gtggacaacg ctctgcagtc cggtaattca    540
caagaatcgg tcaccgaaca agatagcaaa gactctacgt acagtctgag ttccaccctg    600
acgctgagca agcggatta tgaaaaacac aaagtttacg cctgcgaagt tacgcatcag    660
ggtctgtcca gcccggtgac gaaatctttt aatcgtggtg aatgttaatg a             711
```

<210> SEQ ID NO 105
<211> LENGTH: 1416
<212> TYPE: DNA
<213> ORGANISM: Artificial Sequence
<220> FEATURE:
<223> OTHER INFORMATION: Synthetic nucleotide sequence of heavy chain of Trastuzuzumab

<400> SEQUENCE: 105

| | |
|---|---|
| atggagacag acacactcct gctatgggta ctgctgctct ggqttccagg ttccactggt | 60 |
| gacgaagtgc aactggtgga aagtggtggt ggtctggttc aaccgggtgg ctccctgcgt | 120 |
| ctgtcctgtg ctgcgtcggg ttttaacatc aaagatacct atattcattg ggtccgtcag | 180 |
| gcaccgggca aggtctgga tgggtggct cgcatctacc cgaccaacgg ctatacgcgt | 240 |
| tacgcggatt ccgtgaaagg tcgctttacc atttccgcgg acacctcaaa aaacacggcc | 300 |
| tatctgcaga tgaacagcct gcgtgcagaa gacacggctg tttattactg cagtcgctgg | 360 |
| ggcggtgatg gctttatgc catggactac tggggccaag gtaccctggt caccgtgagc | 420 |
| tctgctagca ccaaaggtcc gagcgtgttc ccgctggctc cgagttccaa atcgaccagc | 480 |
| ggcggtacgg cagcactggg ttgtctggtt aaagattatt ttccggaacc ggttaccgtc | 540 |
| tcttggaaca gtggcgcgct gacctctggt gtgcatacgt tcccggccgt tctgcagtca | 600 |
| tcgggcctgt atagcctgag ctctgtggtt accgttccga ttcctcact gggtacccaa | 660 |
| acgtacatct gcaacgtcaa tcacaaaccg agcaatacga agtggacaa aaaagttgaa | 720 |
| ccgaaatcct gcgacaaaac ccatacatgc cctccctgtc cggcgcctga actcctgggt | 780 |
| ggtccgagtg tgttcctctt cctccgaag ccgaaagaca cgctgatgat ttcccgtacg | 840 |
| cccgaagtga cgtgtgttgt cgtagacgtc agccacgaag atccggaagt caaattcaat | 900 |
| tggtacgtcg acggagttga ggtgcataac gcgaaaacta accacgcga gaacagtac | 960 |
| aacagcacgt accgcgtcgt aagtgtcctg actgttctcc accaggattg gctgaatggc | 1020 |
| aaagagtaca atgcaaagt ctcaaacaaa gccctgccag ctccgatcga aaagacgatt | 1080 |
| agcaaagcga aggtcaacc tcgtgaaccc caggtgtata cgctgccacc gtcacgcgag | 1140 |
| gaaatgacca gaatcaggt tagccttaca tgcctggtga agggcttta cccgtcggat | 1200 |
| attgccgtag aatgggaatc caatggtcag ccggagaaca actacaagac aacaccgcca | 1260 |
| gtgctggatt ctgatgggtc cttctttctg tatagcaaac tgaccgttga caaatctcgc | 1320 |
| tggcaacaag caacgtgtt cagctgttcg gtgatgcatg aggccttgca caatcattat | 1380 |
| acccagaaaa gcctgtccct gtcaccgggg taatga | 1416 |

<210> SEQ ID NO 106
<211> LENGTH: 4545
<212> TYPE: DNA
<213> ORGANISM: Artificial Sequence
<220> FEATURE:
<223> OTHER INFORMATION: Synthetic nucleotide sequence of 9 copies of U6-tRNA(Pyl)

<400> SEQUENCE: 106

| | |
|---|---|
| attattgaag catttatcag ggttattgtc tcatgagcgg atacatattt gaatgtattt | 60 |
| agaaaaataa acaaataggg gttccgcgca catttccccg aaaagtgcca cctgacgtct | 120 |
| aagaaaccat tattatcatg acattaacct ataaaaatag gcgtatcacg aggccctttc | 180 |
| gtcttcaaga attcgccacc tgactggaga gggcctattt cccatgattc cttcatattt | 240 |
| gcatatacga tacaaggctg ttagagagat aattagaatt aatttgactg taaacacaaa | 300 |

```
gatattagta caaaatacgt gacgtagaaa gtaataattt cttgggtagt ttgcagtttt    360
aaaattatgt tttaaaatgg actatcatat gcttaccgta acttgaaagt atttcgattt    420
cttggcttta tatatcttgt ggaaaggacg aaacaccgag atcttctaga ctcgagggaa    480
acctgatcat gtagatcgaa tggactctaa atccgttcag ccgggttaga ttcccggggt    540
ttccggacaa gtgcggtttt tttctccagc tcccgaagcc acctgactgg agagggccta    600
tttcccatga ttccttcata tttgcatata cgatacaagg ctgttagaga gataattaga    660
attaatttga ctgtaaacac aaagatatta gtacaaaata cgtgacgtag aaagtaataa    720
tttcttgggt agtttgcagt tttaaaatta tgttttaaaa tggactatca tatgcttacc    780
gtaacttgaa agtatttcga tttcttggct ttatatatct tgtggaaagg acgaaacacc    840
gagatcttct agactcgagg gaaacctgat catgtagatc gaatggactc taaatccgtt    900
cagccgggtt agattcccgg ggtttccgga caagtgcggt tttttctcc agctcccgaa    960 gccacctgac tggagagggc ctatttccca tgattccttc atatttgcat atacgataca   1020
aggctgttag agagataatt agaattaatt tgactgtaaa cacaaagata ttagtacaaa   1080
atacgtgacg tagaaagtaa aatttcttg ggtagtttgc agttttaaaa ttatgtttta    1140
aaatggacta tcatatgctt accgtaactt gaaagtattt cgatttcttg ctttatata    1200 tcttgtggaa aggacgaaac accgagatct tctagactcg agggaaacct gatcatgtag   1260
atcgaatgga ctctaaatcc gttcagccgg gttagattcc ggggtttcc ggacaagtgc    1320 ggttttttc tccagctccc gaagccacct gactggaagc tttaatgcgg tagtttatca    1380
cagttaaatt gctaacgcag tcaggcaccg tgtatgaaat ctaacaatgc gctcatcgtc   1440
atcctcggca ccgtcaccct ggatgctgta ggcataggct tggttatgcc ggtactgccg   1500
ggcctcttgc gggatattat tgaagcattt atcagggtta ttgtctcatg agcggataca   1560
tatttgaatg tatttagaaa aataaacaaa taggggttcc gcgcacattt ccccgaaaag   1620
tgccacctga cgtctaagaa accattatta tcatgacatt aacctataaa aataggcgta   1680
tcacgaggcc ctttcgtctt caagaattcg ccacctgact ggagagggcc tatttcccat   1740
gattccttca tatttgcata tacgatacaa ggctgttaga gagataatta gaattaattt   1800
gactgtaaac acaaagatat tagtacaaaa tacgtgacgt agaaagtaat aatttcttgg   1860
gtagtttgca gttttaaaat tatgttttaa aatggactat catatgctta ccgtaacttg   1920
aaagtatttc gatttcttgg ctttatatat cttgtggaaa ggacgaaaca ccgagatctt   1980
ctagactcga gggaaacctg atcatgtaga tcgaatggac tctaaatccg ttcagccggg   2040
ttagattccc ggggtttccg gacaagtgcg gttttttct ccagctcccg aagccacctg   2100
actggagagg gcctatttcc catgattcct tcatatttgc atatacgata caaggctgtt   2160
agagagataa ttagaattaa tttgactgta aacacaaaga tattagtaca aaatacgtga   2220
cgtagaaagt aataatttct ggggtagttt gcagttttaa aattatgttt taaaatggac   2280
tatcatatgc ttaccgtaac ttgaaagtat ttcgatttct tggctttata tatcttgtgg   2340
aaaggacgaa acaccgagat cttctagact cgagggaaac ctgatcatgt agatcgaatg   2400
gactctaaat ccgttcagcc gggttagatt cccggggttt ccgacaagt gcggttttt    2460 tctccagctc ccgaagccac tgactggag agggcctatt tcccatgatt ccttcatatt   2520
tgcatatacg atacaaggct gttagagaga taattagaat taatttgact gtaaacacaa   2580
agatattagt acaaaatacg tgacgtagaa agtaataatt tcttgggtag tttgcagttt   2640
```

-continued

| | |
|---|---|
| taaaattatg ttttaaaatg gactatcata tgcttaccgt aacttgaaag tatttcgatt | 2700 |
| tcttggcttt atatatcttg tggaaaggac gaaacaccga gatcttctag actcgaggga | 2760 |
| aacctgatca tgtagatcga atggactcta aatccgttca gccgggttag attcccgggg | 2820 |
| tttccggaca agtgcggttt ttttctccag ctcccgaagc cacctgactg gaagctttaa | 2880 |
| tgcggtagtt tatcacagtt aaattgctaa cgcagtcagg caccgtgtat gaaatctaac | 2940 |
| aatgcgctca tcgtcatcct cggcaccgtc accctggatg ctgtaggcat aggcttggtt | 3000 |
| atgccggtac tgccgggcct cttgcgggat attattgaag catttatcag ggttattgtc | 3060 |
| tcatgagcgg atacatattt gaatgtattt agaaaaataa acaaataggg gttccgcgca | 3120 |
| catttccccg aaaagtgcca cctgacgtct aagaaaccat tattatcatg acattaacct | 3180 |
| ataaaaatag gcgtatcacg aggccctttc gtcttcaaga attcgccacc tgactgagag | 3240 |
| gggcctattt cccatgattc cttcatattt gcatatacga tacaaggctg ttagagagat | 3300 |
| aattagaatt aatttgactg taaacacaaa gatattagta caaatacgt gacgtagaaa | 3360 |
| gtaataattt cttgggtagt ttgcagtttt aaaattatgt tttaaaatgg actatcatat | 3420 |
| gcttaccgta acttgaaagt atttcgattt cttggcttta tatatcttgt ggaaaggacg | 3480 |
| aaacaccgag atcttctaga ctcgagggaa acctgatcat gtagatcgaa tggactctaa | 3540 |
| atccgttcag ccgggttaga ttccgggggt ttccggacaa gtgcggtttt tttctccagc | 3600 |
| tcccgaagcc acctgactgg agagggccta tttcccatga ttccttcata tttgcatata | 3660 |
| cgatacaagg ctgttagaga gataattaga attaatttga ctgtaaacac aaagatatta | 3720 |
| gtacaaaata cgtgacgtag aaagtaataa tttcttgggt agtttgcagt tttaaaatta | 3780 |
| tgttttaaaa tggactatca tatgcttacc gtaacttgaa agtatttcga tttcttggct | 3840 |
| ttatatatct tgtggaaagg acgaaacacc gagatcttct agactcgagg gaaacctgat | 3900 |
| catgtagatc gaatggactc taaatccgtt cagccgggtt agattcccgg ggtttccgga | 3960 |
| caagtgcggt ttttttctcc agctcccgaa gccacctgac tggagagggc ctatttccca | 4020 |
| tgattccttc atatttgcat atacgataca aggctgttag agagataatt agaattaatt | 4080 |
| tgactgtaaa cacaaagata ttagtacaaa atacgtgacg tagaaagtaa taatttcttg | 4140 |
| ggtagtttgc agttttaaaa ttatgtttta aaatggacta tcatatgctt accgtaactt | 4200 |
| gaaagtattt cgatttcttg gctttatata tcttgtggaa aggacgaaac accgagatct | 4260 |
| tctagactcg agggaaacct gatcatgtag atcgaatgga ctctaaatcc gttcagccgg | 4320 |
| gttagattcc cggggtttcc ggacaagtgc ggttttttt tccagctccc gaagccacct | 4380 |
| gactggaagc tttaatgcgg tagtttatca cagttaaatt gctaacgcag tcaggcaccg | 4440 |
| tgtatgaaat ctaacaatgc gctcatcgtc atcctcggca ccgtcaccct ggatgctgta | 4500 |
| ggcataggct tggttatgcc ggtactgccg ggcctcttgc gggat | 4545 |

<210> SEQ ID NO 107
<211> LENGTH: 1365
<212> TYPE: DNA
<213> ORGANISM: Artificial Sequence
<220> FEATURE:
<223> OTHER INFORMATION: Synthetic nucleotide sequence of Pyl RS
      (Y306A/Y384F) variant

<400> SEQUENCE: 107

| | |
|---|---|
| atggataaaa aaccactaaa cactctgata tctgcaaccg ggctctggat gtccaggacc | 60 |
| ggaacaattc ataaaataaa acaccacgaa gtctctcgaa gcaaaatcta tattgaaatg | 120 |

```
gcatgcggag accaccttgt tgtaaacaac tccaggagca gcaggactgc aagagcgctc      180
aggcaccaca aatacaggaa gacctgcaaa cgctgcaggg tttcggatga ggatctcaat      240
aagttcctca caaaggcaaa cgaagaccag acaagcgtaa aagtcaaggt cgtttctgcc      300
cctaccagaa cgaaaaaggc aatgccaaaa tccgttgcga gagccccgaa acctcttgag      360
aatacagaag cggcacaggc tcaaccttct ggatctaaat tttcacctgc gataccggtt      420
tccacccaag agtcagtttc tgtcccggca tctgtttcaa catcaatatc aagcatttct      480
acaggagcaa ctgcatccgc actggtaaaa gggaatacga accccattac atccatgtct      540
gcccctgttc aggcaagtgc ccccgcactt acgaagagcc agactgacag gcttgaagtc      600
ctgttaaacc caaagatga gatttccctg aattccggca agcctttcag ggagcttgag       660
tccgaattgc tctctcgcag aaaaaaagac ctgcagcaga tctacgcgga agaaagggag      720
aattatctgg ggaaactcga gcgtgaaatt accaggttct ttgtggacag gggttttctg      780
gaaataaaat ccccgatcct gatccctctt gagtatatcg aaaggatggg cattgataat      840
gataccgaac tttcaaaaca gatcttcagg gttgacaaga acttctgcct gagacccatg      900
cttgctccaa accttgccaa ctacctgcgc aagcttgaca gggccctgcc tgatccaata      960
aaaatttttg aaataggccc atgctacaga aaagagtccg acggcaaaga acacctcgaa      1020
gagtttacca tgctgaactt ctgccagatg ggatcgggat gcacacggga aaatcttgaa      1080
agcataatta cggacttcct gaaccacctg ggaattgatt tcaagatcgt aggcgattcc      1140
tgcatggtct ttggggatac ccttgatgta atgcacggag acctggaact ttcctctgca      1200
gtagtcggac ccataccgct tgaccgggaa tggggtattg ataaaccctg gataggggca      1260
ggtttcgggc tcgaacgcct tctaaaggtt aaacacgact ttaaaaatat caagagagct      1320
gcaaggtccg ggtcttacta taacgggatt tctaccaacc tgtaa                     1365
```

ANTIBODY WITH NON-NATURAL AMINO ACID INTRODUCED THEREIN

CROSS REFERENCE TO RELATED APPLICATIONS

This application is a Divisional Application of U.S. patent application Ser. No. 15/753,724 filed Feb. 20, 2018 (issued as U.S. Pat. No. 10,906,990 on Feb. 2, 2021), which is a National Stage of International Application No. PCT/JP2016/074056 filed Aug. 18, 2016, claiming priority based on Japanese Patent Application No. 2015-162160 filed Aug. 19, 2015.

TECHNICAL FIELD

Related Application

The present application claims priority based on Japanese Patent Application No. 2015-162160 (filed on Aug. 19, 2015), and the contents are incorporated herein by reference.

Technical Field

The present invention relates to a monoclonal antibody or antibody fragment thereof as a human IgG antibody including at least one lysine derivative in a constant region of the human IgG antibody. In addition, the present invention relates to a modified antibody or antibody fragment thereof, wherein the lysine derivative is chemically modified.

BACKGROUND ART

Antibody-drug conjugates (ADCs) are attracting much attention as a novel antibody derivative utilizing the high binding specificity of an antibody. ADCs are capable of specifically delivering a drug, one of functional molecules, included in an antibody derivative into a target cell by utilizing endocytosis of a target antigen due to antibody binding. Mylotarg® (Gemtuzumab Ozogamicin), Kadcyla® (Trastuzumab-DM1), and Adcetris® (Brentuximab vedotin) each have been already approved as an ADC preparation, and many ADC preparations are under clinical development. Thus, ADC preparations are expected to be promising as a form of future pharmaceutical products (Non Patent Literature 1).

In existing ADC preparations, a drug is covalently bonded via the ε-amino group of a lysine residue or the thiol group of a Cys residue in the antibody molecule. Such a modification mode has been revealed to typically lead to formation of a heterogeneous mixture with different numbers of additions per molecule of the antibody, and causes concern over generation of difference in in vivo pharmacokinetics and difficulty in construction of a stable production process (Non Patent Literature 2).

Introduction of a Cys residue into a particular site or particular region of an antibody or antibody fragment has been reported as one of methods for producing an ADC preparation having high homogeneity without affecting the binding affinity, binding specificity, and stability in blood (Patent Literature 8). From various approaches conducted after the report, introduction of a Cys residue into a particular site of the light chain or heavy chain constant region of an antibody or antibody fragment has been reported to enable preparation of a site-specific antibody (Patent Literatures 1, 9).

On the other hand, a method has been developed in which a non-natural amino acid having reactivity differing from those of natural amino acids is introduced into protein and the non-natural amino acid residue is chemically modified in a selective manner. By introduction of acetylphenylalanine as a non-natural amino acid, for example, the pharmaceutical agent molecule auristatin derivative with addition of a linker modified with a reactive group can be specifically bonded to the acetylphenylalanine through reaction called "oxime ligation" (Patent Literature 2, Non Patent Literature 3). However, this technique does not provide sufficient reaction efficiency, and, disadvantageously, requires reaction with an antibody or antibody fragment with acetylphenylalanine introduced therein at a high concentration under acidic conditions for a long period of time, and hence causes concern over influence such as degeneration of an antibody or antibody fragment or a pharmaceutical agent.

Click chemistry which takes place between an azido group and an alkyne is known as a reaction with higher reaction efficiency and high specificity in combination. Actually, chemical modification can be achieved through introduction of a non-natural amino acid modified with an azido group into an antibody or antibody fragment. For example, addition of a pharmaceutical agent molecule through click chemistry to an antibody with azidophenylalanine or azidomethylphenylalanine as a non-natural amino acid introduced therein has been reported (Patent Literature 3, Non Patent Literature 4).

Any of the aforementioned acetylphenylalanine, azidophenylalanine, and azidomethylphenylalanine is introduced by using tyrosyl tRNA synthetase (Tyr RS), and sites near the surface of protein where the ratio of the accessible surface area (ASA), ASA ratio, is relatively high, for example, sites where the ASA ratio is 40% or higher have been primarily reported as the site for introduction. At the same time, a method for introducing a pyrrolysine derivative, which is a non-natural amino acid having a long side chain, by using pyrrolysyl tRNA synthetase (Pyl RS) has been developed, and in addition it has been reported that chemical modification was achieved through click chemistry (Patent Literature 4, Non Patent Literature 5).

In fact, examples in which a pyrrolysine derivative is introduced into an antibody have been reported. With respect to a constant region, the sequence of which is common among antibody species, a site where the ASA ratio is high is targeted and used for introduction of a pyrrolysine derivative (Patent Literature 5, Patent Literature 6).

Site-selective chemical modification through introduction of a non-natural amino acid into an antibody is useful from a viewpoint other than a method for producing an excellent ADC preparation, and, for example, provides a method for producing a recombinant bispecific antibody through chemical conjugation. The term "bispecific antibody" refers to a modified immunoglobulin derivative typically having two different binding paratopes to different antigens or epitopes. To produce stable and homogeneous bispecific antibodies, development has been previously conducted primarily for a novel structure format in which an antigen-binding domain is fused through gene engineering. However, an example in which different antibodies each with the aforementioned acetylphenylalanine introduced therein are heterodimerized through oxime ligation reaction (Non Patent Literature 6) and an example in which different antibodies each with azidohomoalanine introduced therein are heterodimerized through click chemistry (Patent Literature 7) have been also reported as examples in which a bispecific antibody was produced through chemical conjugation.

CITATION LIST

Patent Literature

Patent Literature 1: International Publication No. WO 2011/118739
Patent Literature 2: International Publication No. WO 2013/068874
Patent Literature 3: International Publication No. WO 2014/004639
Patent Literature 4: Japanese Patent Laid-Open No. 2007/37445
Patent Literature 5: International Publication No. WO 2014/044872
Patent Literature 6: International Publication No. WO 2014/124258
Patent Literature 7: National Publication of International Patent Application No. 2013/545438
Patent Literature 8: U.S. Pat. No. 5,219,996
Patent Literature 9: International Publication No. WO 2006/034488

Non Patent Literature

Non Patent Literature 1: Nat Rev Drug Discov., 12, 329-332 (2013)
Non Patent Literature 2: MAbs, 6, 34-45 (2014)
Non Patent Literature 3: Proc Natl Acad Sci USA. 109, 16101-16106 (2012)
Non Patent Literature 4: Bioconjugate Chem., 25, 351-361 (2014)
Non Patent Literature 5: Chem Biol., 15, 1187-1197 (2008)
Non Patent Literature 6: J. Am. Chem. Soc., 134, 9918-9921 (2012)

SUMMARY OF INVENTION

Technical Problem

An object of the present invention is to provide a novel means for site-specific chemical modification without depending on the amino acid sequence of the variable region of an antibody. Another object of the present invention is to provide a novel means for highly-efficient site-specific chemical modification without depending on the amino acid sequence of the variable region of an antibody.

Solution to Problem

As a means to achieve the objects, a lysine derivative is introduced into an antibody or antibody fragment thereof in the present invention. Specifically, a lysine derivative such as a Z-lysine derivative, TCO*-Lys, and BCN-Lys is introduced into an antibody or antibody fragment thereof in the present invention. While several methods in which a non-natural amino acid is introduced into protein and the non-natural amino acid residue is chemically modified in a selective manner have been reported, an example in which a Z-lysine derivative, TCO*-Lys, or BCN-Lys, each of which is one of non-natural amino acids, was introduced into a constant region of an antibody or antibody fragment has not been reported yet.

That is, the present invention relates to a monoclonal antibody or antibody fragment thereof including at least one lysine derivative capable of being chemically modified in a constant region of the antibody, specifically, a monoclonal antibody or antibody fragment thereof including at least one Z-lysine derivative, TCO*-Lys, or BCN-Lys capable of being chemically modified in a constant region of the antibody; a modified antibody or antibody fragment thereof, wherein the lysine derivative is modified; a nucleic acid including a nucleotide sequence encoding the antibody or antibody fragment thereof; a vector including the nucleic acid; a transformed cell obtained by introducing the vector into a host cell; a method for producing the antibody or antibody fragment thereof; and a composition containing the antibody or antibody fragment thereof.

Specifically, the present invention relates to the following (1) to (41).

(1) A monoclonal antibody or antibody fragment thereof as an antibody comprising at least one N6-((benzyloxy)carbonyl)-L-lysine derivative (hereinafter, represented as "Z-lysine derivative") in a constant region of the antibody.

(2) The monoclonal antibody or antibody fragment thereof according to (1), wherein the constant region of the antibody is a constant region of an antibody selected from a human antibody, a rat antibody, a rabbit antibody, and a mouse antibody.

(3) The monoclonal antibody or antibody fragment thereof according to (1) or (2), wherein the constant region of the antibody is at least one constant region selected from the group consisting of a heavy chain constant region and a light chain constant region of the antibody.

(4) The monoclonal antibody or antibody fragment thereof according to any one of (1) to (3), wherein the constant region of the antibody is at least one constant region selected from the group consisting of a CH1 region, a κ chain constant region, and a λ chain constant region.

(5) The monoclonal antibody or antibody fragment thereof according to any one of (1) to (4), wherein at least one amino acid residue selected from the group consisting of the following a) to c) is a Z-lysine derivative:

a) amino acid residues at positions 118, 120, 121, 127, 129, 131, 133, 135, 152, 159, 169, 173, 174, 177, 180, 190, 199, 205, and 210 of a heavy chain of a human IgG antibody according to EU-index numbering by Kabat et al. (hereinafter, represented as "the EU-index numbering");

b) amino acid residues at positions 110, 112, 119, 138, 141, 145, 147, 149, 153, 154, 155, 158, 161, 167, 169, 180, 183, 184, 191, 195, 197, 205, 207, 210, and 211 of a κ chain of a human antibody according to the EU-index numbering; and c) amino acid residues at positions 110, 119, 125, 127, 129, 143, 147, 160, 161, 165, 166, 172, 173, 180, 187, 189, 191, 195, 205, 207, 210, and 215 of a λ chain of a human antibody according to the EU-index numbering.

(6) The monoclonal antibody or antibody fragment thereof according to any one of (1) to (5), wherein at least one amino acid residue selected from the group consisting of amino acid residues at positions 131, 177, and 199 of a heavy chain of a human IgG antibody and amino acid residues at positions 155, 191, and 197 of a κ chain of a human antibody according to the EU-index numbering is a Z-lysine derivative.

(7) The monoclonal antibody or antibody fragment thereof according to any one of (1) to (6), wherein at least one Z-lysine derivative is modified.

(8) The monoclonal antibody or antibody fragment thereof according to (7), wherein the modification is chemical modification with a molecule having reactivity with a Z-lysine derivative.

(9) The monoclonal antibody or antibody fragment thereof according to (8), wherein the molecule having reactivity with a Z-lysine derivative is at least one molecule selected from the group consisting of hydrophilic polymer, amphiphilic polymer, and a functional molecule.

(10) The monoclonal antibody or antibody fragment thereof according to (8) or (9), wherein the molecule having reactivity with a Z-lysine derivative is at least one molecule selected from the group consisting of PEG, an antigen-binding molecule, a drug, and a fluorescent compound.

(11) The monoclonal antibody or antibody fragment thereof according to (10), wherein the antigen-binding molecule is a monoclonal antibody or antibody fragment thereof.

(12) The antibody fragment according to any one of (1) to (11), wherein the antibody fragment is an antibody fragment selected from the group consisting of an Fab, an Fab', an (Fabv)$_2$, a single chain antibody (scFv), a dimerized V region (diabody), a disulfide-stabilized V region (dsFv), and a peptide comprising a CDR.

(13) The monoclonal antibody or antibody fragment thereof according to any one of (1) to (12), wherein the monoclonal antibody is a recombinant antibody.

(14) The monoclonal antibody or antibody fragment thereof according to (13), wherein the recombinant antibody is a mouse antibody, a rat antibody, a rabbit antibody, a chimeric antibody, a humanized antibody, or a human antibody.

(15) A nucleic acid comprising a nucleotide sequence encoding the monoclonal antibody or antibody fragment thereof according to any one of (1) to (14).

(16) A vector comprising the nucleic acid according to (15).

(17) A transformed cell comprising the vector according to (16).

(18) The transformed cell according to (17), wherein the cell is a prokaryotic cell or a eukaryotic cell.

(19) A method for producing the monoclonal antibody or antibody fragment thereof according to any one of (1) to (14), the method comprising culturing the transformed cell according to (17) or (18) in a medium and collecting an antibody or antibody fragment thereof from the culture.

(20) A composition comprising the monoclonal antibody or antibody fragment thereof according to any one of (1) to (14).

(21) A monoclonal antibody or antibody fragment thereof as an antibody comprising at least one lysine derivative selected from the group consisting of N6-(((trans-cyclooct-2-en-1-yl)oxy)carbonyl)-L-lysine (hereinafter, abbreviated as "TCO*-Lys") and N6-((bicyclo[6.1.0]non-4-yn-9-yl-methoxy)carbonyl)-L-lysine (hereinafter, abbreviated as "BCN-Lys") in a constant region of the antibody.

(22) The monoclonal antibody or antibody fragment thereof according to (21), wherein the constant region of the antibody is a constant region of an antibody selected from a human antibody, a rat antibody, a rabbit antibody, and a mouse antibody.

(23) The monoclonal antibody or antibody fragment thereof according to (21) or (22), wherein the constant region of the antibody is at least one constant region selected from the group consisting of a heavy chain constant region and a light chain constant region of the antibody.

(24) The monoclonal antibody or antibody fragment thereof according to any one of (21) to (23), wherein the constant region of the antibody is at least one constant region selected from the group consisting of a CH1 region, a κ chain constant region, and a λ chain constant region.

(25) The monoclonal antibody or antibody fragment thereof according to any one of (21) to (24), wherein at least one amino acid residue selected from the group consisting of the following a) to c) is a lysine derivative:

a) amino acid residues at positions 118, 120, 121, 127, 129, 131, 133, 135, 152, 159, 169, 173, 174, 177, 180, 190, 199, 205, and 210 of a heavy chain of a human IgG antibody according to EU-index numbering by Kabat et al. (hereinafter, represented as "the EU-index numbering");

b) amino acid residues at positions 110, 112, 119, 138, 141, 145, 147, 149, 153, 154, 155, 158, 161, 167, 169, 180, 183, 184, 191, 195, 197, 205, 207, 210, and 211 of a κ chain of a human antibody according to the EU-index numbering; and c) amino acid residues at positions 110, 119, 125, 127, 129, 143, 147, 160, 161, 165, 166, 172, 173, 180, 187, 189, 191, 195, 205, 207, 210, and 215 of a λ chain of a human antibody according to the EU-index numbering.

(26) The monoclonal antibody or antibody fragment thereof according to any one of (21) to (25), wherein at least one lysine derivative is modified.

(27) The monoclonal antibody or antibody fragment thereof according to (26), wherein the modification is chemical modification with a molecule having reactivity with a lysine derivative.

(28) The monoclonal antibody or antibody fragment thereof according to (27), wherein the molecule having reactivity with a lysine derivative is at least one molecule selected from the group consisting of hydrophilic polymer, amphiphilic polymer, and functional molecule.

(29) The monoclonal antibody or antibody fragment thereof according to (27) or (28), wherein the molecule having reactivity with a lysine derivative is at least one molecule selected from the group consisting of PEG, an antigen-binding molecule, a drug, and a fluorescent compound.

(30) The monoclonal antibody or antibody fragment thereof according to (29), wherein the antigen-binding molecule is a monoclonal antibody or antibody fragment thereof.

(31) The antibody fragment according to any one of (21) to (30), wherein the antibody fragment is an antibody fragment selected from the group consisting of an Fab, an Fab', an (Fab')$_2$, a single chain antibody (scFv), a dimerized V region (diabody), a disulfide-stabilized V region (dsFv), and a peptide comprising a CDR.

(32) The monoclonal antibody or antibody fragment thereof according to any one of (21) to (31), wherein the monoclonal antibody is a recombinant antibody.

(33) The monoclonal antibody or antibody fragment thereof according to (32), wherein the recombinant antibody is a mouse antibody, a rat antibody, a rabbit antibody, a chimeric antibody, a humanized antibody, or a human antibody.

(34) A nucleic acid comprising a nucleotide sequence encoding the monoclonal antibody or antibody fragment thereof according to any one of (21) to (33).

(35) A vector comprising the nucleic acid according to (34).

(36) A transformed cell comprising the vector according to (35).

(37) A method for producing the monoclonal antibody or antibody fragment thereof according to any one of (21) to (33), the method comprising culturing the transformed cell according to (36) in a medium and collecting an antibody or antibody fragment thereof from the culture.

(38) A composition comprising the monoclonal antibody or antibody fragment thereof according to any one of (21) to (33).

(39) The monoclonal antibody or antibody fragment thereof according to (1) to (13), wherein the Z-lysine derivative is at least one selected from azido-Z-lysine, ethynyl-Z-lysine, amino-Z-lysine, and formyl-Z-lysine.

(40) The monoclonal antibody or antibody fragment thereof according to (1) to (13), wherein the Z-lysine derivative is at least one of azido-Z-lysine and ethynyl-Z-lysine. (41) The monoclonal antibody or antibody fragment thereof according to (1) to (13), wherein the Z-lysine derivative is azido-Z-lysine.

Advantageous Effects of Invention

The antibody or antibody fragment thereof according to the present invention can be subjected to site-specific chemical modification without depending on the amino acid sequence of the variable region of an antibody, by virtue of the at least one lysine derivative included in a constant region. Specifically, the antibody or antibody fragment thereof according to the present invention can be subjected to site-specific chemical modification without depending on the amino acid sequence of the variable region of an antibody, by virtue of the at least one lysine derivative such as a Z-lysine derivative, TCO*-Lys, and BCN-Lys included in a constant region. That is, a lysine derivative can be site-specifically introduced into any antibody and the antibody can be chemically modified.

DESCRIPTION OF EMBODIMENTS

Figure 1:
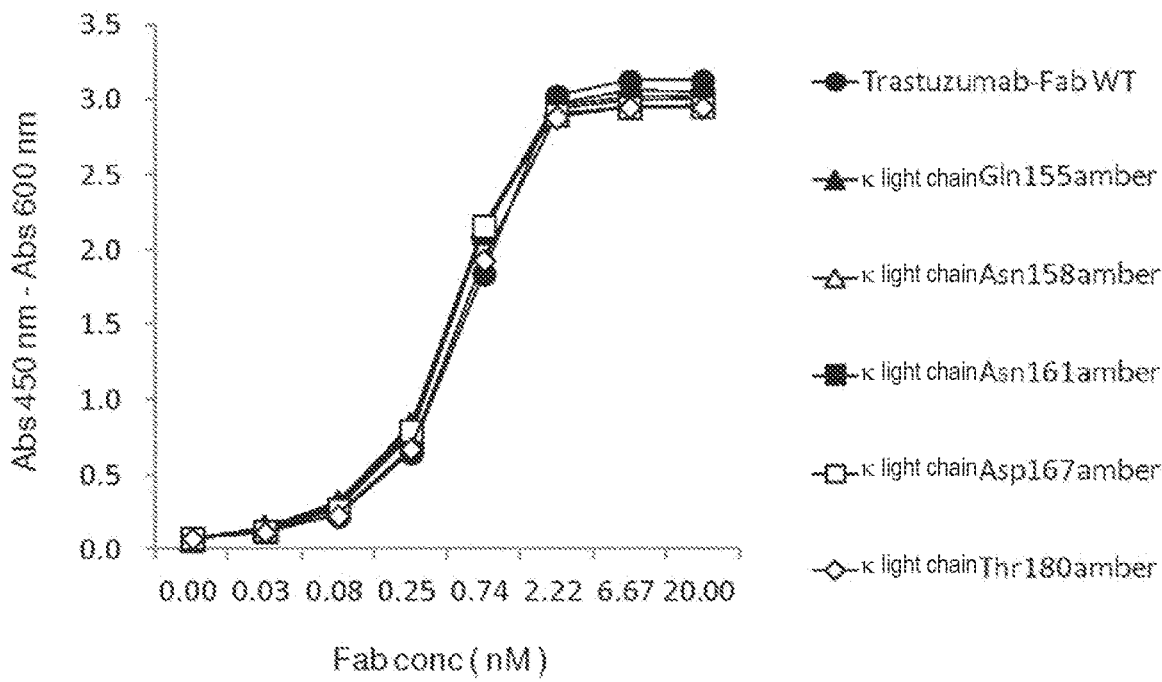
FIG. 1 shows the binding activity of Trastuzumab-Fabs with o-Az-Z-Lys introduced therein to Her2, where the vertical axis represents numerical values calculated by subtracting the absorbance at 600 nm from the absorbance at 450 nm, and the horizontal axis represents Fab concentration (nM).

The present invention relates to an antibody or antibody fragment thereof including a lysine derivative as a non-natural amino acid. Specifically, the present invention relates to an antibody or antibody fragment thereof including an N6-((benzyloxy)carbonyl)-L-lysine derivative (hereinafter, represented as "Z-lysine derivative", where Z-lysine is also referred to as "N$^\varepsilon$-benzyloxycarbonyl-lysine" (WO 2009/038195)), N6-(((trans-cyclooct-2-en-1-yl)oxy)carbonyl)-L-lysine (hereinafter, represented as "TCO*-Lys"), or N$^6$-((bicyclo[6.1.0]non-4-yn-9-ylmethoxy)carbonyl)-L-lysine (hereinafter, represented as "BCN-Lys").

More specifically, the present invention relates to an antibody or antibody fragment thereof as an antibody including at least one lysine derivative such as a Z-lysine derivative, TCO*-Lys, and BCN-Lys in a constant region of the antibody (hereinafter, simply represented as "the antibody or antibody fragment thereof according to the present invention", or occasionally represented as, for example, "the antibody or antibody fragment thereof with a Z-lysine derivative introduced therein", "the antibody or antibody fragment thereof with TCO*-Lys introduced therein", or "the antibody or antibody fragment thereof with BCN-Lys introduced therein").

The term "non-natural amino acid" refers to an amino acid other than amino acids genetically encoded in naturally occurring organisms. The term "amino acids genetically encoded" refers to 22 amino acids consisting of 20 standard amino acids universally utilized by organisms and additional two amino acids of selenomethionine and pyrrolysine.

The term "lysine derivative" refers to a compound which is a non-natural amino acid and in which an atom or group of atoms in lysine is substituted with another atom or group of atoms. In the present invention, the lysine derivative may be any non-natural amino acid having reactivity. The lysine may be either L-lysine or D-lysine. However, the lysine is preferably L-lysine. Specific examples of the lysine derivative include a Z-lysine derivative, TCO*-Lys, and BCN-Lys.

In the present invention, the Z-lysine derivative is a compound represented by the following general formula (I):

[Chemical Formula 1]

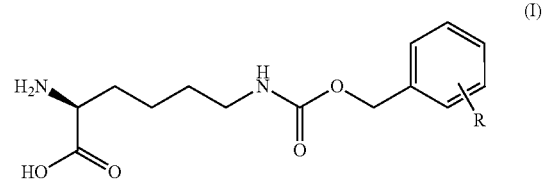

In the general formula (I), R may be any substituent having reactivity. However, R is preferably azido, azido lower alkyl, lower alkynyl, amino, or formyl, and more preferably azido, ethynyl, amino, or formyl. Examples of the lower alkyl moiety of the azido lower alkyl include $C_{2-4}$ alkyl, more specifically, methyl, ethyl, propyl, and butyl. Examples of the lower alkynyl include $C_{2-4}$ alkynyl, more specifically, ethynyl, propynyl, and butynyl. In the general formula (I), one, two, or three R groups may be present. However, substitution with one R group at an ortho position or meta position is preferred. In the case that two or three R groups are present, the R groups may be identical or different.

Specific examples of the Z-lysine derivative to be used in the present invention are listed in Table 1. However, the Z-lysine derivative to be used in the present invention is not limited thereto.

TABLE 1

| Compound name | Chemical structure |
| --- | --- |
| ortho-azido-Z-lysine | 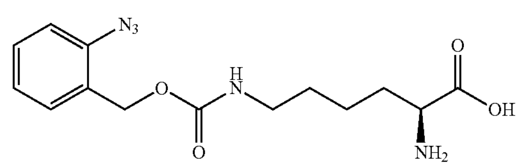 [SMILES: [N-]=[N+]=Nc1ccccc1COC(=O)NCCCC[C@H](N)C(=O)O] |

TABLE 1-continued

| Compound name | Chemical structure |
| --- | --- |
| meta-azido-Z-lysine | (structure) |
| para-azido-Z-lysine | (structure) |
| ortho-ethynyl-Z-lysine | (structure) |
| meta-ethynyl-Z-lysine | (structure) |
| para-ethynyl-Z-lysine | (structure) |
| ortho-amino-Z-lysine | (structure) |
| meta-amino-Z-lysine | (structure) |
| para-amino-Z-lysine | (structure) |

TABLE 1-continued

| Compound name | Chemical structure |
|---|---|
| ortho-formyl-Z-lysine | 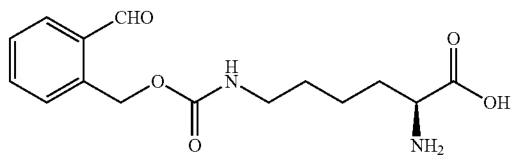 [SMILES: N[C@@H](CCCCNC(=O)OCc1ccccc1C=O)C(=O)O] |
| meta-formyl-Z-lysine | 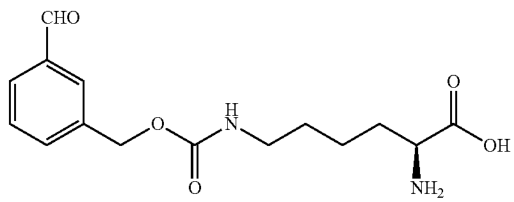 [SMILES: N[C@@H](CCCCNC(=O)OCc1cccc(C=O)c1)C(=O)O] |
| para-formyl-Z-lysine | 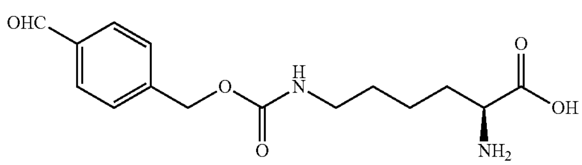 [SMILES: N[C@@H](CCCCNC(=O)OCc1ccc(C=O)cc1)C(=O)O] |

In the present invention, azido-Z-lysine is used as the collective term for ortho-azido-Z-lysine, meta-azido-Z-lysine, and para-azido-Z-lysine; ethynyl-Z-lysine as the collective term for ortho-ethynyl-Z-lysine, meta-ethynyl-Z-lysine, and para-ethynyl-Z-lysine; amino-Z-lysine as the collective term for ortho-amino-Z-lysine, meta-amino-Z-lysine, and para-amino-Z-lysine; and formyl-Z-lysine as the collective term for ortho-formyl-Z-lysine, meta-formyl-Z-lysine, and para-formyl-Z-lysine.

Ortho-azido-Z-lysine and meta-azido-Z-lysine are preferred as azido-Z-lysine; ortho-ethynyl-Z-lysine and meta-ethynyl-Z-lysine are preferred as ethynyl-Z-lysine; ortho-amino-Z-lysine and meta-amino-Z-lysine are preferred as amino-Z-lysine; and ortho-formyl-Z-lysine and meta-formyl-Z-lysine are preferred as formyl-Z-lysine.

Specific examples of the antibody according to the present invention include an antibody including at least one Z-lysine derivative in a constant region thereof. More preferred examples of the antibody according to the present invention include an antibody including at least one Z-lysine derivative having a substituent selected from azido, azido lower alkyl, lower alkynyl, amino, and formyl in a constant region thereof.

More specific examples of the antibody according to the present invention include an antibody including at least one Z-lysine derivative selected from azido-Z-lysine, ethynyl-Z-lysine, amino-Z-lysine, and formyl-Z-lysine. Especially, an antibody including at least one Z-lysine derivative selected from azido-Z-lysine and ethynyl-Z-lysine is preferred, and an antibody including at least one azido-Z-lysine is more preferred.

The antibody and antibody fragment thereof according to the present invention can be subjected to site-specific chemical modification by virtue of at least one Z-lysine derivative included in a constant region of the antibody.

In the case that the Z-lysine derivative is azido-Z-lysine, the antibody and antibody fragment thereof according to the present invention can be subjected to site-specific chemical modification at high efficiency in a simple manner by virtue of at least one azido-Z-lysine included in a constant region of the antibody.

In the case that the Z-lysine derivative is ethynyl-Z-lysine, the antibody and antibody fragment thereof according to the present invention can be subjected to site-specific chemical modification in a simple manner by virtue of at least one ethynyl-Z-lysine included in a constant region of the antibody.

In the case that the Z-lysine derivative is amino-Z-lysine, the antibody and antibody fragment thereof according to the present invention can be subjected to site-specific chemical modification by virtue of at least one amino-Z-lysine included in a constant region of the antibody.

In the case that the Z-lysine derivative is formyl-Z-lysine, the antibody and antibody fragment thereof according to the present invention can be subjected to site-specific chemical modification by virtue of at least one formyl-Z-lysine included in a constant region of the antibody.

Specific examples of the antibody according to the present invention include an antibody or antibody fragment thereof as an antibody including at least one TCO*-Lys or BCN-Lys in a constant region of the antibody.

The chemical structures of TCO*-Lys and BCN-Lys are shown in Table 2.

TABLE 2

| Compound name | Chemical structure |
|---|---|
| TCO*-Lys | (structure shown) |
| BCN-Lys | (structure shown) |

The antibody and antibody fragment thereof according to the present invention can be subjected to site-specific chemical modification by virtue of TCO*-Lys or BCN-Lys included in a constant region of the antibody.

Examples of the constant region of an antibody include a constant region of an antibody derived from an animal species such as a human, a mouse, a rabbit, and a rat, and the constant region of an antibody in the present invention is preferably a constant region of an antibody derived from a human.

Examples of the constant region of an antibody include a heavy chain constant region of an antibody and a light chain constant region of an antibody. Examples of the heavy chain constant region of an antibody include the CH1, hinge, CH2, and CH3 regions, and the heavy chain constant region in the present invention is preferably the CH1 region. Although the subclass of the heavy chain constant region of an antibody is not limited, the subclass is preferably IgG. Examples of the light chain constant region of an antibody include Cκ and Cλ, and the light chain constant region in the present invention may be any of them.

Specific examples of the antibody or antibody fragment according to the present invention include the antibody or antibody fragment thereof selected from the following (a) to (g):

(a) an antibody or antibody fragment thereof in which at least one amino acid residue selected from positions 118, 120, 121, 127, 129, 131, 133, 135, 152, 159, 169, 173, 174, 177, 180, 190, 199, 205, and 210 of the heavy chain of a human IgG antibody according to EU-index numbering by Kabat et al. (hereinafter, represented as "the EU-index numbering") is a Z-lysine derivative;

(b) an antibody or antibody fragment thereof in which at least one amino acid residue selected from positions 118, 127, 129, 131, 133, 135, 159, 173, 174, 177, 180, 199, 205, and 210 of the heavy chain of a human IgG antibody according to the EU-index numbering is a Z-lysine derivative;

(c) an antibody or antibody fragment thereof in which at least one amino acid residue selected from positions 110, 112, 119, 138, 141, 145, 147, 149, 153, 154, 155, 158, 161, 167, 169, 180, 183, 184, 191, 195, 197, 205, 207, 210, and 211 of the κ chain of a human antibody according to the EU-index numbering is a Z-lysine derivative;

(d) an antibody or antibody fragment thereof in which at least one amino acid residue selected from positions 110, 112, 119, 138, 145, 149, 153, 155, 158, 161, 167, 169, 183, 184, 191, 195, 197, 205, 207, 210, and 211 of the κ chain of a human antibody according to the EU-index numbering is a Z-lysine derivative;

(e) an antibody or antibody fragment thereof in which at least one amino acid residue selected from positions 110, 119, 125, 127, 129, 143, 147, 160, 161, 165, 166, 172, 173, 180, 187, 189, 191, 195, 205, 207, 210, and 215 of the λ chain of a human antibody according to the EU-index numbering is a Z-lysine derivative;

(f) an antibody or antibody fragment thereof in which at least one amino acid residue selected from positions 110, 125, 143, 160, 161, 165, 166, 172, 173, 180, 191, 205, 210, and 215 of the λ chain of a human antibody according to the EU-index numbering is a Z-lysine derivative; and (g) an antibody or antibody fragment thereof in which at least one amino acid residue selected from the group consisting of amino acid residues at positions 131, 177, and 199 of the heavy chain of a human IgG antibody and amino acid residues at positions 155, 191, and 197 of the κ chain of a human antibody according to the EU-index numbering is a Z-lysine derivative.

Specific examples of the antibody or antibody fragment according to the present invention include the antibody or antibody fragment thereof selected from the following (a) to (d):

(a) an antibody or antibody fragment thereof in which at least one amino acid residue selected from positions 118, 120, 121, 127, 129, 131, 133, 135, 152, 159, 169, 173, 174, 177, 180, 190, 199, 205, and 210 of the heavy chain of a human IgG antibody according to EU-index numbering by Kabat et al. (hereinafter, represented as "the EU-index numbering") is TCO*-Lys or BCN-Lys;

(b) an antibody or antibody fragment thereof in which at least one amino acid residue selected from positions 110, 112, 119, 138, 141, 145, 147, 149, 153, 154, 155, 158, 161, 167, 169, 180, 183, 184, 191, 195, 197, 205, 207, 210, and 211 of the κ chain of a human antibody according to the EU-index numbering is TCO*-Lys or BCN-Lys;

(c) an antibody or antibody fragment thereof in which at least one amino acid residue selected from positions 110, 119, 125, 127, 129, 143, 147, 160, 161, 165, 166, 172, 173, 180, 187, 189, 191, 195, 205, 207, 210, and 215 of the λ chain of a human antibody according to the EU-index numbering is TCO*-Lys or BCN-Lys; and (d) an antibody or antibody fragment thereof in which at least one amino acid residue selected from the group consisting of amino acid residues at positions 121 and 131 of the heavy chain of a human IgG antibody and an amino acid residue at position 169 of the κ chain of a human antibody according to the EU-index numbering is TCO*-Lys or BCN-Lys.

The term "EU index" in the present invention refers to a position of an amino acid residue as described in Sequence of Proteins of Immunological Interest 5th ed. (1991). Positions of an amino acid residue mentioned hereinafter are all positions of an amino acid residue according to the EU-index numbering, unless otherwise stated.

The antibody molecule is also called "immunoglobulin" (hereinafter, represented as "Ig"), and human antibodies are classified into isotypes of IgA1, IgA2, IgD, IgE, IgG1, IgG2, IgG3, IgG4, and IgM, on the basis of difference in molecular structure. IgG1, IgG2, IgG3, and IgG4, for which the homology of the amino acid sequences is relatively high, are collectively called "IgG" occasionally. The antibody molecule according to the present invention may be either a polyclonal antibody or a monoclonal antibody. However, the antibody molecule according to the present invention is preferably a monoclonal antibody.

The antibody molecule is composed of polypeptides called "heavy chain" (hereinafter, represented as "H chain") and polypeptides called "light chain" (hereinafter, represented as "L chain"). Each H chain is composed of, from the N-terminus side, an H chain variable region (also represented as "VH") and an H chain constant region (also represented as "CH"), and each L chain is composed of, from the N-terminus side, an L chain variable region (also represented as "VL") and an L chain constant region (also represented as "CL"). An α chain, a δ chain, an ε chain, a γ chain, and a μ chain are known as CHs for the respective subclasses. Further, the CH is composed of, from the N-terminus side, a CH1 domain, a hinge domain, a CH2 domain, and a CH3 domain. The term "domain" refers to a functional structural unit constituting each polypeptide of an antibody molecule. The CH2 domain and CH3 domain are collectively called "Fc (Fragment, crystallizable) region" or simply "Fc". For the CL, a Cλ chain and a Cκ chain are known.

In the present invention, the CH1 domain, hinge domain, CH2 domain, CH3 domain, and Fc region can be specified through a position of an amino acid residue from the N-terminus according to the EU-index numbering. Specifically, the CH1 is specified as an amino acid sequence of positions 118 to 215 according to the EU-index numbering; the hinge as an amino acid sequence of positions 216 to 230 according to the EU-index numbering; the CH2 as an amino acid sequence of positions 231 to 340 according to the EU-index numbering; and the CH3 as an amino acid sequence of positions 341 to 447 according to the EU-index numbering, respectively.

Examples of the antibody according to the present invention include a mouse antibody, a rat antibody, a rabbit antibody, a human-type chimeric antibody (hereinafter, simply abbreviated as "chimeric antibody"), a humanized antibody (also referred to as "complementarity-determining region (CDR)-transplanted antibody"), and a recombinant antibody of, for example, a human antibody.

The term "chimeric antibody" refers to an antibody consisting of VHs and VLs of an antibody derived from an animal other than a human (a non-human animal) and CHs and CLs of a human antibody. Any non-human animal which allows production of a hybridoma can be used, and examples thereof include a mouse, a rat, a hamster, and a rabbit.

The term "hybridoma" refers to a cell producing a monoclonal antibody having desired antigen specificity, and is obtained through cell fusion of a B-cell obtained by immunizing a non-human animal with an antigen and a myeloma cell derived from a mouse or the like. Hence, each variable region constituting an antibody produced by a hybridoma consists of an amino acid sequence of a non-human animal antibody.

To produce a human-type chimeric antibody, a hybridoma producing a monoclonal antibody and derived from a non-human animal is used to obtain cDNAs encoding the VH and VL therefrom, and the cDNAs are each inserted into an expression vector for animal cells, the expression vector including a DNA encoding the CH or CL of a human antibody, to construct a human-type chimeric antibody expression vector, which is introduced into an animal cell for expression.

The term "humanized antibody" refers to an antibody obtained by transplanting the amino acid sequences of the CDRs in the VH and VL of a non-human animal antibody into the corresponding CDRs in the VH and VL of a human antibody. A region other than the CDRs in the VH and VL is called "framework region" (hereinafter, represented as "FR").

To produce a humanized antibody, a cDNA encoding a VH amino acid sequence consisting of the amino acid sequences of the CDRs in the VH of a non-human animal antibody and the amino acid sequences of the FRs in the VH of any human antibody, and a cDNA encoding a VL amino acid sequence consisting of the amino acid sequences of the CDRs in the VL of a non-human animal antibody and the amino acid sequences of the FRs in the VL of any human antibody are constructed, and the cDNAs are each inserted into an expression vector for animal cells, the expression vector including a DNA encoding the CH or CL of a human antibody, to construct a humanized antibody expression vector, which is introduced into an animal cell for expression.

Although the term "human antibody" originally refers to an antibody naturally occurring in the human body, the term encompasses, for example, antibodies obtained from a human antibody phage library or human antibody-producing transgenic animal produced by using an advanced gene engineering, cell engineering, or developmental engineering technique.

A human antibody can be obtained through immunization of a mouse possessing a human immunoglobulin gene (Tomizuka K. et al., Proc Natl Acad Sci USA. 97, 722-7, 2000.) with an antigen intended. Further, a human antibody can be obtained without immunization by using a phage display library including antibody genes amplified from human-derived B-cells and selecting a human antibody having desired binding activity (Winter G. et al., Annu Rev Immunol. 12:433-55, 1994). Furthermore, a human antibody can be obtained by producing a cell producing a human antibody having desired binding activity through immortalization of human B-cells with the EB virus (Rosen A. et al., Nature 267, 52-54.1977).

To obtain an antibody present in the human body, lymphocytes isolated from human peripheral blood are infected, for example, with the EB virus to immortalize the lymphocytes, and cloned to obtain lymphocytes producing the antibody, and the antibody is purified from the culture.

The human antibody phage library is a library of phages obtained by introducing an antibody gene prepared from a human B-cell into a phage gene to allow the phage to express an antibody fragment such as an Fab and an scFv on the surface. Phages expressing an antibody fragment having desired antigen-binding activity can be collected from the library by using binding activity to a substrate with an antigen immobilized thereon as an indicator. In addition, the antibody fragment can be further converted into a human antibody molecule consisting of two complete H chains and complete L chains by using a gene engineering technique.

The term "human antibody-producing transgenic animal" refers to an animal such that a human antibody gene is incorporated in a chromosome in the animal as a host. To produce a human antibody-producing transgenic animal, specifically, a human antibody gene is introduced into an ES cell of a mouse, and the ES cell is transplanted into an early embryo of another mouse, and the embryo is developed. To produce a human antibody from a human antibody-producing transgenic animal, a human antibody-producing hybridoma obtained by using a hybridoma production method commonly used for non-human mammals is cultured to allow the hybridoma to produce a human antibody to accumulate the antibody in the culture, and the antibody is purified from the culture.

The amino acid sequences of the VH and VL of the antibody according to the present invention may be any of the amino acid sequences of the VH and VL of a human antibody, the amino acid sequences of the VH and VL of a non-human animal antibody, and the amino acid sequences of the VH and VL of a humanized antibody obtained by transplanting the CDRs of a non-human animal antibody into the framework of a human antibody. Specific examples of the amino acid sequences of the VH and VL of the antibody according to the present invention include the amino acid sequences of the VH and VL of a non-human animal antibody produced by a hybridoma, the amino acid sequences of the VH and VL of a humanized antibody, and the amino acid sequences of the VH and VL of a human antibody.

The concept of the antibody according to the present invention encompasses Fc fusion protein including an Fc and an antibody fragment binding together, Fc fusion protein including an Fc and a naturally occurring ligand or receptor binding together (also referred to as "immunoadhesin"), Fc fusion protein including a plurality of Fc regions fused together, and so on. In addition, for example, an Fc region with an amino acid residue modified to stabilize an antibody and control the half-life in blood can be used for the antibody according to the present invention.

The concept of the antibody or antibody fragment thereof according to the present invention encompasses an antibody with any of the amino acids post-translationally modified. Examples of post-translational modification include deletion of a lysine residue at the C-terminus of an H chain (lysine clipping) and conversion of a glutamine residue at the N-terminus of polypeptide into pyroglutamine (pyroGlu) [Beck et al, Analytical Chemistry, 85, 715-736 (2013)].

The concept of the antibody or antibody fragment thereof according to the present invention encompasses an antibody including a non-natural amino acid other than Z-lysine derivatives, TCO*-Lys, and BCN-Lys. Examples of such a non-natural amino acid include a tyrosine derivative, and a lysine derivative other than Z-lysine derivatives, TCO*-Lys, and BCN-Lys. Examples of the tyrosine derivative include azidophenylalanine, and examples of the lysine derivative other than Z-lysine derivatives, TCO*-Lys, and BCN-Lys include a pyrrolysine derivative.

Examples of the antibody fragment in the present invention include an Fab, an Fab', an F(ab')$_2$, a single chain Fv (scFv), a diabody, a dsFv, and peptide including a plurality of CDRs.

An Fab is one of fragments obtained through treatment of an IgG antibody with the protease papain (cleaved at the amino acid residue at position 224 of an H chain), and is an antibody fragment having a molecular weight of approximately 50000 and having antigen-binding activity, in which approximately half of an H chain in the N-terminus side and the whole L chain are bonded together via a disulfide bond (S—S bond).

An F(ab')$_2$ is one of fragments obtained through treatment of an IgG antibody with the protease pepsin (cleaved at the amino acid residue at position 234 of each H chain), and is an antibody fragment having a molecular weight of approximately 100000 and having antigen-binding activity, and the F(ab')$_2$ is slightly larger than the Fabs bonded together via an S—S bond in the hinge region.

An Fab' is an antibody fragment having a molecular weight of approximately 50000 and having antigen-binding activity, and formed by cleaving the S—S bond in the hinge region of the F(ab')$_2$.

An scFv is a VH-P-VL or VL-P-VH polypeptide in which one VH and one VL are linked together via an appropriate peptide linker (P) such as a linker peptide including an arbitrary number of linkers connected together, each linker consisting of four Gly residues and one Ser residue (G4S), and is an antibody fragment having antigen-binding activity.

A diabody is an antibody fragment which is a dimer of scFvs identical or different in antigen-binding specificity, and has divalent antigen-binding activity to one antigen or antigen-binding activity specific to different antigens.

A dsFv is a product obtained by bonding a polypeptide of a VH with one amino acid residue substituted with a cysteine residue and a polypeptide of a VL with one amino acid residue substituted with a cysteine residue via the S—S bond between the cysteine residues.

A peptide including a CDR has a configuration including at least one or more CDRs of the VH or VL. In a peptide including a plurality of CDRs, the CDRs can be bonded directly or via an appropriate peptide linker. To produce such a peptide, a DNA encoding CDRs of the VH or VL of the antibody according to the present invention are constructed, the DNA is inserted into an expression vector for prokaryotes or expression vector for eukaryotes, and the expression vector is introduced into an prokaryote or eukaryote for expression. Alternatively, a peptide including a CDR can be produced by using a chemical synthesis method such as the Fmoc method and the tBoc method.

The concept of the antibody or antibody fragment thereof according to the present invention encompasses antibodies having any specificity. However, the antibody is preferably an antibody to bind to any of antigens listed below, an antibody to recognize a tumor-associated antigen and bind thereto, an antibody to recognize an antigen associated with allergy or inflammation and bind thereto, an antibody to recognize an antigen associated with viral or bacterial infection and bind thereto, or an antibody to recognize an antigen associated with a cardiovascular disease.

Examples of the antigen to which the antibody according to the present invention binds include CD1a, CD2, CD3, CD4, CD5, CD6, CD7, CD9, CD10, CD13, CD19, CD20, CD21, CD22, CD23, CD24, CD25, CD28, CD30, CD32, CD33, CD37, CD38, CD40, CD40 ligand(CD40L), CD44, CD45, CD46, CD47, CD52, CD53, CD54, CD55, CD59, CD63, CD64, CD66b, CD69, CD70, CD72, CD73, CD74, CDw75, CDw76, CD77, CDw78, CD79a, CD79b, CD80, CD81, CD82, CD83, CDw84, CD85, CD86, CD89, CD95, CD98, CD105, CD134, CD137, CD138, CD147, CD158, CD160, CD162, CD164, CD200, CD227, CD274, adrenomedullin, angiopoietin related protein 4 (ARP4), aurora, B7-H1, B7-H2, B7-H3, B7-H4, B7-DC, ICOS, PD-1, BTLA, OX40, OX40 Ligand(OX40L), integrin, bone marrow stromal antigen 2 (BST2 OR HM1.24), CA125, CA19.9, carbonic anhydrase 9 (CA9), cadherin, cc-chemokine receptor (CCR)4, CCR7, CCR8, CCR10, carcinoembryonic antigen (CEA), cysteine-rich fibroblast growth factor receptor-1 (CFR-1), c-Met, c-Myc, collagen, CTA, connective tissue growth factor (CTGF), CTLA-4, cytokeratin-18, DF3, E-catherin, epidermal growth facter (EGF), epidermal growth facter receptor (EGFR), EGFRvIII, EGFR2 (HER2), EGFR3 (HER3), EGFR4 (HERO), heparin-binding EGF-like growth factor (HB-EGF), endoglin, epithelial cell adhesion molecule (EpCAM), endothelial protein C receptor (EPCR), ephrin, ephrin receptor (Eph), EphA2, endotheliase-2 (ET2), FAM3D, fibroblast activating protein (FAP), Fc receptor homolog 1 (FcRH1), ferritin, fibroblast growth factor-8 (FGF-8), FGF8 receptor, basic FGF (bFGF), bFGF receptor, FGF receptor (FGFR)3, FGFR4, FLT1, FLT3, folate receptor, Frizzled homologue 10 (FZD10), frizzled receptor 4 (FZD-4), G250, G-CSF receptor, ganglioside (e.g., GD2, GD3, GM2, and GM3), globo H, gp75, gp88, GPR-9-6, heparanase I, hepatocyte growth factor (HGF), HGF receptor, HLA antigen (e.g., HLA-DR), human milk fat globule (HMFG), hRS7, heat shock protein 90 (hsp90), idiotype epitope, insulin-like growth factor (IGF), IGF receptor (IGFR), interleukin (e.g., IL-6, IL-12, and IL-15), interleukin receptor (e.g., IL-2R, IL-3R, IL-6R, IL-10R, and IL-15R), Chemokine (e.g., SLC, ELC, 1-309, TARC, MDC, CTACK), integrin, immune receptor translocation associated-4 (IRTA-4), kallikrein 1, KDR, KIR2DL1, KIR2DL2/3, KS1/4, lamp-1, lamp-2, laminin-5, Lewis y, sialyl Lewis x, lymphotoxin-beta receptor (LTBR), LUNX, melanoma-associated chondroitin sulfate proteoglycan (MCSP), mesothelin, MICA, Mullerian inhibiting substance type II receptor (MISIIR), mucin, neural cell adhesion molecule (NCAM), Necl-5, Notch1, osteopontin, platelet-derived growth factor (PDGF), PDGF receptor, platelet factor-4 (PF-4), phosphatidylserine, Prostate Specific Antigen (PSA), prostate stem cell antigen (PSCA), prostate specific membrane antigen (PSMA), Parathyroid hormone related protein/peptide (PTHrP), receptor activator of NF-kappaB (RANK), receptor activator of NF-kappaB ligand (RANKL), Folate receptor, receptor for hyaluronic acid mediated motility (RHAMM), ROBO1, SART3, semaphorin 4B (SEMA4B), secretory leukocyte protease inhibitor (SLPI), SM5-1, sphingosine-1-phosphate, tumor-associated glycoprotein-72 (TAG-72), transferrin receptor (TfR), TGF-beta, Thy-1, Tie-1, Tie2 receptor, T cell immunoglobulin domain and mucin domain 1 (TIM-1), human tissue factor (hTF), Tn antigen, tumor necrosis factor (TNF), Thomsen-Friedenreich antigen (TF antigen), TNF receptor, tumor necrosis factor-related apoptosis-inducing ligand (TRAIL), TRAIL receptor (e.g., DR4 and DR5), system asc amino acid transporter 2 (ASCT2), trkC, TROP-2, TWEAK receptor Fn14, urokinase plasminogen activator receptor (uPAR), type IV collagenase, urokinase receptor, vascular endothelial growth factor (VEGF), VEGF receptor (e.g., VEGFR1, VEGFR2, and VEGFR3), vimentin and VLA-4, erythropoietin (EPO), erythropoietin receptor (EPOR), angiopoietin, angiopoietin receptor, SDF-1, and CXCR4.

Examples of the antibody to recognize a tumor-associated antigen and bind thereto include the anti-GD2 antibody [Anticancer Res., 13, 331 (1993)], anti-GD3 antibody [Cancer Immunol. Immunother. 36, 260 (1993)], anti-GM2 antibody [Cancer Res. 54, 1511 (1994)], anti-HER2 antibody [Proc. Natl. Acad. Sci. USA, 89, 4285 (1992), European Patent No. 882794], anti-CD52 antibody [Proc. Natl. Acad. Sci. USA, 89, 4285 (1992)], anti-CD4 antibody, anti-MAGE antibody [British J. Cancer, 83, 493 (2000)], anti-CCR4 antibody (U.S. Pat. No. 6,989,145, International Publication No. WO 2009/086514), anti-HM1.24 antibody [Molecular Immunol., 36, 387 (1999), International Publication No. WO 2002/057316], anti-parathyroid hormone-related protein (PTHrP) antibody [Cancer, 88, 2909 (2000)], anti-bFGF antibody, anti-FGF-8 antibody [Proc. Natl. Acad. Sci. USA, 86, 9911 (1989)], anti-bFGFR antibody, anti-FGF-8R antibody [J. Biol. Chem., 265, 16455 (1990)], anti-IGF antibody [J. Neurosci. Res., 40, 647 (1995)], anti-IGF-IR antibody [J. Neurosci. Res., 40, 647 (1995)], anti-PSMA antibody [J. Urology, 160, 2396 (1998)], anti-VEGF antibody [Cancer Res., 57, 4593 (1997)], anti-VEGFR antibody [Oncogene, 19, 2138 (2000), International Publication No. WO 96/30046], anti-c-Met antibody (U.S. Pat. No. 7,498,420), anti-CD20 antibody [Rituxan®, Curr. Opin. Oncol., 10, 548 (1998), U.S. Pat. No. 5,736,137], anti-HER2 antibody [Herceptin®, U.S. Pat. No. 5,725,856], anti-HER3 antibody (International Publication No. WO 2008/100624, International Publication No. WO 2007/077028), anti-Bip antibody (International Publication No. WO 2008/105560), anti-CD10 antibody, anti-HB-EGF antibody (International Publication No. WO 2007/142277), anti-EGFR antibody (Erbitux®, International Publication No. WO 1996/402010), anti-Apo-2R antibody (International Publication No. WO 98/51793), anti-ASCT2 antibody (International Publication No. WO 2010/008075), anti-5T4 antibody (U.S. Patent Application Publication No. 2006/0088522), anti-CA9 antibody (U.S. Pat. No. 7,378,091), anti-CEA antibody [Cancer Res., 55 (23 suppl): 5935s-5945s (1995)], anti-LewisY antibody, anti-folate receptor antibody (International Publication No. WO 2005/080431), anti-TROP-2 antibody (U.S. Pat. No. 6,794,494), anti-CD38 antibody, anti-CD33 antibody [Mylotag®], anti-CD22 antibody (Epratuzumab), anti-EpCAM antibody, anti-A33 antibody, anti-IL-3Rα antibody (International Publication No. WO 2010/126066), anti-uPAR antibody (U.S. Patent No. 2008/0152587), and TRAIL2 antibody (International Publication No. WO 2002/94880).

Examples of the antibody to recognize an antigen associated with allergy or inflammation include the anti-interleukin 6 antibody [Immunol. Rev., 127, 5 (1992)], anti-interleukin 6 receptor antibody [Molecular Immunol., 31, 371 (1994)], anti-interleukin 5 antibody [Immunol. Rev., 127, 5 (1992)], anti-interleukin 5 receptor antibody, anti-interleukin 4 antibody [Cytokine, 3, 562 (1991)], anti-interleukin 4 receptor antibody [J. Immunol. Methods, 217, 41 (1998)], anti-interleukin 10 receptor (IL-10R) antibody (International Publication No. WO 2009/154995), anti-tumor necrosis factor antibody [Hybridoma, 13, 183 (1994)], anti-tumor necrosis factor receptor antibody [Molecular Pharmacol., 58, 237 (2000)], anti-CCR4 antibody [Nature 400776, (1999)], anti-CCR5 antibody, anti-CCR6 antibody, and anti-chemokine antibody (Peri et al., J. Immunol. Meth. 174, 249-257, 1994) or anti-chemokine receptor antibody [J. Exp. Med., 186, 1373 (1997)]. Examples of the antibody to recognize an antigen associated with a cardiovascular disease include the anti-GPIIb/IIIa antibody [J. Immunol., 152, 2968 (1994)], anti-platelet-derived growth factor antibody [Science, 253, 1129 (1991)], anti-platelet-derived growth factor receptor antibody [J. Biol. Chem., 272, 17400 (1997)], anti-blood coagulation factor antibody [Circulation, 101, 1158 (2000)], anti-IgE antibody [Xolair®], anti-CD22 antibody (Epratuzumab), anti-BAFF antibody (Belimumab), anti-αVβ3 antibody, and anti-α4β7 antibody.

Examples of the antibody to recognize an antigen associated with viral or bacterial infection and bind thereto include the anti-gp120 antibody [Structure, 8, 385 (2000)], anti-influenza A virus matrix protein 2 (M2, International Publication No. WO 2003/078600), anti-CD4 antibody [J. Rheumatology, 25, 2065 (1998)], anti-CCR5 antibody, and anti-verotoxin antibody [J. Clin. Microbiol., 37, 396 (1999)].

Examples of the antibody to recognize an antigen associated with a cardiovascular disease include the anti-GPIIb/IIIa antibody [J. Immunol., 152, 2968 (1994)], anti-platelet-derived growth factor antibody [Science, 253, 1129 (1991)], anti-platelet-derived growth factor receptor antibody [J. Biol. Chem., 272, 17400 (1997)], anti-blood coagulation factor antibody [Circulation, 101, 1158 (2000)], anti-IgE antibody, anti-αVβ3 antibody, and anti-α4β7.

The concept of the antibody and antibody fragment thereof according to the present invention encompasses a modified antibody and antibody fragment thereof formed by modifying at least one amino acid residue, non-natural amino acid residue, or sugar chain included in the antibody or antibody fragment thereof according to the present invention (hereinafter, represented as "the modified antibody or antibody fragment thereof according to the present invention"). The amino acid residue or sugar chain to be modified may be in the N-terminus side or C-terminus side of the H chain or L chain of the antibody molecule, and may be any amino acid residue or sugar chain present in the antibody molecule. Preferred examples of the amino acid residue include at least one cysteine, tyrosine, phenylalanine, lysine, pyrrolysine, glutamine, asparagine, glutamic acid, aspartic acid, and a derivative of any of them included in the antibody. Preferred examples of the sugar chain include a sugar chain present in the constant region of the antibody.

More preferred examples of the modified antibody and antibody fragment thereof according to the present invention include a modified antibody and antibody fragment thereof with at least one tyrosine derivative such as azidophenylalanine or lysine derivative such as a Z-lysine derivative, TCO*-Lys, and BCN-Lys modified, and most preferred examples include a modified antibody and antibody fragment thereof with at least one lysine derivative such as a Z-lysine derivative, TCO*-Lys, and BCN-Lys modified.

The concept of the modified antibody and antibody fragment thereof according to the present invention further encompasses a modified antibody and antibody fragment thereof with the above-mentioned amino acid residue, non-natural amino acid residue, or sugar chain modified at a plurality of sites.

The method for modifying the antibody or antibody fragment thereof according to the present invention is not limited, and any method allowing modification of an intended amino acid residue or sugar chain can be used. Examples of the method include chemical modification utilizing chemical reaction [Koutai-kougaku Nyuumon (Introduction to Antibody Engineering), Chijinshokan Co., Ltd., (1994), Kolb et al., Angew Chem Int Ed Engl. 40. 2004-21, 2001] and modification through a gene engineering technique in which a recombinant protein expression vector prepared by utilizing recombinant technology is introduced into an appropriate host cell for expression.

Examples of chemical modification of the tyrosine derivative or lysine derivative include modification to bond an azido group of a non-natural amino acid included in the antibody or antibody fragment thereof according to the present invention to a molecule having reactivity with the azido group. Chemical modification to bond the azido group of a non-natural amino acid to a molecule having an alkynyl group is more preferred, because of its high chemical reactivity. Huisgen [3+2] cycloaddition reaction (hereinafter, represented as "click chemistry") [Kolb et al., Angew Chem Int Ed Engl. 40. 2004-21, 2001] can be used for the bonding reaction. Examples of the non-natural amino acid having an azido group in the present invention include azidophenylalanine, azido-Z-lysine, and azido lower alkyl-Z-lysine.

Other examples of chemical modification of the lysine derivative include modification to bond an alkynyl group of a non-natural amino acid included in the antibody or antibody fragment thereof according to the present invention to a molecule having reactivity with the alkynyl group. Examples of the molecule having reactivity with an alkynyl group include a molecule having an azido group, and click chemistry can be used for the bonding reaction. Examples of the non-natural amino acid having an alkynyl group in the present invention include lower alkynyl-Z-lysine such as ethynyl-Z-lysine.

Other examples of chemical modification of the lysine derivative include modification to bond an amino group of a non-natural amino acid included in the antibody or antibody fragment thereof according to the present invention to a molecule having reactivity with the amino group. Examples of the molecule having reactivity with an amino group include a molecule having a formyl group, and reductive amination reaction (Bioconjugate Chem. 2016, 27, 198-206) can be used for the bonding reaction. Examples of the non-natural amino acid having an amino group in the present invention include amino-Z-lysine.

Other examples of chemical modification of the lysine derivative include modification to bond a formyl group of a non-natural amino acid included in the antibody or antibody fragment thereof according to the present invention to a molecule having reactivity with the formyl group. Examples of the molecule having reactivity with a formyl group include a molecule having an amino group, and reductive amination reaction can be used for the bonding reaction. Examples of the non-natural amino acid having a formyl group in the present invention include formyl-Z-lysine.

Other examples of chemical modification of the lysine derivative include modification to bond the trans-cyclooctene ring of TCO*-Lys included in the antibody or antibody fragment thereof according to the present invention to a molecule having reactivity with the trans-cyclooctene ring. Examples of the molecule having reactivity with a trans-cyclooctene ring include a molecule having a 1,2,4,5-tetrazine ring, and inverse electron-demand Diels-Alder reaction (Angew. Chem. Int. Ed. 2014, 53, 2245-2249) can be used for the bonding reaction.

Other examples of chemical modification of the lysine derivative include modification to bond the bicyclo[6.1.0]non-4-yne ring of BCN-Lys included in the antibody or antibody fragment thereof according to the present invention to a molecule having reactivity with the bicyclo[6.1.0]non-4-yne ring. Examples of the molecule having reactivity with a bicyclo[6.1.0]non-4-yne ring include a molecule having a 1,2,4,5-tetrazine ring, and inverse electron-demand Diels-Alder reaction (J. Am. Chem. Soc. 2012, 134, 10317-10320) can be used for the bonding reaction.

Examples of the molecule to modify the antibody and antibody fragment thereof according to the present invention include hydrophilic polymer, amphiphilic polymer, and a functional molecule. Examples of the hydrophilic polymer and amphiphilic polymer include polyoxyalkylene and a molecule including polyol or polysaccharide.

Examples of the polyoxyalkylene include linear or branched polyethylene glycol (hereinafter, abbreviated as "PEG"), polypropylene glycol, and polypropylene-ethylene glycol.

Examples of the molecule including polyol or polysaccharide include homo- or heteropolysaccharide consisting of linear or branched polyglycerol such as amylose, dextran, pullulan, and glycogen.

Although the molecular weight of the molecule including hydrophilic polymer or amphiphilic polymer is not limited, the molecular weight is preferably 100 Da or higher, and, for example, a molecular weight of 100 Da to 100 kDa is preferred.

Examples of the functional molecule include an antigen-binding molecule, an antigen-binding fragment, a drug, a physiologically active peptide, a physiologically active protein, a nucleic acid, a radioactive labeling compound, a sugar chain, a lipid, and a fluorescent compound.

The antigen-binding molecule may be any molecule to specifically bind to an antigen, and examples thereof include an antibody and antibody fragment thereof, a receptor, and a ligand. The antibody may be any of the above-described antibody to bind to any of the above-listed antigens, antibody to recognize a tumor-associated antigen and bind thereto, antibody to recognize an antigen associated with allergy or inflammation and bind thereto, antibody to recognize an antigen associated with viral or bacterial infection and bind thereto, and antibody to recognize an antigen associated with a cardiovascular disease and bind thereto.

The antigen-binding fragment may be any antigen-binding fragment which is a fragment of the antigen-binding molecule and has antigen-binding activity.

Examples of the drug include an anticancer agent such as an alkylating agent, a nitrosourea agent, an antimetabolite, an antiviral agent, an antibiotic, plant alkaloid, a topoisomerase inhibitor, a tubulin polymerization inhibitor, a hormone therapy agent, a hormone antagonist, an aromatase inhibitor, a P-glycoprotein inhibitor, a platinum complex derivative, an M-phase inhibitor, and a kinase inhibitor [Rinsho Syuyo-gaku (Clinical Oncology), Cancer and Chemotherapy K.K. (1996)]; and an anti-inflammatory agent such as a steroidal agent such as hydrocortisone and prednisone, a non-steroidal agent such as aspirin and indomethacin, an immunomodulator such as gold thiomalate and penicillamine, an immunosuppressant such as cyclophosphamide and azathioprine, and an antihistamine such as chlorpheniramine maleate and clemastine [Ensho To Ko-ensho Ryoho (Inflammation and Anti-inflammatory Therapy), Ishiyaku Publishers, Inc. (1982)]. Examples of the anticancer agent include mertansine, emtansine, amifostine (ethyol), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (adriamycin), epirubicin, gemcitabine (Gemzar), daunorubicin, procarbazine, mitomycin, cytarabine, etoposide, 5-fluorouracil, fluorouracil, vinblastine, vincristine, bleomycin, daunomycin, peplomycin, estramustine, paclitaxel (taxol), docetaxel (taxotere), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, tomudex, azacytidine, UFT, oxaloplatin, gefitinib (iressa), imatinib (STI571), erlotinib, an FMS-like tyrosine kinase 3 (Flt3) inhibitor, a vascular endothelial growth factor receptor (VEGFR) inhibitor, a fibroblast growth factor receptor (FGFR) inhibitor, an epidermal growth factor receptor (EGFR) inhibitor such as tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, a progestin, an estrogen, anastrozole (Arimidex), Leuplin, aspirin, indomethacin, celecoxib, azathioprine, penicillamine, gold thiomalate, chlorpheniramine maleate, chlorpheniramine, clemastine, tretinoin, bexarotene, arsenic, bortezomib, allopurinol, calicheamicin, ibritumomab tiuxetan, Targretin, ozogamicin, clarithromycin, leucovorin, ketoconazole, aminoglutethimide, suramin, methotrexate, maytansinoid, and a derivative of any of them.

Examples of the method for bonding the drug and the antibody together include the above-described method, a method of bonding an amino group of the drug and an amino group of the antibody together via glutaraldehyde, and a method of bonding an amino group of the drug and a carboxy group of the antibody together via water-soluble carbodiimide.

Examples of the physiologically active peptide or physiologically active protein include cytokine or growth factor to activate immune cells including NK cells, macrophages, and neutrophils, such as interferon (hereinafter, abbreviated as "IFN")-α, IFN-β, IFN-γ, interleukin (hereinafter, abbreviated as "IL")-2, IL-12, IL-15, IL-18, IL-21, IL-23, granulocyte colony-stimulating factor (G-CSF), granulocyte/macrophage colony-stimulating factor (GM-CSF), and macrophage colony-stimulating factor (M-CSF); protease such as hydrolase, lyase, and isomerase; toxins including bacterial toxins and phytotoxins such as ricin, diphtheria toxin, and ONTAK; antimicrobial peptide having cell membrane-damaging activity; peptide having cell membrane-binding ability or cell membrane permeability; and a derivative of any of them.

The nucleic acid may be any molecule formed through polymerization of nucleotides or molecules each having function equivalent to a nucleotide, and examples thereof include an siRNA, a microRNA, an antisense RNA, and a DNA aptamer.

The radioactive labeling compound may be any nuclide used for diagnosis or therapy, and examples thereof include $^3H$, $^{14}C$, $^{32}P$, $^{33}P$, $^{35}S$, $^{51}Cr$, $^{57}CO$, $^{18}F$, $^{153}Gd$, $^{159}Gd$, $^{64}Cu$, $^{68}Ge$, $^{166}Ho$, $^{115}In$, $^{113}In$, $^{112}In$, $^{111}In$, $^{131}I$, $^{125}I$, $^{123}I$, $^{121}I$, $^{140}La$, $^{177}Lu$, $^{54}Mn$, $^{99}Mo$, $^{103}Pd$, $^{142}Pr$, $^{149}Pm$, $^{186}Re$, $^{188}Re$, $^{211}At$, $^{105}Rh$, $^{97}Ru$, $^{153}Sm$, $^{47}Sc$, $^{75}Se$, $^{85}Sr$, $^{99}Tc$, $^{201}Ti$, $^{113}Sn$, $^{117}Sn$, $^{133}Xe$, $^{169}Yb$, $^{175}Yb$, $^{90}Y$, and $^{65}Zn$, and a compound containing any of the nuclides. The radioactive labeling compound can be bonded directly to the antibody by using a chloramine T method or the like. Alternatively, a substance to chelate the radioactive labeling compound may be bonded to the antibody. Examples of such chelating agents include DOTA, PA-DOTA, TRITA, and DTPA, and the concept of the antibody according to the present invention encompasses an antibody modified with the chelating agent and a modified antibody labeled with the radioactive labeling compound via the chelating agent.

Examples of the sugar chain include monosaccharides, disaccharides, and oligosaccharides including fucose, mannose, glucose, allose, altrose, gulose, idose, galactose, talose, ribose, arabinose, xylose, lyxose, erythrose, erythrose, threose, cellobiose, maltose, isomaltose, lactose, lipoarabinomannan, Lewis-X trisaccharide, and sialyl Lewis-X tetrasaccharide. Alternatively, a natural product containing a sugar chain known as an immunoadjuvant may be used, and examples thereof include β(1→3) glucan (lentinan, schizophyllan) and α galactosylceramide (KRN7000).

Examples of the lipid include an ester of a fatty acid and an alcohol and a simple lipid (a neutral lipid) as an analog thereof, such as fat and oil (e.g., triacylglycerol), wax (a fatty acid ester of a higher alcohol), a sterol ester, a cholesterol ester, a fatty acid ester of a vitamin; a complex lipid having a polar group such as phosphate, saccharide, sulfate, and amine in addition to a fatty acid and an alcohol, such as a phospholipid (e.g., a glycerophospholipid, a sphingophospholipid) and a glycolipid (e.g., a glyceroglycolipid, a sphingoglycolipid); and a derived lipid, which refers to a fat-soluble compound among compounds formed through hydrolysis of simple lipids and complex lipids, such as a fatty acid, a higher alcohol, a fat-soluble vitamin, a steroid, and a hydrocarbon.

Examples of the fluorescent compound include a fluorescein fluorescent dye such as fluorescein isothiocyanate (FITC), rhodamine fluorescent dye, Cy3, Cy5, eosin fluorescent dye, Alexa Fluor fluorescent dye, and NBD fluorescent dye; a luminescent substance such as an acridinium ester and lophine; and a fluorescent protein such as green fluorescent protein (GFP).

The hydrophilic polymer or amphiphilic polymer, and functional molecule can be bonded to the antibody according to the present invention directly or via an appropriate linker. Examples of the linker include an ester, a disulfide, a hydrazone, and a dipeptide.

To produce a fusion antibody through modification of the antibody according to the present invention by using a gene engineering technique, a cDNA encoding a protein is linked to a cDNA encoding the antibody or antibody fragment to construct a DNA encoding a fusion antibody, and the DNA is inserted into an expression vector for prokaryotes or eukaryotes, and the expression vector is introduced into a prokaryote or eukaryote for expression of the fusion antibody.

The composition according to the present invention may be any composition containing the antibody or antibody fragment thereof according to the present invention. That is, the composition according to the present invention may be any composition containing a monoclonal antibody molecule or antibody fragment molecule thereof as an antibody including at least one lysine derivative, specifically, a Z-lysine derivative, TCO*-Lys, or BCN-Lys, in a constant region of the antibody. The composition may contain an appropriate excipient such as a carrier and a stabilizer in addition to the antibody molecule or antibody fragment molecule thereof. Examples of the composition according to the present invention include a therapeutic agent (pharmaceutical composition) containing the antibody or antibody fragment thereof according to the present invention as an active ingredient, and the composition is formulated together with a pharmacologically acceptable carrier into an intended dosage form.

Although the therapeutic agent containing the antibody or antibody fragment thereof according to the present invention may be for any disease involving expression of an antigen to which the antibody specifically binds, the therapeutic agent is preferably for a disease involving expression of any of the above antigens or an antigen associated with cancer, an autoimmune disease, an allergic disease, an inflammatory disease, a cardiovascular disease, or a viral or bacterial infection.

Examples of the cancer include blood cancer, head-and-neck cancer, glioma, tongue cancer, laryngeal cancer, esophageal cancer, stomach cancer, pancreatic cancer (e.g., pancreatic head cancer, pancreatic body cancer, pancreatic tail cancer, and pancreatic duct cancer), small intestine cancer, colorectal cancer, lung cancer (e.g., small-cell lung cancer, large-cell lung cancer, adenocarcinoma, and squamous cell carcinoma), mesothelioma, liver cancer, gallbladder cancer, bile duct cancer, kidney cancer, uterine cancer (e.g., cervical cancer and endometrial cancer), ovarian cancer, ovarian germ cell tumor, prostate cancer, bladder cancer, osteosarcoma, skin cancer, mycosis fungoides, Ewing tumor, malignant bone tumor, and melanoma.

Examples of the blood cancer include leukemia, chronic myelogenous leukemia, acute myelogenous leukemia, chronic lymphatic leukemia, acute lymphatic leukemia, and T-cell-derived cancer. Specific examples of the blood cancer include cutaneous T-cell lymphoma (CTCL), peripheral T-cell lymphoma (PTCL), anaplastic large cell lymphoma (ALCL), acute lymphatic leukemia (ALL), multiple myeloma, Hodgkin's lymphoma, and non-Hodgkin's lymphoma (e.g., Burkitt's lymphoma, lymphoblastic lymphoma, diffuse large B-cell lymphoma, anaplastic large cell lymphoma, MANTL lymphoma, and follicular lymphoma.

Examples of the autoimmune disease include Hashimoto's thyroiditis, Basedow's disease, idiopathic thrombocytopenic purpura, idiopathic neutropenia, megaloblastic anemia, hemolytic anemia, myasthenia gravis, psoriasis, pemphigus, pemphigoid, Crohn's disease, ulcerative colitis, ankylosing spondylitis, multiple sclerosis, type I diabetes mellitus, hepatitis, myocarditis, Sjogren's syndrome, rheumatoid arthritis, systemic lupus erythematosus (SLE), antiphospholipid syndrome, polymyositis, dermatomyositis, systemic scleroderma, and transplant rejection.

Examples of the allergic disease include acute or chronic airway hypersensitivity, bronchial asthma, atopic dermatitis, and allergic rhinitis.

The therapeutic agent containing the antibody or antibody fragment thereof according to the present invention may be a therapeutic agent containing only the antibody or antibody fragment thereof as an active ingredient. However, it is typically desirable to provide the therapeutic agent as a pharmaceutical formulation produced from a mixture of the therapeutic agent and one or more pharmacologically acceptable carriers by using any method known in the field of pharmaceutics.

It is desirable to use the most effective route of administration for the therapy, and examples of the route of administration include oral administration, and parenteral administration such as intraoral administration, intratracheal administration, rectal administration, subcutaneous administration, intramuscular administration, and intravenous administration, and intravenous administration is preferred. Examples of the form of administration include a spray, a capsule, a tablet, a powder, a granule, a syrup, an emulsion, a suppository, an injection, an ointment, and a tape.

The dose or frequency of administration depends on the therapeutic effect intended, administration method, duration of therapy, age, body weight, and so on, and is typically 10 μg/kg to 20 mg/kg per day for an adult.

[Production Method]

The antibody or antibody fragment thereof including a non-natural amino acid according to the present invention can be produced by using any of methods described in Molecular Cloning, second edition, Current Protocols in Molecular Biology; Antibodies, A Laboratory manual, Cold Spring Harbor Laboratory (1988); Monoclonal Antibodies: principles and practice, Third Edition, Acad. Press (1993); Antibody Engineering, A Practical Approach, IRL Press at Oxford University Press (1996), and so on. To produce the antibody or antibody fragment thereof including a non-natural amino acid according to the present invention, for example, an expression vector for the antibody or antibody fragment thereof including a non-natural amino acid according to the present invention, the expression vector described later, is introduced into an appropriate host cell, and the resulting transformant is cultured in a medium with a non-natural amino acid added thereto, and the antibody or antibody fragment thereof is purified from the culture.

Further, the modified antibody or antibody fragment thereof including a non-natural amino acid according to the present invention can be obtained through modification of an amino acid residue, non-natural amino acid residue, or sugar chain of the antibody or antibody fragment thereof including a non-natural amino acid according to the present invention, as described later.

The antibody or antibody fragment thereof including a non-natural amino acid according to the present invention may be either an antibody obtained through substituting an amino acid residue of an antibody as a target for introduction of a non-natural amino acid (hereinafter, represented as "parent antibody") with the non-natural amino acid residue, or an antibody obtained through inserting the non-natural amino acid residue into the amino acid sequence of the parent antibody.

1. Construction of expression vector for antibody or antibody fragment thereof including non-natural amino acid according to present invention (1) Construction of expression vector for antibody or antibody fragment thereof An expression vector according to the purpose or an expression vector suitable for a host cell to express the antibody or antibody fragment thereof including a non-natural amino acid according to the present invention can be appropriately selected for use.

In the case that the expression vector is a recombinant vector, the recombinant vector includes a nucleotide sequence encoding the CL or CH and linked to an appropriate promoter, and preferably includes a transcription termination signal, i.e., a terminator region in the downstream of the polynucleotide according to the present invention.

In addition, the recombinant vector can further include a selectable marker gene to select a transformant (e.g., a drug resistance gene, a gene to complement auxotrophic mutation). The recombinant vector may include, for example, a sequence encoding a tag sequence useful for separation and/or purification of protein expressed.

Insertion of a suitable restriction enzyme recognition sequence at each end of the expression cassette including portions for the light chain or heavy chain of the antibody gene in advance enables incorporation of the expression cassette into an expression vector, for both cases of an antibody expression vector for prokaryotic cells and an antibody expression vector for eukaryotic cells.

In another mode, the expression vector may be an expression vector designed so that only a variable region can be introduced later with use of an appropriate restriction enzyme to construct an expression vector applicable for various antibody variable regions.

In the case that a prokaryotic cell such as *Escherichia coli* is used as a host cell, any expression vector allowing incorporation and expression of a gene encoding the antibody or antibody fragment thereof including a non-natural amino acid according to the present invention can be used, and examples thereof include pFLAG-CTS [SIGMA, Journal of Molecular Recognition, 5, 15 (2002)], pET26b [Novagen, Molecular Immunology, 8, 44 (2007)], pFab1, pFab2, and pFab3 [Protein Expression and Purification, 2, 34 (2004)].

Examples of the promoter to be used for the expression vector for prokaryotic cells include a Tac promoter [Journal of Molecular Recognition, 5, 15 (2002)] and a rhamnose promoter [Journal of Molecular Biology, 234, (1993)].

In addition, the vector may further include a signal sequence for secretion of polypeptide. One example of signal sequences to order the periplasm of *Escherichia coli* to secrete polypeptide is a PelB signal sequence [J. Bacteriol. 169, 4379 (1987)].

In the case that *Escherichia coli* is used as a host cell and the vector is amplified and produced in a large scale in the inside of *Escherichia coli* (e.g., JM109, DH5a, HB101, or XL1Blue), it is required for the vector to include "ori" for amplification in *Escherichia coli* and a marker gene for selection of transformed *Escherichia coli* (e.g., a drug resistance gene selected by a pharmaceutical agent such as ampicillin, tetracycline, kanamycin, and chloramphenicol). Examples of vectors including the marker gene include the M13 series of vectors, the pUC series of vectors, pBR322, and pBluescript.

In the case that an animal cell among eukaryotic cells is used as a host, any expression vector allowing incorporation and expression of a gene encoding the antibody or antibody fragment thereof including a non-natural amino acid according to the present invention can be used.

Examples of the expression vector include pKANTEX93 [Mol. Immunol., 37, 1035 (2000)], pAGE107 [Japanese Patent Laid-Open No. 3-22979, Cytotechnology, 3, 133-140 (1990)], pAGE103 [J. Biochem., 101, 1307 (1987)], pHSG274 [Gene, 27, 223 (1984)], pKCR [Proc. Natl. Acad. Sci. U.S.A., 78, 1527 (1981)], an N5KG1-Val Lark vector [IDEC Pharmaceuticals, a modified vector of N5KG1 (U.S. Pat. No. 6,001,358)], a Tol2 transposon vector [International Publication No. WO 2010/143698], and pSG1βd2-4 [Cytotechnology, 4, 173 (1990)].

Examples of the promoter and enhancer to be used for the expression vector for animal cells include the initial promoter and enhancer of SV40 [J. Biochem., 101, 1307 (1987)], LTR of a Moloney murine leukemia virus [Biochem. Biophys. Res. Commun., 149, 960 (1987)], and immunoglobulin heavy-chain promoter [Cell, 41, 479 (1985)] and enhancer [Cell, 33, 717 (1983)].

Examples of the expression vector for the case that a yeast is used as a host cell include YEP13 (ATCC37115), YEp24 (ATCC37051), and YCp50 (ATCC37419).

The promoter to be used for the expression vector for yeasts may be any promoter capable of being expressed in a yeast strain, and examples thereof include a promoter for a gene associated with glycolysis such as a hexose kinase gene, the PHO5 promoter, PGK promoter, GAP promoter, ADH promoter, gal 1 promoter, gal 10 promoter, heat shock protein promoter, MFal promoter, and CUP 1 promoter.

Examples of the expression vector for the case that an insect cell is used as a host cell include pVL1392, pVL1393, and pBlueBaclll (all from Invitrogen).

Examples of the expression vector for the case that a plant cell is used as a host cell include a Ti plasmid and a tobacco mosaic virus vector.

The promoter to be used for the expression vector for plant cells may be any promoter capable of being expressed in a plant cell, and examples thereof include the 35S promoter of a cauliflower mosaic virus (CaMV) and the rice actin 1 promoter.

The vector for expression of the antibody or antibody fragment thereof including a non-natural amino acid according to the present invention may be either of a type such that a portion for the antibody light chain and a portion for the antibody heavy chain are present in different vectors, or a tandem type such that a portion for the antibody light chain and a portion for the antibody heavy chain are present in one vector [J. Immunol. Methods, 167, 271 (1994)].

Examples of the method for constructing a tandem expression vector include a method in which a DNA encoding the light chain and a DNA encoding the heavy chain each bound to a promoter sequence are linked together by using an appropriate restriction site. Examples of the tandem expression vector include pKANTEX 93 (International Publication No. WO 97/10354), pEE18 [Hybridoma, 559 (1998)], and an N5KG1-Val Lark vector [IDEC Pharmaceuticals, a modified vector of N5KG1 (U.S. Pat. No. 6,001,358)].

Examples of the method for introducing the expression vector into a host cell include a transformation method, electroporation [Japanese Patent Laid-Open No. 2-257891, Cytotechnology, 3, 133 (1990)], and lipofection [Proc. Natl. Acad. Sci. U.S.A., 84, 7413 (1987)].

The expression vector for the antibody or antibody fragment thereof including a non-natural amino acid according to the present invention can be produced through designing a nucleotide sequence of an antibody or antibody fragment thereof including a nonsense codon (also referred to as "stop codon") at a site intended to introduce a non-natural amino acid, on the basis of the nucleotide sequence encoding the amino acid sequence of a parent antibody or antibody fragment thereof. In this case, a codon encoding an amino acid residue of the parent antibody or antibody fragment thereof may be substituted with the nonsense codon, or the nonsense codon may be inserted into the nucleotide sequence encoding the amino acid sequence of the parent antibody or antibody fragment thereof. Examples of the nonsense codon include UAG (amber), UAA (ochre), and UGA (opal). In the present invention, the nonsense codon is preferably a UAG or UGA codon, and more preferably a UAG codon. Alternatively, a codon consisting of four or more nucleotides (preferably, four nucleotides or five nucleotides) (hereinafter, represented as "frameshift codon") can be used in place of the nonsense codon.

Now, the method for producing the antibody including a non-natural amino acid according to the present invention in the case that a UAG codon is allowed to encode a non-natural amino acid will be described. In the case that a non-natural amino acid is introduced into a parent antibody, the non-natural amino acid can be introduced into the parent antibody at an arbitrary site through substitution of a codon encoding an amino acid residue of the parent antibody with a UAG codon encoding the non-natural amino acid, or insertion of UAG encoding the non-natural amino acid into the nucleotide sequence encoding the amino acid sequence of the parent antibody. Also in the case that another nonsense codon or frameshift codon is allowed to encode a non-natural amino acid, the antibody including a non-natural amino acid according to the present invention can be produced by using the same method.

Substitution of a codon encoding an amino acid residue at a site to introduce a non-natural amino acid thereinto with a UAG codon in the nucleotide sequence encoding the amino acid sequence of a parent antibody or antibody fragment thereof can be achieved through site-directed mutagenesis. For example, site-directed mutagenesis can be elicited through designing a primer in which a codon at a site to introduce an intended non-natural amino acid thereinto is replaced with a UAG codon by using a QuikChange II Site-Directed Mutagenesis Kit (Stratagene Calif.) according to the instruction manual.

Alternatively, a nucleotide sequence encoding the CH or CL, where the nucleotide sequence is designed so that a codon at a site for introduction of an intended non-natural amino acid thereinto is UAG, with an appropriate restriction enzyme recognition sequence added to each of the 5'-terminus and the 3'-terminus may be obtained through total synthesis to replace a nucleotide sequence encoding the CH or CL included in an expression vector for a parent antibody with the nucleotide sequence obtained. In this case, the UAG codon may substitute a codon encoding an amino acid residue of the parent antibody, or may be inserted before or after a codon encoding an amino acid residue of the parent antibody.

The presence or absence of a UAG codon introduced can be determined by using a common nucleotide sequence analysis method, for example, through reaction in the dideoxy method by Sanger et al. [Proc. Natl. Acad. Sci. USA., 74, 5463 (1977)] or the like followed by analysis by using an automatic nucleotide sequence analyzer such as an ABI PRISM377 DNA sequencer (from Applied Biosystems).

The expression vector constructed for the antibody or antibody fragment thereof including a non-natural amino acid according to the present invention can be used for expression of a recombinant antibody of a mouse antibody, rat antibody, rabbit antibody, hamster antibody, monkey antibody, human-type chimeric antibody, humanized antibody, or human antibody, or an antibody fragment of any of them, produced by using a gene recombinant technique for prokaryotic cells or eukaryotic cells as described later.

The expression vector includes a nucleotide sequence encoding a tRNA linked to an appropriate promoter to recognize a UAG codon (hereinafter, simply represented as "tRNA") and the nucleotide sequence encoding the amino acid sequence of aminoacyl tRNA synthetase to acylate the tRNA with a non-natural amino acid (hereinafter, simply represented as "aminoacyl tRNA synthetase").

The nucleotide sequence encoding the tRNA and the nucleotide sequence encoding the amino acid sequence of the aminoacyl tRNA synthetase may be included in an expression vector different from the expression vector for the antibody or antibody fragment thereof including a non-natural amino acid according to the present invention, or separately included in different expression vectors, and any of these modes may be employed.

In the case that a plurality of expression vectors is introduced into a host cell for transgenesis, the transgenesis may be in a simultaneous manner or in a separate manner. For example, transgenesis with the expression vector for the antibody or antibody fragment thereof including a non-natural amino acid according to the present invention may be achieved in a manner such that a transformant obtained by introducing an expression vector for the tRNA and/or aminoacyl tRNA synthetase into a host cell is cryopreserved and the cell is thawed, as necessary.

In the present invention, the tRNA is capable of binding to a non-natural amino acid intended and recognizing a UAG codon included in the nucleotide sequence encoding the antibody or antibody fragment thereof including a non-natural amino acid according to the present invention in the presence of the aminoacyl tRNA synthetase.

For the tRNA and aminoacyl tRNA synthetase, suitable ones can be appropriately selected for use according to the type of a non-natural amino acid to be introduced into the antibody and the type of a host cell. In the case that a Z-lysine derivative such as azido-Z-lysine, ethynyl-Z-lysine, amino-Z-lysine, and formyl-Z-lysine, TCO*-Lys, or BCN-Lys is introduced into the antibody, for example, the wild-type pyrrolysine tRNA (Pyl tRNA, tRNA$^{Pyl}$) from *Methanosarcina mazei* (SEQ ID NO: 1) and a Y384F/Y306 Å double mutant of the pyrrolysyl tRNA synthetase (Pyl RS) from *Methanosarcina mazei* [Yanagisawa T. et al, Chem. Biol., 15, 1187-1197 (2008)] (SEQ ID NO: 8) can be used.

In the case that Z-lysine is introduced into the antibody, the wild-type pyrrolysine tRNA derived from the methanogenic archaeon *Methanosarcina mazei* and a L309A/C348V double mutant of the pyrrolysyl tRNA synthetase from *Methanosarcina mazei* [International Publication No. WO 2009/038195] can be used. In the case that azidotyrosine or azidophenylalanine is introduced into the antibody, BYR as a mutant of the tyrosine tRNA (Tyr tRNA, tRNA$^{Tyr}$) from the gram-positive bacterium *Geobacillus stearothermophilus* and a mutant of the tyrosyl tRNA synthetase (Tyr RS) from *Escherichia coli* (V37C195), EYR as a mutant of the tyrosine tRNA from *Escherichia coli* and a fusion protein of the proofreading domains of a mutant of the tyrosyl tRNA synthetase from *Escherichia coli* (V37C195) and the phenylalanyl tRNA synthetase from the hyperthermophilic archaeon *Pyrococcus horikoshii* [Japanese Patent Laid-Open No. 2009-207490].

It is preferred for the tRNA and aminoacyl tRNA synthetase not to interact with an endogenous tRNA and aminoacyl tRNA synthetase, in other words, to be what is called orthogonal.

In the case that the pyrrolysine tRNA is derived from a methanogenic archaeon and an expression vector including a nucleotide sequence encoding the pyrrolysine tRNA is introduced into an animal cell for transgenesis, it is preferred that a nucleotide sequence encoding a tRNA from a eukaryote or a promoter sequence for the U6 snRNA gene be bound to the 5'-terminus of the nucleotide sequence encoding the pyrrolysine tRNA. The nucleotide sequence encoding a tRNA from a eukaryote is preferably a nucleotide sequence encoding the human valine tRNA. It is more preferred that a transcription termination sequence be bound to the 3'-terminus of the nucleotide sequence encoding the pyrrolysine tRNA. An expression vector including the nucleotide sequence encoding the tRNA may include a nucleotide sequence cluster which consists of a plurality of repeated nucleotide sequences each encoding pyrrolysine tRNA and includes a nucleotide sequence encoding a tRNA from a eukaryote and a promoter sequence for the U6 snRNA gene bound thereto.

The expression vector including the nucleotide sequence encoding the pyrrolysine tRNA can be produced according to a method described in WO 2007/099854 or Mukai et al. [Biochem. Biophys. Res. Commmun, 371, 818-822 (2008)], and thereby the pyrrolysine tRNA can be efficiently expressed in an animal cell.

A Promoter sequence derived from a bacteriophage may be bound to the 5'-terminus of the nucleotide sequence encoding the pyrrolysine tRNA derived from the methanogenic archaeon. Examples of the promoter derived from a bacteriophage include a T7 promoter. An expression vector including such a nucleotide sequence can be similarly produced according to the method described in WO 2007/099854, and thereby the pyrrolysine tRNA can be efficiently expressed in an animal cell.

The antibody or antibody fragment thereof including a lysine derivative according to the present invention can be efficiently produced in an animal cell through efficient expression of the pyrrolysine tRNA in an animal cell.

In the case that the tyrosine tRNA is derived from *Escherichia coli* and an expression vector including a nucleotide sequence encoding the tyrosine tRNA is introduced into an animal cell for transgenesis, it is similarly preferred that a promoter sequence for the U1 snRNA gene, U6 snRNA gene, T7, or the like be bounded to the 5'-terminus of the nucleotide sequence encoding the tyrosine tRNA. It is more preferred that a transcription termination factor be bound to the 3'-terminus of the nucleotide sequence encoding the tyrosine tRNA. An expression vector including such a nucleotide sequence can be similarly produced according to the method described in WO 2007/099854. Thereby, the antibody or antibody fragment thereof including a tyrosine derivative according to the present invention can be efficiently produced in an animal cell through efficient expression of the tyrosine tRNA in an animal cell.

(2) Acquisition of cDNA Encoding V Region of Antibody

A cDNA encoding the VL or VH of an antibody can be obtained as follows.

An mRNA extracted from an antibody-producing cell or hybridoma cell producing an arbitrary antibody is used as a template to synthesize a cDNA. The synthesized cDNA is inserted into a vector such as a phage and plasmid to produce a cDNA library.

With use of a DNA encoding the C region or V region of an antibody derived from an existing animal species as a probe, a recombinant phage or recombinant plasmid including a cDNA encoding the heavy chain V region and a recombinant phage or recombinant plasmid including a cDNA encoding the light chain V region are isolated from the library.

The complete nucleotide sequences for the VL and VH of the intended antibody on the recombinant phages or recombinant plasmids are determined, and the complete amino acid sequences of the VL and VH are estimated from the nucleotide sequences.

To obtain hybridoma cells producing an antibody from an arbitrary non-human animal, a non-human animal is immunized with an antigen to which the antibody binds, and hybridoma cells are produced from the antibody-producing cells of the immunized animal and myeloma cells according to a well-known method [Molecular Cloning, second edition, Current Protocols in Molecular Biology, Antibodies, Monoclonal Antibodies, Antibody Engineering]; subsequently, a hybridoma isolated as a single cell is selected, cultured, and purified from the culture supernatant.

The non-human animal to be used may be any animal allowing production of a hybridoma cell such as a mouse, a rat, a hamster, a monkey, a camel, and a rabbit. A human antibody can be produced in the same manner as in production of an antibody derived from a non-human animal, through production of a hybridoma via immunization of a recombinant animal such as a human antibody-producing mouse with an antigen. In addition, a human antibody can be established through immortalization of a human peripheral blood cell or a human immune cell producing a human antibody.

Examples of methods for preparing a total RNA from a hybridoma cell or antibody-producing cell include the guanidine thiocyanate-cesium trifluoroacetate method [Methods in Enzymol., 154, 3 (1987)].

Examples of methods for preparing an mRNA from a total RNA include the oligo (dT)-immobilized cellulose column method [Molecular Cloning: A Laboratory Manual, Cold Spring Harbor Lab. Press New York, 1989].

Examples of kits for preparing an mRNA from a hybridoma cell include a Fast Track mRNA Isolation Kit (from Invitrogen) and a Quick Prep mRNA Purification Kit (from Pharmacia).

Examples of methods for synthesizing a cDNA and producing a cDNA library include a conventional method [Cloning: A Laboratory Manual, Cold Spring Harbor Lab. Press New York, 1989; Current Protocols in Molecular Biology, Supplement 1-34] and a method with a commercially available kit. Examples of the commercially available kit include a Super Scrip™ Lim Plasmid System for cDNA Synthesis and Plasmid Cloning (from GIBCO BRL) and a ZAP-cDNA Synthesis Kit (from Stratagene Calif.).

In production of a cDNA library, the vector to incorporate therein a cDNA synthesized by using an mRNA extracted from a hybridoma cell as a template may be any vector allowing incorporation of the cDNA therein.

Examples of the vector include ZAP Express [Strategies, 5, 58 (1992)], pBluescript II SK(+) [Nucleic Acids Research, 17, 9494 (1989)], λZAP II (from Stratagene Calif.), λgt10, λgt11 [DNA Cloning: A Practical Approach, I, 49 (1985)], Lambda BlueMid (from Clontech Laboratories, Inc.), λExCell, pT7T3 18U (from Pharmacia), pcD2 [Cell. Biol., 3, 280 (1983)], and pUC18 [Gene, 33, 103 (1985)].

*Escherichia coli* to introduce a cDNA library constructed with a phage or plasmid vector therein may be any one allowing introduction, expression, and maintenance of the cDNA library.

Examples of such *Escherichia coli* include the strains XL1-Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], and JM105 [Gene, 38, 275 (1985)].

A cDNA clone encoding the VL or VH of an antibody can be selected from a cDNA library by using a colony hybridization method or plaque hybridization method with a probe labeled with an isotope, fluorescence, or the like [Molecular Cloning: A Laboratory Manual, Cold Spring Harbor Lab. Press New York (1989)].

Alternatively, a cDNA encoding the VL or VH can be prepared through PCR with a primer prepared and a cDNA or cDNA library as a template PCR [Molecular Cloning: A Laboratory Manual, Cold Spring Harbor Lab. Press New York, (1989), Current Protocols in Molecular Biology, Supplement 1-34].

The cDNA selected by using the above method is cleaved with an appropriate restriction enzyme or the like, and then cloned into a plasmid of pBluescript SK(–) (from Stratagene Calif.) or the like, and the nucleotide sequence of the cDNA can be determined by using the nucleotide sequence analysis method described in 1-(1).

The complete amino acid sequence of the VH or VL is estimated from the nucleotide sequence determined, and whether the cDNA obtained is encoding an amino acid sequence completely including the VL or VH of an antibody including a secretion signal sequence can be determined through comparison with the complete amino acid sequences of the VL or VH of a known antibody [Sequences of Proteins of Immunological Interest, US Dept. Health and Human Services (1991)].

In addition, in the case that the amino acid sequence of a variable region of an antibody or the nucleotide sequence of a DNA encoding the variable region is already known, the cDNA can be prepared by using the following method.

In the case that the amino acid sequence is known, a DNA sequence encoding the variable region is designed in consideration of the frequency of codon usage [Sequences of Protein of Immunological Interest, US Dept. Health and Human Services (1991)], and several synthetic DNAs each consisting of around 100 nucleotides are synthesized on the basis of the designed DNA sequence, from which the DNA can be obtained through PCR. In the case that the nucleotide sequence is known, several synthetic DNAs each consisting of around 100 nucleotides are synthesized on the basis of the information, from which the DNA can be obtained through PCR. Alternatively, a DNA of interest can be obtained through total synthesis of a nucleotide sequence of interest.

(3) Analysis of Amino Acid Sequence of V Region of Antibody

Regarding the complete amino acid sequence of the VL or VH of the antibody including a secretion signal sequence, the length of the secretion signal sequence and the amino acid sequence at the N-terminus can be estimated through comparison with the amino acid sequence of the VL or VH of a known antibody [Sequences of Proteins of Immunological Interest, US Dept. Health and Human Services (1991)], and, in addition, the subgroup to which the antibody belongs can be clarified. The amino acid sequence of each CDR of the VL or VH can be similarly revealed by using the same method.

(4) Construction of Expression Vector for Human-Type Chimeric Antibody or Antibody Fragment Thereof In the case that the V region amino acid sequence of the antibody acquired in 1-(3) is the V region amino acid sequence of the V region of a nonhuman antibody, a human-type chimeric antibody can be produced by using the sequences for the VL and VH of the antibody. A cDNA encoding the VL or VH of an antibody from a non-human animal is inserted into the upstream of a gene encoding the CL or CH in the expression vector for the antibody or antibody fragment thereof described in 1-(1), and thus an expression vector for a human-type chimeric antibody or antibody fragment thereof can be constructed.

For example, a cDNA encoding the VL or VH of an antibody from a non-human animal is linked to a synthetic DNA consisting of a 3'-side nucleotide sequence for the VL or VH of an antibody from a non-human animal and a 5'-side nucleotide sequence for the CL or CH of an antibody from a human antibody and including an appropriate restriction enzyme recognition sequence at each terminus. The linked cDNA encoding the VL or VH is further inserted into the upstream of a gene encoding the CL or CH of a human antibody in the expression vector for the antibody or antibody fragment thereof including a non-natural amino acid according to the present invention described in 1-(1) in a manner such that the resultant is expressed in an appropriate manner, and thus an expression vector for a human-type chimeric antibody or antibody fragment thereof can be constructed.

(5) Construction of cDNA Encoding V Region of Humanized Antibody

A cDNA encoding the VL or VH of a humanized antibody can be constructed as follows. First, amino acid sequences are selected for the FRs of the VL or VH of a human antibody to transplant CDRs of the VL or VH of an intended antibody from a non-human animal.

The amino acid sequences to be used for the FRs of the VL or VH of a human antibody may be any amino acid sequences from a human antibody. Examples thereof include amino acid sequences of the FRs of the VL or VH of a human antibody registered in a data base such as PDB and amino acid sequences of the FRs of the VL or VH of a human antibody common among subgroups [Sequences of Proteins of Immunological Interest, US Dept. Health and Human Services (1991)]. Especially, it is preferred for production of a humanized antibody having sufficient activity to select amino acid sequences having homology as high as possible (at least 60% or higher) with amino acid sequences of the FRs of the VL or VH of an intended antibody from a non-human animal.

Subsequently, the amino acid sequences of CDRs of the VL or VH of an intended antibody from a non-human animal is transplanted into the selected amino acid sequences of the FRs of the VL or VH of a human antibody to design the amino acid sequence of the VL or VH of a humanized antibody. The designed amino acid sequence is converted into a DNA sequence in consideration of the frequency of codon usage [Sequences of Proteins of Immunological Interest, US Dept. Health and Human Services (1991)] observed for the nucleotide sequence of the gene for the antibody to design a DNA sequence encoding the amino acid sequence of the VL or VH of a humanized antibody.

Several synthetic DNAs each consisting of around 100 nucleotides are synthesized on the basis of the designed DNA sequence, and PCR is performed for the synthetic DNAs. In this case, it is preferred to design four to six synthetic DNAs for each of the heavy chain and light chain, in view of the reaction efficiency in PCR and the length of a DNA synthesizable.

Introduction of an appropriate restriction enzyme recognition sequence at the 5'-terminus of a synthetic DNA positioned at each end facilitates cloning into the expression vector for the antibody or antibody fragment thereof according to the present invention, the expression vector constructed in 1-(1). Alternatively, an intended DNA sequence can be obtained through total synthesis.

After the PCR, the amplified product is cloned into a plasmid such as pBluescript SK(−) (from Stratagene Calif.), the nucleotide sequence is determined by using the nucleotide sequence analysis method described in 1-(1), and a plasmid including a DNA sequence encoding the amino acid sequence of the VL or VH of an intended humanized antibody is obtained.

(6) Modification of Amino Acid Sequence of V Region of Humanized Antibody

It is known that a humanized antibody with only the CDRs of the VL and VH of an antibody from a non-human animal transplanted therein has antigen-binding activity lower than that of the original non-human animal [BIO/TECHNOLOGY, 9, 266 (1991)].

Regarding the cause, it is believed that not only CDRs but also some amino acid residues in the FRs of the VL and VH of an antibody of an original non-human animal are directly or indirectly associated with antigen-binding activity, and the amino acid residues change to different amino acid residues in the FRs of the VL and VH of a human antibody in association with transplantation of the CDRs.

To solve this problem, for a humanized antibody, amino acid residues directly involved in binding to an antigen, amino acid residues to interact with the amino acid residues of CDRs, amino acid residues indirectly involved in binding to an antigen through maintaining the three-dimensional structure of the antibody, and so on, in the amino acid sequences of the FRs of the VL and VH of a human antibody are identified, and they are each modified into amino acid resides derived from the antibody from the original non-human animal to increase the lowered antigen-binding activity [BIO/TECHNOLOGY, 9, 266 (1991)].

In production of a humanized antibody, efficient identification of amino acid residues associated with the antigen-binding activity in the FRs is the most critical, and thus construction and analysis of the three-dimensional structure of an antibody are carried out through X-ray crystallography [J. Mol. Biol., 112, 535 (1977)] or computer modeling [Protein Engineering, 7, 1501 (1994)], etc.

The information on the three-dimensional structures of antibodies has provided much useful information for production of a humanized antibody. However, a humanized antibody production method applicable to any antibody has not been established yet. Currently, various trial and errors are required, for example, such that several variants are produced for each antibody and the correlation of antigen-binding activity among them is examined.

Modification of amino acid residues in the FRs of the VL and VH of a humanized antibody can be achieved through the PCR described in 1-(5) with a synthetic DNA for modification. The nucleotide sequence of the amplified product after the PCR is determined by using the method described in 1-(1) to confirm achievement of the intended modification.

(7) Construction of Expression Vector for Humanized Antibody or Antibody Fragment Thereof An expression vector for a humanized antibody or antibody fragment thereof can be constructed through insertion of a cDNA encoding the VL or VH of the humanized antibody constructed in 1-(5) or 1-(6) into the upstream of a gene encoding the CL or CH of a human antibody in the expression vector described in 1-(1) for the antibody or antibody fragment thereof.

For example, an appropriate restriction enzyme recognition sequence is introduced at the 5'-terminus of a synthetic DNA positioned at each end, among the synthetic DNAs to be used in construction of the VH or VL of a humanized antibody in 1-(5) or 1-(6), to insert into the upstream of a gene encoding the CH or CL of a human antibody in the expression vector described in 1-(1) for the antibody or antibody fragment thereof in a manner such that the resultant is expressed in an appropriate manner. In this manner, an expression vector for a humanized antibody or antibody fragment thereof can be constructed.

2. Production of Antibody or Antibody Fragment Thereof Including Non-Natural Amino Acid According to Present Invention In order to obtain the antibody or antibody fragment thereof including a non-natural amino acid according to the present invention, a transformant obtained by introducing the expression vector produced in 1. for the antibody or antibody fragment thereof according to the present invention is introduced into an appropriate host cell is cultured in a medium with an intended non-natural amino acid added thereto to allow the host cell to produce the antibody or antibody fragment thereof including a non-natural amino acid according to the present invention to accumulate it in the culture, which is purified from the culture.

The host cell in the present invention may be any host cell commonly used for production of recombinant protein, such as a prokaryotic cell and a eukaryotic cell.

(1) For Prokaryotic Host Cell

In the case that the host cell in the present invention is a prokaryotic cell, the prokaryotic cell to be used may be any prokaryotic cell capable of producing a recombinant antibody. Examples of the prokaryotic cell include *Escherichia coli*, *Bacillus subtilis*, *Salmonella* spp., *Serratia* spp., and *Pseudomonas* spp. Among them, *Escherichia coli* is preferred.

In the case that the host cell is a prokaryotic cell, it is preferred that the activity of a release factor (hereinafter, abbreviated as "RF") to terminate translation at a UAG codon in the cell be lowered or lost, and it is more preferred that the activity of the release factor be lost.

It is known that the release factor and a tRNA to bind to a UAG codon, the tRNA expressed through transgenesis with an expression vector, competitively recognize a UAG codon in a host cell. Accordingly, an intended antibody can be efficiently expressed in a cell with the activity of the release factor lowered or lost.

Examples of the technique to cause lowering or loss of the activity of the release factor include genetic modification such as addition, deletion, and substitution for a gene encoding the release factor. Specific examples thereof include deletion of a part or the whole of a gene encoding the release factor to cause lowering or loss of the activity of the release factor, introduction of a point mutation to cause lowering or loss of the activity of the release factor, insertion of an unnecessary sequence to cause lowering or loss of the activity of the release factor, highly excessive expression of a tRNA to bind to a UAG codon to cause a dominant-negative phenotype, and use of an siRNA, antisense RNA, or the like to cause lowering or loss of expression of the release factor on a transcription level. Any of these methods may be used as long as lowering or loss of the activity of the release factor is successfully caused.

Further, the host cell to be used in the present invention is preferably a cell capable of expressing the function of one or more genes selected from a gene group to lose the function through lowering or loss of the activity of the release factor to terminate translation at a UAG codon, or lowering or loss of expression of a gene encoding the release factor, in the absence of the release factor. Specific examples thereof include a cell with a bacterial artificial chromosome (hereinafter, abbreviated as "BAC") incorporating one or more genes selected from a gene group to lose the function through lowering or loss of the activity of the release factor to terminate translation at a UAG codon, or lowering or loss of expression of a gene encoding the release factor, the one or more genes including substitution of a UAG codon with a UGA or UAA codon. The cell can be produced according to a method described in WO 2011/158895.

Examples of the gene group to lose the function through deletion of a gene encoding the release factor to terminate translation at a UAG codon in the present invention include a gene group to cause death through single deletion of the gene and a gene group to lose the function through deletion of the gene and thereby cause lowering of the growth rate of prokaryotic cells.

The gene group to cause death through single deletion of the gene include coaD, murF, hda, mreC, lpxK, hemA, and lolA of *Escherichia coli*; the genes accD, acpS, cspR, dapB, divIC, dnaA, fmt, folD, ftsA, map, mrpD, murE, murG, plsX, ppnK, racE, resB, resC, rnpA, rplX, rpmGB, rpmH, rpsG, secA, secY, topA, trmD, yacM, ydiC, yloQ, ypuH, and ysxC of *Bacillus subtilis*; and the genes mreD and hemK of *Escherichia coli*.

The gene group to lose the function through deletion of the gene and thereby cause lowering of the growth rate of prokaryotic cells include fliN, fliP, fliQ, sucB, ubiF, ulaF, atpE, and fabH of *Escherichia coli*, and the gene sucB is preferred among them.

In the case of *Escherichia coli*, specifically, it is preferred to select eight genes of coaD, hda, hemA, mreC, murF, lolA, lpxK, and SucB for the one or more genes selected from a gene group to lose the function through deletion of a gene encoding the release factor.

Examples of the release factor to terminate translation at a UAG codon in the case of bacteria such as *Escherichia coli* and *Bacillus subtilis* include RF-1, and examples of the gene encoding RF-1 include the gene prfA.

Any method capable of introducing a DNA into the host cell can be used to introduce the expression vector. Examples thereof include a method with calcium ions [Proc. Natl. Acad. Sci. USA, 69, 2110 (1972)], a method described in [Gene, 17, 107 (1982), Molecular & General Genetics, 168, 111 (1979)], and electroporation [Japanese Patent Laid-Open No. 2-257891, Cytotechnology, 3, 133 (1990)].

After introduction of the expression vector, a transformant stably producing the antibody or antibody fragment thereof including a non-natural amino acid according to the present invention can be selected by using a medium for culturing prokaryotic cells, the medium containing a pharmaceutical agent such as ampicillin.

Examples of the medium for culturing prokaryotic cells include an LB medium (from Becton, Dickinson and Company), an NZYM GIT medium (from Nihon Pharmaceutical Co., Ltd.), a Terrific Broth medium (from Applichem GmbH), an SOB medium (from Applichem GmbH), an SOC medium (from Ampliqon A/S), and a medium obtained by adding an antibiotic such as ampicillin to any of these media.

The transformant obtained is cultured in a medium with an intended non-natural amino acid added thereto to allow the transformant to produce an antibody or antibody fragment thereof with the intended non-natural amino acid introduced therein at an intended position to accumulate it in the culture supernatant. In the case that the transformant is derived from transformation by using a recombinant vector with an inducible promoter as the promoter, an inducer may be added to a medium, as necessary.

Examples of the inducer when a microorganism transformed by using a recombinant vector with a tac promoter include isopropyl-β-D-thiogalactopyranoside, and examples of the inducer when a microorganism transformed by using a recombinant vector with a trp promoter include indoleacrylic acid.

The amount of production and antigen-binding activity of the antibody or antibody fragment thereof according to the present invention in the transformant of a prokaryotic cell or in the culture medium can be measured, for example, through enzyme-linked immunosorbent assay [hereinafter, abbreviated as "ELISA", Antibodies: A Laboratory Manual, Cold Spring Harbor Laboratory, Chapter 14 (1998), Monoclonal Antibodies: Principles and Practice, Academic Press Limited (1996)].

The antibody or antibody fragment thereof including a non-natural amino acid according to the present invention in the transformant of a prokaryotic cell or in the culture supernatant can be purified from an *Escherichia coli* extract or a periplasm extract fraction through affinity purification with protein G, or through affinity purification with a tag such as a histidine tag sequence (a tag sequence consisting of six consecutive His, hereinafter, abbreviated as "His tag") bound to the C-terminus of the constant region.

Alternatively, a purification method commonly used for purification of protein can be used. For example, purification can be performed by using combination of gel filtration, ion exchange chromatography, hydrophobic chromatography, ultrafiltration, and so on.

The molecular weight of the light chain, the heavy chain, or the whole molecule of the antibody or antibody fragment thereof including a non-natural amino acid according to the present invention after purification can be measured, for example, through denaturing SDS-polyacrylamide gel electrophoresis (hereinafter, abbreviated as "SDS-PAGE") [Nature, 227, 680 (1970)] and Western blotting [Antibodies: A Laboratory Manual, Cold Spring Harbor Laboratory, Chapter 12 (1988), Monoclonal Antibodies: Principles and Practice, Academic Press Limited (1996)].

Whether the antibody or antibody fragment thereof including a non-natural amino acid according to the present invention is successfully produced can be determined through measurement of the molecular weight by mass spectrometry to compare with the theoretical molecular weight.

(2) For Eukaryotic Cell

In the case that the host cell is a eukaryotic cell, the eukaryotic cell to be used may be any eukaryotic cell capable of producing a recombinant antibody. Specific examples thereof include an animal cell, a yeast cell, an insect cell, and a plant cell.

Examples of the animal cell in the present invention include an NS0 cell as a mouse myeloma cell; an SP2/0 cell; a CHO/dhfr(-) cell, a CHO/DG44 cell, and a CHO-K1 cell each as a Chinese hamster ovarian cell; a YB2/0 cell as a rat myeloma cell; an IR983F cell; a BHK cell, derived from a Syrian hamster's kidney; an HEK293 cell, derived from a human kidney; and a Namalwa cell as a human myeloma cell.

Preferred among them are animal cells including the CHO/DG44 cell and CHO-K1 cell each as a Chinese hamster ovarian cell, the HEK293 cell, derived from a human kidney, and the rat myeloma YB2/0 cell. Alternatively, a cell to express a recombinant antibody having high ADCC activity, the cell described in International Publication Nos. WO 00/61739 and WO 02/31140, can be used for the host cell.

Any method capable of introducing a DNA into the host cell can be used to introduce the expression vector. Examples thereof include a method with calcium ions [Proc. Natl. Acad. Sci. USA, 69, 2110 (1972)], a method described in [Gene, 17, 107 (1982), Molecular & General Genetics, 168, 111 (1979)], electroporation [Japanese Patent Laid-Open No. 2-257891, Cytotechnology, 3, 133 (1990)], and lipofection [Proc. Natl. Acad. Sci. U.S.A., 84, 7413 (1987)].

After introduction of the expression vector, a transformant stably producing the antibody or antibody fragment thereof including a non-natural amino acid according to the present invention can be selected by using a medium for culturing animal cells, the medium containing a pharmaceutical agent such as G418 sulfate (hereinafter, abbreviated as "G418") (from Sigma-Aldrich Co., LLC.) according to a method disclosed in Japanese Patent Laid-Open No. 2-257891.

Examples of the medium for animal cells include an RPMI1640 medium (from NISSUI PHARMACEUTICAL CO., LTD.), a GIT medium (from Nihon Pharmaceutical Co., Ltd.), an EX-CELL302 medium (from JRH Biosciences), an IMDM medium (from GIBCO BRL), a Hybridoma-SFM medium (from GIBCO BRL), a FreeStyle™ 293 Expression Medium (from Invitrogen), and a FreeStyle™ CHO Expression Medium (from Invitrogen), and a medium obtained by adding an additive such as fetal calf serum (hereinafter, abbreviated as "FCS") to any of these media.

The amount of production of the antibody or antibody fragment thereof according to the present invention by the transformant can be increased, for example, by using a dihydrofolate reductase (DHFR) gene amplification system according to a method disclosed in Japanese Patent Laid-Open No. 2-257891.

The transformant obtained is cultured in a medium with an intended non-natural amino acid added thereto to allow the transformant to produce an antibody or antibody fragment thereof with the intended non-natural amino acid introduced therein at an intended position to accumulate it in the culture supernatant.

Examples of the method for producing the antibody or antibody fragment thereof according to the present invention with an animal cell include a method described in Mukai et al. [Biochem. Biophys. Res. Commmun, 371, 818-822 (2008)].

The antibody or antibody fragment thereof including a non-natural amino acid according to the present invention can be purified from the culture supernatant, for example, through affinity purification with protein G, or through affinity purification with a tag such as a histidine tag sequence (a tag sequence consisting of six consecutive His, hereinafter, abbreviated as "His tag") bound to the C-terminus of the constant region.

Alternatively, a purification method commonly used for purification of protein can be used. For example, purification can be performed by using combination of gel filtration, ion exchange chromatography, hydrophobic chromatography, ultrafiltration, and so on.

The molecular weight of the light chain, the heavy chain, or the whole molecule of the antibody or antibody fragment thereof including a non-natural amino acid according to the present invention after purification can be measured, for example, through SDS-polyacrylamide gel electrophoresis (hereinafter, abbreviated as "SDS-PAGE") [Nature, 227, 680 (1970)] and Western blotting [Antibodies: A Laboratory Manual, Cold Spring Harbor Laboratory, Chapter 12 (1988), Monoclonal Antibodies: Principles and Practice, Academic Press Limited (1996)].

Whether the antibody or antibody fragment thereof including a non-natural amino acid according to the present invention is successfully produced can be determined through measurement of the molecular weight by mass spectrometry to compare with the theoretical molecular weight.

Examples of the medium to culture the transformant obtained from an animal cell as the host cell include media commonly used including an RPMI1640 medium [The Journal of the American Medical Association, 199, 519 (1967)], an Eagle's MEM medium [Science, 122, 501 (1952)], a Dulbecco's modified MEM medium [Virology, 8, 396 (1959)], a 199 medium [Proceeding of the Society for the Biological Medicine, 73, 1 (1950)], a Whitten medium [Hassei-kogaku Jikken Manual—Transgenic Mouse no Tsukuri-kata (Manual for Developmental Engineering Experiment—How to Produce Transgenic Mouse) (KODANSHA LTD.), edited by Motoya Katsuki (1987)], a FreeStyle™ 293 Expression Medium (from Invitrogen), and a FreeStyle™ CHO Expression Medium (from Invitrogen), and a medium obtained by adding fetal calf serum or the like to any of these media.

It is typically preferred to culture, for example, under conditions of pH 6.0 to 8.0 and 30 to 40° C. in the presence of 5% $CO_2$ for 1 to 7 days.

An antibiotic such as kanamycin and penicillin may be added to the medium during culturing, as necessary.

The amount of production and antigen-binding activity of the antibody or antibody fragment thereof including a non-natural amino acid according to the present invention in the culture supernatant can be measured, for example, through ELISA [Antibodies: A Laboratory Manual, Cold Spring Harbor Laboratory, Chapter 14 (1998), Monoclonal Antibodies: Principles and Practice, Academic Press Limited (1996)].

The antibody or antibody fragment thereof including a non-natural amino acid according to the present invention in the culture supernatant can be purified from the culture supernatant for the transformant by using a protein A column [Antibodies: A Laboratory Manual, Cold Spring Harbor Laboratory, Chapter 8 (1988), Monoclonal Antibodies: Principles and Practice, Academic Press Limited (1996)].

Alternatively, a purification method commonly used for purification of protein can be used. For example, purification can be performed by using combination of gel filtration, ion exchange chromatography, hydrophobic chromatography, ultrafiltration, and so on.

The molecular weight of the light chain, the heavy chain, or the whole molecule of the antibody or antibody fragment thereof including a non-natural amino acid according to the present invention after purification can be measured, for example, through SDS-PAGE [Nature, 227, 680 (1970)] and Western blotting [Antibodies: A Laboratory Manual, Cold Spring Harbor Laboratory, Chapter 12 (1988), Monoclonal Antibodies: Principles and Practice, Academic Press Limited (1996)].

Whether the antibody or antibody fragment thereof including a non-natural amino acid according to the present invention is successfully produced can be determined through measurement of the molecular weight by mass spectrometry to compare with the theoretical molecular weight.

In the case of another type of eukaryotic cell such as a yeast, an insect cell, and a plant cell, the antibody or antibody fragment thereof according to the present invention can be produced by using the same method as for the animal cell.

Examples of the host cell for the case that a yeast is used include microorganisms belonging to the genus *Saccharomyces*, the genus *Schizosaccharomyces*, the genus *Kluyveromyces*, the genus *Trichosporon*, and the genus *Schwanniomyces*. Examples of the microorganism include *Saccharomyces cerevisiae*, *Schizosaccharomyces pombe*, *Kluyveromyces lactis*, *Trichosporon pullulans*, and *Schwanniomyces alluvius*.

Any method capable of introducing a DNA into a yeast can be used to introduce the expression vector. Examples thereof include electroporation [Methods. Enzymol., 194, 182 (1990)], a spheroplast method [Proc. Natl. Acad. Sci. U.S.A, 84, 1929 (1978)], and a lithium acetate method [J. Bacteriology, 153, 163 (1983), Proc. Natl. Acad. Sci. U.S.A, 75, 1929 (1978)].

A transformant obtained from a yeast as the host cell is cultured in a medium with an intended non-natural amino acid added thereto to allow the transformant to produce an antibody or antibody fragment thereof with the intended non-natural amino acid introduced therein at an intended position and accumulate it in the culture, from which the antibody or antibody fragment thereof is collected. In this manner, the antibody or antibody fragment thereof according to the present invention can be produced. Culture of the transformant can be performed according to a conventional method used for culturing a yeast.

Any natural medium or synthetic medium containing a carbon source, a nitrogen source, an inorganic salt, and so on, which the organism can assimilate, and allowing efficient culture of the transformant may be used for the medium to culture the transformant obtained from a yeast as the host cell.

The carbon source may be any carbon source which the organism can assimilate, and examples thereof include glucose, fructose, sucrose, a syrup containing any of them, a carbohydrate such as starch and starch hydrolyzate, an organic acid such as acetic acid and propionic acid, and an alcohol such as ethanol and propanol.

Examples of the nitrogen source include ammonia, an ammonium salt of an inorganic acid or organic acid such as ammonium chloride, ammonium sulfate, ammonium acetate, and ammonium phosphate, a nitrogen-containing compound other than them, peptone, meat extract, yeast extract, corn steep liquor, casein hydrolyzate, a soybean cake, a soybean cake hydrolyzate, and bacterial cells of a fermentative bacterium and a digested product thereof.

Examples of the inorganic salt include monopotassium phosphate, dipotassium phosphate, magnesium phosphate, magnesium sulfate, sodium chloride, ferrous sulfate, manganese sulfate, copper sulfate, and calcium carbonate.

Culture is typically performed under aerobic conditions through shaking culture, stirring culture with deep aeration, or the like. The culture temperature is preferably 15 to 40° C., and the culture duration is preferably 16 hours to 7 days in typical cases. It is preferred to retain the pH at 3.0 to 9.0 during culturing. It is preferred to adjust the pH, for example, with an inorganic or organic acid, alkaline solution, urea, calcium carbonate, or ammonia.

An antibiotic such as ampicillin and tetracycline may be added to the medium during culturing, as necessary.

In this case, the antibody or antibody fragment thereof including a non-natural amino acid according to the present invention can be collected from the culture supernatant. Specifically, the culture is treated, for example, by means of centrifugation, as described above, to obtain the culture supernatant, from which a purified preparation of the antibody or antibody fragment thereof including a non-natural amino acid according to the present invention can be obtained by using the isolation and/or purification method described above.

In the case that an insect cell is used as the host cell, the antibody or antibody fragment thereof according to the present invention can be expressed, for example, by using any of methods described in Current Protocols in Molecular Biology, Supplement 1-34; Baculovirus Expression Vectors, A Laboratory Manual, W. H. Freeman and Company, New York (1992); Bio/Technology, 6, 47 (1988), and so on.

For expression of the antibody or antibody fragment thereof according to the present invention, specifically, an expression vector and a baculovirus are co-introduced into an insect cell to obtain a recombinant virus in the culture supernatant for the insect cell, and further an insect cell is infected with the recombinant cell.

Examples of the baculovirus include the *Autographa californica* nuclear polyhedrosis virus, which is a virus to infect insects belonging to the family Hadeninae.

Examples of the insect cell include Sf9 and Sf21, each as an ovarian cell of Spodopterafrugiperda [Current Protocols in Molecular Biology, Supplement 1-34; Baculovirus Expression Vectors, A Laboratory Manual, W. H. Freeman and Company, New York (1992)], and High 5 (Invitrogen), as an ovarian cell of Trichoplusiani.

Examples of the method for co-introducing an expression vector and a baculovirus into an insect cell to prepare a recombinant virus include a calcium phosphate method (Japanese Patent Laid-Open No. 2-227075) and lipofection [Proc. Natl. Acad. Sci. U.S.A., 84, 7413 (1987)].

The transformant obtained from an insect cell as the host cell is cultured in a medium with an intended non-natural amino acid added thereto to allow the transformant to produce an antibody or antibody fragment thereof with the intended non-natural amino acid introduced therein at an intended position to accumulate it in the culture, from which the antibody or antibody fragment thereof is collected. In this manner, the antibody or antibody fragment thereof according to the present invention can be produced. Culture of the transformant can be performed according to a conventional method used for culturing an insect cell.

Examples of the medium to culture the transformant obtained from an insect cell as the host cell include media commonly used including a TNM-FH medium (from PharMingen); an Sf-900 II SFM medium (Life Technologies); an ExCell400 and ExCell405 (each from JRH Biosciences); and a Grace's Insect Medium [Nature, 195, 788 (1962)].

It is typically preferred to culture, for example, under conditions of pH 6.0 to 7.0 and 25 to 30° C. for 1 to 5 days. An antibiotic such as gentamicin may be added to the medium during culturing, as necessary.

In this case, the antibody or antibody fragment thereof including a non-natural amino acid according to the present invention can be collected from the culture supernatant. Specifically, the culture is treated, for example, by means of centrifugation, as described above, to obtain the culture supernatant, from which a purified preparation of the antibody or antibody fragment thereof including a non-natural amino acid according to the present invention can be obtained by using the isolation and/or purification method described above.

Examples of the host cell for the case that a plant cell is used include cells derived from the tobacco, potato, tomato, carrot, soybean, rape, alfalfa, rice, wheat, and barley.

Any method capable of introducing a DNA into a plant cell can be used to introduce a recombinant vector. Examples thereof include *Agrobacterium* (Japanese Patent Laid-Open Nos. 59-140885 and 60-70080, International Publication No. WO 94/00977), electroporation (Japanese Patent Laid-Open No. 60-251887), and a method with a particle gun (gene gun) (Japanese Patent Nos. 2606856 and 2517813).

Any method capable of introducing a DNA into a plant cell can be used to introduce the expression vector. Examples thereof include electroporation [Cytotechnology, 3, 133 (1990)], a calcium phosphate method (Japanese Patent Laid-Open No. 2-227075), lipofection [Proc. Natl. Acad. Sci. U.S.A., 84, 7413 (1987)], injection [Manipulating the Mouse Embryo A Laboratory Manual, Second Edition, Cold Spring Harbor Laboratory Press (1994)], a method with a particle gun (gene gun) [Japanese Patent Nos. 2606856 and 2517813], a DEAE-dextran method [Bio-manual series 4—Idenshi-donyu to Hatsugen, Kaiseki-Ho (Bio-manual series 4—Transgenesis and Expression, Analysis Method) (YODOSHA CO., LTD.), edited by Takeshi Yokota and Kenichi Arai (1994)], and a virus vector method [Manipulating the Mouse Embryo A Laboratory Manual, Second Edition, Cold Spring Harbor Laboratory Press (1994)].

A transformant obtained from a plant cell as the host cell is cultured in a medium with an intended non-natural amino acid added thereto to allow the transformant to produce an antibody or antibody fragment thereof with the intended non-natural amino acid introduced therein at an intended position to accumulate it in the culture, from which the antibody or antibody fragment thereof is collected. In this manner, the antibody or antibody fragment thereof including a non-natural amino acid according to the present invention can be produced. Culture of the transformant can be performed according to a conventional method used for culturing a plant cell.

The transformant obtained from a plant cell as the host cell can be cultured as a cell, or can be differentiated into a plant cell or organ and cultured. Examples of the medium to culture the transformant include media commonly used including a Murashige and Skoog (MS) medium and a White medium, and a medium obtained by adding a plant hormone such as auxin and cytokinin to any of these media.

It is typically preferred to culture, for example, under conditions of pH 5.0 to 9.0 and 20 to 40° C. for 3 to 60 days. An antibiotic such as kanamycin and hygromycin may be added to the medium during culturing, as necessary.

In this case, the antibody or antibody fragment thereof including a non-natural amino acid according to the present invention can be collected from the culture supernatant. Specifically, the culture is treated, for example, by means of centrifugation, as described above, to obtain the culture supernatant, from which a purified preparation of the antibody or antibody fragment thereof including a non-natural amino acid according to the present invention can be obtained by using the isolation and/or purification method described above.

(3) For Cell-Free Expression System

In the method for producing the antibody or antibody fragment thereof including a non-natural amino acid according to the present invention, a cell-free protein synthesis system (also referred to as "cell-free expression system") can be employed. The cell-free protein synthesis system is a system for synthesizing intended protein in vitro by using protein factors required for protein translation, where the protein factors are those taken as a cell extract. Extracts derived from various species can be used to configure the cell-free system, and examples thereof include extracts from eukaryotic cells or prokaryotic cells with high protein synthesis activity, for example, bacteria such as *Escherichia coli* and thermophilic bacteria, wheat germs, rabbit reticulocytes, mouse L-cells, Ehrlich ascites carcinoma cells, HeLa cells, CHO cells, and budding yeasts (Clemens, M. J., Transcription and Translation—A Practical Approach, (1984), pp. 231-270, Henes, B. D. et al. eds., IRL Press, Oxford).

The antibody or antibody fragment thereof including a non-natural amino acid according to the present invention can be produced in the cell-free expression system through preparing an extract from the transformant capable of producing the antibody or antibody fragment thereof including a non-natural amino acid according to the present invention, the transformant obtained in (1) or (2).

In the case that *Escherichia coli* is used, the antibody or antibody fragment thereof including a non-natural amino acid according to the present invention may be produced in an extract from a recombinant bacterial strain prepared according to a method disclosed in Zubay et al., (Zubay et al., Ann. Rev. Genet. Vol. 7, pp. 267-287 (1973)), Pratt et al.

(Pratt, J. M. et al., Transcription and Translation—A practical approach, (1984), pp. 179-209, Henes, B. D. et al. eds., IRL Press, Oxford), or Kigawa et at. (Kigawa, T. et al, J. Struct. Funct. Genomics, Vol. 5, pp 63-68 (2004)).

The extract from a transformant for producing the antibody or antibody fragment thereof including a non-natural amino acid according to the present invention can be prepared, for example, by using the following preparation method. In the case that a Z-lysine derivative such as azido-Z-lysine, ethynyl-Z-lysine, amino-Z-lysine, and formyl-Z-lysine, TCO*-Lys, or BCN-Lys is introduced into an antibody, a transformant of a cell capable of forming a Y384F/Y306A double mutant of pyrrolysyl tRNA synthetase from *Methanosarcina mazei* is cultured, and the transformant is collected through centrifugation. In the case that a non-natural amino acid other than Z-lysine derivatives such as azido-Z-lysine, ethynyl-Z-lysine, amino-Z-lysine, and formyl-Z-lysine, TCO*-Lys, and BCN-Lys is introduced into an antibody, a suitable aminoacyl tRNA synthetase is selected as described above, and a transformant of a cell capable of forming the aminoacyl tRNA synthetase is collected.

The cell collected is washed, resuspended in a buffer, and pulverized by using a French press, glass beads, a Waring blender, etc. The insoluble fraction of the cell is removed through centrifugation, and incubated. Endogenous nucleic acids (DNA and RNA) can be decomposed through this incubation. The endogenous nucleic acids can be further decomposed through further addition of a calcium salt or nuclease from *Micrococcus* or the like to the incubation solution. After the incubation, endogenous amino acids, nucleic acids, nucleosides, and so on are removed through dialysis to prepare an extract.

In production of the antibody or antibody fragment thereof including a non-natural amino acid according to the present invention in the cell-free system, the following production method can be employed. A tRNA appropriately selected according to the type of the non-natural amino acid, as described above, a commercially available tRNA fraction, and a template DNA/RNA are added to the above extract. Here, the intended non-natural amino acid is added, and energy, ions, a buffer, an ATP-regenerating system, a nuclease inhibitor, a reductant, polyethylene glycol, cAMP, a folate, or an antibiotic, etc., may be further added, according to the types of the protein and production system. In the case that a DNA is used as a template, it is preferred to add an RNA synthesis system (substrate, polymerase, and so on).

(4) General Method for Producing Each Non-Natural Amino Acid

In the present invention, each non-natural amino acid can be synthesized according to any of methods described in WO 2013/068874, WO 2014/004639, WO 2014/044872, WO 2014/124258, and so on. Alternatively, a commercially available non-natural amino acid can be used.

The Z-lysine derivative represented by the general formula (I) can be produced, for example, by using a production method illustrated below. If the defined group changes under conditions for the production method or is inappropriate for performing the production method, a targeted compound can be produced, for example, by using a method for introducing and removing a protective group conventionally used in synthetic organic chemistry [e.g., a method described in Protective Groups in Organic Synthesis, third edition, written by T. W. Greene, John Wiley & Sons Inc. (1999)]. The order of reaction steps including introduction of a substituent can be changed, as necessary.

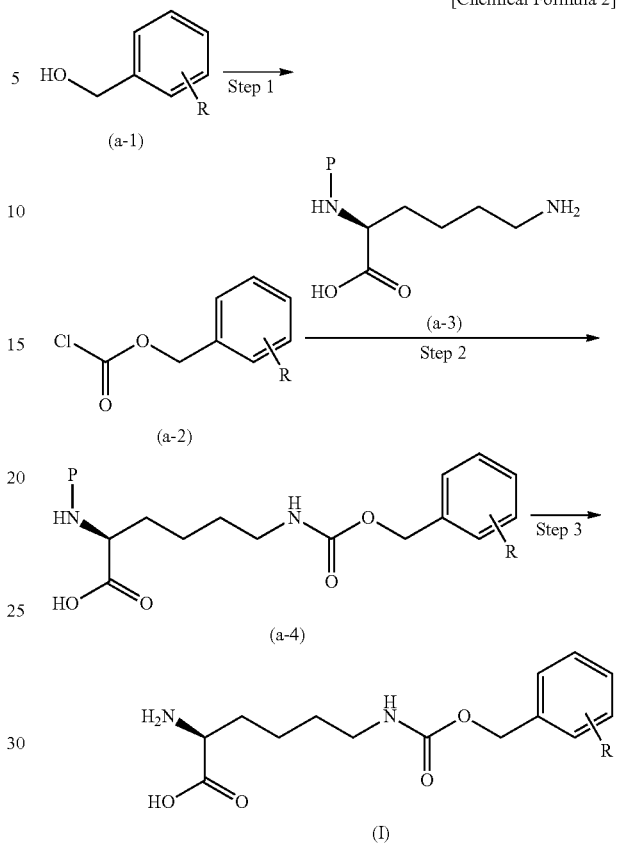

[Chemical Formula 2]

In the formula, R is as defined above, and P represents a protective group such as benzyloxycarbonyl (Cbz), tert-butoxycarbonyl (Boc), and 9-fluorenylmethyloxycarbonyl (Fmoc). Hereinafter, the compound represented by the general formula (a-1) is referred to as "Compound (a-1)". The same is applied to compounds of different formula numbers.

(Step 1)

To produce Compound (a-2), Compound (a-1) and 1 to 20 equivalents of an acid chloride-forming agent are reacted in a solvent in the presence of 1 to 50 equivalents of an additive, as necessary, at a temperature between −20° C. and the boiling point of the solvent for 5 minutes to 72 hours.

Compound (a-1) can be obtained as a commercially available product, or by using a known method [e.g., The Fifth Series of Experimental Chemistry, Volume 16, p. 1, MARUZEN CO., LTD. (2005)] or a method according thereto.

Examples of the acid chloride-forming agent include phosgene, triphosgene, and trichloromethylchloroformate.

Examples of the solvent include dichloromethane, chloroform, 1,2-dichloroethane, toluene, acetonitrile, diethyl ether, tetrahydrofuran (THF), 1,2-dimethoxyethane (DME), dioxane, N,N-dimethylformamide (DMF), N,N-dimethylacetamide (DMA), N-methylpyrrolidone (NMP), and pyridine, and one of them is used singly, or any mixture of them is used.

Examples of the additive include pyridine, triethylamine, N,N-diisopropylethylamine, 1,8-diazabicyclo[5.4.0]-7-undecene (DBU), sodium hydroxide, potassium hydroxide, sodium carbonate, potassium carbonate, and cesium carbonate.

(Step 2)

To produce Compound (a-4), Compound (a-2) and 1 to 10 equivalents of Compound (a-3) are reacted in a solvent in the presence of 1 to 50 equivalents of an additive, as necessary, at a temperature between −20° C. and the boiling point of the solvent for 5 minutes to 72 hours.

Compound (a-3) can be obtained as a commercially available product, or by using a known method [e.g., Amino Acid, Peptides and Proteins in Organic Chemistry, Volume 4, Protection Reactions, Medicinal Chemistry, Combinatorial Synthesis, Andrew B. Hughes, 2011, ISBN: 978-3-527-32103-2] or a method according thereto.

Examples of the solvent include dichloromethane, chloroform, 1,2-dichloroethane, toluene, acetonitrile, ethyl acetate, diethyl ether, THF, DME, dioxane, DMF, DMA, NMP, pyridine, and water, and one of them is used singly, or any mixture of them is used.

Examples of the additive include pyridine, triethylamine, N,N-diisopropylethylamine, DBU, sodium hydroxide, potassium hydroxide, sodium carbonate, potassium carbonate, and cesium carbonate.

(Step 3)

To produce Compound (I), Compound (a-4) is reacted in a solvent in the presence of 1 to 50 equivalents of an additive at a temperature between −20° C. and the boiling point of the solvent for 5 minutes to 72 hours.

Examples of the solvent include dichloromethane, chloroform, 1,2-dichloroethane, toluene, acetonitrile, ethyl acetate, diethyl ether, THF, DME, dioxane, DMF, DMA, NMP, pyridine, and water, and one of them is used singly, or any mixture of them is used.

For the additive, a suitable one according to the type of the protective group P can be selected, and, more specifically, examples thereof include an additive necessary for deprotection reaction, for example, described in Protective Groups in Organic Synthesis, third edition, written by T. W. Greene, John Wiley & Sons Inc. (1999). In the case that P is Boc, for example, an acid such as hydrochloric acid is preferred.

Any of the intermediates and targeted compound in the production methods can be isolated and/or purified through a method of isolation and/or purification conventionally used in synthetic organic chemistry, such as filtration, extraction, washing, drying, concentration, recrystallization, and various chromatographies. Each of the intermediates can be subjected to the next reaction without any purification.

To obtain a salt of Compound (I), purification can be suitably performed in the case that Compound (I) is obtained as a salt; in the case that Compound (I) is obtained as a free form, Compound (I) is dissolved or suspended in an appropriate solvent, and an acid or base is added to form a salt, which can be suitably isolated and/or purified.

3. Production of Modified Antibody or Antibody Fragment Thereof Including Non-Natural Amino Acid According Present Invention The modified antibody or antibody fragment thereof including a non-natural amino acid according to the present invention can be produced through modification of at least one amino acid residue, non-natural amino acid residue, or sugar chain included in the above-described antibody or antibody fragment thereof including a non-natural amino acid according to the present invention by using chemical modification or a gene engineering technique. The chemical modification can be achieved by using a method described in [Koutai-kougaku Nyuumon (Introduction to Antibody Engineering), Chijinshokan Co., Ltd., (1994) Kolb et al., Angew Chem Int Ed Engl. 40. 2004-21, 2001], and examples of the gene engineering technique include, but are not limited to, a method in which an expression vector for recombinant protein is introduced into an appropriate host cell for expression.

The amino acid residue to be modified is preferably cysteine, tyrosine, phenylalanine, lysine, pyrrolysine, glutamine, asparagine, glutamic acid, aspartic acid, or a derivative or the like of any of them, more preferably a tyrosine derivative such as azidophenylalanine or a lysine derivative such as a Z-lysine derivative, TCO*-Lys, and BCN-Lys, and the most preferably a lysine derivative such as a Z-lysine derivative, TCO*-Lys, and BCN-Lys. The sugar chain to be modified is preferably a sugar chain present in the constant region of an antibody.

The modified antibody or antibody fragment thereof including a non-natural amino acid according to the present invention may be any one, for example, formed by chemically modifying the antibody or antibody fragment thereof according to the present invention with a molecule having reactivity with an intended amino acid residue, amino acid derivative, non-natural amino acid residue, or a non-natural amino acid derivative included in the antibody or antibody fragment thereof according to the present invention.

The modified antibody or antibody fragment thereof including a non-natural amino acid according to the present invention can be produced, for example, by bonding an azido group included in an intended amino acid residue, amino acid derivative, non-natural amino acid residue, or a non-natural amino acid derivative included in the antibody or antibody fragment thereof including a non-natural amino acid according to the present invention, to a molecule having reactivity with the azido group through chemical reaction.

The molecule having reactivity with an azido group is preferably a molecule having an alkynyl group, and examples of the molecule having an alkynyl group include a commercially available molecule such as Alexa Fluor 488 DIBO Alkyne (Life Technologies) and a molecule which can be prepared by using a known method, for example, described in Synlett 1996; 1996(6): 521-522, or Chem. Commun.; 2010; 46, 97-99. The molecule having an azido group and molecule having an alkynyl group can be bonded together, for example, by using chemical reaction called "click chemistry" described in [Kolb et al., Angew Chem Int Ed Engl. 40. 2004-21, 2001].

The modified antibody or antibody fragment thereof including a non-natural amino acid according to the present invention can be produced, for example, by bonding an alkynyl group included in an intended amino acid residue, amino acid derivative, non-natural amino acid residue, or a non-natural amino acid derivative included in the antibody or antibody fragment thereof including a non-natural amino acid according to the present invention, to a molecule having reactivity with the alkynyl group through chemical reaction.

The molecule having reactivity with an alkynyl group is preferably a molecule having an azido group, and examples of the molecule having an azido group include a commercially available molecule such as Click-IT Azide Alexa Fluor 488 (from Life Technologies) and a molecule prepared by using a known method. The molecule having an alkynyl group and molecule having an azido group can be bonded together, for example, by using chemical reaction called "click chemistry" described in [Kolb et al., Angew Chem Int Ed Engl. 40. 2004-21, 2001].

The modified antibody or antibody fragment thereof including a non-natural amino acid according to the present invention can be produced, for example, by bonding an amino group included in an intended amino acid residue, amino acid derivative, non-natural amino acid residue, or a non-natural amino acid derivative included in the antibody or antibody fragment thereof including a non-natural amino acid according to the present invention, to a molecule having reactivity with the amino group through chemical reaction.

The molecule having reactivity with an amino group is preferably a molecule having a formyl group, and examples of the molecule having a formyl group include a commercially available molecule such as Fluorescein PEG aldehyde (from Nanocs Inc.) and a molecule which can be prepared by using a known method. The molecule having an amino group and molecule having a formyl group can be bonded together, for example, by using chemical reaction called "reductive amination reaction" (Bioconjugate Chem. 2016, 27, 198-206).

The modified antibody or antibody fragment thereof including a non-natural amino acid according to the present invention can be produced, for example, by bonding a formyl group included in an intended amino acid residue, amino acid derivative, non-natural amino acid residue, or a non-natural amino acid derivative included in the antibody or antibody fragment thereof including a non-natural amino acid according to the present invention, to a molecule having reactivity with the formyl group through chemical reaction.

The molecule having reactivity with a formyl group is preferably a molecule having an amino group, and examples of the molecule having an amino group include a commercially available molecule such as Fluorescein PEG amine (from Nanocs Inc.) and a molecule which can be prepared by using a known method. The molecule having a formyl group and molecule having an amino group can be bonded together, for example, by using chemical reaction called "reductive amination reaction".

The modified antibody or antibody fragment thereof including a non-natural amino acid according to the present invention can be produced, for example, by bonding the trans-cyclooctene ring of TCO*-Lys included in the antibody or antibody fragment thereof according to the present invention, to a molecule having reactivity with the trans-cyclooctene ring through chemical reaction.

The molecule having reactivity with a trans-cyclooctene ring is preferably a molecule having a 1,2,4,5-tetrazine ring, and examples of the molecule having a 1,2,4,5-tetrazine ring include a commercially available molecule such as Cy3 Tetrazine (from Click Chemistry Tools LLC.) and a molecule which can be prepared by using a known method. The molecule having a trans-cyclooctene ring and molecule having a 1,2,4,5-tetrazine ring can be bonded together, for example, by using chemical reaction called "inverse electron-demand Diels-Alder reaction" (Angew. Chem. Int. Ed. 2014, 53, 2245-2249).

The modified antibody or antibody fragment thereof including a non-natural amino acid according to the present invention can be produced, for example, by bonding the bicyclo[6.1.0]non-4-yne ring of BCN-Lys included in the antibody or antibody fragment thereof according to the present invention, to a molecule having reactivity with the bicyclo[6.1.0]non-4-yne ring through chemical reaction.

The molecule having reactivity with a bicyclo[6.1.0]non-4-yne ring is preferably a molecule having a 1,2,4,5-tetrazine ring, and examples of the molecule having a 1,2,4,5-tetrazine ring include a commercially available molecule such as Cy3 Tetrazine (from Click Chemistry Tools LLC.) and a molecule which can be prepared by using a known method. The molecule having a bicyclo[6.1.0]non-4-yne ring and molecule having a 1,2,4,5-tetrazine ring can be bonded together, for example, by using chemical reaction called "inverse electron-demand Diels-Alder reaction" (J. Am. Chem. Soc. 2012, 134, 10317-10320).

Chemical modification of the antibody or antibody fragment thereof including a non-natural amino acid according to the present invention is performed preferably with 1 to 1000 mol, more preferably 1 to 50 mol, of the molecule having reactivity with the antibody or antibody fragment thereof according to the present invention per 1 mol of the antibody or antibody fragment thereof.

The degree of chemical modification of the modified antibody or antibody fragment thereof including a non-natural amino acid according to the present invention, in other words, the reactivity of the molecule having reactivity with an intended amino acid residue, amino acid derivative, non-natural amino acid residue, or non-natural amino acid derivative included in the antibody or antibody fragment thereof according to the present invention, can be arbitrarily selected through controlling the mole ratio of the molecule to be reacted, reaction temperature, pH, reaction time, and so on.

The reactivity between an amino acid residue, amino acid derivative, non-natural amino acid residue, or non-natural amino acid derivative having an azido group included in the antibody or antibody fragment thereof according to the present invention and the molecule having an alkynyl group can be confirmed according to a method, for example, described in Bioconjugate Chem. 2014, 25, 351-361. In the case that the antibody or antibody fragment thereof includes a non-natural amino acid residue having one azido group, for example, the reactivity between the non-natural amino acid residue and Alexa 488, which is a fluorescent dye having an alkynyl group, can be confirmed by using a method described below. In the case that the molecule having an alkynyl group is not Alexa 488, the reactivity can be similarly confirmed according to a method described below.

The antibody or antibody fragment thereof at an appropriate concentration is prepared with DPBS, and Alexa Fluor 488 DIBO Alkyne (Life Technologies) is added thereto, and reacted at room temperature overnight. Thereafter, the optical densities of the reaction solution at wavelengths of 280 nm and 495 nm are monitored through cation exchange chromatography. The reactivity (%) between the antibody or antibody fragment thereof and Alexa 488 is calculated from equations below with the area values of the optical densities obtained. For example, when one molecule of Alexa 488 bonds to one molecule of an Fab including a non-natural amino acid, the reactivity reaches 100%.

> Concentration of antibody or antibody fragment thereof (M)={(area value at wavelength of 280 nm)−0.11×(area value at wavelength of 495 nm)}/molar extinction coefficient of antibody or antibody fragment thereof > Reactivity (%)=[area value at wavelength of 495 nm/(molar extinction coefficient of Alexa 488× concentration of antibody or antibody fragment thereof (M) obtained from above equation)/ number of molecules of non-natural amino acid per molecule of antibody or antibody fragment thereof]×100

The reactivity between an amino acid residue, amino acid derivative, non-natural amino acid residue, or non-natural amino acid derivative having an alkynyl group included in the antibody or antibody fragment thereof according to the present invention and the molecule having an azido group can be similarly confirmed by using the above method. For the substance to be reacted with the antibody or antibody fragment thereof according to the present invention, for example, Click-IT Azide Alexa Fluor 488 (from Life Technologies) can be used.

The reactivity between an amino acid residue, amino acid derivative, non-natural amino acid residue, or non-natural amino acid derivative having an amino group included in the antibody or antibody fragment thereof according to the present invention and the molecule having a formyl group can be confirmed by using a method described in the following.

The antibody or antibody fragment thereof according to the present invention at an appropriate concentration is prepared with an appropriate solvent, for example, a solvent containing 50 mM trisodium citrate (from Wako Pure Chemical Industries, Ltd.) and 50 mM citric acid (from NACALAI TESQUE, INC.) at pH 4.0. To the antibody solution, Fluorescein PEG aldehyde (from Nanocs Inc.) and 2-Methylpyridine borane complex (from Sigma-Aldrich Co. LLC.) are added, and the resultant is reacted at 4° C. overnight.

Thereafter, unreacted Fluorescein PEG aldehyde is removed through ultrafiltration, and then analysis is performed by using the spectrophotometer UV-1800 (from Shimadzu Corporation). In the case that the antibody or antibody fragment thereof according to the present invention includes a non-natural amino acid residue having one amino group, the reactivity (%) can be calculated from equations below. In the case that one molecule of the antibody according to the present invention includes two molecules of a non-natural amino acid introduced therein, the reactivity reaches 100% when two molecules of Fluorescein are added to the antibody.

Concentration of antibody or antibody fragment thereof (M)={(area value at wavelength of 280 nm)−0.30×(area value at wavelength of 495 nm)}/molar extinction coefficient of antibody or antibody fragment thereof Reactivity (%)=[area value at wavelength of 495 nm/(molar extinction coefficient of Fluorescein×concentration of antibody or antibody fragment thereof (M) obtained from above equation)/number of molecules of non-natural amino acid per molecule of antibody or antibody fragment thereof]×100

When a parent antibody (or a wild-type antibody) including no non-natural amino acid and Fluorescein PEG aldehyde are reacted together, a value obtained by subtracting the reactivity between the parent antibody and Fluorescein PEG aldehyde from the reactivity between the antibody or antibody fragment thereof according to the present invention and Fluorescein PEG aldehyde as calculated from the above equations is the reactivity (%) between a non-natural amino acid included in the antibody according to the present invention and Fluorescein PEG aldehyde.

The reactivity between an amino acid residue, amino acid derivative, non-natural amino acid residue, or non-natural amino acid derivative having a formyl group included in the antibody or antibody fragment thereof according to the present invention and the molecule having an amino group can be similarly confirmed by using the above method. For the substance to be reacted with the antibody or antibody fragment thereof according to the present invention, for example, Fluorescein PEG amine can be used.

The reactivity between TCO*-Lys included in the antibody or antibody fragment thereof according to the present invention and the molecule having a 1,2,4,5-tetrazine ring, and the reactivity between BCN-Lys included in the antibody or antibody fragment thereof according to the present invention and the molecule having a 1,2,4,5-tetrazine ring can be similarly measured according to the method for measuring the reactivity between the antibody or antibody fragment thereof according to the present invention and the molecule having an azido group or alkynyl group. For the substance to be reacted with the antibody or antibody fragment thereof according to the present invention in this case, for example, Cy3 Tetrazine (from Click Chemistry Tools LLC.) can be used, and the reactivity in this case is calculated from the following equations.

Concentration of antibody or antibody fragment thereof (M)={(area value at wavelength of 280 nm)−0.08×(area value at wavelength of 550 nm)}/molar extinction coefficient of antibody or antibody fragment thereof Reactivity (%)=[area value at wavelength of 550 nm/(molar extinction coefficient of Cy3×concentration of antibody or antibody fragment thereof (M) obtained from above equation)/number of molecules of non-natural amino acid per molecule of antibody or antibody fragment thereof]×100

The solvent to be used in the modification reaction may be any solvent which does not interfere with the reaction. For example, the solvent is selected from phosphate buffer, borate buffer, Tris-hydrochloride buffer, sodium hydrogen carbonate aqueous solution, sodium acetate buffer, citrate buffer, water, N,N-dimethylformamide, dimethylsulfoxide, methanol, acetonitrile, dioxane, and tetrahydrofuran, and a mixed solvent of any of them [see Zoku Tanpaku-shitsu Hybrid (Protein Hybrid Part II), edited by Yuji Inada and Hiroshi Maeda, KYORITSU SHUPPAN CO., LTD. (1988)]

With respect to the temperature, pH, and the reaction time, any conditions may be employed such that the activities of the antibody or antibody fragment thereof according to the present invention to be used for the chemical modification and the molecule to be used for the chemical modification are not deteriorated. For example, a temperature between 0 to 50° C., a reaction time of 10 minutes to 100 hours, and a pH of 4 to 10 are preferred.

The modified antibody or antibody fragment thereof including a non-natural amino acid according to the present invention as obtained in the above chemical reaction can be purified according to a conventional method with use of any one of gel filtration, ion exchange chromatography, reverse-phase high-performance liquid chromatography, affinity chromatography, hydrophobic chromatography, ultrafiltration, and so on, or with use of any combination of them. The modified antibody or antibody fragment thereof including a non-natural amino acid according to the present invention, for example, with any chemical modification ratio can be purified through fractionation with any of these purification methods.

The structure of the modified antibody or antibody fragment thereof including a non-natural amino acid according to the present invention after purification can be confirmed, for example, through mass spectrometry, nuclear magnetic resonance (NMR), and amino acid composition analysis with an amino acid analyzer. For example, the structure can be confirmed through amino acid sequence analysis in which phenylthiohydantoin (PTH)-amino acid obtained through Edman degradation by using a gas-phase protein sequencer is analyzed through reverse-phase high-performance liquid chromatography (HPLC).

4. Method for Controlling Effector Activity of Antibody

Examples of the method for controlling the effector activity of the antibody or antibody fragment thereof including a non-natural amino acid according to the present invention include a method of controlling the amount of fucose to bond via α-1,6 bonding to N-acetylglucosamine (GlcNAc) present in the reducing terminus of an N-bound composite sugar chain bonding to asparagine (Asn) at position 297 of the constant region of an antibody (also referred to as "core fucose") (International Publication Nos. WO 2005/035586, WO 2002/31140, WO 00/61739), and a controlling method through modification of an amino acid residue in the Fc region of an antibody. The effector activity of the antibody including a non-natural amino acid according to the present invention can be controlled by using any of the methods.

"Effector activity" refers to antibody-dependent activity caused via the Fc region of an antibody. Examples of the effector activity include antibody-dependent cellular cytotoxicity activity (ADCC activity), complement-dependent cytotoxicity activity (CDC activity), and antibody-dependent phagocytosis (ADP activity) by a phagocyte such as a macrophage and a dendritic cell.

The effector activity of an antibody can be increased or decreased through controlling the content of fucose adding to N-acetylglucosamine at the reducing terminus of an N-bound composite sugar chain on the Fc region. Examples of the method for decreasing the content of fucose adding to an N-bound composite sugar chain bound to the Fc region of an antibody include a method in which an antibody including no fucose bound thereto is obtained through expression of the antibody by using a CHO cell with the α1,6-fucose transferase gene deleted. The antibody including no fucose bound thereto has high ADCC activity.

On the other hand, examples of the method for increasing the content of fucose adding to an N-bound composite sugar chain bound to the Fc region of an antibody include a method in which an antibody including fucose bound thereto is obtained through expression of the antibody by using a host cell including an α1,6-fucose transferase gene introduced therein. The antibody including fucose bound thereto has ADCC activity lower than that of an antibody including no fucose bound thereto.

Alternatively, the ADCC activity or CDC activity can be increased or decreased through modification of an amino acid residue in the Fc region of an antibody. For example, the CDC activity of an antibody can be increased by using an amino acid sequence of the Fc region described in U.S. Patent Application Publication No. 2007/0148165. The ADCC activity or CDC activity can be increased or decreased through amino acid modification described in any of U.S. Pat. Nos. 6,737,056, 7,297,775, and 7,317,091.

Further, an antibody having controlled effector activity can be obtained by using any combination of the above methods for one antibody.

5. Evaluation of Activity of Antibody or Antibody Fragment Thereof Including Non-Natural Amino Acid According to Present Invention after Purification Evaluation of the activity of the antibody or antibody fragment thereof including a non-natural amino acid according to the present invention after purification can be performed as follows.

The binding activity to an antigen or binding activity to a cultured antigen-positive cell strain can be measured, for example, by using any of a binding assay, fluorescent antibody method [Cancer Immunol. Immunother., 36, 373 (1993)], surface plasmon resonance method with a Biacore system or the like, and so on.

For the antigen, for example, a transgenic cell obtained by introducing an expression vector including a cDNA encoding an antigen into any of *Escherichia coli*, a yeast, an insect cell, an animal cell, and so on, recombinant protein, or purified polypeptide or partial peptide obtained from a human tissue can be used.

In the case that the antigen is partial peptide, a conjugate with carrier protein such as BSA and KLH can be produced for use.

The procedure of the binding assay is as follows. An antigen is aliquoted into a plate such as a 96-well plate and immobilized, and then a test substance such as serum, culture supernatant for a hybridoma, and a purified monoclonal antibody is aliquoted thereto as a first antibody to react together. After thorough washing with PBS, PBS containing 0.05% tween 20 (PBS-Tween), or the like, an anti-immunoglobulin antibody labeled with, for example, biotin, an enzyme, a chemiluminescent substance, or a radioactive compound is aliquoted as a second antibody to react together. After thorough washing with PBS-Tween, the antigen-binding activity of the test substance is measured through detection reaction according to the labeling substance for the second antibody.

The ADCC activity or CDC activity to a cultured antigen-positive cell strain is measured by using a known measurement method [Cancer Immunol. Immunother., 36, 373 (1993)].

The binding activity of the antibody according to the present invention to FcγR and FcR can be confirmed through production of recombinant FcγR IIIA protein or recombinant neonatal FcR (neonatal Fc receptor, FcRn) protein followed by measurement of the binding activity thereto (U.S. Patent Application Publication No. 2004/0259150).

In the case that a modified antibody or modified antibody fragment is produced by modifying the antibody or antibody fragment thereof according to the present invention with a pharmaceutical agent having cell-killing activity, the cell-killing activity of the modified antibody or antibody fragment thereof can be measured by using the following method.

Appropriate cells to which the modified antibody or antibody fragment thereof is to bind are seeded in a plate such as a 96-well plate. Thereto, the modified antibody or antibody fragment thereof in an appropriate concentration is added, and incubated. Thereafter, the survival of each cell in the plate is detected with a reagent capable of detecting the survival of a cell such as CellTiter-Glo™ (from Promega Corporation), and the viability (%) of the cells is calculated.

6. Use of Antibody or Antibody Fragment Thereof Including Non-Natural Amino Acid According to Present Invention for Medicine The antibody or antibody fragment thereof including a non-natural amino acid according to the present invention can be used for a medicine such as a diagnostic agent and a therapeutic agent.

The medicine containing the antibody or antibody fragment thereof including a non-natural amino acid according to the present invention can be administered singly as a therapeutic agent. However, it is preferred in common cases to provide the medicine as a composition produced from a mixture of the medicine and one or more pharmacologically acceptable carriers by using any method well known in the field of pharmaceutics, that is, as a pharmaceutical formulation.

It is desirable to use the most effective route of administration for the therapy, and examples of the route of administration include oral administration, and parenteral administration such as intraoral administration, intratracheal administration, rectal administration, subcutaneous administration, intramuscular administration, and intravenous administration. For an antibody formulation, intravenous administration is preferred.

Examples of the form of administration include a spray, a capsule, a tablet, a granule, a syrup, an emulsion, a suppository, an injection, an ointment, and a tape.

Examples of the formulation suitable for oral administration include an emulsion, a syrup, a capsule, a tablet, a powder, and a granule.

A liquid preparation such as an emulsion and a syrup can be produced by using an excipient, examples of which include water, a saccharide such as sucrose, sorbitol, and fructose, a glycol such as polyethylene glycol and propylene glycol, an oil such as sesame oil, olive oil, and soybean oil, a preservative such as p-hydroxybenzoate, and a flavor such as strawberry flavor and peppermint flavor.

A capsule, a tablet, a powder, a granule, and so on, can be produced by using an excipient, examples of which include a diluent such as lactose, glucose, sucrose, and mannitol, a disintegrator such as starch and sodium alginate, and a lubricant such as magnesium stearate and talc, a binder such as polyvinyl alcohol, hydroxypropyl cellulose, and gelatin, a surfactant such as fatty acid ester, and a plasticizer such as glycerin.

Examples of the formulation suitable for parenteral administration include an injection, a suppository, and a spray.

An injection is prepared by using a carrier or the like consisting of salt solution, glucose solution, or a mixture of them. Alternatively, a powder injection can be prepared through freeze-drying the antibody or antibody fragment thereof according to the present invention according to a conventional method followed by adding sodium chloride thereto.

A suppository is prepared by using a carrier such as cacao butter, hydrogenated fat, and carboxylic acid.

A spray is prepared by using a carrier or the like which neither stimulates the antibody or antibody fragment thereof according to the present invention itself nor irritates the oral cavity and airway mucosa, and is capable of dispersing the antibody or antibody fragment thereof according to the present invention as fine particles therein to facilitate absorption thereof.

Specific examples of the carrier include lactose and glycerin. An aerosol formulation, a dry powder formulation, and the like can be produced if the characteristics of the antibody or antibody fragment thereof according to the present invention and the carrier to be used permit. The components exemplified as excipients for oral agents can be similarly added to any of these parenteral agents.

The dose or frequency of administration depends on the therapeutic effect intended, administration method, duration of therapy, age, body weight, and so on, and is typically 10 μg/kg to 20 mg/kg per day for an adult as an amount of active ingredient.

In the case that the antibody or antibody fragment thereof according to the present invention is used as an antitumor agent, examples of the method for examining the antitumor effect to various tumor cells include a method with an in vitro experiment or an in vivo experiment.

Examples of the in vitro experiment include cytotoxic activity measurement, CDC activity measurement, and ADCC activity measurement. Examples of the in vivo experiment include an antitumor experiment with a tumor system in an experimental animal such as a mouse.

EXAMPLES

Hereinafter, the present invention will be described with reference to Examples. However, the present invention is never limited to the following Examples.

Example 1

Production of Recombinant *Escherichia coli* by Using *Escherichia coli* W3110 Strain as Host To produce an antibody with ortho-azido-Z-lysine (hereinafter, represented as "o-Az-Z-Lys"), a non-natural amino acid, introduced therein, a recombinant *Escherichia coli* (hereinafter, represented as "W3110RF-Zero strain") was produced according to the following method by using an *Escherichia coli* W3110 strain (ATCC) as a parent strain for host cells.

According to a method described in WO 2011/158895, a bacterial artificial chromosome (BAC) with the gene prfA, which is possessed by a wild-type W3110 strain and encodes the release factor RF-1, deleted and with the nonsense codon of each of the genes coaD, hda, hemA, mreC, murF, lolA, lpxK, and SucB, which loses the function through deletion of the prfA gene, modified from TAG to TAA was introduced to produce a W3110RF-Zero cell.

Example 2

Construction of Expression Vector for Anti-Her2 Humanized Antibody-Fab (Trastuzumab-Fab) with o-Az-Z-Lys Introduced Therein Obtained by Substituting Lys Residue with o-Az-Z-Lys According to the following method, Trastuzumab-Fabs with o-Az-Z-Lys introduced therein was produced from the Trastuzumab-Fab, which is the Fab of an anti-Her2 humanized antibody (IgG1, κ), by substituting a Lys residue in the CH1 or Cκ with o-Az-Z-Lys.

First, the method for producing an expression vector for the Fab for *Escherichia coli* is described in the following.

(1) Construction of Basic Expression Vector for Fab with o-Az-Z-Lys Introduced Therein for *Escherichia coli*

The commercially available vector pFLAG-CTS (from Sigma-Aldrich Co., LLC.) was used for the basic expression vector for the Fab with o-Az-Z-Lys introduced therein for *Escherichia coli*. A Nucleotide sequence of pyrrolysine tRNA (hereinafter, also represented as "Pyl tRNA" or "tRNA$^{Pyl}$") and a nucleotide sequence encoding pyrrolysyl tRNA synthetase (hereinafter, also represented as "Pyl RS") were inserted into the direct downstream of the lac repressor gene lad of the pFLAG-CTS according to a method described in a literature [Mukai et al, Biochem Biophys Res Commun 411, 757-761, 2011]. Hereinafter, the expression vector is represented as "pFLAG-CTS PylTS". For the nucleotide sequence of Pyl tRNA and the nucleotide sequence encoding Pyl RS, the nucleotide sequence encoding wild-type Pyl tRNA derived from *Methanosarcina mazei* (SEQ ID NO: 1) and the nucleotide sequence encoding the amino acid sequence of a mutant of Pyl RS derived from *Methanosarcina mazei* (Y306A/Y384F) [Yanagisawa et al, Chem Biol., 15, 1187-1197, 2008] (SEQ ID NO: 8) were used, respectively.

(2) Construction of Expression Vector for Trastuzumab-Fab with o-Az-Z-Lys Introduced Therein for *Escherichia coli*

(2-1) Construction of Expression Vector for Wild-Type Trastuzumab-Fab

A Nucleotide sequence encoding the Trastuzumab-Fab was designed on the basis of the amino acid sequence of the light chain region of the Fab of Trastuzumab (SEQ ID NO: 2) and the amino acid sequence of the heavy chain region of the Fab of Trastuzumab (SEQ ID NO: 3) each described in Proc. Natl. Acad. Sci. U.S.A., 89, 4285 (1992).

The nucleotide sequence was designed so that a BsiWI restriction enzyme recognition sequence was positioned at the boundary between the light chain variable region and the light chain constant region and an NheI restriction enzyme recognition sequence was positioned at the boundary between the heavy chain variable region and the heavy chain constant region.

For both the light chain and the heavy chain, a PelB secretion signal (SEQ ID NO: 5) was linked under control by a nucleotide sequence consisting of a Tac promoter and a Shine-Dalgarno sequence (SEQ ID NO: 4).

For the light chain, a nucleotide sequence formed by adding an NdeI restriction enzyme recognition sequence to the 5'-terminus of the nucleotide sequence for the light chain of the Fab and adding an HindIII restriction enzyme recognition sequence to the 3'-terminus (SEQ ID NO: 6) was obtained through total synthesis. With use of a restriction enzyme NdeI site and HindIII site, the nucleotide sequence was inserted into the pFLAG-CTS PylTS produced in (1).

For the heavy chain, a nucleotide sequence formed by adding an NdeI restriction enzyme recognition sequence to the 5'-terminus of the nucleotide sequence for the heavy chain of the Fab and adding a His tag and an SalI restriction enzyme recognition sequence to the 3'-terminus (SEQ ID NO: 7) was obtained through total synthesis. With use of a restriction enzyme NdeI site and EcoRI site, the nucleotide sequence was inserted into pFLAG-CTS-H obtained by inserting a known EcoRI restriction enzyme recognition sequence into the upstream of the Taq promoter of the pFLAG-CTS.

(2-2) Introduction of Amber (TAG) Codon Mutation

The expression vectors for Trastuzumab-Fabs with o-Az-Z-Lys introduced therein listed in Table 3 were produced by using the following method.

On the basis of the nucleotide sequence encoding the light chain or heavy chain of the wild-type Trastuzumab-Fab produced in (2-1), nucleotide sequences each with the codon corresponding to a site for introduction of o-Az-Z-Lys substituted with an amber (TAG) codon (SEQ ID NOs: 9 to 62) were obtained through total synthesis. The thus-produced Trastuzumab-Fabs with o-Az-Z-Lys introduced therein and the nucleotide sequences with a TAG codon introduced therein obtained through total synthesis for production of the Fabs are listed in Table 3.

Each of the nucleotide sequences shown in SEQ ID NOs: 9 to 16 and 28 to 47 is a nucleotide sequence obtained by setting the 5'-terminus of the nucleotide sequence for the light chain constant region of Trastuzumab to a BsiWI restriction enzyme recognition sequence and adding an HindIII restriction enzyme recognition sequence to the 3'-terminus. Through treatment of the nucleotide sequence with the restriction enzymes BsiWI and HindIII, the nucleotide sequence included in the pFLAG-CTS PylTS produced in (2-1) for the light chain constant region of the wild-type Fab was substituted with a nucleotide sequence for the light chain constant region with a TAG codon introduced therein.

Each of the nucleotide sequences shown in SEQ ID NOs: 17 to 23, 26, 27, and 48 to 62 is a nucleotide sequence obtained by setting the 5'-terminus of the nucleotide sequence for the heavy chain constant region of Trastuzumab to an NheI restriction enzyme recognition sequence and adding an SalI restriction enzyme recognition sequence to the 3'-terminus. Through treatment of the nucleotide sequence with the restriction enzymes NheI and SalI, the nucleotide sequence included in the pFLAG-CTS-H produced in (2-1) for the heavy chain constant region of the wild-type Fab was substituted with a nucleotide sequence for the heavy chain constant region with a TAG codon introduced therein.

Each of the nucleotide sequences shown in SEQ ID NOs: 24 and 25 is a nucleotide sequence obtained by adding an NdeI restriction enzyme recognition sequence to the 5'-terminus of the nucleotide sequence for the heavy chain constant region and heavy chain variable region of Trastuzumab with the codon corresponding to a site for introduction of o-Az-Z-Lys substituted with a TAG codon and adding a His tag and an SalI restriction enzyme recognition sequence to the 3'-terminus.

(2-3) Construction of Expression Vector for Trastuzumab-Fab with o-Az-Z-Lys Introduced Therein for *Escherichia coli*

Trastuzumab-Fab expression vectors were constructed through treatment of the vectors obtained in (2-1) and (2-2) (each vector including one of the nucleotide sequences shown in SEQ ID NOs: 9 to 23 and 26 to 62) with the restriction enzymes EcoRI and SalI followed by insertion of a nucleotide sequence for an intended heavy chain into each pFLAG-CTS PylTS including a nucleotide sequence for an intended light chain inserted thereinto.

Each of the nucleotide sequences shown in SEQ ID NOs: 24 and 25 obtained through total synthesis was inserted into the pFLAG-CTS-H with use of a restriction enzyme NdeI site and EcoRI site to construct the expression vector.

Example 3

Preparation of Wild-Type Trastuzumab-Fab and Trastuzumab-Fab with o-Az-Z-Lys Introduced Therein To prepare a Trastuzumab-Fab with o-Az-Z-Lys introduced therein, each of the Trastuzumab-Fab expression vectors for *Escherichia coli* constructed in Example 2 was introduced into the W3110 RF-zero strain produced in Example 1.

Each of the Trastuzumab-Fab expression vectors was suspended in sterile distilled water to a concentration of 10 ng/μL. This DNA solution in a volume of 3 μL was added to 50 μL of competent cells, and the resultant was gently mixed together, and aliquoted into Eppendorf tubes, which were maintained on ice for 30 minutes. Subsequently, the Eppendorf tubes were maintained in a water bath at 42° C. for 30 seconds, and then left to stand on ice again for 2 minutes.

After 500 μL of a sterile LB medium (from DIFCO) with Z-Lys (from Bachem) at a final concentration of 0.1 mg/mL added thereto was added, shaking culture was performed in an incubator set at 37° C. for 60 minutes. After the culturing, the cultured product was totally plated in an LB plate [1.5% (W/V) agarose] with Z-Lys (from Bachem) at a final concentration of 0.1 mg/mL and ampicillin (from Wako Pure Chemical Industries, Ltd.) at a final concentration of 100 μg/mL added thereto. Culturing was performed in an incubator set at 37° C. overnight, and the *Escherichia coli* growing in the plate was selected as a strain for transgenesis.

The thus-obtained transformed strain was subjected to shaking culture by using 10 mL of an LB medium with Z-Lys at a final concentration of 0.1 mg/mL added thereto at 37° C. overnight. The resulting bacterial cell solution was seeded in 100 mL of Super Broth [MOPS (from NACALAI TESQUE, INC.): 1 g, Tryptone (from DIFCO): 3 g, Yeast Extract (from DIFCO): 2 g] with o-Az-Z-Lys (synthesized by GVK Biosciences Private Limited according to a method described in Reference Example 1) at a final concentration of 1 mM and ampicillin (from Wako Pure Chemical Industries, Ltd.) at a final concentration of 100 μg/mL added thereto, and cultured at 37° C.

When the optical density value of the bacterial cell solution at 600 nm (hereinafter, represented as "OD600") reached 2.0, the culturing was stopped, and the bacterial cell solution was left to stand at room temperature for approximately 15 minutes. Isopropyl-β-thiogalactopyranoside (IPTG) (from NACALAI TESQUE, INC.) at a final concentration of 1.0 mmol/L was added to the bacterial cell solution, and the bacterial cell solution was subjected to shaking culture in a BioShaker set at 22° C. at 50 rpm overnight for expression of the Fab.

The bacterial cell solution after the culturing was subjected to centrifugation [CR21E (from Hitachi, Ltd.), 7000 rpm, 4° C., 5 minutes], and the weight of the resulting precipitate was measured, and a buffer containing 20 mM citric acid (from NACALAI TESQUE, INC.), 150 mM NaCl (from NACALAI TESQUE, INC.), and 2 mM EDTA (from NACALAI TESQUE, INC.) at pH 6.0 (hereinafter, represented as "citrate buffer") in a volume of 10 mL per 1 g of Escherichia coli was added thereto, and the precipitate was sufficiently suspended. The suspension was subjected to shaking culture with warming by using a thermostatic chamber with a shaker (from Yamato Scientific Co., Ltd.) set at 63° C. for 15 minutes. Thereafter, the bacterial cells were precipitated through centrifugation [CR21E (from Hitachi, Ltd.), 7000 rpm, 4° C., 15 minutes], and the resulting supernatant was filtered through a filter [Millex-G 0.22 μm (from Millipore Corporation)] and used for purification described in the following.

A Poly-Prep column (from Bio-Rad Laboratories, Inc.) was packed with 0.5 mL of Prosep G resin (from Millipore Corporation), and washed with 10 mL of the citrate buffer. The Fab-expressing culture supernatant prepared in the above was applied to the column, and washed with 10 mL of the citrate buffer, and then washed sequentially with 2 mL of a buffer containing 100 mM citric acid (from NACALAI TESQUE, INC.), 150 mM NaCl (from NACALAI TESQUE, INC.), and 2 mM EDTA (from NACALAI TESQUE, INC.) at pH 5.0, and 2 mL of a buffer containing 100 mM citric acid (from NACALAI TESQUE, INC.), 150 mM NaCl (from NACALAI TESQUE, INC.), and 2 mM EDTA (from NACALAI TESQUE, INC.) at pH 3.5, in the order presented. Thereafter, elution was performed with 2 mL of a buffer containing 100 mM citric acid (from NACALAI TESQUE, INC.), 150 mM NaCl (from NACALAI TESQUE, INC.), and 2 mM EDTA (from NACALAI TESQUE, INC.) at pH 3.0, and immediately 700 μL of 1.0 M Tris-HCl (from NACALAI TESQUE, INC.) was added to the eluted fraction to neutralize it.

The eluted fraction was subjected to buffer exchange with a buffer containing 20 mM citric acid (from NACALAI TESQUE, INC.) and 150 mM NaCl (from NACALAI TESQUE, INC.) at pH 6.0 (hereinafter, represented as "storage citrate buffer") by using an Amicon Ultra-4 30K (from Millipore Corporation). Centrifugal concentration [CF15R (from Hitachi, Ltd.), 15000 rpm, 4° C., 5 minutes] was performed four times with filling with an appropriate amount of a buffer, and the supernatant was collected and used as a final sample in the subsequent experiment.

Mass spectrometry was performed for the thus-obtained Fabs with o-Az-Z-Lys introduced therein according to a conventional method by using the mass spectrometer Synapt G2 HDMS from Waters Corporation to find that the measured value coincided with the theoretical molecular weight for any of the Fabs. This result confirmed that one molecule of o-Az-Z-Lys was introduced into one molecule of the Trastuzumab-Fab, and thus the Fabs with o-Az-Z-Lys introduced therein were successfully produced.

Example 4

Analysis of Reactivity Between Trastuzumab-Fab with o-Az-Z-Lys Introduced Therein and Alexa 488 DIBO The reactivity between each of the Trastuzumab-Fabs with o-Az-Z-Lys introduced therein obtained in Example 3 and Alexa 488 DIBO was measured by using a method described below. Click chemistry was used for the reaction.

Each Trastuzumab-Fab with o-Az-Z-Lys introduced therein obtained in Example 3 at a concentration of 5 μM was prepared with DPBS (from NACALAI TESQUE, INC.). Thereto, 40 equivalents of Click-IT Alexa Fluor 488 DIBO Alkyne (from Life Technologies) with respect to each Trastuzumab-Fab with o-Az-Z-Lys introduced therein was added, and reacted at room temperature overnight.

The resulting reaction solution was analyzed by using cation exchange chromatography to measure the reactivity between the Trastuzumab-Fab with o-Az-Z-Lys introduced therein and Alexa 488. The cation exchange chromatography was performed by using a Prominence (from Shimadzu Corporation) under conditions as follows: column: TSKgel SP-5PW (from Tosoh Corporation); eluent A: 20 mM acetate buffer (pH 5.0); eluent B: 1M NaCl, 20 mM acetate buffer (pH 5.0); flow rate: 1 mL/min; temperature: 25° C. An SPD-M10A (from Shimadzu Corporation) was used as a detector, and monitoring was performed for the optical densities at wavelengths of 280 nm and 495 nm. By using the area values at the optical densities, the reactivity (%) was calculated from equations below. The results are listed in Table 3. The reactivity reaches 100% when one molecule of Alexa 488 is added to one molecule of the Trastuzumab-Fab with o-Az-Z-Lys introduced therein.

Fab concentration (M)={(area value at wavelength of 280 nm)−0.11×(area value at wavelength of 495 nm)}/67980

Reactivity (%)=[area value at wavelength of 495 nm/(71,000×Fab concentration (M))]×100

Here, the value 67980 is the molar extinction coefficient of the Trastuzumab-Fab, and the value 71,000 is the molar extinction coefficient of Alexa 488.

Table 3 shows the accessible surface area ratio (hereinafter, represented as "ASA Ratio (S)") of the side chain of a Lys residue substituted with o-Az-Z-Lys for each Trastuzumab-Fab in combination. Each ASA Ratio (S) was determined by dividing the accessible surface area of the side chain of an amino acid residue of interest in the protein by the accessible surface area of the side chain of X in Gly-X-Gly (X is an amino acid residue of interest). The accessible surface area of the side chain of an amino acid residue of interest in each Trastuzumab-Fab was calculated by using three-dimensional structure data of PDB ID: 1N8Z registered in the Protein Data Bank (PDB) [http://www.rcsb.org/pdb] and an MOE ASA Calculator program (provided by Ryoka Systems Inc. (2011)) to operate under a Molecular Operating Environment (MOE) 2013.08 from Chemical Computing Group ULC in Canada. A larger value for the ASA Ratio(S) of an amino acid residue of interest indicates that the amino acid residue of interest is present near the surface of the protein.

TABLE 3

| Constant region | Site for introduction of o-Az-Z-Lys (EU numbering) | Amino acid residue substituted with o-Az-Z-Lys | Nucleotide sequence with TAG codon introduced therein | ASA Ratio(S) | Reactivity (%) |
| --- | --- | --- | --- | --- | --- |
| Cκ | 126 | Lys | SEQ ID NO: 9 | 0.65 | 63.8 |
| Cκ | 145 | Lys | SEQ ID NO: 10 | 0.64 | 90.9 |
| Cκ | 149 | Lys | SEQ ID NO: 11 | 0.35 | 94.3 |
| Cκ | 169 | Lys | SEQ ID NO: 12 | 0.91 | 92.6 |
| Cκ | 183 | Lys | SEQ ID NO: 13 | 0.48 | 98.5 |
| Cκ | 188 | Lys | SEQ ID NO: 14 | 0.64 | 74.5 |
| Cκ | 190 | Lys | SEQ ID NO: 15 | 0.57 | 70.3 |
| Cκ | 207 | Lys | SEQ ID NO: 16 | 0.20 | 104.0 |
| $CH_1$ | 121 | Lys | SEQ ID NO: 17 | 0.73 | 87.2 |
| $CH_1$ | 133 | Lys | SEQ ID NO: 18 | 0.44 | 102.2 |
| $CH_1$ | 147 | Lys | SEQ ID NO: 19 | 0.08 | 32.0 |
| $CH_1$ | 205 | Lys | SEQ ID NO: 20 | 0.62 | 96.4 |
| $CH_1$ | 210 | Lys | SEQ ID NO: 21 | 0.66 | 91.3 |
| $CH_1$ | 213 | Lys | SEQ ID NO: 22 | 0.36 | 9.7 |
| $CH_1$ | 214 | Lys | SEQ ID NO: 23 | 0.53 | 66.4 |
| $CH_1$ | 118 | Ala | SEQ ID NO: 24 | 0.55 | 92.9 |
| $CH_1$ | 119 | Ser | SEQ ID NO: 25 | 1.00 | 69.9 |
| $CH_1$ | 162 | Ala | SEQ ID NO: 26 | 0.92 | 55.1 |
| $CH_1$ | 176 | Ser | SEQ ID NO: 27 | 1.00 | 34.9 |

As shown in Table 3, the reactivity between a Trastuzumab-Fab with o-Az-Z-Lys introduced therein and Alexa 488 depended on the site for introduction of o-Az-Z-Lys. Other Fabs with an amino acid residue having an ASA Ratio (S) of 0.9 or lower substituted with o-Az-Z-Lys tended to have higher reactivity with Alexa 488 than Fabs with an amino acid residue having an ASA Ratio (S) of 0.9 to 1 substituted with o-Az-Z-Lys. Especially, Fabs with an amino acid residue having an ASA Ratio (S) of 0.2 to 0.4 substituted with o-Az-Z-Lys tended to have even higher reactivity with Alexa 488.

Example 5

Construction of expression vector for Trastuzumab-Fab with o-Az-Z-Lys introduced therein and anti-IGF-1R human antibody-Fab (Cixutumumab-Fab) with o-Az-Z-Lys introduced therein, each with amino acid residue having ASA Ratio (S) of 0.2 to 0.4 or hydrophobic amino acid residue substituted with o-Az-Z-Lys In view of the results in Example 4, the following experiment was carried out to find out a site for introduction of o-Az-Z-Lys useful for production of an antibody-Fab with o-Az-Z-Lys introduced therein which allows chemical modification at high efficiency.

Various Fabs with o-Az-Z-Lys introduced therein were produced through substitution of every single amino acid residue having an ASA Ratio (S) of 0.2 to 0.4 or hydrophobic amino acid residue, regardless of its ASA Ratio (S), present in the heavy chain or light chain constant region of each Fab, and the reactivity with Alexa 488 was measured for each of the Fabs.

An expression vector for each Trastuzumab-Fab with o-Az-Z-Lys introduced therein for *Escherichia coli*, in which an amino acid residue having an ASA Ratio (S) of 0.2 to 0.4 or hydrophobic amino acid residue in the (κ light chain constant region or heavy chain constant region CH1 was substituted with o-Az-Z-Lys, was constructed by using the method in Example 2. The thus-produced Trastuzumab-Fabs with o-Az-Z-Lys introduced therein and nucleotide sequences with a TAG codon introduced therein for the light chain or heavy chain (SEQ ID NOs: 28 to 62), the nucleotide sequences obtained through total synthesis for production of expression vectors for the Fabs, are listed in Tables 4 and 5.

In addition, an expression vector for each anti-IGF-1R human antibody (IgG1, λ)-Fab (hereinafter, represented as "Cixutumumab-Fab") with an amino acid residue having an ASA Ratio (S) of 0.2 to 0.4 or hydrophobic amino acid residue in the λ light chain constant region substituted with o-Az-Z-Lys was produced by using the method in Example 2.

The expression vectors for the Cixutumumab-Fab and Cixutumumab-Fab with o-Az-Z-Lys introduced therein were designed on the basis of the amino acid sequence of the light chain region of the Fab of Cixutumumab (SEQ ID NO: 63) and the amino acid sequence of the heavy chain region of the Fab of Cixutumumab (SEQ ID NO: 64) [WHO Drug Information., 22, 317 (2008)].

For the light chain, the nucleotide sequence for the light chain region of the Fab of Cixutumumab and nucleotide sequences each formed by adding an NdeI restriction enzyme recognition sequence to the 5'-terminus of a nucleotide sequence obtained by introducing a TAG mutation into the nucleotide sequence for the light chain region of the Fab of Cixutumumab and adding an HindIII restriction enzyme recognition sequence to the 3'-terminus (SEQ ID NOs: 65, 67 to 93) were obtained through total synthesis. The Cixutumumab-Fabs with o-Az-Z-Lys introduced therein and nucleotide sequences with a TAG mutation introduced therein for the light chain, the nucleotide sequences obtained through total synthesis for production of expression vectors for the Fabs, are listed in Table 6. For the heavy chain, a nucleotide sequence shown in SEQ ID NO: 66 was obtained through total synthesis.

Each of the nucleotide sequences for the light chain shown in SEQ ID NOs: 65 and 67 to 93 was introduced into the pFLAG-CTS PylTS with use of a restriction enzyme NdeI site and HindIII site. The nucleotide sequence for the heavy chain shown in SEQ ID NO: 66 was introduced into each of the vectors obtained with use of a restriction enzyme EcoRI site and SalI site, and thus expression vectors for the Cixutumumab-Fab and Cixutumumab-Fabs with o-Az-Z-Lys introduced therein of interest were constructed.

Example 6

Preparation of Trastuzumab-Fab with o-Az-Z-Lys Introduced Therein and Cixutumumab-Fab with o-Az-Z-Lys Introduced Therein By using the vectors produced in Example 5, Trastuzumab-Fabs with o-Az-Z-Lys introduced therein and Cixutumumab-Fabs with o-Az-Z-Lys introduced therein were prepared in the same manner as in Example 3.

Mass spectrometry was performed for the thus-prepared Cixutumumab-Fabs with o-Az-Z-Lys introduced therein by using the method in Example 3 to find that the measured value coincided with the theoretical molecular weight for any of the Fabs. This result confirmed that one molecule of o-Az-Z-Lys was introduced into one molecule of the Cixutumumab-Fab, and thus the Fabs with o-Az-Z-Lys introduced therein were successfully produced.

Example 7

Analysis of Reactivity Between Trastuzumab-Fab with o-Az-Z-Lys Introduced Therein or Cixutumumab-Fab with o-Az-Z-Lys Introduced Therein and Alexa 488 DIBO The reactivity between each of the Trastuzumab-Fabs with o-Az-Z-Lys introduced therein and Cixutumumab-Fabs with o-Az-Z-Lys introduced therein obtained in Example 6 and Alexa 488 DIBO was measured in the same manner as in Example 4. A value of 74820 was used for the molar extinction coefficient of the Cixutumumab-Fab. Click chemistry was used for reaction between each Fab with o-Az-Z-Lys introduced therein and Alexa 488.

Tables 4 and 5 show the reactivity of each Trastuzumab-Fab with o-Az-Z-Lys introduced therein, and Table 6 shows the reactivity of each Cixutumumab-Fab with o-Az-Z-Lys introduced therein. In addition, the accessible surface area ratio (ASA Ratio (S)) of the side chain of an amino acid residue substituted with o-Az-Z-Lys was calculated for each Fab by using the method in Example 4. The results are listed in Tables 4 to 6. In calculation of the ASA Ratio (S), the three-dimensional structure data of PDB ID: 1N8Z were used for the Trastuzumab-Fabs with o-Az-Z-Lys introduced therein, and three-dimensional structure data of PDB ID: 3n9g were used for the Cixutumumab-Fabs with o-Az-Z-Lys introduced therein.

TABLE 4

| Constant region | Site for introduction of o-Az-Z-Lys (EU numbering) | Amino acid residue substituted with o-Az-Z-Lys | Nucleotide sequence with TAG codon introduced therein | ASA Ratio (S) | Reactivity (%) |
|---|---|---|---|---|---|
| Cκ | 119 | Pro | SEQ ID NO: 28 | 0.24 | 106.4 |
| Cκ | 138 | Asn | SEQ ID NO: 29 | 0.37 | 91.1 |
| Cκ | 141 | Pro | SEQ ID NO: 30 | 0.30 | 86.0 |
| Cκ | 147 | Gln | SEQ ID NO: 31 | 0.30 | 86.9 |
| Cκ | 155 | Gln | SEQ ID NO: 32 | 0.21 | 106.6 |
| Cκ | 158 | Asn | SEQ ID NO: 33 | 0.22 | 101.5 |
| Cκ | 161 | Glu | SEQ ID NO: 34 | 0.39 | 103.5 |
| Cκ | 167 | Asp | SEQ ID NO: 35 | 0.35 | 103.2 |
| Cκ | 180 | Thr | SEQ ID NO: 36 | 0.26 | 88.8 |
| Cκ | 191 | Val | SEQ ID NO: 37 | 0.38 | 104.3 |
| Cκ | 195 | Glu | SEQ ID NO: 38 | 0.26 | 108.1 |
| Cκ | 197 | Thr | SEQ ID NO: 39 | 0.30 | 99.4 |
| Cκ | 210 | Asn | SEQ ID NO: 40 | 0.40 | 109.7 |
| Cκ | 211 | Arg | SEQ ID NO: 41 | 0.30 | 101.2 |
| Cκ | 110 | Val | SEQ ID NO: 42 | 0.60 | 101.2 |
| Cκ | 112 | Ala | SEQ ID NO: 43 | 0.64 | 93.2 |
| Cκ | 153 | Ala | SEQ ID NO: 44 | 0.89 | 97.1 |
| Cκ | 154 | Leu | SEQ ID NO: 45 | 0.61 | 81.9 |
| Cκ | 184 | Ala | SEQ ID NO: 46 | 1.00 | 93.5 |
| Cκ | 205 | Val | SEQ ID NO: 47 | 0.43 | 100.4 |

TABLE 5

| Constant region | Site for introduction of o-Az-Z-Lys (EU numbering) | Amino acid residue substituted with o-Az-Z-Lys | Nucleotide sequence with TAG codon introduced therein | ASA Ratio (S) | Reactivity (%) |
|---|---|---|---|---|---|
| CH$_1$ | 120 | Thr | SEQ ID NO: 48 | 0.31 | 80.6 |
| CH$_1$ | 127 | Pro | SEQ ID NO: 49 | 0.22 | 90.8 |
| CH$_1$ | 131 | Ser | SEQ ID NO: 50 | 0.31 | 96.1 |
| CH$_1$ | 135 | Thr | SEQ ID NO: 51 | 0.24 | 96.3 |
| CH$_1$ | 148 | Asp | SEQ ID NO: 52 | 0.36 | 79.8 |
| CH$_1$ | 152 | Glu | SEQ ID NO: 53 | 0.29 | 81.9 |
| CH$_1$ | 159 | Asn | SEQ ID NO: 54 | 0.22 | 90.4 |
| CH$_1$ | 169 | Thr | SEQ ID NO: 55 | 0.28 | 82.6 |
| CH$_1$ | 173 | Val | SEQ ID NO: 56 | 0.26 | 93.7 |
| CH$_1$ | 177 | Ser | SEQ ID NO: 57 | 0.39 | 93.8 |
| CH$_1$ | 180 | Tyr | SEQ ID NO: 58 | 0.28 | 102.0 |
| CH$_1$ | 190 | Ser | SEQ ID NO: 59 | 0.35 | 83.0 |

TABLE 5-continued

| Constant region | Site for introduction of o-Az-Z-Lys (EU numbering) | Amino acid residue substituted with o-Az-Z-Lys | Nucleotide sequence with TAG codon introduced therein | Reactivity (%) ASA Ratio (S) | Reactivity (%) |
|---|---|---|---|---|---|
| CH₁ | 199 | Ile | SEQ ID NO: 60 | 0.38 | 101.2 |
| CH₁ | 129 | Ala | SEQ ID NO: 61 | 0.46 | 101.6 |
| CH₁ | 174 | Leu | SEQ ID NO: 62 | 0.64 | 98.5 |

TABLE 6

| Constant region | Site for introduction of o-Az-Z-Lys (EU numbering) | Amino acid residue substituted with o-Az-Z-Lys | Nucleotide sequence with TAG codon introduced therein | ASA Ratio (S) | Reactivity (%) |
|---|---|---|---|---|---|
| Cλ | 110 | Lys | SEQ ID NO: 67 | 0.57 | 92.3 |
| Cλ | 129 | Lys | SEQ ID NO: 68 | 0.65 | 87.4 |
| Cλ | 149 | Lys | SEQ ID NO: 69 | 0.22 | 75.4 |
| Cλ | 156 | Lys | SEQ ID NO: 70 | 0.82 | 76.7 |
| Cλ | 166 | Lys | SEQ ID NO: 71 | 0.17 | 94.1 |
| Cλ | 172 | Lys | SEQ ID NO: 72 | 0.45 | 90.0 |
| Cλ | 187 | Lys | SEQ ID NO: 73 | 0.70 | 82.6 |
| Cλ | 207 | Lys | SEQ ID NO: 74 | 0.51 | 84.8 |
| Cλ | 119 | Pro | SEQ ID NO: 75 | 0.24 | 80.5 |
| Cλ | 125 | Leu | SEQ ID NO: 76 | 0.28 | 116.0 |
| Cλ | 137 | Ser | SEQ ID NO: 77 | 0.28 | 32.0 |
| Cλ | 160 | Glu | SEQ ID NO: 78 | 0.24 | 92.8 |
| Cλ | 161 | Thr | SEQ ID NO: 79 | 0.24 | 90.5 |
| Cλ | 165 | Ser | SEQ ID NO: 80 | 0.29 | 92.9 |
| Cλ | 173 | Tyr | SEQ ID NO: 81 | 0.24 | 90.8 |
| Cλ | 180 | Ser | SEQ ID NO: 82 | 0.38 | 91.9 |
| Cλ | 189 | His | SEQ ID NO: 83 | 0.35 | 83.4 |
| Cλ | 191 | Ser | SEQ ID NO: 84 | 0.29 | 99.8 |
| Cλ | 195 | Gln | SEQ ID NO: 85 | 0.24 | 88.5 |
| Cλ | 197 | Thr | SEQ ID NO: 86 | 0.40 | 77.4 |
| Cλ | 205 | Val | SEQ ID NO: 87 | 0.34 | 93.6 |
| Cλ | 210 | Ala | SEQ ID NO: 88 | 0.33 | 135.2 |
| Cλ | 215 | Ser | SEQ ID NO: 89 | 0.36 | 108.6 |
| Cλ | 127 | Ala | SEQ ID NO: 90 | 0.57 | 84.9 |
| Cλ | 143 | Ala | SEQ ID NO: 91 | 1.00 | 92.1 |
| Cλ | 147 | Ala | SEQ ID NO: 92 | 0.60 | 88.0 |
| Cλ | 157 | Ala | SEQ ID NO: 93 | 1.00 | 65.6 |

As shown in Tables 4 and 5, most of the Fabs with o-Az-Z-Lys introduced therein, each with an amino acid residue having an ASA Ratio (S) of 0.2 to 0.4 or hydrophobic amino acid substituted with o-Az-Z-Lys, exhibited reactivity of as high as 80% or higher with Alexa 488, for both cases of substitution in the CH1 and κ chain constant region of the Trastuzumab-Fab. In addition, over half of the Fabs with o-Az-Z-Lys introduced therein exhibited very high reactivity of 90% or higher with Alexa 488. As shown in Table 4, similar results were obtained for the λ chain constant region of the Cixutumumab-Fab.

Since click chemistry was used for the reaction, production of a chemically modified product of an Fab with o-Az-Z-Lys introduced therein was achieved in a simple manner.

From these results, many sites for introduction of o-Az-Z-Lys which allow site-specific chemical modification with Alexa 488 at high efficiency were found for the CH1, Cκ, and Cλ of the Fab.

Example 8

Measurement of Antigen-Binding Activity of Each Trastuzumab-Fab with o-Az-Z-Lys Introduced Therein The antigen-binding activity of each of the Trastuzumab-Fabs with o-Az-Z-Lys introduced therein and wild-type Trastuzumab-Fab produced in Examples 3 and 6 was measured by using the following method.

Recombinant Her2 extracellular domain protein prepared according to a description in Protein Eng. Des. Sel., 17, 455 (2004) was diluted with DPBS (from NACALAI TESQUE, INC.) to a concentration of 1 μg/mL, and added to a 96-well ELISA plate (from Greiner Bio-One International GmbH) at 50 μL/well, and immobilized at 4° C. overnight. After washing with DPBS, DPBS containing 1% bovine serum albumin (BSA) (1%-BSA-PBS) (from Sigma-Aldrich Co., LLC.) was added at 150 μL/well, and the plate was left to stand at room temperature for 1 hour for adsorption.

After washing with DPBS, diluted solution of each of the Trastuzumab-Fabs obtained in Examples 3 and 6 was added at 50 μL/well and reacted at room temperature for 1 hour. After the reaction, washing was performed with PBS containing 0.05% Tween20 (from NACALAI TESQUE, INC.) (PBST), and peroxidase-labeled mouse anti-His tag antibody solution (from QIAGEN) diluted by 1000-fold with 1%-BSA-PBS was added at 50 μL/well, and the plate was left to stand at room temperature for 1 hour for reaction.

After the reaction, washing was performed with PBST, and the chromogenic substrate TMB (from Dako) was added at 50 μL/well, and the plate was left to stand at room temperature for 10 minutes for chromogenic reaction, and then 1N sulfuric acid (from NACALAI TESQUE, INC.) was added at 50 µL/well to terminate the chromogenic reaction. Thereafter, the antigen-binding activity was calculated for each Trastuzumab-Fab by using, as the measurement, a numerical value obtained by subtracting the absorbance at wavelength of 600 nm from the absorbance at wavelength of 450 nm, each acquired with the plate reader iMark (from Bio-Rad Laboratories, Inc.).

FIG. 1 shows representative examples of the antigen-binding activity calculated for the Trastuzumab-Fabs. As shown in FIG. 1, the Trastuzumab-Fabs with o-Az-Z-Lys introduced therein in each of which an amino acid residue at position 155, 158, 161, 167, or 180 of the κ light chain of the Trastuzumab-Fab was substituted with o-Az-Z-Lys each possessed binding activity equivalent to that of the wild-type Trastuzumab-Fab. Similar results were obtained for all of the other Trastuzumab-Fabs with o-Az-Z-Lys introduced therein listed in Tables 3 to 5.

These results demonstrate that introduction of o-Az-Z-Lys at any of the specified sites listed in Tables 3 to 5 in the CH1 or κ chain constant region of the Trastuzumab-Fab does not affect the antigen-binding activity of the Fab.

Example 9

Measurement of Antigen-Binding Activity of Each Cixutumumab-Fab with o-Az-Z-Lys Introduced Therein The antigen-binding activity of each of the Cixutumumab-Fabs with o-Az-Z-Lys introduced therein and the wild-type Cixutumumab-Fab produced in Example 6 was measured by using the method in Example 8.

Recombinant IGF-1R extracellular domain (from Research And Diagnostic Systems, Inc.) was diluted with DPBS (from NACALAI TESQUE, INC.) to a concentration of 2 µg/mL, and added to a 96-well ELISA plate (from Greiner Bio-One International GmbH) at 50 µL/well, and immobilized at 4° C. overnight. After washing with DPBS, 1%-BSA-PBS was added at 150 µL/well, and the plate was left to stand at room temperature for 1 hour for adsorption.

After washing with DPBS, diluted solution of each of the Cixutumumab-Fabs obtained in Example 6 was added at 50 µL/well and reacted at room temperature for 1 hour. After the reaction, washing was performed with PBST, and peroxidase-labeled mouse anti-His tag antibody solution (from QIAGEN) diluted by 1000-fold with 1%-BSA-PBS was added at 50 µL/well, and the plate was left to stand at room temperature for 1 hour for reaction.

After the reaction, washing was performed with PBST, and the chromogenic substrate TMB (from Dako) was added at 50 µL/well, and the plate was left to stand at room temperature for 10 minutes for chromogenic reaction, and then 1N sulfuric acid (from NACALAI TESQUE, INC.) was added at 50 µL/well to terminate the chromogenic reaction. Thereafter, the antigen-binding activity was calculated for each Cixutumumab-Fab by using, as the measurement, a numerical value obtained by subtracting the absorbance at wavelength of 600 nm from the absorbance at wavelength of 450 nm, each acquired with the plate reader iMark (from Bio-Rad Laboratories, Inc.).

Figure 2:
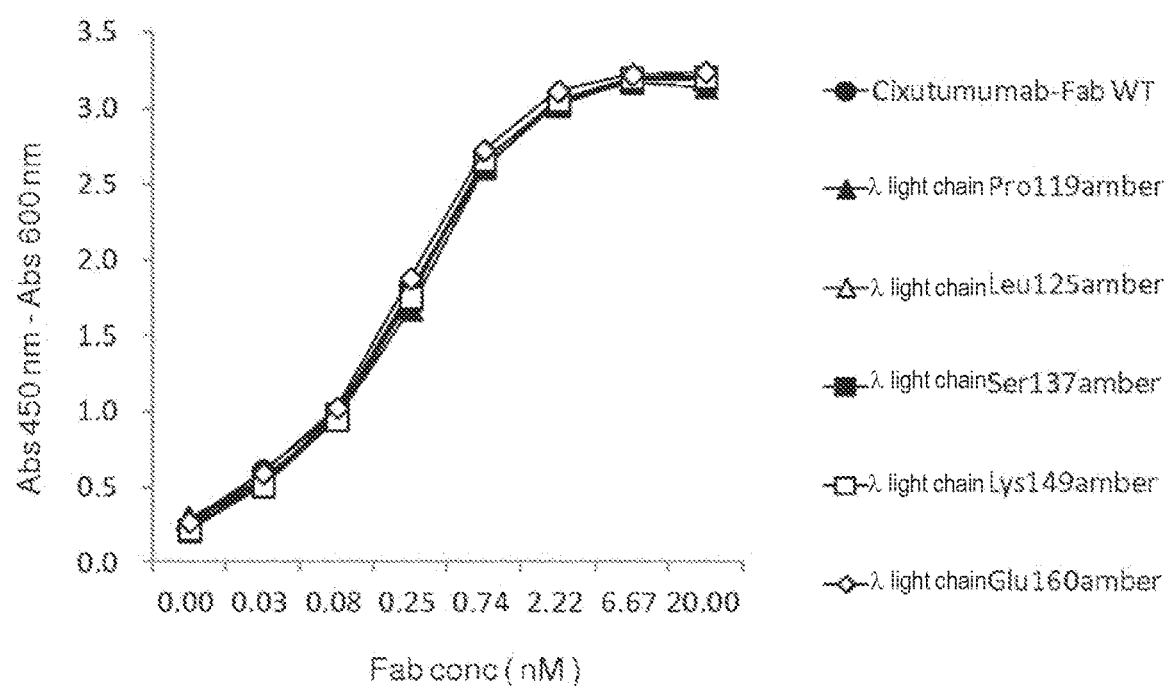
FIG. 2 shows the binding activity of Cixutumumab-Fabs with o-Az-Z-Lys introduced therein to IGF-1R, where the vertical axis represents numerical values calculated by subtracting the absorbance at 600 nm from the absorbance at 450 nm, and the horizontal axis represents Fab concentration (nM).

FIG. 2 shows representative examples of the antigen-binding activity calculated for the Cixutumumab-Fabs. As shown in FIG. 2, the Cixutumumab-Fabs with o-Az-Z-Lys introduced therein in each of which an amino acid residue at position 119, 125, 137, 149, or 160 of the λ light chain of the wild-type Cixutumumab-Fab was substituted with o-Az-Z-Lys each possessed binding activity equivalent to that of the wild-type Cixutumumab-Fab. Similar results were obtained for all of the other Cixutumumab-Fabs with o-Az-Z-Lys introduced therein listed in Table 6.

These results demonstrate that introduction of o-Az-Z-Lys at any of the specified sites listed in Table 6 in the λ chain constant region of the Cixutumumab-Fab does not affect the antigen-binding activity of the Fab.

Example 10

Production of Fabs with o-Az-Z-Lys Introduced Therein by Using Various Fabs and Measurement of Reactivity Thereof Among the Trastuzumab-Fabs with o-Az-Z-Lys introduced therein listed in Tables 3 to 5, six sites for introduction of o-Az-Z-Lys are listed in Table 7. Different Fabs with o-Az-Z-Lys introduced at a site listed in Table 7 were produced by using Fabs other than the Trastuzumab-Fab, and the reactivity was measured for each of the Fabs.

The Fabs used were the Farletuzumab-Fab, as the Fab of the anti-Folate Receptor 1 humanized antibody Farletuzumab (IgG1, κ); the Adalimumab-Fab, as the Fab of the anti-TNF-α human antibody Adalimumab (IgG1, κ); the Rituximab-Fab, as the Fab of the anti-CD-20 chimeric antibody Rituximab (IgG1, κ); and the Bevacizumab-Fab, as the Fab of the anti-VEGF humanized antibody (IgG1, κ) Bevacizumab.

Sequence information on DNAs encoding the amino acid sequences of the Fabs was acquired from WO 2005/080431 A2 for the Farletuzumab-Fab (SEQ ID NOs: 94 and 95); from [Marisic J. et al, J. Biol. Chem. 287, 8613-8620 (2012)] for the Adalimumab-Fab (SEQ ID NOs: 96 and 97); from [Du J. et al, J. Biol. Chem. 282, 15073-15080 (2007)] for the Rituximab-Fab (SEQ ID NOs: 98 and 99); and from [Chung C. et al, J. Biol. Chem. 291, 5500-5511 (2016)] for the Bevacizumab-Fab (SEQ ID NOs: 100 and 101). On the basis of the information, expression vectors for various Fabs with o-Az-Z-Lys introduced therein were produced by using the method in Example 2.

Each Fab expression vector obtained was introduced into the W3110 RF-zero strain produced in Example 1 to prepare each Fab with o-Az-Z-Lys introduced therein in the same manner as in Example 3.

Mass spectrometry was performed for the thus-obtained Fabs with o-Az-Z-Lys introduced therein in the same manner as in Example 3 to find that the measured value coincided with the theoretical molecular weight for any of the Fabs. This result confirmed that one molecule of o-Az-Z-Lys was introduced into one molecule of each Fab, and thus the Fabs with o-Az-Z-Lys introduced therein were successfully produced.

Thereafter, the reactivity between each Fab with o-Az-Z-Lys introduced therein and Alexa 488 in click chemistry was measured by using the method in Example 4. The results are shown in Table 7. Any of the Fabs with o-Az-Z-Lys introduced therein was found to react with Alexa 488 at high efficiency as with the case of the Trastuzumab-Fabs with o-Az-Z-Lys introduced therein.

These results demonstrate that an Fab with o-Az-Z-Lys introduced therein at position 197, 155, or 191 of the Cκ or at position 177, 199, or 131 of the CH1 according to the EU numbering allows production of its chemically modified product at high efficiency, regardless of the amino acid sequence of the variable region.

TABLE 7

| Constant region | Site for introduction of o-Az-Z-Lys (EU numbering) | Amino acid residue substituted with o-Az-Z-Lys | Reactivities of different Fabs with o-Az-Z-Lys introduced therein | | | | |
|---|---|---|---|---|---|---|---|
| | | | Trastuzumab-Fab | Farletuzumab-Fab | Adalimumab-Fab | Rituximab-Fab | Bevacizumab-Fab |
| Cκ | 197 | Thr | 103.3 | 90.1 | 89.5 | 71.9 | 69.0 |
| Cκ | 155 | Gln | 109.3 | 94.0 | 104.1 | 93.3 | 97.1 |
| Cκ | 191 | Val | 113.2 | 100.4 | 97.1 | 93.6 | 102.4 |
| CH1 | 177 | Ser | 100.7 | 84.8 | 86.7 | 89.0 | 72.3 |
| CH1 | 199 | Ile | 111.6 | 105.1 | 85.4 | 88.7 | 106.2 |
| CH1 | 131 | Ser | 112.0 | 93.9 | 105.2 | 117.6 | 99.9 |

Example 11

Production of Fab Homodimer

Feasibility of dimerization of Fabs via a linker was examined by using Trastuzumab-Fabs with o-Az-Z-Lys introduced therein. By using the methods in Examples 2 and 3, six Trastuzumab-Fabs with o-Az-Z-Lys introduced therein were produced through introducing o-Az-Z-Lys at each of six sites shown in Table 7, and an Fab homodimer as a product resulting from dimerization of identical Fabs was produced for each of the six Trastuzumab-Fabs with o-Az-Z-Lys introduced therein by using the following method.

A solution of each Trastuzumab-Fab with o-Az-Z-Lys introduced therein at a concentration of 100 µM was prepared, and mixed with 20 equivalents of the linker DBCO-PEG4-DBCO (from Click Chemistry Tools LLC.) and reacted at room temperature overnight. Thereafter, the unreacted linker was removed through ultrafiltration by using an Amicon Ultra-0.5 30K (from Millipore Corporation), and the resultant was mixed with 2 equivalents of the same Trastuzumab-Fab with o-Az-Z-Lys introduced therein and reacted at room temperature overnight. The reaction solution was purified through gel filtering by using a Superdex 200 column (from GE Healthcare) and fractionated to collect a fraction corresponding to the Fab dimer, and the fraction was concentrated by using an Amicon Ultra-0.5 30K, and the molecular weight was determined through SDS-PAGE.

A band at a molecular weight corresponding to the Fab dimer was found in the SDS-PAGE, and thus it was demonstrated that a dimer (Fab homodimer) of Trastuzumab with o-Az-Z-Lys introduced therein can be produced via a linker.

Example 12

Production of Fabs with o-Az-Z-Lys Introduced Therein at Plurality of Sites and Measurement of Reactivity Thereof Fabs each as a Trastuzumab-Fab with o-Az-Z-Lys introduced therein at a plurality of sites were produced, and the reactivity of each of the Fabs was measured. Trastuzumab-Fab expression vectors with codons at a plurality of sites substituted with an amber codon were produced by using the method in Example 2 with use of nucleotide sequences with TAG codons introduced therein as shown in Table 8. Each of the Fab expression vectors obtained was introduced into the 3110 RF-zero strain produced in Example 1, and different Fabs with o-Az-Z-Lys introduced therein were obtained by using the method in Example 3.

Mass spectrometry was performed for the thus-obtained Trastuzumab-Fabs with o-Az-Z-Lys introduced therein in the same manner as in Example 3 to find that the measured value coincided with the theoretical molecular weight for any of the Fabs. This result confirmed that an intended number of molecules of o-Az-Z-Lys were introduced into one molecule of the Fab.

The reactivity between each Trastuzumab-Fab with o-Az-Z-Lys introduced therein obtained and Alexa 488 in click chemistry was evaluated by using the method in Example 4. The reactivity (%) was calculated from equations below. In the case that two molecules of o-Az-Z-Lys are introduced into one molecule of the Trastuzumab-Fab, for example, the reactivity reaches 100% when two molecules of Alexa 488 are added to the Trastuzumab-Fab with o-Az-Z-Lys introduced therein, and the reactivity reaches 50% when one molecule of 488 is added.

Fab concentration (M)={(area value at wavelength of 280 nm)−0.11×(area value at wavelength of 495 nm)}/67980

Reactivity (%)=[area value at wavelength of 495 nm/(71,000×Fab concentration (M) calculated from above equation)/number of molecules of non-natural amino acid per molecule of Fab]× 100

The value 67980 is the molar extinction coefficient of the Fab, and the value 71,000 is the molar extinction coefficient of Alexa 488.

Table 8 shows the results. The results confirmed that even in the case that o-Az-Z-Lys is introduced into the Trastuzumab-Fab at four or fewer sites in total, the Fab with o-Az-Z-Lys introduced therein can react with Alexa 488 at high efficiency.

TABLE 8

Fabs with o-Az-Z-Lys introduced therein

| | Cκ | | | CH1 | | | |
|---|---|---|---|---|---|---|---|
| Antibody No. | Site for introduction of o-Az-Z-Lys (EU numbering) | Amino acid substituted with o-Az-Z-Lys | Nucleotide sequence with TAG codon introduced therein | Site for introduction of o-Az-Z-Lys (EU numbering) | Amino acid substituted with o-Az-Z-Lys | Nucleotide sequence with TAG codon introduced therein | Reactivity (%) |
| 1 | 155 | Gln | SEQ ID NO: 32 | 177 | Ser | SEQ ID NO: 57 | 84.2 |
| 2 | 155 | Gln | SEQ ID NO: 32 | 177 131 | Ser Ser | SEQ ID NO: 102 | 79.2 |
| 3 | 155 | Gln | SEQ ID NO: 32 | 177 199 131 | Ser Ile Ser | SEQ ID NO: 103 | 71.1 |
| 4 | 191 | Val | SEQ ID NO: 37 | 177 | Ser | SEQ ID NO: 57 | 92.8 |
| 5 | 191 | Val | SEQ ID NO: 37 | 177 131 | Ser Ser | SEQ ID NO: 102 | 82.2 |
| 6 | 191 | Val | SEQ ID NO: 37 | 177 199 131 | Ser Ile Ser | SEQ ID NO: 103 | 81.2 |

Example 13

Production of Chemically Modified Products of Trastuzumab-Fab with o-Az-Z-Lys Introduced Therein and Measurement of Cytotoxic Activity Thereof Each of the Trastuzumab-Fabs with o-Az-Z-Lys introduced therein at one or two site(s) produced in Example 3 and Example 12 was reacted with Mertansine (DM1-SH) to produce a chemically modified product of the Trastuzumab-Fab, and the cytotoxic activity was measured.

The six Fabs listed in Table 7, each as a Trastuzumab-Fab with o-Az-Z-Lys introduced therein at one site, were used. The two Fabs Antibody No. 1 and Antibody No. 4 listed in Table 8, each as a Trastuzumab-Fab with o-Az-Z-Lys introduced therein at two sites, were used.

Production of a chemically modified product and measurement of the cytotoxic activity were according to the following method.

A solution of each Trastuzumab-Fab with o-Az-Z-Lys introduced therein at a concentration of 20 μM was prepared with a buffer containing 20 mM citric acid (from NACALAI TESQUE, INC.), 150 mM NaCl (from NACALAI TESQUE, INC.), and 2 mM EDTA (from NACALAI TESQUE, INC.) at pH 4.0, and mixed with 8 equivalents of the linker DBCO-PEG4-Maleimide (from Click Chemistry Tools LLC.) and reacted at 4° C. overnight. Thereafter, the unreacted linker was removed through ultrafiltration by using an Amicon Ultra-0.5 30K (from Millipore Corporation), and the concentration of the resulting solution was adjusted to 30 μM with the citrate buffer described in Example 3, and the solution was mixed with 10 equivalents of the thiol group-containing pharmaceutical agent Mertansine (DM1-SH, from Santa Cruz Biotechnology, Inc.) and reacted at room temperature overnight. Thereafter, the unreacted pharmaceutical agent was removed through ultrafiltration by using an Amicon Ultra-0.5 30K (from Millipore Corporation). Mass spectrometry was performed in the same manner as in Example 3 to confirm that one or two molecule(s) of Mertansine was/were introduced into one molecule of each Trastuzumab-Fab with o-Az-Z-Lys introduced therein as expected.

Subsequently, the cytotoxic activity of each of the obtained chemically modified products of the Trastuzumab-Fab was measured with the Her2-expressing cell strain SK-BR-3. SK-BR-3 (ATCC) cells were diluted to 5000 cells/well with an RPMI 1640 medium containing 10% bovine serum (from Life Technologies) and seeded in a 96-well plate, and each of the chemically modified products of the Trastuzumab-Fab was diluted to an appropriate concentration with the same medium and added to the wells. After incubation at 37° C. in the presence of 5% $CO_2$ for 5 days, the number of cells was counted by using a CellTiter-Glo™ (from Promega Corporation), and the viability was calculated as the viability of a control well with addition only of the medium was defined as 100%.

Figure 3:
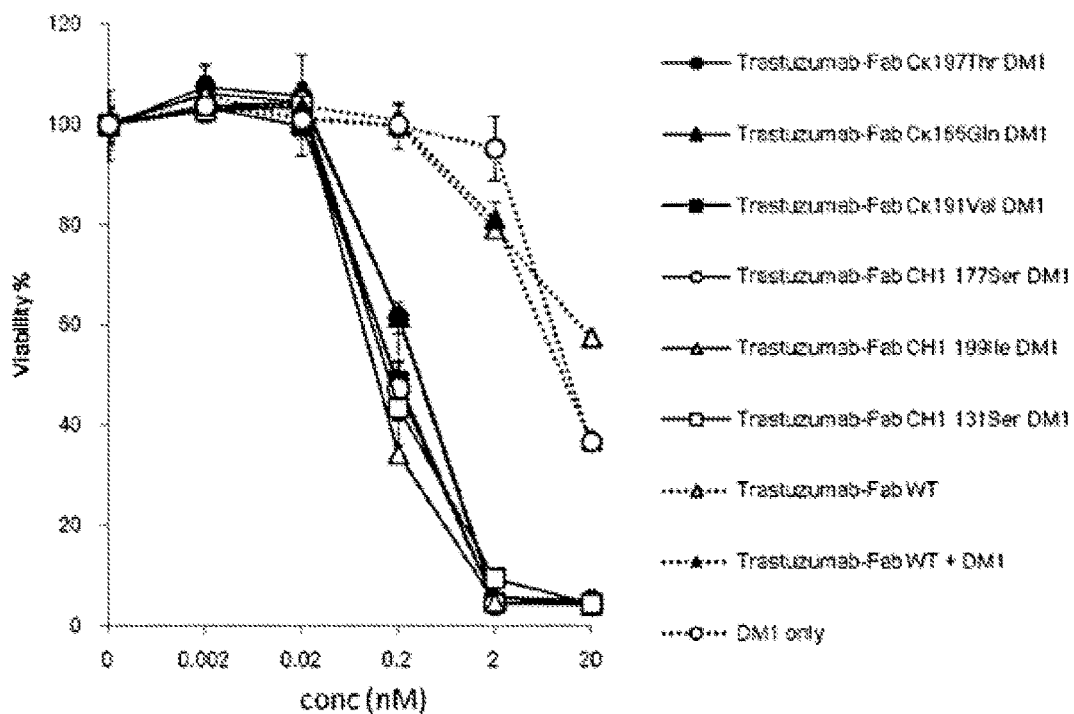
FIG. 3 shows the cytotoxic activity of modified antibodies of Trastuzumab-Fabs with o-Az-Z-Lys introduced therein, where the vertical axis represents the viability (%) of cells, and the horizontal axis represents Fab or DM1 concentration (nM).
Figure 4:
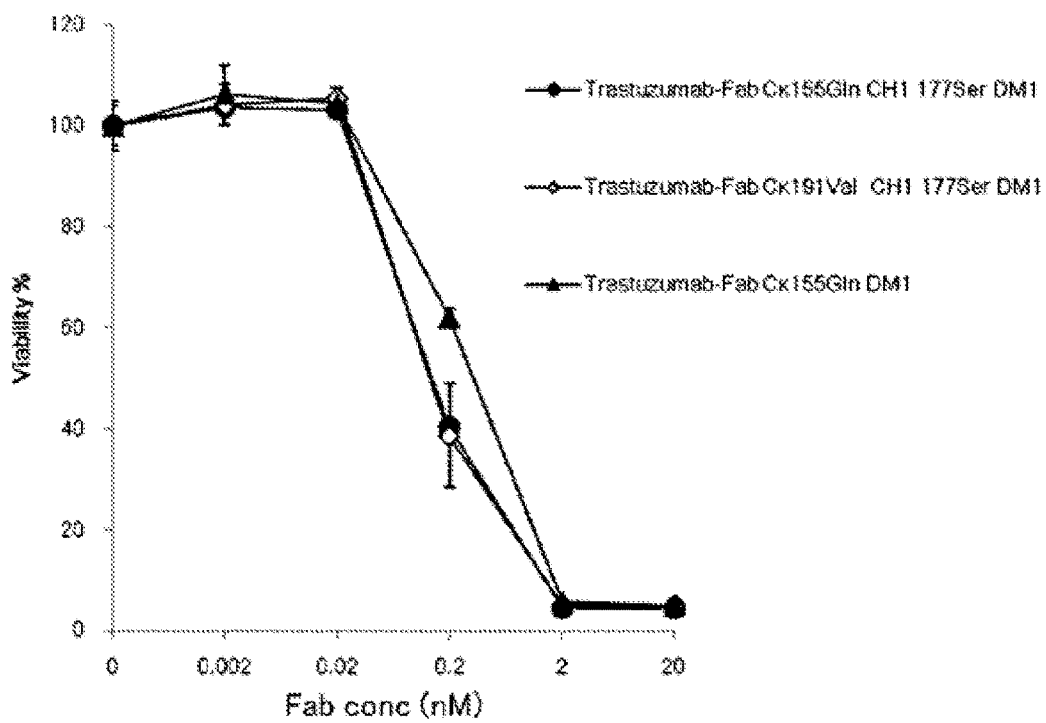
FIG. 4 shows the cytotoxic activity of modified antibodies of Trastuzumab-Fabs with o-Az-Z-Lys introduced therein, where the vertical axis represents the viability (%) of cells, and the horizontal axis represents Fab concentration (nM).

FIGS. 3 and 4 show the results, where the chemically modified product in which the amino acid residue at position 197 of the Cκ of the Trastuzumab-Fab is o-Az-Z-Lys is represented as "Trastuzumab-Fab Cκ197Thr DM1", and the other modified products are represented in the same manner, and the wild-type Trastuzumab-Fab is represented as "Trastuzumab-Fab WT", combination of the wild-type Trastuzumab-Fab and DM1 as "Trastuzumab-Fab WT+DM1", and single DM1 as "DM1 only".

These results confirmed that any of the chemically modified products of the Trastuzumab-Fab has higher cytotoxic activity than the wild-type Trastuzumab-Fab and combination of the wild-type Trastuzumab-Fab and Mertansine (FIGS. 3 and 4).

Example 14

Production of Trastuzumab IgG Antibodies with o-Az-Z-Lys Introduced Therein and Measurement of Reactivity Thereof Six IgG antibodies, each as a Trastuzumab IgG antibody with o-Az-Z-Lys introduced therein at a site as listed in Table 7, were produced, and the reactivity between each of the antibodies and Alexa 488 was measured.

A gene encoding the heavy chain of Trastuzumab, a gene encoding the light chain of Trastuzumab, nine copies of U6-tRNA$^{Pyl}$ (9×U6-tRNA$^{Pyl}$) (SEQ ID NO: 106), and a gene encoding pyrrolysyl tRNA synthetase (derived from *Methanosarcina mazei*, Y306A/Y384F double mutant)

(SEQ ID NO: 107) were each introduced into a pOriP vector according to the method in Example 2 and a method described in Mukai T. et al [Biochem. Biophys. Res. Commmun, 371, 818-822 (2008)], and thus four vectors were produced. The nucleotide sequence of the heavy chain of Trastuzumab and the nucleotide sequence of the light chain of Trastuzumab were produced on the basis of the nucleotide sequences shown in SEQ ID NO: 104 and SEQ ID NO: 105, respectively.

These expression vectors were introduced into an Expi293 cell (from Life Technologies) by using a Transfection Kit with the transfection reagent ExpiFectamine™ 293 (from Life Technologies), and the culture supernatant was collected after culturing for 6 days, and the antibody was purified with Protein G resin. After the purification, SDS-PAGE was performed to confirm that the antibody was expressed as expected.

Mass spectrometry was performed for the thus-obtained Trastuzumab IgG antibodies with o-Az-Z-Lys introduced therein in the same manner as in Example 3 to find that the measured value coincided with the theoretical molecular weight for any of the antibodies. This result confirmed that two molecules of o-Az-Z-Lys were introduced into one molecule of each Trastuzumab IgG antibody with o-Az-Z-Lys introduced therein, and thus the Trastuzumab IgG antibodies with o-Az-Z-Lys introduced therein were successfully produced.

In addition, the reactivity between each of the IgG antibodies with o-Az-Z-Lys introduced therein and Alexa 488 in click chemistry was measured by using the method in Example 4. The reactivity (%) was calculated from the following equations.

Antibody concentration (M)={(area value at wavelength of 280 nm)−0.11×(area value at wavelength of 495 nm)}/204080

Reactivity (%)=[area value at wavelength of 495 nm/(71,000×antibody concentration (M) calculated from above equation)/2]×100

Here, the value 204080 is the molar extinction coefficient of Trastuzumab. The reactivity reaches 100% when two molecules of Alexa 488 are added to one molecule of a Trastuzumab IgG antibody with o-Az-Z-Lys introduced therein.

Table 9 shows the results. The reactivity with Alexa 488 was high for any of the Trastuzumab IgG antibodies with o-Az-Z-Lys introduced therein. These results demonstrate that not only an Fab but also an IgG antibody with o-Az-Z-Lys introduced therein at position 197, 155, or 191 of the Cκ or at position 177, 199, or 131 of the CH1 according to the EU numbering allows production of its chemically modified product at high efficiency.

Example 15

Production of Various Trastuzumab-Fabs with Non-Natural Amino Acid Introduced Therein and Measurement of Reactivity Thereof Trastuzumab-Fabs with a Z-Lys derivative synthesized according to Reference Examples 2 to 7, the Lys derivative BCN-Lys (from Scientific & Chemical Supplies Ltd.), or the Lys derivative TCO*-Lys (from Scientific & Chemical Supplies Ltd.) introduced therein were produced by using a method described below, and the reactivity of each of the Fabs was measured. The Trastuzumab-Fabs with a non-natural amino acid introduced therein produced are listed in Table 10.

Fab expression vectors were produced by using the method in Example 2 with use of the nucleotide sequences with a TAG codon introduced therein as listed in Table 10, and Fabs with a non-natural amino acid introduced therein were obtained by using the method in Example 3. In culturing the W3110 RF-Zero strain with an expression vector for the Trastuzumab-Fab introduced therein, a non-natural amino acid listed in Table 10 at a concentration of 1 mM was added to the medium in place of o-Az-Z-Lys.

Mass spectrometry was performed to find that the measured value coincided with the theoretical molecular weight for any of the Fabs with a non-natural amino acid introduced therein, and confirmed that one molecule of a non-natural amino acid was introduced into one molecule of the Trastuzumab-Fab.

The reactivity of each of the obtained Trastuzumab-Fabs with a non-natural amino acid introduced therein was measured by using the following method.

The reactivity of the Trastuzumab-Fab with m-Az-Z-Lys introduced therein was measured by using the method in Example 4. Click chemistry was used for the reaction.

The reactivity of each of the Trastuzumab-Fabs with o-Ethynyl-Z-Lys or m-Ethynyl-Z-Lys introduced therein was measured by using a method below. Click chemistry was used for the reaction.

A solution of each Trastuzumab-Fab with o-Ethynyl-Z-Lys or m-Ethynyl-Z-Lys introduced therein at a concentration of 40 μM was prepared with DPBS (from NACALAI TESQUE, INC.). To each antibody solution, 40 equivalents of Click-IT Azide Alexa Fluor 488 (from Life Technologies), CuSO$_4$ (from Wako Pure Chemical Industries, Ltd.) at a final concentration of 1 mM, Sodium Ascorbate (from Tokyo Chemical Industry Co., Ltd.) at a final concentration of 50 mM, THPTA [Tris(3-hydroxypropyltriazolylmethyl) amine](from Sigma-Aldrich Co. LLC.) at a final concentration of 250 μM, and Aminoguanidine bicarbonate (from Wako Pure Chemical Industries, Ltd.) at a final concentration of 1 mM were added, and reacted at room temperature

TABLE 9

| Antibody No. | Constant region | Site for introduction of o-Az-Z-Lys (EU numbering) | Amino acid residue substituted with o-Az-Z-Lys | Reactivity (%) |
|---|---|---|---|---|
| 7 | Cκ | 197 | Thr | 90.1 |
| 8 | Cκ | 155 | Gln | 88.4 |
| 9 | Cκ | 191 | Val | 85.8 |
| 10 | CH1 | 177 | Ser | 91.4 |
| 11 | CH1 | 199 | Ile | 97.7 |
| 12 | CH1 | 131 | Ser | 91.2 | overnight. Thereafter, the unreacted Click-IT Azide Alexa Fluor 488 was removed through ultrafiltration by using an Amicon Ultra-0.5 30K (from Millipore Corporation), and then analysis was performed through cation exchange chromatography in the same manner as in Example 4 to measure the reactivity with Alexa 488.

The reactivity of each of the Trastuzumab-Fabs with m-Amino-Z-Lys introduced therein was measured by using a method below. Reductive amination reaction was used for the reaction.

A solution of each Trastuzumab-Fab with m-Amino-Z-Lys introduced therein at a concentration of 20 µM was prepared with a buffer containing 50 mM trisodium citrate (from Wako Pure Chemical Industries, Ltd.) and 50 mM citric acid (from NACALAI TESQUE, INC.) at pH 4.0. To the solution, 2 equivalents of Fluorescein PEG aldehyde (from Nanocs Inc.) and 2-Methylpyridine borane complex (from Sigma-Aldrich Co. LLC.) at a final concentration of 1.5 mM were added and reacted at 4° C. overnight. Thereafter, the unreacted Fluorescein PEG aldehyde was removed through ultrafiltration by using an Amicon Ultra-0.5 30K (from Millipore Corporation), and then analysis was performed by using the spectrophotometer UV-1800 (from Shimadzu Corporation), and the reactivity (%) was calculated from equations below.

The reactivity reaches 100% when one molecule of Fluorescein is added to one molecule of a Trastuzumab-Fab with m-Amino-Z-Lys introduced therein.

Fab concentration (M)={(area value at wavelength of 280 nm)–0.30×(area value at wavelength of 495 nm)}/67980

Reactivity (%)=[area value at wavelength of 495 nm/(70,000×Fab concentration (M) calculated from above equation)]×100

Here, the value 70,000 is the molar extinction coefficient of Fluorescein. The value 67980 is the molar extinction coefficient of the Trastuzumab-Fab.

Then, addition of Fluorescein probably due to reaction with a wild-type amino acid was found also for the wild-type Trastuzumab-Fab without introduction of m-Amino-Z-Lys. For this reason, the difference between the reactivity of each Fab with m-Amino-Z-Lys introduced therein and the reactivity of the wild-type Trastuzumab-Fab was calculated as the reactivity of m-Amino-Z-Lys in the Fab with m-Amino-Z-Lys introduced therein. The results are listed in Table 10.

The reactivity of each of the Trastuzumab-Fabs with BCN-Lys or TCO*-Lys introduced therein was measured by using a method below. Inverse electron-demand Diels-Alder reaction was used for the reaction.

A solution of each Trastuzumab-Fab with BCN-Lys or TCO*-Lys introduced therein at a concentration of 40 µM was prepared with DPBS (from NACALAI TESQUE, INC.). To each antibody solution, 40 equivalents of Cy3 Tetrazine (from Click Chemistry Tools LLC.) was added and reacted at room temperature overnight. Thereafter, the unreacted Cy3 Tetrazine was removed through ultrafiltration by using an Amicon Ultra-0.5 30K (from Millipore Corporation), and then analysis was performed through cation exchange chromatography in the same manner as in Example 4, and the reactivity with Cy3 was measured.

Then, the optical densities at wavelengths of 280 nm and 550 nm were monitored, and the reactivity (%) was calculated from equations below with the area values at the optical densities. The reactivity reaches 100% when one molecule of Cy3 is added to one molecule of a Trastuzumab-Fab with BCN-Lys or TCO*-Lys introduced therein.

Fab concentration (M)={(area value at wavelength of 280 nm)–0.08×(area value at wavelength of 550 nm)}/67980

Reactivity (%)=[area value at wavelength of 550 nm/(150,000×Fab concentration (M))]×100

Here, the value 150,000 is the molar extinction coefficient of Cy3. The value 67980 is the molar extinction coefficient of the Trastuzumab-Fab.

Table 10 shows the results. The Fab with m-Az-Z-Lys introduced therein (Antibody No. 14) was found to have high reactivity with Alexa 488, as the Fab with o-Az-Z-Lys introduced therein (Antibody No. 13). Further, reactivity with Alexa 488 was found for the Fabs with o-Ethynyl-Z-Lys introduced therein (Antibody Nos. 15, 16) and the Fabs with m-Ethynyl-Z-Lys introduced therein (Antibody Nos. 17, 18), reactivity with PEG was found for the Fabs with m-Amino-Z-Lys introduced therein (Antibody Nos. 19, 20), and reactivity with Cy3 was found for the Fabs with BCN-Lys introduced therein (Antibody Nos. 21 to 23) and the Fabs with TCO*-Lys introduced therein (Antibody Nos. 24 to 26).

These results demonstrate that an Fab with m-Az-Z-Lys introduced therein allows production of its chemically modified product at high efficiency in a simple manner as with the case of the Fabs with o-Az-Z-Lys introduced therein, and that an Fab with o-Ethynyl-Z-Lys introduced therein, an Fab with m-Ethynyl-Z-Lys introduced therein, an Fab with m-Amino-Z-Lys introduced therein, an Fab with BCN-Lys introduced therein, and an Fab with TCO*-Lys introduced therein each allows production of its chemically modified product similarly.

TABLE 10

| Antibody No. | Constant region | Site for introduction of non-natural amino acid (EU numbering) | Amino acid residue substituted with non-natural amino acid | Nucleotide sequence with TAG codon introduced therein | Non-natural amino acid introduced | Reactivity (%) |
| --- | --- | --- | --- | --- | --- | --- |
| 13 | Cκ | 155 | Gln | SEQ ID NO: 32 | o-Az-Z-Lys | 101.4 |
| 14 | Cκ | 155 | Gln | SEQ ID NO: 32 | m-Az-Z-Lys | 93.7 |
| 15 | Cκ | 155 | Gln | SEQ ID NO: 32 | o-Ethynyl-Z-Lys | 54.2 |
| 16 | CH1 | 131 | Ser | SEQ ID NO: 50 | o-Ethynyl-Z-Lys | 40.2 |
| 17 | Cκ | 155 | Gln | SEQ ID NO: 32 | m-Ethynyl-Z-Lys | 62.8 |
| 18 | CH1 | 131 | Ser | SEQ ID NO: 50 | m-Ethynyl-Z-Lys | 51.8 |
| 19 | Cκ | 155 | Gln | SEQ ID NO: 32 | m-Amino-Z-Lys | 28.2 |
| 20 | CH1 | 131 | Ser | SEQ ID NO: 50 | m-Amino-Z-Lys | 33.9 |
| 21 | Cκ | 169 | Lys | SEQ ID NO: 12 | BCN-Lys | 36.9 |
| 22 | CH1 | 121 | Lys | SEQ ID NO: 17 | BCN-Lys | 24.9 |

TABLE 10-continued

| Antibody No. | Constant region | Site for introduction of non-natural amino acid (EU numbering) | Amino acid residue substituted with non-natural amino acid | Nucleotide sequence with TAG codon introduced therein | Non-natural amino acid introduced | Reactivity (%) |
|---|---|---|---|---|---|---|
| 23 | CH1 | 131 | Ser | SEQ ID NO: 50 | BCN-Lys | 35.2 |
| 24 | Cκ | 169 | Lys | SEQ ID NO: 12 | TCO*-Lys | 61.3 |
| 25 | CH1 | 121 | Lys | SEQ ID NO: 17 | TCO*-Lys | 52.0 |
| 26 | CH1 | 131 | Ser | SEQ ID NO: 50 | TCO*-Lys | 49.2 |

Example 16

Production of Trastuzumab-Fabs with Formyl-Z-Lysine Introduced Therein

Trastuzumab-Fabs with m-formyl-Z-Lys introduced therein were produced by using the method in Example 15, where the m-formyl-Z-Lys was synthesized according to Reference Example 8. The Fabs with m-formyl-Z-Lys introduced therein produced and nucleotide sequences used for the antibody production are listed in Table 11.

TABLE 11

| Constant region | Site for introduction of m-formyl-Z-Lys (EU numbering) | Amino acid residue substituted with m-formyl-Z-Lys | Nucleotide sequence with TAG codon introduced therein |
|---|---|---|---|
| Cκ | 155 | Gln | SEQ ID NO: 32 |
| CH1 | 131 | Ser | SEQ ID NO: 50 |

Mass spectrometry was performed for the Fabs with m-formyl-Z-Lys introduced therein to find that the measured value coincided with the theoretical molecular weight for any of the Fabs, and confirmed that one molecule of m-formyl-Z-Lys was introduced into one molecule of the Trastuzumab-Fab.

Hydrochlorides of ortho-azido-Z-lysine, meta-azido-Z-lysine, para-azido-Z-lysine, ortho-ethynyl-Z-lysine, meta-ethynyl-Z-lysine, para-ethynyl-Z-lysine, meta-amino-Z-lysine, and meta-formyl-Z-lysine, each as a lysine derivative used in the present invention, were obtained according to Reference Examples described below. However, the lysine derivative to be used in the present invention is not limited to them. Proton nuclear resonance spectra PH NMR) used in Reference Examples were acquired through measurement at 300 MHz or 400 MHz, and no exchangeable proton may be observed for some compounds or in some measurement conditions. The multiplicity of a signal is represend with a commonly used simbol, and "br" represents an apparently broad signal. ChemBioDraw Ultra 14.0.0.117 was used for nomenclature of compounds.

Reference Example 1

N6-{[(2-azidobenzyl)oxy]carbonyl}-L-lysine hydrochloride (ortho-azido-Z-lysine hydrochloride)

Ortho-azido-Z-lysine hydrochloride was obtained by using (2-aminophenyl)methanol as a raw material according to a method for synthesizing mAzZLys described in a literature (Bioconjugate Chem. 2016, 27, 198).

ESIMS m/z: 322 (M–HCl)$^+$; $^1$H NMR (400 MHz, DMSO-d$_6$, D$_2$O, δ): 1.23-1.45 (m, 4H), 1.68-1.82 (m, 2H), 2.97-3.01 (m, 2H), 3.57-3.60 (m, 1H), 4.95 (s, 2H), 7.18-7.24 (m, 1H), 7.31-7.47 (m, 3H).

Reference Example 2

N6-{[(3-azidobenzyl)oxy]carbonyl}-L-lysine hydrochloride (meta-azido-Z-lysine hydrochloride)

Meta-azido-Z-lysine hydrochloride was obtained according to a method for synthesizing mAzZLys described in a literature (Bioconjugate Chem. 2016, 27, 198).

Reference Example 3

N6-{[(4-azidobenzyl)oxy]carbonyl}-L-lysine hydrochloride (para-azido-Z-lysine hydrochloride)

Para-azido-Z-lysine hydrochloride was obtained by using (4-aminophenyl)methanol as a raw material according to a method for synthesizing mAzZLys described in a literature (Bioconjugate Chem. 2016, 27, 198).

ESIMS m/z: 322 (M–HCl)$^+$; $^1$H NMR (400 MHz, DMSO-d$_6$, D$_2$O, δ): 1.22-1.44 (m, 4H), 1.58-1.78 (m, 2H), 2.94-3.02 (m, 2H), 3.24-3.28 (m, 1H), 4.97 (s, 2H), 7.12 (d, J=8.4 Hz, 2H), 7.39 (d, J=8.4 Hz, 2H).

Reference Example 4

N6-{[(2-ethynylbenzyl)oxy]carbonyl}-L-lysine hydrochloride (ortho-ethynyl-Z-lysine hydrochloride)

(Step 1)

Commercially available (2-iodophenyl)methanol (75.0 g, 0.321 mol) was dissolved in triethylamine (1 L), and ethynyltrimethylsilane (34.7 g, 0.353 mol) and bistriphenylphosphine-palladium (II) chloride (4.51 g, 6.40 mmol) were added thereto, and the resultant was stirred at room temperature under a nitrogen atmosphere for 10 minutes. Copper (I) iodide (0.61 g, 3.20 mmol) was added to the reaction mixture, which was stirred at room temperature for 2 hours. The reaction mixture was filtered through a Celite, and the filtrate was concentrated under reduced pressure. The resulting residue was purified by using silica gel column chromatography (ethyl acetate/petroleum ether=5/95 to 10/90) to afford {2-[(trimethylsilyl)ethynyl]phenyl}methanol (60 g, 92%). ESIMS m/z: 205 (M+H)$^+$.

(Step 2)

In tetrahydrofuran (THF) (350 mL), {2-[(trimethylsilyl)ethynyl]phenyl}methanol (36.0 g, 0.176 mol) obtained in Step 1 was dissolved, and phosgene (20% toluene solution, 174 mL, 0.352 mol) was added thereto under ice cooling, and the resultant was stirred at room temperature for 16 hours. The reaction mixture was concentrated under reduced pressure to afford a crude product of 2-[(trimethylsilyl)ethynyl]benzyl carbonochloridate (47.0 g). The crude product obtained was directly used for the next step.
(Step 3)

The crude product of 2-[(trimethylsilyl)ethynyl]benzyl carbonochloridate (47.0 g, 0.158 mol) obtained in Step 2 was dissolved in THF (500 mL) to afford a solution of 2-[(trimethylsilyl)ethynyl]benzyl carbonochloridate. Commercially available (tert-butoxycarbonyl)-L-lysine (39.0 g, 0.158 mol) was dissolved in 1 mol/L NaOH aqueous solution (470 mL) and THF (250 mL) to afford a solution of (tert-butoxycarbonyl)-L-lysine. The solution of 2-[(trimethylsilyl)ethynyl]benzyl carbonochloridate was added dropwise to the solution of (tert-butoxycarbonyl)-L-lysine under ice cooling over 10 minutes, and the resultant was stirred at room temperature for 2 hours. The reaction mixture was cooled, and diethyl ether was added thereto, and extraction was performed with water. To the aqueous layer obtained, 1 mol/L hydrochloric acid aqueous solution was added so that the pH reached 1 to 2, and extraction was performed with ethyl acetate. The organic layer was dried over anhydrous sodium sulfate, and the solvent was distilled off under reduced pressure. The resulting residue was dissolved in THF (85 mL), and 1 mol/L tetrabutylammonium fluoride solution (28 mL) was added thereto under ice cooling, and the resultant was stirred at room temperature for 2 hours. To the reaction mixture, 1 mol/L hydrochloric acid aqueous solution was added, and extraction was performed with ethyl acetate. The organic layer was dried over anhydrous sodium sulfate, and the solvent was distilled off under reduced pressure. The resulting residue was purified by using silica gel column chromatography (dichloromethane/methanol=98/2 to 97/3) to afford N2-(tert-butoxycarbonyl)-N6-{[(2-ethynylbenzyl)oxy]carbonyl}-L-lysine (16.0 g, total yield in two steps: 22%).

ESIMS m/z: 405 (M+H)$^+$.
(Step 4)

N2-(tert-butoxycarbonyl)-N6-{[(2-ethynylbenzyl)oxy]carbonyl}-L-lysine (16.0 g, 0.039 mol) obtained in Step 3 was dissolved in 1,4-dioxane (30 mL), and hydrochloric acid/dioxane solution (30 mL) was gradually added dropwise thereto, and the resultant was stirred at room temperature for 16 hours. The solvent in the reaction mixture was distilled off under reduced pressure, and the resulting residue was purified through reslurrying with diethyl ether to afford ortho-ethynyl-Z-lysine hydrochloride (11.8 g, 99%).

ESIMS m/z: 305 (M–HCl)$^+$; $^1$H NMR (400 MHz, DMSO-d$_6$, D$_2$O, δ): 1.28-1.50 (m, 4H), 1.71-1.86 (m, 2H), 2.97-3.01 (m, 2H), 3.85-3.90 (m, 1H), 4.37 (S, 1H), 5.14 (s, 2H), 7.34-7.47 (m, 3H), 7.52-7.54 (m, 1H).

Reference Example 5

N6-{[(3-ethynylbenzyl)oxy]carbonyl}-L-lysine hydrochloride (meta-ethynyl-Z-lysine hydrochloride)

(Step 1)
With use of commercially available (3-iodophenyl)methanol (75.0 g, 0.321 mol), {3-[(trimethylsilyl)ethynyl]phenyl}methanol (60.0 g, 91%) was obtained in the same manner as in Step 1 of Reference Example 4.

ESIMS m/z: 205 (M+H)$^+$.
(Step 2)

In methanol (1 L), {3-[(trimethylsilyl)ethynyl]phenyl}methanol (60 g, 0.293 mol) obtained in Step 1 was dissolved, and potassium carbonate (20.3 g, 0.146 mol) was added thereto, and the resultant was stirred at room temperature for 3 hours. The reaction mixture was concentrated under reduced pressure, and the resulting residue was purified by using silica gel column chromatography (ethyl acetate/petroleum ether=30/70 to 40/60) to afford (3-ethynylphenyl)methanol (33 g, 83%).

ESIMS m/z: 133 (M+H)$^+$.
(Step 3)

With use of (3-ethynylphenyl)methanol (33.0 g, 0.249 mol) obtained in Step 2, a crude product of 3-ethynylbenzyl carbonochloridate (40.0 g) was obtained in the same manner as in Step 2 of Reference Example 4. The crude product obtained was directly used for the next step.
(Step 4)

The crude product of 3-ethynylbenzyl carbonochloridate (40 g, 0.205 mol) obtained in Step 3 was dissolved in THF (50 mL) to afford a solution of 3-ethynylbenzyl carbonochloridate. Commercially available (tert-butoxycarbonyl)-L-lysine (50.4 g, 0.205 mol) was dissolved in 1 mol/L NaOH aqueous solution (500 mL) and THF (200 mL) to afford a solution of (tert-butoxycarbonyl)-L-lysine. The solution of 3-ethynylbenzyl carbonochloridate was added dropwise to the solution of (tert-butoxycarbonyl)-L-lysine under ice cooling over 10 minutes, and the resultant was stirred at room temperature for 2 hours. The reaction mixture was cooled, and diethyl ether was added thereto, and extraction was performed with water. To the aqueous layer obtained, 1 mol/L hydrochloric acid aqueous solution was added so that the pH reached 1 to 2, and extraction was performed with ethyl acetate. The organic layer was dried over anhydrous sodium sulfate, and the solvent was distilled off under reduced pressure. The resulting residue was purified by using silica gel column chromatography (dichloromethane/methanol=98/2 to 97/3) to afford N2-(tert-butoxycarbonyl)-N6-{[(3-ethynylbenzyl)oxy]carbonyl}-L-lysine (20 g, total yield in two steps: 25%).

ESIMS m/z: 405 (M+H)$^+$.
(Step 5)

With use of N2-(tert-butoxycarbonyl)-N6-{[(3-ethynylbenzyl)oxy]carbonyl}-L-lysine (17.0 g, 0.042 mol) obtained in Step 4, meta-ethynyl-Z-lysine hydrochloride (11.1 g, 87%) was obtained in the same manner as in Step 4 of Reference Example 4.

ESIMS m/z: 305 (M–HCl)$^+$; $^1$H NMR (400 MHz, DMSO-d$_6$, D$_2$O, δ): 1.28-1.50 (m, 4H), 1.70-1.85 (m, 2H), 2.97-3.01 (m, 2H), 3.83-3.90 (m, 1H), 4.21 (S, 1H), 5.01 (s, 2H), 7.28-7.47 (m, 4H).

Reference Example 6

N6-{[(4-ethynylbenzyl)oxy]carbonyl}-L-lysine hydrochloride (para-ethynyl-Z-lysine hydrochloride)

(Step 1)
Commercially available 4-ethynylbenzaldehyde (5.00 g, 38.5 mmol) was dissolved in ethanol (100 mL), and sodium borohydride (4.40 g, 116 mmol) was added thereto under ice cooling, and the resultant was stirred at 0° C. for 2 minutes. Ammonium chloride aqueous solution was added to the reaction mixture, and extraction was performed with dichloromethane. The organic layer was washed with water and saturated sodium chloride aqueous solution, dried over anhydrous sodium sulfate, and the solvent was distilled off under reduced pressure. The resulting residue was purified by using silica gel column chromatography (ethyl acetate/petroleum ether=20/80) to afford (4-ethynylphenyl)methanol (5.00 g, 100%). ESIMS m/z: 133 (M+H)$^+$.

(Step 2)

In dichloromethane (100 mL), (4-ethynylphenyl)methanol (7.80 g, 58.7 mmol) obtained in Step 1 was dissolved, and pyridine (10 mL) and commercially available 4-nitrophenylchloroformate (11.8 g, 58.7 mmol) were added thereto at room temperature, and the resultant was stirred overnight. Water was added to the reaction mixture, and extraction was performed with dichloromethane. The organic layer was washed with water and saturated sodium chloride aqueous solution, dried over anhydrous sodium sulfate, and the solvent was distilled off under reduced pressure to afford a crude product of 4-ethynylbenzyl (4-nitrophenyl)carbonate (17.5 g). The crude product obtained was directly used for the next step.

(Step 3)

In THF (100 mL), 4-ethynylbenzyl (4-nitrophenyl)carbonate (7.50 g, 25.0 mmol) obtained in Step 2 was dissolved, and diisopropylethylamine (6.40 g, 50.0 mmol) and commercially available (tert-butoxycarbonyl)-L-lysine (6.20 g, 25.0 mmol) were added thereto, and the resultant was stirred at room temperature overnight. To the reaction mixture, 4 mol/L hydrochloric acid aqueous solution was added so that the pH reached 3, and extraction was performed with dichloromethane. The organic layer was washed with water and saturated sodium chloride aqueous solution, dried over anhydrous sodium sulfate, and the solvent was distilled off under reduced pressure. The resulting residue was purified by using silica gel column chromatography (dichloromethane/methanol=98/2 to 97/3) to afford N2-(tert-butoxycarbonyl)-N6-{[(4-ethynylbenzyl)oxy]carbonyl}-L-lysine (4.00 g, total yield in two steps: 40%).

ESIMS m/z: 405 (M+H)$^+$.

(Step 4)

N2-(tert-butoxycarbonyl)-N6-{[(4-ethynylbenzyl)oxy]carbonyl}-L-lysine (3.40 g, 8.30 mmol) obtained in Step 3 was dissolved in hydrochloric acid-ethyl acetate solution (25 mL), and the resultant was stirred at room temperature for 2 hours. The reaction mixture was concentrated under reduced pressure, and the resulting residue was purified by using reverse phase preparative chromatography to afford para-ethynyl-Z-lysine hydrochloride (1.30 g, 50%).

ESIMS m/z: 305 (M−HCl)$^+$; $^1$H NMR (300 MHz, DMSO-d$_6$, δ): 1.26-1.50 (m, 4H), 1.70-1.84 (m, 2H), 2.94-3.04 (m, 2H), 3.80-3.90 (m, 1H), 4.20 (s, 1H), 5.02 (s, 2H), 7.28-7.38 (m, 3H), 7.47 (d, J=8.1 Hz, 2H), 8.20-8.36 (br, 3H).

Reference Example 7

N6-{[(3-aminobenzyl)oxy]carbonyl}-L-lysine hydrochloride (meta-amino-Z-lysine hydrochloride)

(Step 1)

With use of commercially available (3-aminophenyl)methanol (3.24 g, 26.3 mmol), tert-butyl [3-(hydroxymethyl)phenyl]carbamate (7 g, quant.) was obtained according to a synthesis method described in a literature (Chem. Mater. 2011, 23, 4844.).

ESIMS m/z: 224 (M+H)$^+$.

(Step 2)

With use of tert-butyl [3-(hydroxymethyl)phenyl]carbamate (1.49 g, 6.70 mmol) obtained in Step 1, a crude product of tert-butyl [3-({[(4-nitrophenoxy)carbonyl]oxy}methyl)phenyl]carbamate (2.35 g) was obtained in the same manner as in Step 2 of Reference Example 6. The crude product obtained was directly used for the next step.

(Step 3)

With use of the crude product of tert-butyl [3-({[(4-nitrophenoxy)carbonyl]oxy}methyl)phenyl]carbamate (2.35 g) obtained in Step 2, N2-(tert-butoxycarbonyl)-N6-[({3-[(tert-butoxycarbonyl)amino]benzyl}oxy)carbonyl]-L-lysine (2.90 g, total yield in two steps: 87%) was obtained in the same manner as in Step 3 of Reference Example 6.

ESIMS m/z: 496 (M+H)$^+$.

(Step 4)

With use of N2-(tert-butoxycarbonyl)-N6-[({3-[(tert-butoxycarbonyl)amino]benzyl}oxy)carbonyl]-L-lysine (2.80 g, 5.65 mmol) obtained in Step 3, meta-amino-Z-lysine hydrochloride (1.15 g, 70%) was obtained in the same manner as in Step 4 of Reference Example 4.

ESIMS m/z: 296 (M−HCl)$^+$; $^1$H NMR (400 MHz, DMSO-d$_6$, δ): 1.24-1.42 (m, 4H), 1.62-1.80 (m, 2H), 2.50 (br s, 2H), 2.93-3.01 (m, 2H), 3.59 (t, J=5.6 Hz, 1H), 4.84 (s, 2H), 6.42-6.53 (m, 3H), 6.97 (t, J=7.6 Hz, 1H), 7.17 (t, J=5.6 Hz, 1H).

Reference Example 8

N6-{[(3-formylbenzyl)oxy]carbonyl}-L-lysine hydrochloride (meta-formyl-Z-lysine hydrochloride)

(Step 1)

Commercially available (3-iodophenyl)methanol (1.00 g, 4.25 mmol) was dissolved in THF (15 mL), and mesitylene (0.3 mL, 2.12 mmol), triethylamine (0.6 mL, 4.25 mmol), and triethylsilane (1.3 mL, 8.40 mmol) were added thereto, and the resultant was stirred at room temperature for 5 minutes. To the reaction mixture, [1,1'-bis(diphenylphosphino)ferrocene]dichloropalladium (II) (0.700 g, 1.06 mmol) was added, and the resultant was stirred under carbon monoxide capping (70 psi) at 100° C. for 16 hours. The reaction mixture was concentrated under reduced pressure, and the resulting residue was purified by using silica gel column chromatography (ethyl acetate/petroleum ether=5/95) to afford 3-(hydroxymethyl)benzaldehyde (512 mg, 88%). ESIMS m/z: 137 (M+H)$^+$.

(Step 2)

With use of 3-(hydroxymethyl)benzaldehyde (510 mg, 3.75 mmol) obtained in Step 1, a crude product of 3-formylbenzyl carbonochloridate (410 mg) was obtained in the same manner as in Step 2 of Reference Example 4. The crude product obtained was directly used for the next step.

(Step 3)

With use of the crude product of 3-formylbenzyl carbonochloridate (410 mg) obtained in Step 2, N2-(tert-butoxycarbonyl)-N6-{[(3-formylbenzyl)oxy]carbonyl}-L-lysine (540 mg, total yield in two steps: 66%) was obtained in the same manner as in Step 4 of Reference Example 5.

ESIMS m/z: 409 (M+H)$^+$.

(Step 4)

With use of N2-(tert-butoxycarbonyl)-N6-{[(3-formylbenzyl)oxy]carbonyl}-L-lysine (540 mg, 1.32 mmol) obtained in Step 3, meta-formyl-Z-lysine hydrochloride (130 mg, 29%) was obtained in the same manner as in Step 4 of Reference Example 4.

ESIMS m/z: 309 (M−HCl)$^+$; $^1$H NMR (400 MHz, DMSO-d$_6$, δ): 1.30-1.50 (m, 4H), 1.70-1.85 (m, 2H), 2.90-3.10 (m, 2H), 3.85 (br s, 1H), 5.10 (s, 2H), 7.33 (t, J=5.2 Hz, 1H), 7.55-7.75 (m, 2H), 7.80-7.94 (m, 2H), 8.28 (br s, 2H), 10.02 (s, 1H), 13.8 (br s, 1H).

For TCO*-Lys and BCN-Lys, commercially available products (from Scientific & Chemical Supplies Ltd.) can be used.

INDUSTRIAL APPLICABILITY

The present invention can provide a monoclonal antibody or antibody fragment thereof as a human IgG antibody including at least one lysine derivative in a constant region of the human IgG antibody; a modified antibody or antibody fragment thereof, wherein the lysine derivative is chemically modified; a nucleic acid including a nucleotide sequence encoding the antibody or antibody fragment thereof; a vector including the nucleic acid; a transformed cell obtained by introducing the vector into a host cell; a method for producing the antibody or antibody fragment thereof; and a composition containing the antibody or antibody fragment thereof.

All of the publications, patents, and patent applications recited herein are to be directly incorporated herein as reference.

Sequence Listing Free Text

Description of SEQ ID NO: 2-artificial sequence: amino acid sequence of Trastuzumab-Fab light chain region Description of SEQ ID NO: 3-artificial sequence: amino acid sequence of Trastuzumab-Fab heavy chain region Description of SEQ ID NO: 4-artificial sequence: nucleotide sequence consisting of Tac promoter and Shine-Dalgarno sequence Description of SEQ ID NO: 5-artificial sequence: nucleotide sequence encoding PelB secretion signal Description of SEQ ID NO: 6-artificial sequence: nucleotide sequence encoding Trastuzumab-Fab light chain region Description of SEQ ID NO: 7-artificial sequence: nucleotide sequence encoding Trastuzumab-Fab heavy chain region Description of SEQ ID NO: 8-artificial sequence: amino acid sequence of mutant of Pyl RS derived from *Methanosarcina mazei* (Y306A/Y384F)

Description of SEQ ID NO: 9-artificial sequence: nucleotide sequence for Trastuzumab-Fab light chain constant region with amber codon introduced at 126 Lys site of κ light chain Description of SEQ ID NO: 10-artificial sequence: nucleotide sequence for Trastuzumab-Fab light chain constant region with amber codon introduced at 145 Lys site of κ light chain Description of SEQ ID NO: 11-artificial sequence: nucleotide sequence for Trastuzumab-Fab light chain constant region with amber codon introduced at 149 Lys site of κ light chain Description of SEQ ID NO: 12-artificial sequence: nucleotide sequence for Trastuzumab-Fab light chain constant region with amber codon introduced at 169 Lys site of κ light chain Description of SEQ ID NO: 13-artificial sequence: nucleotide sequence for Trastuzumab-Fab light chain constant region with amber codon introduced at 183 Lys site of κ light chain Description of SEQ ID NO: 14-artificial sequence: nucleotide sequence for Trastuzumab-Fab light chain constant region with amber codon introduced at 188 Lys site of κ light chain Description of SEQ ID NO: 15-artificial sequence: nucleotide sequence for Trastuzumab-Fab light chain constant region with amber codon introduced at 190 Lys site of κ light chain Description of SEQ ID NO: 16-artificial sequence: nucleotide sequence for Trastuzumab-Fab light chain constant region with amber codon introduced at 207 Lys site of κ light chain Description of SEQ ID NO: 17-artificial sequence: nucleotide sequence for Trastuzumab-Fab heavy chain constant region with amber codon introduced at 121 Lys site of heavy chain CH1

Description of SEQ ID NO: 18-artificial sequence: nucleotide sequence for Trastuzumab-Fab heavy chain constant region with amber codon introduced at 133 Lys site of heavy chain CH1

Description of SEQ ID NO: 19-artificial sequence: nucleotide sequence for Trastuzumab-Fab heavy chain constant region with amber codon introduced at 147 Lys site of heavy chain CH1

Description of SEQ ID NO: 20-artificial sequence: nucleotide sequence for Trastuzumab-Fab heavy chain constant region with amber codon introduced at 205 Lys site of heavy chain CH1

Description of SEQ ID NO: 21-artificial sequence: nucleotide sequence for Trastuzumab-Fab heavy chain constant region with amber codon introduced at 210 Lys site of heavy chain CH1

Description of SEQ ID NO: 22-artificial sequence: nucleotide sequence for Trastuzumab-Fab heavy chain constant region with amber codon introduced at 213 Lys site of heavy chain CH1

Description of SEQ ID NO: 23-artificial sequence: nucleotide sequence for Trastuzumab-Fab heavy chain constant region with amber codon introduced at 214 Lys site of heavy chain CH1

Description of SEQ ID NO: 24-artificial sequence: nucleotide sequence for Trastuzumab-Fab heavy chain variable region and constant region with amber codon introduced at 118 Ala site of heavy chain CH1

Description of SEQ ID NO: 25-artificial sequence: nucleotide sequence for Trastuzumab-Fab heavy chain variable region and constant region with amber codon introduced at 119 Ser site of heavy chain CH1

Description of SEQ ID NO: 26-artificial sequence: nucleotide sequence for Trastuzumab-Fab heavy chain constant region with amber codon introduced at 162 Ala site of heavy chain CH1

Description of SEQ ID NO: 27-artificial sequence: nucleotide sequence for Trastuzumab-Fab heavy chain constant region with amber codon introduced at 176 Ser site of heavy chain CH1

Description of SEQ ID NO: 28-artificial sequence: nucleotide sequence for Trastuzumab-Fab light chain constant region with amber codon introduced at 119 Pro site of κ light chain Description of SEQ ID NO: 29-artificial sequence: nucleotide sequence for Trastuzumab-Fab light chain constant region with amber codon introduced at 138 Asn site of κ light chain Description of SEQ ID NO: 30-artificial sequence: nucleotide sequence for Trastuzumab-Fab light chain constant region with amber codon introduced at 141 Pro site of κ light chain Description of SEQ ID NO: 31-artificial sequence: nucleotide sequence for Trastuzumab-Fab light chain constant region with amber codon introduced at 147 Gln site of κ light chain Description of SEQ ID NO: 32-artificial sequence: nucleotide sequence for Trastuzumab-Fab light chain constant region with amber codon introduced at 155 Gln site of κ light chain Description of SEQ ID NO: 33-artificial sequence: nucleotide sequence for Trastuzumab-Fab light chain constant region with amber codon introduced at 158 Asn site of κ light chain Description of SEQ ID NO: 34-artificial sequence: nucleotide sequence for Trastuzumab-Fab light chain constant region with amber codon introduced at 161 Glu site of κ light chain Description of SEQ ID NO: 35-artificial sequence: nucleotide sequence for Trastuzumab-Fab light chain constant region with amber codon introduced at 167 Asp site of κ light chain Description of SEQ ID NO: 36-artificial sequence: nucleotide sequence for Trastuzumab-Fab light chain constant region with amber codon introduced at 180 Thr site of κ light chain Description of SEQ ID NO: 37-artificial sequence: nucleotide sequence for Trastuzumab-Fab light chain constant region with amber codon introduced at 191 Val site of κ light chain Description of SEQ ID NO: 38-artificial sequence: nucleotide sequence for Trastuzumab-Fab light chain constant region with amber codon introduced at 195 Glu site of κ light chain Description of SEQ ID NO: 39-artificial sequence: nucleotide sequence for Trastuzumab-Fab light chain constant region with amber codon introduced at 197 Thr site of κ light chain Description of SEQ ID NO: 40-artificial sequence: nucleotide sequence for Trastuzumab-Fab light chain constant region with amber codon introduced at 210 Asn site of κ light chain Description of SEQ ID NO: 41-artificial sequence: nucleotide sequence for Trastuzumab-Fab light chain constant region with amber codon introduced at 211 Arg site of κ light chain Description of SEQ ID NO: 42-artificial sequence: nucleotide sequence for Trastuzumab-Fab light chain constant region with amber codon introduced at 110 Val site of κ light chain Description of SEQ ID NO: 43-artificial sequence: nucleotide sequence for Trastuzumab-Fab light chain constant region with amber codon introduced at 112 Ala site of κ light chain Description of SEQ ID NO: 44-artificial sequence: nucleotide sequence for Trastuzumab-Fab light chain constant region with amber codon introduced at 153 Ala site of κ light chain Description of SEQ ID NO: 45-artificial sequence: nucleotide sequence for Trastuzumab-Fab light chain constant region with amber codon introduced at 154 Leu site of κ light chain Description of SEQ ID NO: 46-artificial sequence: nucleotide sequence for Trastuzumab-Fab light chain constant region with amber codon introduced at 184 Ala site of κ light chain Description of SEQ ID NO: 47-artificial sequence: nucleotide sequence for Trastuzumab-Fab light chain constant region with amber codon introduced at 205 Val site of κ light chain Description of SEQ ID NO: 48-artificial sequence: nucleotide sequence for Trastuzumab-Fab heavy chain constant region with amber codon introduced at 120 Thr site of heavy chain CH1

Description of SEQ ID NO: 49-artificial sequence: nucleotide sequence for Trastuzumab-Fab heavy chain constant region with amber codon introduced at 127 Pro site of heavy chain CH1

Description of SEQ ID NO: 50-artificial sequence: nucleotide sequence for Trastuzumab-Fab heavy chain constant region with amber codon introduced at 131 Ser site of heavy chain CH1

Description of SEQ ID NO: 51-artificial sequence: nucleotide sequence for Trastuzumab-Fab heavy chain constant region with amber codon introduced at 135 Thr site of heavy chain CH1

Description of SEQ ID NO: 52-artificial sequence: nucleotide sequence for Trastuzumab-Fab heavy chain constant region with amber codon introduced at 148 Asp site of heavy chain CH1

Description of SEQ ID NO: 53-artificial sequence: nucleotide sequence for Trastuzumab-Fab heavy chain constant region with amber codon introduced at 152 Glu site of heavy chain CH1

Description of SEQ ID NO: 54-artificial sequence: nucleotide sequence for Trastuzumab-Fab heavy chain constant region with amber codon introduced at 159 Asn site of heavy chain CH1

Description of SEQ ID NO: 55-artificial sequence: nucleotide sequence for Trastuzumab-Fab heavy chain constant region with amber codon introduced at 169 Thr site of heavy chain CH1

Description of SEQ ID NO: 56-artificial sequence: nucleotide sequence for Trastuzumab-Fab heavy chain constant region with amber codon introduced at 173 Val site of heavy chain CH1

Description of SEQ ID NO: 57-artificial sequence: nucleotide sequence for Trastuzumab-Fab heavy chain constant region with amber codon introduced at 177 Ser site of heavy chain CH1

Description of SEQ ID NO: 58-artificial sequence: nucleotide sequence for Trastuzumab-Fab heavy chain constant region with amber codon introduced at 180 Tyr site of heavy chain CH1

Description of SEQ ID NO: 59-artificial sequence: nucleotide sequence for Trastuzumab-Fab heavy chain constant region with amber codon introduced at 190 Ser site of heavy chain CH1

Description of SEQ ID NO: 60-artificial sequence: nucleotide sequence for Trastuzumab-Fab heavy chain constant region with amber codon introduced at 199 Ile site of heavy chain CH1

Description of SEQ ID NO: 61-artificial sequence: nucleotide sequence for Trastuzumab-Fab heavy chain constant region with amber codon introduced at 129 Ala site of heavy chain CH1

Description of SEQ ID NO: 62-artificial sequence: nucleotide sequence for Trastuzumab-Fab heavy chain region with amber codon introduced at 174 Leu site of heavy chain CH1

Description of SEQ ID NO: 63-artificial sequence: amino acid sequence of Cixutumumab-Fab light chain region Description of SEQ ID NO: 64-artificial sequence: amino acid sequence of Cixutumumab-Fab heavy chain region Description of SEQ ID NO: 65-artificial sequence: nucleotide sequence encoding Cixutumumab-Fab light chain region Description of SEQ ID NO: 66-artificial sequence: nucleotide sequence encoding Cixutumumab-Fab heavy chain region Description of SEQ ID NO: 67-artificial sequence: nucleotide sequence for Cixutumumab-Fab light chain region with amber codon introduced at 110 Lys site of λ light chain Description of SEQ ID NO: 68-artificial sequence: nucleotide sequence for Cixutumumab-Fab light chain region with amber codon introduced at 129 Lys site of λ light chain Description of SEQ ID NO: 69-artificial sequence: nucleotide sequence for Cixutumumab-Fab light chain region with amber codon introduced at 149 Lys site of λ light chain Description of SEQ ID NO: 70-artificial sequence: nucleotide sequence for Cixutumumab-Fab light chain region with amber codon introduced at 156 Lys site of λ light chain Description of SEQ ID NO: 71-artificial sequence: nucleotide sequence for Cixutumumab-Fab light chain region with amber codon introduced at 166 Lys site of λ light chain Description of SEQ ID NO: 72-artificial sequence: nucleotide sequence for Cixutumumab-Fab light chain region with amber codon introduced at 172 Lys site of λ light chain Description of SEQ ID NO: 73-artificial sequence: nucleotide sequence for Cixutumumab-Fab light chain region with amber codon introduced at 187 Lys site of λ light chain Description of SEQ ID NO: 74-artificial sequence: nucleotide sequence for Cixutumumab-Fab light chain region with amber codon introduced at 207 Lys site of λ light chain Description of SEQ ID NO: 75-artificial sequence: nucleotide sequence for Cixutumumab-Fab light chain region with amber codon introduced at 119 Pro site of λ light chain Description of SEQ ID NO: 76-artificial sequence: nucleotide sequence for Cixutumumab-Fab light chain region with amber codon introduced at 125 Leu site of λ light chain Description of SEQ ID NO: 77-artificial sequence: nucleotide sequence for Cixutumumab-Fab light chain region with amber codon introduced at 137 Ser site of λ light chain Description of SEQ ID NO: 78-artificial sequence: nucleotide sequence for Cixutumumab-Fab light chain region with amber codon introduced at 160 Glu site of λ light chain Description of SEQ ID NO: 79-artificial sequence: nucleotide sequence for Cixutumumab-Fab light chain region with amber codon introduced at 161 Thr site of λ light chain Description of SEQ ID NO: 80-artificial sequence: nucleotide sequence for Cixutumumab-Fab light chain region with amber codon introduced at 165 Ser site of λ light chain Description of SEQ ID NO: 81-artificial sequence: nucleotide sequence for Cixutumumab-Fab light chain region with amber codon introduced at 173 Tyr site of λ light chain Description of SEQ ID NO: 82-artificial sequence: nucleotide sequence for Cixutumumab-Fab light chain region with amber codon introduced at 180 Ser site of λ light chain Description of SEQ ID NO: 83-artificial sequence: nucleotide sequence for Cixutumumab-Fab light chain region with amber codon introduced at 189 His site of λ light chain Description of SEQ ID NO: 84-artificial sequence: nucleotide sequence for Cixutumumab-Fab light chain region with amber codon introduced at 191 Ser site of λ light chain Description of SEQ ID NO: 85-artificial sequence: nucleotide sequence for Cixutumumab-Fab light chain region with amber codon introduced at 195 Gln site of λ light chain Description of SEQ ID NO: 86-artificial sequence: nucleotide sequence for Cixutumumab-Fab light chain region with amber codon introduced at 197 Thr site of λ light chain Description of SEQ ID NO: 87-artificial sequence: nucleotide sequence for Cixutumumab-Fab light chain region with amber codon introduced at 205 Val site of λ light chain Description of SEQ ID NO: 88-artificial sequence: nucleotide sequence for Cixutumumab-Fab light chain region with amber codon introduced at 210 Ala site of λ light chain Description of SEQ ID NO: 89-artificial sequence: nucleotide sequence for Cixutumumab-Fab light chain region with amber codon introduced at 215 Ser site of λ light chain Description of SEQ ID NO: 90-artificial sequence: nucleotide sequence for Cixutumumab-Fab light chain region with amber codon introduced at 127 Ala site of λ light chain Description of SEQ ID NO: 91-artificial sequence: nucleotide sequence for Cixutumumab-Fab light chain region with amber codon introduced at 143 Ala site of λ light chain Description of SEQ ID NO: 92-artificial sequence: nucleotide sequence for Cixutumumab-Fab light chain region with amber codon introduced at 147 Ala site of λ light chain Description of SEQ ID NO: 93-artificial sequence: nucleotide sequence for Cixutumumab-Fab light chain region with amber codon introduced at 157 Ala site of λ light chain Description of SEQ ID NO: 94-artificial sequence: nucleotide sequence for VL of Farletuzumab-Fab Description of SEQ ID NO: 95-artificial sequence: nucleotide sequence for VH of Farletuzumab-Fab Description of SEQ ID NO: 96-artificial sequence: nucleotide sequence for VL of Adalimumab-Fab Description of SEQ ID NO: 97-artificial sequence: nucleotide sequence for VH of Adalimumab-Fab Description of SEQ ID NO: 98-artificial sequence: nucleotide sequence for VL of Rituximab-Fab Description of SEQ ID NO: 99-artificial sequence: nucleotide sequence for VH of Rituximab-Fab Description of SEQ ID NO: 100-artificial sequence: nucleotide sequence for VL of Bevacizumab-Fab Description of SEQ ID NO: 101-artificial sequence: nucleotide sequence for VH of Bevacizumab-Fab Description of SEQ ID NO: 102-artificial sequence: nucleotide sequence for heavy chain of Antibody No. 2 or 5

Description of SEQ ID NO: 103-artificial sequence: nucleotide sequence for heavy chain of Antibody No. 3 or 6

Description of SEQ ID NO: 104-artificial sequence: nucleotide sequence for light chain of Trastuzumab Description of SEQ ID NO: 105-artificial sequence: nucleotide sequence for heavy chain of Trastuzumab Description of SEQ ID NO: 106-artificial sequence: nucleotide sequence of nine copies of U6-tRNA$^{Pyl}$ Description of SEQ ID NO: 107-artificial sequence: nucleotide sequence for mutant of Pyl RS (Y306A/Y384F)

The invention claimed is:

1. A polynucleotide comprising a nucleotide sequence encoding a monoclonal IgG antibody or antigen-binding fragment thereof which comprises at least one lysine derivative,
   at positions selected from the group consisting of 131, 177, and 199 of a heavy chain of a human IgG antibody and at positions 155, 191, and 197 of a κ chain of a human antibody numbering according to the EU-index,
   wherein said lysine derivative is encoded by a nonsense codon, and
   wherein said lysine derivative is selected from the group consisting of a Z-lysine derivative, N6-(((trans-cyclooct-2-en-1-yl)oxy)carbonyl)-L-lysine (hereinafter, abbreviated as "TCO*-Lys"), and N6-((bicyclo[6.1.0]non-4-yn-9-ylmethoxy)carbonyl)-L-lysine (hereinafter, abbreviated as "BCN-Lys").

2. A vector comprising the polynucleotide according to claim 1.

3. A transformed cell comprising the vector according to claim 2.

4. The transformed cell according to claim 3, wherein the cell is a prokaryotic cell or a eukaryotic cell.

5. A method for producing a monoclonal IgG antibody or antigen-binding fragment thereof which comprises at least one lysine derivative,
   wherein the method comprises culturing the transformed cell according to claim 3 in a medium, and collecting the monoclonal IgG antibody or antigen-binding fragment thereof which comprises at least one lysine derivative from the culture,
   wherein said at least one lysine residue is at positions selected from the group consisting of 131, 177, and 199 of a heavy chain of a human IgG antibody and at positions 155, 191, and 197 of a κ chain of a human antibody numbering according to the EU-index, and
   wherein said lysine derivative is selected from the group consisting of a Z-lysine derivative, N6-(((trans-cyclooct-2-en-1-yl)oxy)carbonyl)-L-lysine (hereinafter, abbreviated as "TCO*-Lys"), and N6-((bicyclo[6.1.0]non-4-yn-9-ylmethoxy)carbonyl)-L-lysine (hereinafter, abbreviated as "BCN-Lys").

6. The method according to claim 1, wherein the nonsense codon is an amber codon.

7. The method according to claim 1, wherein said lysine derivative is a Z-lysine derivative.

8. The method according to claim 1, wherein said lysine derivative is TCO*-Lys or BCN-Lys.

9. The vector according to claim 2, wherein said vector further comprises at least one of: a nucleotide sequence encoding a tRNA; and a nucleotide sequence encoding an aminoacyl tRNA synthetase.

10. The vector according to claim 2, wherein said vector further comprises at least one of: a nucleotide sequence encoding a pyrrolysine tRNA; and a nucleotide sequence encoding a pyrrolysyl tRNA synthetase.

11. The vector according to claim 10, wherein the nucleotide sequence encoding the pyrrolysine tRNA comprises the nucleotide sequence of SEQ ID NO: 1 or 106, and wherein the nucleotide sequence encoding the pyrrolysyl tRNA synthetase comprises the nucleotide sequence of SEQ ID NO: 107.

12. The transformed cell according to claim 3, wherein said transformed cell further comprises at least one of: a nucleotide sequence encoding a tRNA; and a nucleotide sequence encoding an aminoacyl tRNA synthetase.

13. The transformed cell according to claim 3, wherein said transformed cell further comprises at least one of: a nucleotide sequence encoding a pyrrolysine tRNA; and a nucleotide sequence encoding a pyrrolysyl tRNA synthetase.

14. The transformed cell according to claim 13, wherein the nucleotide sequence encoding the pyrrolysine tRNA comprises the nucleotide sequence of SEQ ID NO: 1 or 106, and wherein the nucleotide sequence encoding the pyrrolysyl tRNA synthetase comprises the nucleotide sequence of SEQ ID NO: 107.

* * * * *